US012492257B2

(12) United States Patent
Van Dijk et al.

(10) Patent No.: US 12,492,257 B2
(45) **Date of Patent: *Dec. 9, 2025**

(54) ANTI-CTLA-4 ANTIBODIES AND METHODS OF USE THEREOF

(71) Applicants: AGENUS INC., Lexington, MA (US); Ludwig Institute for Cancer Research Ltd., Zurich (CH); Memorial Sloan-Kettering Cancer Center, New York, NY (US)

(72) Inventors: Marc Van Dijk, Bosch en Duin (NL); Cornelia Anne Mundt, Lörrach (DE); Gerd Ritter, New York, NY (US); David Schaer, Mamaroneck, NY (US); Jedd David Wolchok, New York, NY (US); Taha Merghoub, Jersey City, NJ (US); David Adam Savitsky, Boxford, MA (US); Nicholas Stuart Wilson, San Carlos, CA (US)

(73) Assignees: AGENUS INC., Lexington, MA (US); LUDWIG INSTITUTE FOR CANCER RESEARCH LTD., Zurich (CH); MEMORIAL SLOAN-KETTERING CANCER CENTER, New York, NY (US)

( * ) Notice: Subject to any disclaimer, the term of this patent is extended or adjusted under 35 U.S.C. 154(b) by 930 days.

This patent is subject to a terminal disclaimer.

(21) Appl. No.: 17/582,839

(22) Filed: Jan. 24, 2022

(65) Prior Publication Data

US 2022/0267443 A1 Aug. 25, 2022

Related U.S. Application Data

(63) Continuation of application No. 16/858,195, filed on Apr. 24, 2020, now Pat. No. 11,267,889, which is a continuation of application No. 16/572,216, filed on Sep. 16, 2019, now abandoned, which is a continuation of application No. 16/165,833, filed on Oct. 19, 2018, now Pat. No. 10,479,833, which is a continuation of application No. 15/166,305, filed on May 27, 2016, now Pat. No. 10,144,779.

(60) Provisional application No. 62/323,226, filed on Apr. 15, 2016, provisional application No. 62/294,558, filed on Feb. 12, 2016, provisional application No. 62/292,500, filed on Feb. 8, 2016, provisional application No. 62/280,263, filed on Jan. 19, 2016, provisional application No. 62/257,202, filed on Nov. 18, 2015, provisional application No. 62/190,653, filed on Jul. 9, 2015, provisional application No. 62/182,363, filed on Jun. 19, 2015, provisional application No. 62/168,391, filed on May 29, 2015.

(51) Int. Cl.

| | |
|---|---|
| ***C07K 16/28*** | (2006.01) |
| ***A61K 47/68*** | (2017.01) |
| ***A61K 51/10*** | (2006.01) |
| ***A61P 35/00*** | (2006.01) |
| ***A61P 37/04*** | (2006.01) |
| ***C12N 15/85*** | (2006.01) |
| *A61K 39/00* | (2006.01) |

(52) U.S. Cl.
CPC ...... *C07K 16/2818* (2013.01); *A61K 47/6849* (2017.08); *A61K 51/1027* (2013.01); *A61P 35/00* (2018.01); *A61P 37/04* (2018.01); *C07K 16/283* (2013.01); *A61K 2039/505* (2013.01); *C07K 2317/21* (2013.01); *C07K 2317/33* (2013.01); *C07K 2317/34* (2013.01); *C07K 2317/41* (2013.01); *C07K 2317/52* (2013.01); *C07K 2317/56* (2013.01); *C07K 2317/565* (2013.01); *C07K 2317/567* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,811,097 | A | 9/1998 | Allison et al. |
| 5,977,318 | A | 11/1999 | Linsley et al. |
| 6,207,156 | B1 | 3/2001 | Kuchroo et al. |
| 6,383,492 | B1 | 5/2002 | Srivastava et al. |
| 6,391,306 | B1 | 5/2002 | Srivastava et al. |
| 6,403,095 | B1 | 6/2002 | Srivastava et al. |
| 6,410,026 | B1 | 6/2002 | Srivastava |
| 6,436,404 | B1 | 8/2002 | Srivastava et al. |

(Continued)

FOREIGN PATENT DOCUMENTS

| | | | |
|---|---|---|---|
| CN | 101074264 | B | 6/2007 |
| CN | 102134276 | A | 7/2011 |

(Continued)

OTHER PUBLICATIONS

"A comprehensive immune-oncology Ecosystem" Cowen and Company 36th Annual Health Care Conference Mar. 2016.
Abdallah A-O., et al., (2016) "Ipilimumab-induced necrotic myelopathy in a patient with metastatic melanoma: A case report and review of literature" Journal of Oncology Pharmacy Practice 22(3):537-542.
Acuto, O., et al., (2003) "CD28-mediated co-stimulation: a quantitative support for TCR signaling" Nature Reviews Immunology 3:939-951.

(Continued)

*Primary Examiner* — Ilia I Ouspenski
(74) *Attorney, Agent, or Firm* — Dechert LLP

(57) ABSTRACT

The instant disclosure provides antibodies that specifically bind to human CTLA-4 and antagonize CTLA-4 function. Also provided are pharmaceutical compositions comprising these antibodies, nucleic acids encoding these antibodies, expression vectors and host cells for making these antibodies, and methods of treating a subject using these antibodies.

20 Claims, 39 Drawing Sheets

Specification includes a Sequence Listing.

(56) References Cited

U.S. PATENT DOCUMENTS

| | | | |
|---|---|---|---|
| 6,447,780 | B1 | 9/2002 | Srivastava et al. |
| 6,447,781 | B1 | 9/2002 | Srivastava |
| 6,610,659 | B1 | 8/2003 | Pramod |
| 6,682,736 | B1 | 1/2004 | Hanson et al. |
| 6,719,972 | B1 | 4/2004 | Gribben et al. |
| 6,808,710 | B1 | 10/2004 | Wood et al. |
| 7,034,121 | B2 | 4/2006 | Carreno et al. |
| 7,332,582 | B2 | 2/2008 | Hardy et al. |
| 7,452,535 | B2 | 11/2008 | Davis et al. |
| 7,465,446 | B2 | 12/2008 | Lowry et al. |
| 7,488,802 | B2 | 2/2009 | Collins et al. |
| 7,605,238 | B2 | 10/2009 | Korman et al. |
| 7,943,743 | B2 | 5/2011 | Korman et al. |
| 8,008,449 | B2 | 8/2011 | Korman et al. |
| 8,039,592 | B2 | 10/2011 | Lazar et al. |
| 8,114,845 | B2 | 2/2012 | Langermann et al. |
| 8,119,129 | B2 | 2/2012 | Jure-Kunkel et al. |
| 8,168,179 | B2 | 5/2012 | Honjo et al. |
| 8,168,757 | B2 | 5/2012 | Finnefrock et al. |
| 8,217,149 | B2 | 7/2012 | Irving et al. |
| 8,263,073 | B2 | 9/2012 | Korman et al. |
| 8,354,509 | B2 | 1/2013 | Carven et al. |
| 8,388,955 | B2 | 3/2013 | Lazar et al. |
| 8,449,886 | B2 | 5/2013 | Jure-Kunkel |
| 8,552,154 | B2 | 10/2013 | Freeman et al. |
| 8,686,119 | B2 | 4/2014 | Rotem-Yehudar et al. |
| 8,697,845 | B2 | 4/2014 | Ward et al. |
| 8,728,474 | B2 | 5/2014 | Honjo et al. |
| 8,735,553 | B1 | 5/2014 | Li et al. |
| 8,747,847 | B2 | 6/2014 | Rotem-Yehudar et al. |
| 8,779,105 | B2 | 7/2014 | Korman et al. |
| 8,779,108 | B2 | 7/2014 | Queva et al. |
| 8,927,697 | B2 | 1/2015 | Davis et al. |
| 8,981,063 | B2 | 3/2015 | Chen |
| 8,993,731 | B2 | 3/2015 | Tyson |
| 9,102,727 | B2 | 8/2015 | Freemn et al. |
| 9,119,839 | B2 | 9/2015 | Huang et al. |
| 9,132,281 | B2 | 9/2015 | Zeng et al. |
| 9,175,082 | B2 | 11/2015 | Zhou et al. |
| 9,205,148 | B2 | 12/2015 | Langermann et al. |
| 9,241,992 | B2 | 1/2016 | Ponte et al. |
| 9,244,059 | B2 | 1/2016 | Triebel et al. |
| 9,273,135 | B2 | 3/2016 | Korman et al. |
| 9,358,289 | B2 | 6/2016 | Korman et al. |
| 9,457,080 | B2 | 10/2016 | Freeman et al. |
| 9,714,290 | B2 | 7/2017 | Jones et al. |
| 9,758,583 | B2 | 9/2017 | Wang et al. |
| 9,856,320 | B2 | 1/2018 | Cogswell et al. |
| 10,144,779 | B2 * | 12/2018 | van Dijk ................. A61P 35/00 |
| 10,479,833 | B2 * | 11/2019 | van Dijk ................. A61P 37/04 |
| 10,912,831 | B1 | 2/2021 | Van Dijk et al. |
| 11,013,802 | B2 | 5/2021 | Van Dijk et al. |
| 11,267,889 | B2 * | 3/2022 | Van Dijk ................ A61P 31/00 |
| 11,638,755 | B2 * | 5/2023 | van Dijk ............ C07K 16/2818 424/136.1 |
| 11,993,653 | B2 * | 5/2024 | Van Dijk ......... A61K 39/39558 |
| 2003/0086930 | A1 | 5/2003 | Mueller et al. |
| 2003/0232323 | A1 | 12/2003 | Freeman et al. |
| 2005/0277173 | A1 | 12/2005 | Chin et al. |
| 2006/0034844 | A1 | 2/2006 | Allison et al. |
| 2006/0093612 | A1 | 5/2006 | Srivastava |
| 2006/0240006 | A1 | 10/2006 | Chu et al. |
| 2009/0123477 | A1 | 5/2009 | Hanke et al. |
| 2009/0214553 | A1 | 8/2009 | Chin et al. |
| 2010/0203056 | A1 | 8/2010 | Irving et al. |
| 2011/0150892 | A1 | 6/2011 | Thudium et al. |
| 2013/0202623 | A1 | 8/2013 | Chomont et al. |
| 2013/0291136 | A1 | 10/2013 | Freeman et al. |
| 2013/0323249 | A1 | 12/2013 | Zhou et al. |
| 2014/0044738 | A1 | 2/2014 | Langermann |
| 2014/0093511 | A1 | 4/2014 | Lonberg et al. |
| 2014/0220021 | A1 | 8/2014 | Shibayama |
| 2014/0286935 | A1 | 9/2014 | Hamblin et al. |
| 2014/0341917 | A1 | 11/2014 | Nastri et al. |
| 2014/0356363 | A1 | 12/2014 | Zhou et al. |
| 2015/0203580 | A1 | 7/2015 | Papadopoulo |
| 2015/0225483 | A1 | 8/2015 | Lo et al. |
| 2015/0259420 | A1 | 9/2015 | Triebel et al. |
| 2015/0273033 | A1 | 10/2015 | Bosch et al. |
| 2015/0283237 | A1 | 10/2015 | Felder et al. |
| 2015/0346208 | A1 | 12/2015 | Couto et al. |
| 2015/0352206 | A1 | 12/2015 | Gajewski et al. |
| 2015/0355184 | A1 | 12/2015 | Pierce et al. |
| 2016/0060344 | A1 | 3/2016 | Narwal et al. |
| 2016/0075753 | A1 | 3/2016 | Altman et al. |
| 2016/0075783 | A1 | 3/2016 | King et al. |
| 2016/0185870 | A1 | 6/2016 | Van Eenennaam et al. |
| 2016/0193239 | A1 | 7/2016 | Baylin et al. |
| 2016/0200814 | A1 | 7/2016 | Smythe |
| 2016/0222121 | A1 | 8/2016 | Johnson et al. |
| 2016/0237154 | A1 | 8/2016 | Gray et al. |
| 2016/0243225 | A1 | 8/2016 | Ioffe et al. |
| 2016/0272708 | A1 | 9/2016 | Chen |
| 2016/0289327 | A1 | 10/2016 | Hermans et al. |
| 2016/0347848 | A1 | 12/2016 | Hammond et al. |
| 2016/0362492 | A1 | 12/2016 | Freeman et al. |
| 2016/0375115 | A1 | 12/2016 | Binder et al. |
| 2016/0376367 | A1 | 12/2016 | Yuan et al. |
| 2017/0037132 | A1 | 2/2017 | Manekas et al. |
| 2017/0088626 | A1 | 3/2017 | Jure-Kunkel et al. |
| 2017/0114364 | A9 | 4/2017 | Allison et al. |
| 2017/0157188 | A1 | 6/2017 | Silvestre et al. |
| 2017/0158776 | A1 | 6/2017 | Feltquate et al. |
| 2017/0209574 | A1 | 7/2017 | Cao et al. |
| 2017/0210806 | A1 | 7/2017 | Liu |
| 2017/0216433 | A1 | 8/2017 | Li et al. |
| 2017/0224734 | A1 | 8/2017 | Chapman et al. |
| 2017/0233476 | A1 | 8/2017 | Zhou et al. |
| 2017/0253655 | A1 | 9/2017 | Bakacs et al. |
| 2017/0296659 | A1 | 10/2017 | Lebwohl et al. |
| 2017/0340733 | A1 | 11/2017 | Cao |
| 2018/0118836 | A1 | 5/2018 | Bernett et al. |
| 2018/0127501 | A1 | 5/2018 | Bernett et al. |
| 2020/0024350 | A1 | 1/2020 | Van Dijk et al. |
| 2021/0205451 | A1 | 7/2021 | Van Dijk et al. |
| 2023/0330225 | A1 | 10/2023 | Van Dijk et al. |

FOREIGN PATENT DOCUMENTS

| | | | |
|---|---|---|---|
| EP | 1137436 | B1 | 10/2001 |
| EP | 1262193 | A1 | 12/2002 |
| EP | 2100615 | B1 | 9/2009 |
| EP | 3206711 | A1 | 8/2017 |
| EP | 3218004 | A1 | 9/2017 |
| EP | 3218408 | A1 | 9/2017 |
| EP | 3233123 | A2 | 10/2017 |
| EP | 3240551 | A1 | 11/2017 |
| JP | 2006327937 | A | 12/2006 |
| JP | 2009213478 | A | 9/2009 |
| JP | 2012100674 | A | 5/2012 |
| JP | 2014167029 | A | 9/2014 |
| WO | WO1999047558 | A2 | 9/1999 |
| WO | WO2001079300 | A1 | 10/2001 |
| WO | WO2002043478 | A2 | 6/2002 |
| WO | WO2004029069 | A2 | 4/2004 |
| WO | WO2005092380 | A2 | 10/2005 |
| WO | WO2006028999 | A2 | 3/2006 |
| WO | WO2006029219 | A2 | 3/2006 |
| WO | WO2006096491 | A2 | 9/2006 |
| WO | WO2007056539 | A2 | 5/2007 |
| WO | WO2007067959 | A2 | 6/2007 |
| WO | WO2007076354 | A2 | 7/2007 |
| WO | WO2007113648 | A2 | 10/2007 |
| WO | WO2007126805 | A2 | 11/2007 |
| WO | WO2008100562 | A2 | 8/2008 |
| WO | WO2009019312 | A2 | 2/2009 |
| WO | WO2009089260 | A2 | 7/2009 |
| WO | WO2009100140 | A1 | 8/2009 |
| WO | 2010014784 | A2 | 2/2010 |
| WO | WO2011020024 | A2 | 2/2011 |
| WO | WO2011061487 | A1 | 5/2011 |
| WO | WO2011120135 | A1 | 10/2011 |
| WO | WO2012120125 | A1 | 9/2012 |
| WO | WO2012162277 | A1 | 11/2012 |

(56) References Cited

FOREIGN PATENT DOCUMENTS

| | | | |
|---|---|---|---|
| WO | WO201 3022091 | A1 | 2/2013 |
| WO | WO2013043569 | A1 | 3/2013 |
| WO | WO2013126809 | A1 | 8/2013 |
| WO | WO2013169388 | A1 | 11/2013 |
| WO | WO2013173223 | A1 | 11/2013 |
| WO | WO2013142796 | A2 | 12/2013 |
| WO | WO2014022758 | A2 | 4/2014 |
| WO | WO2014055897 | A2 | 4/2014 |
| WO | WO2014066532 | A1 | 5/2014 |
| WO | WO2014100079 | A1 | 6/2014 |
| WO | WO2014144960 | A2 | 9/2014 |
| WO | WO2014179664 | A2 | 11/2014 |
| WO | WO2014206107 | A1 | 12/2014 |
| WO | WO2014209804 | A1 | 12/2014 |
| WO | WO2015009856 | A2 | 1/2015 |
| WO | WO2015036394 | A1 | 3/2015 |
| WO | WO2015042246 | A1 | 3/2015 |
| WO | WO2015058573 | A1 | 4/2015 |
| WO | WO2015061668 | A1 | 4/2015 |
| WO | WO2015085847 | A1 | 6/2015 |
| WO | WO2015109124 | A2 | 7/2015 |
| WO | WO2015116539 | A1 | 8/2015 |
| WO | WO2015195163 | A1 | 12/2015 |
| WO | WO2015200119 | A1 | 12/2015 |
| WO | WO2016000619 | A1 | 1/2016 |
| WO | WO2016015685 | A1 | 2/2016 |
| WO | WO2016020856 | A1 | 2/2016 |
| WO | WO2016028672 | A1 | 2/2016 |
| WO | WO2016030350 | A1 | 3/2016 |
| WO | WO2016149387 | A1 | 9/2016 |
| WO | WO2016168809 | A1 | 10/2016 |
| WO | WO2016179576 | A1 | 11/2016 |
| WO | WO2016183469 | A1 | 11/2016 |
| WO | WO2016196237 | A1 | 12/2016 |
| WO | WO2016196389 | A1 | 12/2016 |
| WO | WO2016197067 | A1 | 12/2016 |
| WO | WO201 7021913 | A1 | 2/2017 |
| WO | WO201 7025871 | A1 | 2/2017 |
| WO | WO201 7062615 | A2 | 4/2017 |
| WO | WO2017079303 | A1 | 5/2017 |
| WO | WO2017106372 | A1 | 6/2017 |
| WO | WO2017120612 | A1 | 7/2017 |
| WO | WO2017129790 | A1 | 8/2017 |
| WO | WO201 7160717 | A2 | 9/2017 |
| WO | WO2017149150 | A1 | 9/2017 |
| WO | WO2017156349 | A1 | 9/2017 |
| WO | WO2017198212 | A1 | 11/2017 |
| WO | WO2017201502 | A1 | 11/2017 |
| WO | 2017218707 | A2 | 12/2017 |
| WO | WO2018106864 | A1 | 6/2018 |

OTHER PUBLICATIONS

"Agenus Announces Clearance of Investigational New Drug Applications by the FDA for anti-CTLA-4 and anti-GITR Antibodies" Jan. 21, 2016 (Business Wire).

"Agenus Commences Phase 1 Clinical Trial of its CTLA-4 Checkpoint Antibody to Treat Solid Tumors" Apr. 27, 2016 (Business Wire).

Agenus Investor Relations Deck May 15, 2015.

Agenus News vol. 1 Issue 1 (2018).

Agenus News vol. 1 Issue 2 (2018).

Agenus News vol. 1 Issue 3 (2018).

"Agenus Presents Posters on Checkpoint Antibody Product Candidates at the American Association for Cancer Research (AACR) 2016 Annual Meeting" Apr. 18, 2016 (Business Wire).

"Agenus R&D Day" Nov. 19, 2015 New York, NY.

"Agonist Checkpoint Modulators: Challenges and Opportunities" PEGS Boston May $8^{1h}$, 2015.

Alegre, M.L., et al., (2001) "T-cell regulation by CD28 and CTLA-4" Nat Rev Immunol 1(3):220-8.

Ampie L., et al., (2015) "Heat shock protein vaccines against glioblastoma: from bench to bedside" J. Neurooncol. 123:441-8.

Arnold, D., et al., (1997) "Influences of Transporter Associated with Antigen Processing (TAP) on the Repertoire of Peptides Associated with the Endoplasmic Reticulum-resident Stress Protein gp96" J. Exp. Med. vol. 186(3):461-466.

Azuma, M., et al., (1993) "B70 antigen is a second ligand for CTLA-4 and CD28" Nature 366:76-79.

Ban-Hoefen M., et al., (2016) "Ipilimumab-Induced Neutropenia in Melanoma." Journal of Investigative Medicine High Impact Case Reports 4(3):1-5.

Bartkowiak, T., et al., (2015) "Unique potential of 4-1BB agonist antibody to promote durable regression of HPV+ tumors when combined with an E6/E7 peptide vaccine" PNAS E5290-E5299.

Binder, R.J., (2014) "Functions of heat shock proteins in pathways of the innate and adaptive immune system" J. Immunol. 193:5765-5771.

Binder, R.J., et al., (2005) "Peptides chaperoned by heat-shock proteins are a necessary and sufficient source of antigen in the cross-priming of CD8+ T Cells" Nature Immunology 6(6):593-599.

Blachere, N.E., et al., (1993) "Heat Shock Protein Vaccines Against Cancer" Journal of Immunotherapy 14:352-356.

Boise, L.H., et al., (1995) "CD28 costimulation can promote T cell survival by enhancing the expression of Bcl-XL" Immunity 3:87-98.

Bouchez, C., et al., (2012) "Development of a Delayed-Type Hypersensitivity (DTH) Model in the Cynomolgus Monkey" J. Toxicol. Pathol. 25:183-188.

Boussiotis, V.A., et al., (2014) "Somatic Mutations and Immunotherapy Outcome with CTLA-4 Blockade in Melanoma" N. Engl. J. Med. 371:2189-2199.

Boutros, C., et al., (2016) "Safety profiles of anti-CTLA-4 and anti-PD-1 antibodies alone and in combination" Nature Reviews 13:473-86.

Bowes, J., et al., (2012) "Reducing safety-related drug attrition: the use of in vitro pharmacological profiling" Nature Reviews Drug Discovery 11:909-922.

Braster, R., et al., (2014) "Myeloid cells as effector cells for monoclonal antibody therapy of cancer" Methods 65:28-37.

Brem, H., et al., (1995) "Placebo-controlled trial of safety and efficacy of intraoperative controlled delivery by biodegradable polymers of chemotherapy for recurrent gliomas" Lancet 345:1008-12.

Brennan, F.R., et al., (2010) "Safety and immunotoxicity assessment of immunomodulatory monoclonal antibodies" MAbs 2:233-255.

Breous-Nystrom, E., et al., (2014) "Retrocyte Display@ technology: generation and screening of a high diversity cellular antibody library" Methods 65:57-67.

Bretscher, P.A., (1999) "A two-step, two-signal model for the primary activation of precursor helper T cells" Proc. Natl. Acad. Sci. USA 96:185-90.

Bristol-Myers Squibb. Yervoy (ipilimumab) United States Prescribing Information.

Brown, S.D., (2014) "Neo-antigens predicted by tumor genome meta-analysis correlate with increased patient survival" Genome Res. 24:743-750.

Bruhns, O., et al., (2009) "Specificity and affinity of human Fcgamma receptors and their polymorphic variants for human IgG subclasses" Blood 113:3716-3752.

Brunet, J.F., et al., (1987) "A new member of the immunoglobulin superfamily—CTLA-4" Nature 328:267-270.

Bryceson, Y.T., et al., (2006) "Activation, coactivation, and costimulation of resting human natural killer cells" Immunol Rev 214:73-91.

Buchbinder, E.I., et al., (2016) "CTLA-4 and PD-1 Pathways: Similarities, Differences, and Implications of Their Inhibition" American Journal of Clinical Oncology 39(1):98-106.

Bukau, B., et al., (1998) "The HSP70 and HSp60 Chaperone Machines" Cell 92:351-366.

Bulliard, Y., et al., (2013) "Activating Fc gamma receptors contribute to the antitumor activities of immunoregulatory receptor-targeting antibodies" J. Exp. Med. 210:1685-1693.

Bulliard, Y., et al., (2014) "OX40 engagement depletes intratumoral Tregs via activating FcyRs, leading to antitumor efficacy" Immunology and Cell Biology 92:475-480.

(56) References Cited

OTHER PUBLICATIONS

Callahan, M.K., (2015) "CTLA-4 and PD-1 Pathway Blockade: Combinations in the Clinic" Front Oncol 4(385):1-6.
Callahan, M.K., et al., (2010) "Anti-CTLA-4 Antibody Therapy: Immune Monitoring During Clinical Development of a Novel Immunotherapy" Semin. Oncol. Oct. 37(5):473-484.
Camacho, L.H., (2015) "CTLA-4 blockade with ipilimumab: biology, safety, efficacy, and future considerations" Cancer Medicine 4(5):661-672.
Caravella et al., (2010) "Structure-Guided Design of Antibodies" Current Computer-Aided Drug Design 6(2):128-138.
Carthon, B.C., et al., (2010) "Preoperative CTLA-4 Blockade: Tolerability and Immune Monitoring in the Setting of a Presurgical Clinical Trial" Clinical Cancer Res. 16(10):286171.
Cartron, G., et al., (2002) "Therapeutic activity of humanized anti-CD20 monoclonal antibody and polymorphism in IgG Fc receptor FcyRIIIa gene" Blood 99:754-758.
Castle J.C., et al., (2014) "Immunomic, genomic and transcriptomic characterization of CT26 colorectal carcinoma" BMC Genomics 15:190.
Caudill et al., (2001) "HSPPC-96: a personalized cancer vaccine," Exp. Opin. Biol. Ther. 1(3):539-547.
Ceuppens, J.L., et al., (1988) "Human T cell activation with phytohemagglutinin. The function of 1-6 as an accessory signal" J. Immunol. 141:3868-3874.
Chaft, J.E., (Mar. 30, 2017) "Immunotherapy for lung cancer and the landscape of combinations" Thoracic Oncology Service Memorial Sloan Kettering Cancer Center.
Chapman, K., et al., (2007) "Preclinical safety testing of monoclonal antibodies: the significance of species relevance" Nat. Rev. Drug Discov. 6:120-126.
Chen, D.S., et al., (2013) "Oncology Meets Immunology: The Cancer-Immunity Cycle" Immunity 39:1-10.
Cheng, Z.J., et al., (2014) "Development of a robust reporter-based ADCC assay with frozen, thaw-and-use cells to measure Fc effector function of therapeutic antibodies" Journal of Immunological Methods 414: 69-81.
Choe J.H., et al., (2016) "Autoimmune meningoencephalitis in a melanoma patient treated with ipilimumab." Immunotherapy 8(10):1163-1167.
Choueiri, T.K., et al., (2015) "Abstract 1306: Biomarker results from a clinical trial of nivolumab in patients (pts) with metastatic renal cell carcinoma (mRCC) (CA209009): Gene expression, serum profiling for immune markers, and multiplex tissue immunohistochemistry (IHC)" Cancer Res. 75:1306.
Chung, C.H., (2008) "Managing premedications and the risk for reactions to infusional monoclonal antibody therapy" The Oncologist 13(6):725-732.
Coiffier, B., (2007) "Rituximab therapy in malignant lymphoma" Oncogene 26:3603-3613.
Collins, A.V., et al., (2002) "The Interaction Properties of Costimulatory Molecules Revisited" Immunity 17:201-210.
Curran, M.A., et al., (2010) "PD-1 and CTLA-4 combination blockade expands infiltrating T cells and reduces regulatory T and myeloid cells within B16 melanoma tumors" Proc. Natl. Acad. Sci. USA 107:4275-4280.
Curti B.D., et al., (2013) "OX40 is a potent immune-stimulating target in late-stage cancer patients" Cancer Res. 73:7189-98.
Dangl, J.L., et al., (1988) "Segmental flexibility and complement fixation of genetically engineered chimeric human, rabbit and mouse antibodies" EMBO J. 7:1989-1994.
Dariavach, P., et al., (1988) "Human Ig superfamily CTLA-4 gene: chromosomal localization and identity of protein sequence between murine and human CTLA-4 cytoplasmic domains" Eur. J. Immunol. 18:1901-1905.
Das, R., et al., (2015) "Combination therapy with anti-CTLA-4 and anti-PD-1 leads to distinct immunologic changes in vivo" Journal of Immunology 194(3):950-959.
Dasanu, C., et al., (2016) "Late-onset pericardial tamponade, bilateral pleural effusions and recurrent immune monoarthritis induced by ipilimumab use for metastatic melanoma" Journal of Oncology Pharmacy Practice 23(3):231-234.
Davis, TA, et al., "MDX-010 (human anti-CTLA4): a phase 1 trial in hormone refractory prostate carcinoma (HRPC)" ASCO 38$^{th}$ Annual Meeting (May 18-21, 2002) Orlando FL.
Dick, L.W., et al., (2008) "C-Terminal Lysine Variants in Fully Human Monoclonal Antibodies: Investigation of Test Methods and Possible Causes" Biotechnology and Bioengineering 100(6):1132-1143.
Drouin, et al., (Apr. 16-20, 2016) "AGEN1884 and AGEN2041: Two functionally distinct anti-CTLA-4 antagonist antibodies," Poster No. 5005 Presented at the American Association for Cancer Research Annual Meeting 2016, New Orleans, LA, USA.
Duraiswamy, J., et al., (2013) "Dual Blockade of PD-1 and CTLA-4 Combined with Tumor Vaccine Effectively Restores T-Cell Rejection Function in Tumors" Cancer Res 73(12):3591-603.
Ehrenstein, MR, et al., (2010) "The importance of natural IgM: scavenger, protector and regulator" Nat. Rev. Immunol. 10(11):778-86.
Eisenhauer, E.A., et al., (2009) "New response evaluation criteria in solid tumours: revised RECIST guideline (version 1.1)" European Journal of Cancer 45(2):228-247.
"Emerging Leader In Immuno-Oncology" Nov. 2015, Lexington, MA.
Epstein, L.B., et al., (1971) "The interaction of human macrophages and lymphocytes in the phytohemagglutinin-stimulated production of interferon" J. Clin. Invest. 50:744-753.
Finco, D., et al., (2014) "Cytokine release assays: current practices and future directions" Cytokine 66:143-155.
Freedman, A.S., et al., (1991) "Selective induction of B7/BB-1 on interferon-gamma stimulated monocytes: a potential mechanism for amplification of T cell activation through the CD28 pathway" Cell Immunol 137:429-437.
Friedman, H.S., et al., (2009) "Bevacizumab Alone and in Combination With Irinotecan in Recurrent Glioblastoma" J Clin Oncol 27(28):4733-40.
Furness, A.J.S., et al., (2014) "Impact of tumour microenvironment and Fc receptors on the activity of immunomodulatory antibodies" Trends in Immunology 35(7):290-298.
Gombos, R.B., et al., (2018) "Toxicological and pharmacological assessment of AGEN1884, a novel human IgG1 anti-CTLA-4 antibody" PLoS One 13(4): e0191926.
Grosso, J.F., et al., (2013) "CTLA-4 blockade in tumor models: an overview of preclinical and translational research" Cancer Immunol. 13:5-19.
Guilliams, M., et al., (2014) "The function of Fcy receptors in dendritic cells and macrophages" Nature Reviews 14:94-109.
Hahn, L., et al., (2016) "Bilateral neuroretinitis and anterior uveitis following ipilimumab treatment for metastatic melanoma" Journal of Ophthalmic Inflammation and Infection 6(14):1-4.
Hall, W., et al., (2008) "Tissue Cross-Reactivity Studies for Monoclonal Antibodies: Predictive Value and Use for Selection of Relevant Animal Species for Toxicity Testing. In Preclinical Safety Evaluation of Biopharmaceuticals: A Science-Based Approach to Facilitating Clinical Trials" J.A.Cavagnaro, ed. (John Wiley & Sons, Inc.) pp. 208-240.
Hanahan, D., et al., (2011) "Hallmarks of cancer: the next generation" Cell 144:646-674.
Hathcock, K.S., et al., (1993) "Identification of an alternative CTLA-4 ligand costimulatory for T cell activation" Science 262:905-907.
Heemskerk, B., et al., (2013) "The cancer antigenome" EMBO J. 32:194-203.
Heinzerling, L., et al., (2016) "Cardiotoxicity associated with CTLA4 and PD1 blocking immunotherapy." Journal for Immuno Therapy of Cancer 4(1):1-11.
Hellmann, M.D., et al., (2016) "CheckMate 012: safety and efficacy of first-line nivolumab and ipilimumab in advanced NSCLC" In ASCO Annual Meeting. Chicago: Proc. Am. Soc. Clin. Oncol.
Herrero-Beaumont, G., et al., (2012) "Abatacept mechanism of action: concordance with its clinical profile" Reumatol. Clin. 8:78-83.

(56) References Cited

OTHER PUBLICATIONS

Hodi, F.S., et al., (2010) “Improved survival with ipilimumab in patients with metastatic melanoma” N. Engl. J. Med. 363:711-723.
Hogarth, PM, et al., (2012) “Fc receptor-targeted therapies for the treatment of inflammation, cancer and beyond” Nat. Rev. Drug Discov. 11(4):311-31.
Hurwitz, A.A., et al., (2000) “Combination Immunotherapy of Primary Prostate Cancer in a Transgenic Mouse Model Using CTLA-4 Blockade” Cancer Res. 60:2444-2448.
Hurwitz, A.A., et al., (1998) “CTLA-4 blockade synergizes with tumor-derived granulocyte-macrophage colony-stimulating factor for treatment of an experimental mammary carcinoma” Proc. Natl. Acad. Sci. USA 95:10067-10071.
Idusogie, E.E., et al., (2000) “Mapping of the Cq Binding Site on Rituxan a Chimeric Antibody with a Human IgG1 Fc” J. Immunol. 164:4178-4184.
Ikemizu, S., et al., (2000) “Structure and Dimerization of a Soluble Form of B7-1” Immunity 12:51-60.
“Immuno-Oncology” RBS Immunotherapy Conference Mar. 27, 2014.
“Integrated Approach to Immuno-Oncology” Blair Maidstone 1-O Conference NYC Mar. 31, 2016.
“Integrated Solutions in Immuno-Oncology” Apr. 2016.
“Integrated Solutions in Immuno-Oncology” May 2016.
International Search Report with Written Opinion corresponding to International Patent Application No. PCT/US2016/034508, mailed Aug. 5, 2016.
Jacobsen, F.W., et al., (2011) “Molecular and functional characterization of cynomolgus monkey IgG subclasses” J. Immunol. 186:341-349.
Jiang, H., et al., (2015) “Elevated chronic inflammatory factors and myeloid-derived suppressor cells indicate poor prognosis in advanced melanoma patients” Int. J. Cancer 136:2352-2360.
Keler, T., (2003) “Activity and safety of CTLA-4 blockade combined with vaccines in cynomolgus macaques” J. Immunol. 171:6251-6259.
Kesari, S., et al., (2007) “Phase II study of metronomic chemotherapy for recurrent malignant gliomas in adults” Neuro-Oncology 9:354-363.
Kim, J.M., et al., (2013) “Fcy receptors enable anticancer action of proapoptotic and immune-modulatory antibodies” J. of Exp. Med. 210(9):1647.
Koene, H.R., et al., (1997) “Fc gammaRIIIa-158V/F polymorphism influences the binding of IgG by natural killer cell Fc gammaRlla, independently of the Fc gammaRIIIa-48L/R/H phenotype” Blood 90:1109-1114.
Kreisl, T.N., et al., (2008) “Phase II Trial of Single-Agent Bevacizumab Followed by Bevacizumab Plus Irinotecan at Tumor Progression in Recurrent Glioblastoma” J. Clin. Oncol. 27:740-745.
Krummel, M.F., et al., (1995) “CD28 and CTLA-4 have opposing effects on the response of T cells to stimulation” J. Exp. Med. 182:459-465.
Kuehn, H.S., et al., (2014) “Immune dysregulation in human subjects with heterozygous germline mutations in CTLA4” Science 345:1623-1627.
Kuiper, H.M., et al., (1995) “Activated T cells can induce high levels of CTLA-4 expression on B cells” J Immunol 155:1776-1783.
Kumaraguru, U., et al., (2002) “Immunization with Chaperone-Peptide Complex Induces Low-Avidity Cytotoxic T Lymphocytes Providing Transient Protection against Herpes Simplex Virus Infection” Journal of Virology 76(1):136-141.
Lammert, E., et al., (1997) “The endoplasmic reticulum-resident stress protein gp96 binds peptides translocated by TAP” Eur. J. Immunol. 27:923-927.
Langer, C.J., et al., (2016) “Carboplatin and pemetrexed with or without pembrolizumab for advanced, non-squamous non-small-cell lung cancer: a randomised, phase 2 cohort of the open-label KEYNOTE-021 study” The Lancet Oncology, 17(11):1497-1508.
Larkin, J., et al., (2015) “Combined Nivolumab and Ipilimumab or Monotherapy in Untreated Melanoma” New England Journal of Medicine 373(1):23-34.
Le Arnold-Schild, D., et al., (2000) “One-Step Single-Chain Fv Recombinant Antibody-based Purification of pg96 for Vaccine Development” Cancer Research 60:4175-4178.
Leach, D.R., et al., (1996) “Enhancement of Antitumor Immunity by CTLA-4 Blockade” Science 271:1734-36.
Leach, M.W., et al., (2010) “Use of tissue cross-reactivity studies in the development of antibody-based biopharmaceuticals: history, experience, methodology, and future directions.” Toxicol. Pathol. 38:1138-1166.
Li, Z., et al., (1993) “Tumor rejection antigen gp96/grp94 is an ATPase: implications for protein folding and antigen presentation” EMBO Journal 12(8):3143-3151.
Lindquist, S., (1986) “The heat-shock response” Ann. Rev. Biochem. 55:1151-91.
Lindsley, P.S., et al., (1992) “Coexpression and Functional Cooperation of CTLA-4 and CD28 on Activated T Lymphocytes” J Exp Med 176:1595-1604.
Lindsley, P.S., et al., (1996) “Intracellular Trafficking of CTLA-4 and Focal Localization Towards Sites of TCR Engagement” Immunity 4:535-543.
Lindsten, T., et al., (1993) “Characterization of CTLA-4 Structure and Expression on Human T Cells” Journal of Immunology 51(7):3489-99.
Long, G.V., et al., (2016) “Pembrolizumab (pembro) plus ipilimumab (ipi) for advanced melanoma: Results of the KEYNOTE-029 expansion cohort” Journal of Clinical Oncology 34(15_suppl):9506-9506.
Mangsbo, S.M., et al., (2010) “Enhanced Tumor Eradication by Combining CTLA-4 or PD-1 Blockade With CpG Therapy” J. Immunother. 33:225-235.
Marabelle, A., et al., (2013) “Depleting tumor-specific Tregs at a single site eradicates disseminated tumors” J. Clin. Invest. 123:2447-2463.
Marrack, P., et al., (1990) “The toxicity of Staphylococcal Enterotoxin B in Mice is Mediated by T Cells” J. Exp. Med. 171:455-464.
McCoy, K.D., et al., (1999) “The role of CTLA-4 in the regulation of T cell immune responses” Immunol Cell Biol. 77:1-10.
Merck Sharp & Dohme USA, 2017. Keytruda® (pembrolizumab) Package Insert.
Metzler, W.J., et al., (1997) “Solution structure of human CTLA-4 and delineation of a CD80/CD86 binding site conserved in CD28” Nat. Struct. Biol. 4:527-531.
Moreau, T., et al., (1996) “Transient increase in symptoms associated with cytokine release in patients with multiple sclerosis” Brain 119 (Pt 1):225-237.
Newton, D.W., et al., (1996) “Mutations in the MHC Class II Binding Domains of Staphylococcal Enterotoxin A Differentially Affect T Cell Receptor VI3 Specificity” The Journal of Immunology 157:3988-3994.
Nimmerjahn, F., et al., (2006) “Fcgamma receptors: old friends and new family members” Immunity 24:19-28.
Nimmerjahn, F., et al., (2007) “Antibodies, Fc receptors and cancer” Current Opinion in Immunology 19:239-245.
Nimmerjahn, F., et al., (2008) “Fcy receptors as regulators of immune responses” Nature Reviews 8:34-47.
Nimmerjahn, F., et al., (2012) “Translating basic mechanisms of IgG effector activity into next generation cancer therapies” Cancer Immun. 12:13.
Okada, H., et al., (2015) “Immunotherapy response assessment in neuro-oncology: a report of the RANO working group” Lancet Oncol. 16:e534-42.
Oken, M.M., et al., (1982) “Toxicity and response criteria of the Eastern Cooperative Oncology Group” American Journal of Clinical Oncology 5(6):649-655.
Ostrom, Q.T., et al., (2013) “CBTRUS Statistical Report: Primary Brain and Central Nervous System Tumors Diagnosed in the United States in 2006-2010” Neuro-Oncology 15:ii1-ii56.
Ott, P.A., et al., (2013) “CTLA-4 and PD-1/PD-L1 blockade: new immunotherapeutic modalities with durable clinical benefit in melanoma patients” Clin. Cancer Res. 19:5300-5309.

(56) References Cited

OTHER PUBLICATIONS

Page, D.B., et al., (2013) "Checkpoint modulation in melanoma: an update on ipilimumab and future directions" Curr. Oncol. Rep. 15:500-8.
Parekh, B.S., et al., (2012) "Development and validation of an antibody-dependent cell-mediated cytotoxicity-reporter gene assay" mAbs 4:3, 310-318.
Peggs, K.S., et al., (2006) "Principles and use of anti-CTLA4 antibody in human cancer immunotherapy" Current Opinion in Immunology 18:206-213.
Peggs, K.S., et al., (2008) "Cell intrinsic mechanisms of T-cell inhibition and application to cancer therapy" Immunological Reviews 224:141-165.
Peggs, K.S., et al., (2009) "Cancer immunotherapy: co-stimulatory agonists and co-inhibitory antagonists" Clin. Exp. Immunol. 157:9-19.
Petersson, K., (2002) "Crystal structure of a SEA variant in complex with MHC class II reveals the ability of SEA to crosslink MHC molecules" Structure 10:1619-1626.
Phan, et al., (Jul. 8, 2003) "Cancer regression and autoimmunity induced by cytotoxic T lymphocyte-associated antigen 4 blockade in patients with metastatic melanoma" PNAS 100(14):8372-77.
Postow, M.A., et al., (2015) "Nivolumab and ipilimumab versus ipilimumab in untreated melanoma" N. Engl. J. Med. 372:2006-2017.
Presta, L.G., (2008) "Molecular engineering and design of therapeutic antibodies" Curr. Opin. Immunol. 20:460-470.
Preusser, M., et al., (2015) "Prospects of immune checkpoint modulators in the treatment of glioblastoma" Nat. Rev. Neurol. 11(9):504-14.
Qureshi, O.S., et al., (2011) "Trans-endocytosis of CD80 and CD86: a molecular basis for the cell-extrinsic function of CTLA-4" Science 332:600-603.
Regnault, M.M., et al., (2016) "Tumour lysis syndrome: an unexpected adverse event associated with ipilimumab" Journal of the European Academy of Dermatology and Venereology 31(2).
Reubern, J.M., et al., (2006) "Biologic and Immunomodulatory Events after CTLA-4 Blockade with Ticilimumab in Patients with Advanced Malignant Melanoma" Cancer 106:2437-44.
Riley, J.L., et al., (2005) "The CD28 family: a T-cell rheostat for therapeutic control of T-cell activation" Blood 105:13-21.
Robert, C., et al., (2015) "Pembrolizumab versus Ipilimumab in Advanced Melanoma." New England Journal of Medicine 372(26):2521-2532.
Robert, C., et al., (2011) "Ipilimumab plus dacarbazine for previously untreated metastaic melanoma" N. Engl. J. Med. 364:2517-2526.
Robert, L., et al., (2014) "Distinct immunological mechanisms of CTLA-4 and PD-1 blockade revealed by analyzing TCR usage in blood lymphocytes" Oncoimmunology 3:e29244.
Rodman & Renshaw Annual Global Investment Conference Sep. 2015.
Rogers, L.M., et al., (2014) "Complement in Monoclonal Antibody Therapy of Cancer" Immunol Res. 59(0):203-210.
Romano, E., et al., (2015) "Ipilimumab-dependent cell-mediated cytotoxicity of regulatory T cells ex vivo by nonclassical monocytes in melanoma patients" Proc. Natl. Acad. Sci. USA 112:6140-6145.
Roth, M.E., et al., (2016) "Left Ventricular Dysfunction After Treatment With Ipilimumab for Metastatic Melanoma" American Journal of Therapeutics 23(6).
Rothstein, D.M., et al., (2003) "T-cell costimulatory pathways in allograft rejection and tolerance" Immunological Reviews 196: 85-108.
Sampson, J.H., et al., (2010) "Immunologic escape after prolonged progression-free survival with epidermal growth factor receptor variant III peptide vaccination in patients with newly diagnosed glioblastoma" J. Clin. Oncol. 28:4722-4729.
Sarma, J.V., et al., (2011) "The complement system" Cell Tissue Res. 343(1): 227-235.
Sathornsumetee, S., et al., (2010) "Phase II trial of bevacizumab and erlotinib in patients with recurrent malignant glioma" Neuro-Oncology 12(12):1300-1310.
Schandendorf, D., et al., (2015) "Pooled Analysis of Long-Term Survival Data From Phase II and Phase III Trials of Ipilimumab in Unresectable or Metastatic Melanoma" J. Clin. Oncol. 33:1889-1894.
Selby, M.J., et al., (2013) "Anti-CTLA-4 antibodies of IgG2a isotype enhance antitumor activity through reduction of intratumoral regulatory T cells" Cancer Immunol. Res. 1:3242.
Sharma, P. & Allison, J.P., (2015) "The future of immune checkpoint therapy" Science 348(6230):56-61.
Sharpe, A.H., et al., (2002) "The B7-CD28 superfamily" Nat. Rev. Immunol. 2:116-126.
Sheridan (Apr. 7, 2015) "IDO inhibitors move center stage in immuno-oncology" Nat. Biotechnol. 33(4):321-322.
Shields, R.L., et al., (2001) "High resolution mapping of the binding site on human IgG1 for Fc gamma RI, Fc gamma RII, Fc gamma RIII, and FcRn and design of IgG1 variants with improved binding to the Fc gamma R." The Journal of Biological Chemistry 276:6591-6604.
Sica, G.L., et al., (Jun. 2003) "B7—H4, a Molecule of the B7 Family, Negatively Regulates T Cell Immunity" Immunity 18:849-861.
Simpson, T.T., et al., (2013) "Fc-dependent depletion of tumor-infiltrating regulatory T cells co-defines the efficacy of anti-CTLA-4 therapy against melanoma" J. Exp. Med. 210:1695-1710.
Snyder, A., et al., (2014) "Genetic basis for clinical response to CTLA-4 blockade in melanoma" N. Engl. J. Med. 371:2189-2199.
Srivastava, P.K., (2009) et al., "Treating human cancers with heat shock protein-peptide complexes: the road ahead" Expert Opin. Biol. Ther. 9:179-186.
Stamper, C.C., et al., (2001) "Crystal structure of the B7-1/CTLA-4 complex that inhibits human immune responses" Nature 410:608-611.
Stebbings, R., et al., (2007) 'Cytokine Storm' in the phase I trial of monoclonal antibody TGN1412: better understanding the causes to improve preclinical testing of immunotherapeutics J. Immunol. 179:3325-3331.
Stupp, R., et al., (2005) "Radiotherapy plus Concomitant and Adjuvant Temozolomide for Glioblastoma" N. Engl. J. Med. 352(10):987-96.
Tai, X., et al., (2012) "Basis of CTLA-4 function in regulatory and conventional CD4(+) T cells" Blood 119:5155-5163.
Tamura, Y., et al., (1997) "Immunotherapy of tumors with autologous tumor-derived heat shock protein preparations" Science 278:117-120.
"Targeting TNFR family members: Therapeutic opportunities in immuno-oncology and immuno-inflammation" PEGS Boston 2016.
Tivol, E.A., et al., (1995) "Loss of CTLA-4 leads to massive lymphoproliferation and fatal multiorgan tissue destruction, revealing a critical negative regulatory role of CTLA-4" Immunity 3:541-547.
Topalian, S.L., et al., (2015) "Immune checkpoint blockade: a common denominator approach to cancer therapy" Cancer Cell, 27(4):450-461.
Udono, H., et al., (1993) "Cellular requirements for tumor-specific immunity elicited by heat shock proteins: Tumor rejection antigen gp96 primes CDS+ T cells in vivo" Proc. Natl. Acad. Sci. USA 91:3077-3081.
Udono, H., et al., (1994) "Heat Shock Protein 70-associated Peptides Elicit Specific Cancer Immunity" J. Exp. Med. 178:1391-96.
US Food and Drug Administration (FDA) (1997a). Guidance for Industry: S6 Preclinical Safety Evaluation of Biotechnology-Derived Pharmaceuticals. Center for Drug Evaluation and Research (CDER) and Center for Biologics Evaluation and Research (CBER).
US Food and Drug Administration (FDA) (1997b). Points to Consider in the Manufacture and Testing of Monoclonal Antibody Products for Human Use. Center for Biologics Evaluation and Research (CBER).
US Food and Drug Administration (FDA) (2012). Guidance for Industry: S6 Addendum to Preclinical Safety Evaluation of Bio-

(56) References Cited

OTHER PUBLICATIONS technology-Derived Pharmaceuticals. Center for Drug Evaluation and Research (CDER) and Center for Biologics Evaluation and Research (CBER).
Van Den Bent, M.J., et al., (2009) "Randomized Phase II Trial of Erlotinib Versus Temozolomide or Carmustine in Recurrent Glioblastoma: EORTC Brain Tumor Group Study 26034" Journal of Clinical Oncology 27(8):1268-1274.
Van Der Merwe, P.A., et al., (1997) "CD80 (B7-1) Binds Both CD28 and CTLA-4 with a Low Affinity and Very Fast Kinetics" J. Exp. Med. 185(3):393-403.
Van Elsas A, et al., (1999) "Combination Immunotherapy of B16 Melanoma Using Anti-Cytotoxic T Lymphocyte-associated Antigen 4 (CTLA-4) and Granulocyte/ Macrophage Colony-Stimulating Factor (GM-CSF)-producing Vaccines Induces Rejection of Subcutaneous and Metastatic Tumors Accompanied by Autoimmune Depigmentation" J. Exp. Med. 190(3):355-366.
Vessillier, S., et al., (2015) "Cytokine release assays for the prediction of therapeutic mAB safety in first-in man trials—Whole blood cytokine release assays are poorly predictive for IGN1412 cytokine storm" J Immunol Methods 424:43-52.
Victor, C.T., et al., (2015) "Radiation and dual checkpoint blockade activate non-redundant immune mechanisms in cancer" Nature 520(7547):373-7.
Vidal, J.M., et al., (2010) "In vitro cytokine release assays for predicting cytokine release syndrome: the current state-of-the-science" Report of a European Medicines Agency Workshop. Cytokine 51:213-215.
Vidarsson, G., et al., (2014) "IgG subclasses and allotypes: from structure to effector functions" Frontiers in Immunology 5(520):1-17.
Vredenburgh, J.J., et al., (2007) "Bevacizumab Plus Irinotecan in Recurrent Glioblastoma Multiforme" Journal of Clinical Oncology 25(30):4722-4729.
Waight, J.D., et al., (2015) "Cutting edge: epigenetic regulation of Foxp3 defines a stable population of CD4+ regulatory T cells in tumors from mice and humans" J. Immunol. 194:878-882.
Waight, J.D., et al., (2018) "Selective FcgR Co-engagement on APCs Modulates the Activity of Therapeutic Antibodies Targeting T Cell Antigens" Cancer Cell 33:1033-1047.
Waldhauer, I. et al., (2008) "NK cells and cancer immunosurveillance" Oncogene 27:5932-5943.
Walker et al. (2011) "The emerging role of CTLA4 as a cell-extrinsic regulator of T cell responses" Nat. Rev. Immunol. 11(12):852-63.
Walker, L.S., et al., (2015) Confusing signals: recent progress in CTLA-4 biology Trends in immunology 36:63-70.
Wang, W., et al., (2012) "Biomarkers on melanoma patient T cells associated with ipilimumab treatment" J. Transl. Med. 10:146.
Wang, C., et al., (2014) "In vitro characterization of the anit-PD-1 antibody nivolumab, BMS-936558, and in vivo toxicology in non-human primates" Cancer Immunol. Res. 2:846-856.
Warncke, M., et al., (2012) "Different adaptations of IgG effector function in human and nonhuman primates and implications for therapeutic antibody treatment" J. Immunol. 188:4405-4411.
Waterhouse, P., et al., (1995) "Lymphoproliferative disorders with early lethality in mice deficient in Ctla-4" Science 270:985-988.
Weber, J.S., et al., (2012) "Management of immune-related adverse events and kinetics of response with ipilimumab" Journal of Clinical Oncology 30(21):2691-2697.
Weng, W., et al., (2004) "Clinical Outcome of Lymphoma Patients After Idiotype Vaccination Is Correlated With Humoral Immune Response and Immunoglobulin G Fc Receptor Genotype" J. Clin. Oncol. 22:4717-4724.
Weng, W.K., et al., (2003) "Two immunoglobulin G fragment C receptor polymorphisms independently predict response to rituximab in patients with follicular lymphoma" J. Clin. Oncol. 21:3940-3947.
Willman, J.H., et al., (2001) "Multiplex Analysis of Heterophil Antibodies in Patients With Indeterminate HIV Immunoassay Results" Am. J. Clin. Pathol. 115:764-769.
Wilson, N.S., et al., (2005) "Regulation of antigen presentation and cross-presentation in the dendritic cell network: facts, hypothesis, and immunological implications" Adv. Immunol. 86:241-305.
Wilson, N.S., et al., (2011) "An Fcgamma receptor-dependent mechanism drives antibody-mediated target-receptor signaling in cancer cells" Cancer Cell 19:101-113.
Wing, K., et al., (2008) "CTLA-4 control over FOXp3+ regulatory T cell function" Science 322:271-275.
Wolchok, J.D., et al., (2009) "Guidelines for the evaluation of immune therapy activity in solid tumors: immune-related response criteria" Clin. Cancer Res. 15:7412-20.
Wolchok, J.D., et al., (2010) "Ipilimumab monotherapy in patients with pretreated advanced melanoma: a randomised, double-blind, multicentre, phase 2, dose-ranging study" The Lancet Oncology 11(2):155-64.
Wolchok, J.D., et al., (2016) "Updated results from a phase III trial of nivolumab (NIVO) combined with ipilimumab (IPI) in treatment-naive patients (pts) with advanced melanoma (MEL) (CheckMate 067)" Journal of Clinical Oncology 34(15 suppl):9505.
Wong, E.T., et al., (1999) "Outcomes and Prognostic Factors in Recurrent Glioma Patients Enrolled Onto Phase II Clinical Trials" J. Clin. Oncol. 17:2572-2578.
Wu, J., et al., (1997) "A Novel Polymorphism of FcyRIIIa (CD16) Alters Receptor Function and Predisposes to Autoimmune Disease" J. Clin. Invest. 100(5):1059-1070.
Wu, L.X., et al., (2005) "CD28 Regulates the Translation of BcLXL via the Phosphatidylinositol 3-inase/Mammalian Target Rapamycin Pathway" J. Immunol. 174:180-194.
Wu et al. (May 1, 2013) "Eradication of melanoma by intratumoral injection of attenuated vaccinia virus requires CD8+ T cells and combination of anti-CTLA-4 blockade and virotherapy enhances therapeutic efficacy in advanced melanoma" J. Invest. Dermatol. 133(Suppl 1):5241. Abstract No. 1415.
Xu, et al., (2012) "Affinity and cross-reactivity engineering of CTLA4-19 to modulate T cell costimulation" J. Immunol. 189(9):4470-7.
Yamaguchi, T., et al., (2013) "Construction of self-recognizing regulatory T cells from conventional T cells by controlling CTLA-4 and IL-2 expression" Proc. Natl. Acad. Sci. USA 110:E2116-2125.
Yang, J.C., et al., (2007) "Ipilimumab (Anti-CTLA4 Antibody) Causes Regression of Metastatic Renal Cell Cancer Associated With Enteritis and Hypophysitis" J. Immunother. 30(8):825-830.
Yao, S., et al., (2013) "Advances in targeting cell surface signaling molecules for immune modulation" Nat Rev Drug Discov. 12:130-146.
Zhang, X., et al., (2003) "Crystal structure of the receptor-binding domain of human B72: insights into organization and signaling" Proc. Natl. Acad. Sci. USA 100:2586-2591.
Zipfel, P.F., et al., (2009) "Complement regulators and inhibitory proteins" Nat. Rev. Immunol. 9:729-740.
Zitvogel, L., et al., (2006) "Cancer despite immunosurveillance: immunoselection and immunosubversion" Nature Reviews 6:715-727.
Zou, W., (2006) "Regulatory T cells, tumour immunity and immunotherapy" Nat. Rev. Immunol. 6:295-307.
Feb. 28, 2016 Q4 2015 Results—Earnings Call Transcript.
Aug. 3, 2017 Q2 2017 Results—Earnings Call Transcript.
Nov. 7, 2017 Q3 2017 Results—Earnings Call Transcript.
Barthelemy et al., "Comprehensive Analysis of the Factors Contributing to the Stability and Solubility of Autonomous Human VH Domains", The Journal of Biological Chemistry, Feb. 8, 2008, 283(6):3639-3654.
Beiboer et al., "Guided Selection of a Pan Carcinoma Specific Antibody Reveals Similar Binding Characteristics yet Structural Divergence Between the Original Murine Antibody and its Human Equivalent", Journal of Molecular Biology, 2000, 296(3):833-849.
Choi et al., "Predicting antibody complementarity determining region structures without classification", Molecular Biosystems, 2011, 7(12):3327-3334.
De Genst et al., "Antibody repertoire development in camelids", Developmental and Comparative Immunology, 2006, 30(1-2):187-198.

(56) References Cited

OTHER PUBLICATIONS

Edwards et al., "The remarkable flexibility of the human antibody repertoire; isolation of over one thousand different antibodies to a single protein, BLyS", Journal of Molecular Biology, 2003, 334(1):103-118.
Griffiths et al., "Human anti-self antibodies with high specificity from phage display libraries", The EMBO Journal, 1993, 12(2):725-734.
Klimka et al., "Human anti-CD30 recombinant antibodies by guided phage antibody selection using cell panning", British Journal of Cancer, 2000, 83(2):252-260.
Lee et al., "Molecular Interactions of Antibody Drugs Targeting PD-1, PD-L1, and CTLA-4 in Immuno-Oncology", Molecules, 2019, 24(6):1190, pp. 1-16.
Lloyd et al., "Modelling the human immune response: performance of a 1011 human antibody repertoire against a broad panel of therapeutically relevant antigens", Protein Engineering, Design & Selection, 2009, 22(3):159-168.
Malia et al., "Epitope mapping and structural basis for the recognition of phosphorylated tau by the anti-tau antibody AT8", Proteins, 2016, 84(4):427-434.
Ward et al., "Binding activities of a repertoire of single immunoglobulin variable domains secreted from *Escherichia coli*", Nature, Oct. 12, 1989, 341(6242):544-546.
International Preliminary Report on Patentability received for PCT Application No. PCT/US2016/034508, mailed on Dec. 14, 2017, 10 pages.
International Preliminary Report on Patentability received for PCT Application No. PCT/US2017/065011, mailed on Jun. 20, 2019, 12 pages.
International Search Report with Written Opinion received for PCT Application No. PCT/US2017/065011 , mailed on Mar. 13, 2018, 17 pages.

* cited by examiner

Surface Plasmon Resonance ($K_D$)

| | Human | | Cynomolgus | | Mouse | Rat | |
|---|---|---|---|---|---|---|---|
| | CTLA-4 | | CTLA-4 | | CTLA-4 | CTLA-4 | |
| | dimer | monomer | dimer | monomer | dimer | dimer | monomer |
| AGEN1884 | 0.6 nM | 0.8 nM | 6.2 nM | 1.6 nM | 9.9 nM | No binding | No binding |
| Reference Antibody (IgG1) | 0.54 nM | 1.2 nM | 1.2 nM | 0.75 nM | 1.2 nM | 26 nM | 22 nM |

CTLA-4 Expressing Cells

Figure 1C

CTLA-4 Selectivity Assay

| | Conc. in ng/ml | rhCTLA-4 Fc (R&D) | rcCTLA-4 Fc (Sino) | rhCD28 Fc (R&D) | rhICOS Fc (R&D) | rhBTLA Fc (Sino) | rhPD-1 Fc (R&D) | rcPD-1 Fc (4AB) |
|---|---|---|---|---|---|---|---|---|
| AGEN1884 | 1000 | 22729 | 16557 | 45 | 43 | 87 | 15 | 32 |
| | 100 | 20859 | 12676 | 48 | 47 | 115 | 25 | 41 |
| | 10 | 7820 | 4096 | 77 | 60 | 95 | 32 | 46 |
| Reference Antibody (IgG1) | 1000 | 20845 | 21580 | 52 | 46 | 97 | 24 | 40 |
| | 100 | 19131 | 19810 | 55 | 53 | 87 | 28 | 41 |
| | 10 | 6825 | 7245 | 65 | 57 | 92 | 35 | 41 |
| Isotype Control (IgG1) | 1000 | 79 | 154 | 57 | 34 | 73 | 31 | 49 |
| | 100 | 75 | 166 | 67 | 67 | 123 | 39 | 45 |
| | 10 | 88 | 175 | 52 | 48 | 91 | 31 | 30 |

Figure 1D

Relative Binding Affinity

| | AGEN1884 | Reference Antibody (IgG1) | Isotype Control (IgG1) |
|---|---|---|---|
| rhCTLA-4 | +++ | +++ | — |
| rcCTLA-4 | +++ | +++ | — |
| rhCD28 | — | — | — |
| rhICOS | — | — | — |
| rhBTLA | — | — | — |
| rhPD-1 | — | — | — |
| rcPD-1 | — | — | — |

Primary Human T Cells
(Surface)

Primary Cynomolgus T cells
(Intracellular)

Figure 5A
Surface Plasmon Resonance ($K_D$)
| | Human CTLA-4 | | Cynomolgus CTLA-4 | |
|---|---|---|---|---|
| | dimer | monomer | dimer | monomer |
| AGEN2041w | 1.7 nM | 2.0 nM | 4.4 nM | 2.1 nM |
| Reference Antibody (IgG1) | 0.5 nM | 1.2 nM | 1.2 nM | 0.8 nM |
| Reference Antibody (IgG2) | 1.5 nM | 1.6 nM | 3.1 nM | 1.5 nM |
Figure 5B
CTLA-4 expressing cells
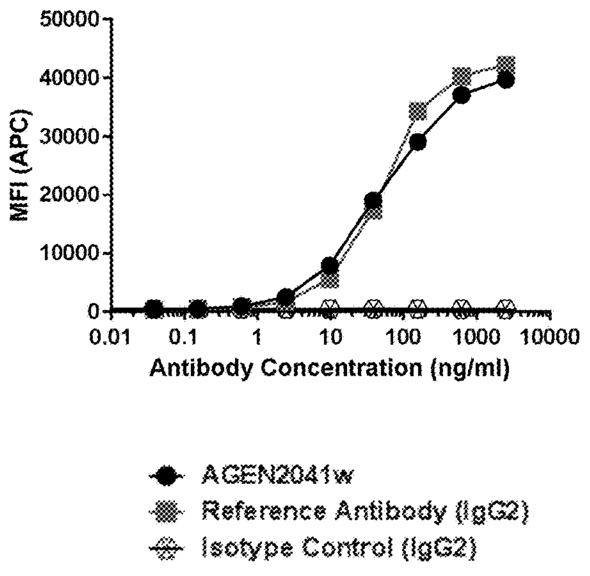
Figure 5C
Inhibition of CD80 and CD86 binding to CTLA-4
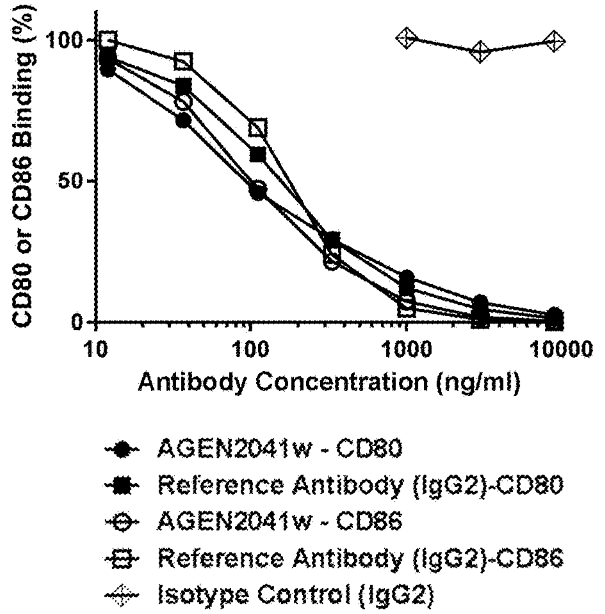

Figure 5D

CTLA-4 Selectivity Assay

| | Conc. in ng/ml | rhCTLA-4 Fc (R&D) | rcCTLA-4 Fc (Sino) | rhCD28 Fc (R&D) | rhICOS Fc (R&D) | rhBTLA Fc (Sino) | rhPD-1 Fc (R&D) | rcPD-1 Fc (4AB) |
|---|---|---|---|---|---|---|---|---|
| AGEN2041w | 1000 | 16693 | 13885 | 58 | 48 | 95 | 30 | 31 |
| | 100 | 15890 | 9949 | 42 | 43 | 104 | 19 | 27 |
| | 10 | 7737 | 3684 | 73 | 55 | 89 | 32 | 29 |
| Reference Antibody (IgG2) | 1000 | 17288 | 16442 | 58 | 49 | 106 | 33 | 39 |
| | 100 | 13932 | 13721 | 62 | 47 | 102 | 43 | 50 |
| | 10 | 4846 | 5143 | 71 | 59 | 111 | 36 | 60 |
| Isotype Control (IgG2) | 1000 | 79 | 158 | 64 | 41 | 93 | 36 | 41 |
| | 100 | 83 | 184 | 52 | 57 | 88 | 94 | 96 |
| | 10 | 80 | 187 | 55 | 58 | 99 | 79 | 70 |

Figure 5E

Relative Binding Affinity

| | AGEN2041w | Reference Antibody (IgG2) | Isotype Control (IgG2) |
|---|---|---|---|
| rhCTLA-4 | +++ | +++ | — |
| rcCTLA-4 | +++ | +++ | — |
| rhCD28 | — | — | — |
| rhICOS | — | — | — |
| rhBTLA | — | — | — |
| rhPD-1 | — | — | — |
| rcPD-1 | — | — | — |

Figure 14
IL-2 (pg/ml)
5000
4000
3000
2000
1000
0
no Ab
Isotype Control (IgG1)
AGEN1884w
AGEN1884w-N297A
AGEN1884w-S267E/L328F
AGEN1884w-S239D/A330L/I332E
Isotype Control (IgG2)
AGEN2041w

*Walker and Sansom Nat. Rev. Immunology 2011*

| CTLA-4-Ig | $K_D$ (nM) |
|---|---|
| CD80-Fc-His* | 0.3 nM |
| CD86-Fc-His* | 3.6 nM |
| Reference Antibody (IgG1) | 0.5 nM |
| AGEN1884 | 0.6 nM |

**Modified from: Xu et al., JI 2012*

Figure 17A

```
P16410 CTLA4_HUMAN   1   MACLGFQRHKAQLNLATRTWPCTLLFFLLFIPVFCKAMHVAQPAVVLASSRGIASFVCEY   60
G7PL88 CTLA4_MACFA   1   ...........R.......R.Y....S.......S.............N...........   60
P09793 CTLA4_MOUSE   1   .....LR.Y....Q.PS....FVA.LT.......SE.IQ.T..S......H.V...P...   60
Q62859 CTLA4_RAT     1   .....L..Y.TH.Q.PS....FGV.LS.....I.SE.IQ.T..S......H.V...P...   60
                         *****:.*:*::*:* :** *    *: *****:*.:*::*:**:****.*:*:*** ***

P16410 CTLA4_HUMAN   61  ASPGKATEVRVTVLRQADSQVTEVCAATYMMGNELTFLDDSICTGTSSGNQVNLTIQGLR   120
G7PL88 CTLA4_MACFA   61  ............................................................   120
P09793 CTLA4_MOUSE   61  SPSHNTD.........TND.M.....T.FTEK.TVG...YPF.S..FNESR.........   120
Q62859 CTLA4_RAT     61  ..SHNTD.........TND.......T.FTVK.T.G....PF.S..FNESR.........   120
                         :   :: *********:.*:*****:*:    * : ***  :*:**  .  .:*********

P16410 CTLA4_HUMAN   121 AMDTGLYICKVELMYPPPYYLGIGNGTQIYVIDPEPCPDSDFLLWILAAVSSGLFFYSFL   180
G7PL88 CTLA4_MACFA   121 ....................M.......................................   180
P09793 CTLA4_MOUSE   121 .V.....L...........FV.M........................V...L........   180
Q62859 CTLA4_RAT     121 .A.....F...........FV.M.....................................   180
                         * *****:***********::*:***********************.*** ********

P16410 CTLA4_HUMAN   181 LTAVSLSKMLKKRSPLTTGVYYVKMPPTEPECEKQFQPYFIPIN   223
G7PL88 CTLA4_MACFA   181 ............................................   223
P09793 CTLA4_MOUSE   181 VS..........................................   223
Q62859 CTLA4_RAT     181 V.....NRT...................................   223
                         ::****.: **********************************
```

Figure 17B

```
SP|P16410|CTLA4_HUMAN  MACLGFQRHKAQLNLATRTWPCTLLFFLLFIP--VFC--------KAMHVAQPAVVLA--- 48
TR|G7PL88|G7PL88_MACFA MACLGFQRHKARLNLATRTRPYTLLFSLLFIP--VFS--------KAMHVAQPAVVLA--- 48
SP|P10747|CD28_HUMAN   -----------------------MLRLLLALN--LFPS-IQVTGNKILVKQSP-MLV--- 30
SP|Q9Y6W8|ICOS_HUMAN   --------------MKSGLWY---------FF--LFCLRIKVLTGEINGSANYEMFI--- 32
SP|Q7Z6A9|BTLA_HUMAN   ----------------MKTLPAMLGTGKLFWV---FFLIPYLDIWNIHGKESCDVQLYIK 41
SP|Q15116|PDCD1_HUMAN  ------------MQIPQAPWPVVWAVLQLGWRPGWFLDSPD-RPWNPPTFSPALLVV--- 44
                                                    *                  :

SP|P16410|CTLA4_HUMAN  --------SSRGIASFVCEYASPGKA---TEVRVTVLRQADSQVTEVCAATYMMGNE--LT 96
TR|G7PL88|G7PL88_MACFA --------NSRGIASFVCEYASPGKA---TEVRVTVLRQADSQVTEVCAATYMMGNE--LT 96
SP|P10747|CD28_HUMAN   --------AYDNAVNLSCKYSYNLFS---REFRASLHKGLDSA-VEVCVVYGNYSQQLQVY 79
SP|Q9Y6W8|ICOS_HUMAN   --------FHNGGVQILCKYPD--IV---QQFKMQLLKGGQ----ILCDLTKTKGSGNTVS 76
SP|Q7Z6A9|BTLA_HUMAN   RQSEHSILAGDPFELECPVKYCANRPHVTWCKLN---GT-------TCVKLEDRQ------ 86
SP|Q15116|PDCD1_HUMAN  --------TEGDNATFTCSFSNTSESFVLNWYRMSPSNQTDK----LAAFPEDR------- 86
                                    : *                 :               .

SP|P16410|CTLA4_HUMAN  FLDDSICT----GTSSGNQVNLTI---QGLRAMDTGLYICKVELMYPPPYYLGIG------ 144
TR|G7PL88|G7PL88_MACFA FLDDSICT----GTSSGNQVNLTI---QGLRAMDTGLYICKVELMYPPPYYMGIG------ 144
SP|P10747|CD28_HUMAN   SKTGFNCD----GKLGNESVTFYL---QNLYVNQTDIYFCKIEVMYPPPYLDNEK------ 127
SP|Q9Y6W8|ICOS_HUMAN   IKSLKFCH----SQLSNNSVSFFL---YNLDHSHANYYFCNLSIFDPPPFKVTLT------ 124
SP|Q7Z6A9|BTLA_HUMAN   ------------TSWKEEKNISFFILHFEPVLPNDNGSYRCSANFQSNL---IE------- 125
SP|Q15116|PDCD1_HUMAN  SQPGQDCRFRVTQLPNGRDFHMSV----VRARRNDSGTYLCGAISLAPKAQIKESLRAELR 143
                                       ... : :          .   * *
```

Figure 17C

```
SP|P16410|CTLA4_HUMAN  -NGTQIYVIDP-----EPCPDS-----DFLLWILAAVSSGLFFYSFLLTAVSL--S-KML 190
TR|G7PL88|G7PL88_MACFA -NGTQIYVIDP-----EPCPDS-----DFLLWILAAVSSGLFFYSFLLTAVSL--S-KML 190
SP|P10747|CD28_HUMAN   SNGTIIHVKGK-----HLCPSPLFPGPSKPFWVLVVVGGVLACYSLLVTVAFI--IFWVR 180
SP|Q9Y6W8|ICOS_HUMAN   --GGYLHIYES-----QLCCQL-------KFWLPIGCAA---FVVVCILGCIL--ICWLT 165
SP|Q7Z6A9|BTLA_HUMAN   SHSTTLYVTDVKSASERPSKDEMASR-PWLLYRLLPLGG----LPLLITTCFCLFCCLRR 180
SP|Q15116|PDCD1_HUMAN  VTERRAEVPTA-----HPSPSPRPAG-QFQTLVVGVVGGLLGSLVLLVWVLAV--ICSRA 195
                              :        . . .                ..      . :

SP|P16410|CTLA4_HUMAN  KKRSP----LTTGVYVKMPPTE-----PEC-EKQFQPYFIPIN----------------- 223
TR|G7PL88|G7PL88_MACFA KKRSP----LTTGVYVKMPPTE-----PEC-EKQFQPYFIPIN----------------- 223
SP|P10747|CD28_HUMAN   SKRSR----LLHSDYMNMTPRR-----PGPTRKHYQPYAPPRD--FAAYRS--------- 220
SP|Q9Y6W8|ICOS_HUMAN   KKKYSSSVHDPNGEYMFMRAVN-----TAKKSRLTDVTL--------------------- 199
SP|Q7Z6A9|BTLA_HUMAN   HQGKQNELSDTAGREINLVDAHLKSEQTEASTRQNSQVLLSETGIYDNDPDLCFRMQEGS 240
SP|Q15116|PDCD1_HUMAN  ARG-------TIG------ARR-----TGQP-LKEDPSAVPVF--SVDYGELDFQWREKT 234
                        :          .        .             .

SP|P16410|CTLA4_HUMAN  ----------------------------------------------------------
TR|G7PL88|G7PL88_MACFA ----------------------------------------------------------
SP|P10747|CD28_HUMAN   ----------------------------------------------------------
SP|Q9Y6W8|ICOS_HUMAN   ----------------------------------------------------------
SP|Q7Z6A9|BTLA_HUMAN   EVYSNPCLEENKP--GIVYASLNHSVIGPNSRLARNVKEAPTEYASI------CVRS- 289
SP|Q15116|PDCD1_HUMAN  PEPPVPCVPEQTEYATIVFP----SGMGTSSPARRGSADGPRSAQPLRPEDGHCSWPL 288
```

Figure 19A

```
                                        CDRH1                 CDRH2
                       10        20        30        40        50        60
              ---------+---------+---------+---------+---------+---------+
BADD411-2354 EVQLVESGGGLVKPGGSLRLSCAASGFTFSSYSMNWVRQAPGKGLEWVSSISSSSSYIYY   60
BADD412-2356 ....L.......Q...................A.S..........V..............   60
BADD412-2357 ............................................................   60
BADD412-2358 ....L.......................................................   60
BADD412-2359 ....L.......Q...................A.S..........V..............   60
BADD412-2360 ............Q.....T.........................................   60

                                                    CDRH3
                       70        80        90        100       110
              ---------+---------+---------+---------+---------+--------
BADD411-2354 ADSVKGRFTISRDNAKNSLYLQMNSLRAEDTAVYYCARVGLMGPFDIWGQGTMVTVSS   118
BADD412-2356 ..........................................................   118
BADD412-2357 .................T........................................   118
BADD412-2358 ..........................................................   118
BADD412-2359 .............................................N............   118
BADD412-2360 ..........................................................   118
```

Figure 19B

```
                                    CDRL1             CDRL2
                     10        20        30        40        50        60
               ---------+---------+---------+---------+---------+---------+
BADD412-2376   EIVLTQSPGTLSLSPGERATLSCRASQSVSRYLGWYQQKPGQAPRLLIYGASTRATGIPD   60
BADD412-2367   ........A....................GT..A..H..V............R.......   60
BADD412-2382   ........A.....................S..A..........S....AT.S.......   60
BADD412-2384   ........A...F.................S..A..................S.......   60
BADD412-2390   ........A...V.................S..A...............A..........   60
BADD412-2393   ........A.....................S..A..................N......A   60

                                          CDRL3
                     70        80        90        100
               ---------+---------+---------+---------+-------
BADD412-2376   RFSGSGSGTDFTLTITRLEPEDFAVYYCQQYGSSPWTFGQGTKVEIK   107
BADD412-2367   ...............S...............................   107
BADD412-2382   .....V.........S................T..............   107
BADD412-2384   ............F..S...................F...P....D..   107
BADD412-2390   .....A.........S...............................   107
BADD412-2393   ...............SS..................F...P....D..   107
```

ANTI-CTLA-4 ANTIBODIES AND METHODS OF USE THEREOF

RELATED APPLICATIONS

This application is a continuation of U.S. patent application Ser. No. 16/858,195, filed Apr. 24, 2020, which is a continuation of U.S. patent application Ser. No. 16/572,216, filed Sep. 16, 2019, which is a continuation of U.S. patent application Ser. No. 16/165,833, filed Oct. 19, 2018, now U.S. Pat. No. 10,479,833, which is a continuation of U.S. patent application Ser. No. 15/166,305, filed May 27, 2016, now U.S. Pat. No. 10,144,779, which claims the benefit of U.S. Provisional Application Nos: 62/168,391, filed May 29, 2015; 62/182,363, filed Jun. 19, 2015; 62/190,653, filed Jul. 9, 2015; 62/257,202, filed Nov. 18, 2015; 62/280,263, filed Jan. 19, 2016; 62/292,500, filed Feb. 8, 2016; 62/294,558, filed Feb. 12, 2016; 62/323,226, filed Apr. 15, 2016, each of which is incorporated by reference herein in its entirety.

SEQUENCE LISTING

The sequence listing attached herewith, named 404299_AGBW_004USC4_188778_Sequence_Listing and created on Apr. 24, 2020, is herein incorporated by reference in its entirety.

1. FIELD

The instant disclosure relates to antibodies that specifically bind to human CTLA-4 and methods of using the same.

2. BACKGROUND

T-lymphocytes are central to the adaptive immune response to antigen. At least two signals are required for full activation of naive T-cells (Bretscher 1999, Proc Natl Acad Sci USA 96:185-90). A first, antigen-specific signal is provided by interaction of the T-cell receptor (TCR) with MHC/peptide complex on an antigen-presenting cell (APC). A second, co-stimulatory signal is provided by the interactions between receptors on the T-cell and their ligands on an antigen presenting cell (APC). Engagement of both TCR/MHC and co-stimulatory interactions leads to T-cell activation via a number of intracellular pathways, including calcium-calcineurin and RAS mitogen-activated protein kinase, and subsequent activation of transcription factors for a number of effector compounds, including cytokines such as IL-2. These events lead to T-cell proliferation, generation of a $CD4^+$ helper T-cell ($T^H$) pool, and expansion of activated $CD8^+$ cytotoxic T-cells. Not only is co-stimulation critical for full T-cell activation, its absence during TCR/MHC engagement results in anergy and/or apoptosis.

Multiple positive and negative co-stimulatory pathways are involved in T-cell regulation, however, the most critical are between CD28 on T-cells and B7-1 (CD80) and B7-2 (CD86) on APCs. CD28 promotes T-cell differentiation into TH1 phenotype cells and enhances antibody production by B cells and activation of T-cells. B7-1 and B7-2, expressed on APCs such as dendritic cells (DC) and B cells, have overlapping but distinct functions. B7-2 is constitutively expressed and is rapidly upregulated on APCs coincident with TCR/MHC engagement (signal 1). B7-1 expression is very low on the resting cell, but is typically induced after prolonged T-cell stimulation. These differences suggest that while B7-2 may be important in initialization of T-cell activation, B7-1 may play a greater role in perpetuating the immune response.

After T-cell activation, a negative regulatory receptor Cytotoxic T-Lymphocyte Antigen 4 (CTLA-4) is upregulated on T-cells (Alegre et al., 2001, Nat Rev Immunol 1:220-8). CTLA-4 is structurally homologous to CD28 but binds more tightly to both B7-1 and B7-2 ligands. CTLA-4 inhibits the immune response in several ways: it competes with CD28 for the B7 ligands and thus blocks co-stimulation; it negatively signals to inhibit T-cell activation; and it can capture CD80 and CD86 from opposing cells by trans-endocytosis, resulting in impaired costimulation via CD28 (Krummel and Allison, 1995, J Exp Med 182:459-465; Walunas et al., 1994, Immunity 1:405-413; Qureshi et al., 2011, Science 332:600-603).

Given the critical role of the B7 co-stimulatory pathway in promoting and maintaining an immune response, therapeutic agents designed to antagonize this pathway are promising for the treatment of autoimmune diseases and disorders.

3. SUMMARY

The instant disclosure provides antibodies that specifically bind to human CTLA-4 and antagonize CTLA-4 function, e.g., CTLA-4-mediated immune suppression. Also provided, are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T-cell activation in response to an antigen (e.g., a tumor antigen) and/or decreasing Treg-mediated immune suppression, and hence for treating cancer in a subject.

Accordingly, in one aspect the instant disclosure provides an isolated antibody comprising a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of $SYX_1MX_2$ (SEQ ID NO: 22), wherein $X_1$ is S or A; and $X_2$ is N or S;

(b) CDRH2 comprises the amino acid sequence of SISSSSSYIYYADSVKG (SEQ ID NO: 2);

(c) CDRH3 comprises the amino acid sequence of VGLMGPFXI (SEQ ID NO: 23), wherein X is D or N;

(d) CDRL1 comprises the amino acid sequence of $RASQSVX_1X_2YLX_3$ (SEQ ID NO: 24), wherein $X_1$ is S or G; $X_2$ is R, S, or T; and $X_3$ is G or A;

(e) CDRL2 comprises the amino acid sequence of $X_1X_2SX_3RAT$ (SEQ ID NO: 25), wherein $X_1$ is G or A; $X_2$ is A or T; and $X_3$ is T, S, R, or N; and (f) CDRL3 comprises the amino acid sequence of $QQYGX_1SPX_2T$ (SEQ ID NO: 26), wherein $X_1$ is S or T; and $X_2$ is W or F.

In certain embodiments, the CDRH1 comprises an amino acid sequence selected from the group consisting of SEQ ID NOs: 1 and 27. In certain embodiments, the CDRH3 comprises an amino acid sequence selected from the group consisting of SEQ ID NOs: 3 and 28. In certain embodiments, the CDRL1 comprises an amino acid sequence selected from the group consisting of SEQ ID NOs: 4, 29, and 30. In certain embodiments, the CDRL2 comprises an amino acid sequence selected from the group consisting of SEQ ID NOs: 5 and 31-35. In certain embodiments, the CDRL3 comprises an amino acid sequence selected from the group consisting of SEQ ID NOs: 6, 36, and 37. In certain embodiments, CDRH1, CDRH2 and CDRH3 comprise the CDRH1, CDRH2 and CDRH3 amino acid sequences, respectively, set forth in SEQ ID NOs: 1, 2, and 3; 27, 2, and 3; or, 27, 2, and 28. In certain embodiments, CDRL1, CDRL2 and CDRL3 comprise the CDRL1, CDRL2 and CDRL3 amino acid sequences, respectively, set forth in SEQ ID NOs: 4, 5, and 6; 29, 32, and 36; 29, 33, and 37; 30, 31, and 6; 29, 34, and 6; or, 29, 35, and 37. In certain embodiments, CDRH1, CDRH2, CDRH3, CDRL1, CDRL2, and CDRL3 comprise the amino acid sequences set forth in SEQ ID NOs: 1, 2, 3, 4, 5, and 6, respectively.

In another aspect, the instant disclosure provides an isolated antibody that specifically binds to human CTLA-4 protein, comprising a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of $SYX_1MX_2$ (SEQ ID NO: 22), wherein $X_1$ is S or A; and $X_2$ is N or S;

(b) CDRH2 comprises the amino acid sequence of SISSSSSYIYYADSVKG (SEQ ID NO: 2);

(c) CDRH3 comprises the amino acid sequence of VGLMGPFXI (SEQ ID NO: 23), wherein X is D or N;

(d) CDRL1 comprises the amino acid sequence of $RASQSVX_1X_2YLX_3$ (SEQ ID NO: 24), wherein $X_1$ is S or G; $X_2$ is R, S, or T; and $X_3$ is G or A;

(e) CDRL2 comprises the amino acid sequence of $X_1X_2SX_3RAT$ (SEQ ID NO: 25), wherein $X_1$ is G or A; $X_2$ is A or T; and $X_3$ is T, S, R, or N; and (f) CDRL3 comprises the amino acid sequence of $QQYGX_1SPX_2T$ (SEQ ID NO: 26), wherein $X_1$ is S or T; and $X_2$ is W or F.

In certain embodiments, the CDRH1 comprises an amino acid sequence selected from the group consisting of SEQ ID NOs: 1 and 27. In certain embodiments, the CDRH3 comprises an amino acid sequence selected from the group consisting of SEQ ID NOs: 3 and 28. In certain embodiments, the CDRL1 comprises an amino acid sequence selected from the group consisting of SEQ ID NOs: 4, 29, and 30. In certain embodiments, the CDRL2 comprises an amino acid sequence selected from the group consisting of SEQ ID NOs: 5 and 31-35. In certain embodiments, the CDRL3 comprises an amino acid sequence selected from the group consisting of SEQ ID NOs: 6, 36, and 37. In certain embodiments, CDRH1, CDRH2 and CDRH3 comprise the CDRH1, CDRH2 and CDRH3 amino acid sequences, respectively, set forth in SEQ ID NOs: 1, 2, and 3; 27, 2, and 3; or, 27, 2, and 28. In certain embodiments, CDRL1, CDRL2 and CDRL3 comprise the CDRL1, CDRL2 and CDRL3 amino acid sequences, respectively, set forth in SEQ ID NOs: 4, 5, and 6; 29, 32, and 36; 29, 33, and 37; 30, 31, and 6; 29, 34, and 6; or, 29, 35, and 37.

In another aspect, the instant disclosure provides an isolated antibody that specifically binds to human CTLA-4 protein, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 4, 5, and 6, respectively.

In certain embodiments, the antibody comprises a heavy chain variable region comprising the amino acid sequence of SEQ ID NO: 72. In certain embodiments, the antibody comprises a heavy chain variable region comprising an amino acid sequence which is at least 75%, 80%, 85%, 90%, 95%, or 100% identical to an amino acid sequence selected from the group consisting of SEQ ID NOs: 7 and 38-42. In certain embodiments, the heavy chain variable region comprises an amino acid sequence selected from the group consisting of SEQ ID NOs: 7 and 38-42. In certain embodiments, the heavy chain variable region comprises the amino acid sequence of SEQ ID NO: 7. In certain embodiments, the antibody comprises a heavy chain comprising the amino acid sequence of SEQ ID NO: 12. In certain embodiments, the antibody comprises a heavy chain comprising the amino acid sequence of SEQ ID NO: 93. In certain embodiments, the antibody comprises a heavy chain comprising the amino acid sequence of SEQ ID NO: 14. In certain embodiments, the antibody comprises a heavy chain comprising the amino acid sequence of SEQ ID NO: 94. In certain embodiments, the antibody comprises a heavy chain comprising the amino acid sequence of SEQ ID NO: 76. In certain embodiments, the antibody comprises a heavy chain comprising the amino acid sequence of SEQ ID NO: 97. In certain embodiments, the antibody comprises a heavy chain variable region having an amino acid sequence derived from a human IGHV3-21 germline sequence (e.g., IGHV3-21*01, e.g., having amino acid sequence of SEQ ID NO: 9).

In certain embodiments, the antibody comprises a light chain variable region comprising the amino acid sequence of SEQ ID NO: 73. In certain embodiments, the antibody comprises a light chain variable region comprising an amino acid sequence which is at least 75%, 80%, 85%, 90%, 95%, or 100% identical to an amino acid sequence selected from the group consisting of SEQ ID NOs: 8 and 43-47. In certain embodiments, the antibody comprises a light chain variable region comprising an amino acid sequence selected from the group consisting of SEQ ID NOs: 8 and 43-47. In certain embodiments, the antibody comprises a light chain variable region comprising the amino acid sequence of SEQ ID NO: 8. In certain embodiments, the antibody comprises a light chain comprising the amino acid sequence of SEQ ID NO: 13. In certain embodiments, the antibody comprises a light chain comprising the amino acid sequence of SEQ ID NO: 15. In certain embodiments, the antibody comprises a light chain variable region having an amino acid sequence derived from a human IGKV3-20 germline sequence (e.g., IGKV3-20*01, e.g., having amino acid sequence of SEQ ID NO: 10) or a human IGKV3-11 germline sequence (e.g., IGKV3-11*01, e.g., having amino acid sequence of SEQ ID NO: 11).

In another aspect, the instant disclosure provides an isolated antibody that specifically binds to human CTLA-4 protein, comprising a heavy chain variable region comprising an amino acid sequence selected from the group consisting of SEQ ID NOs: 7 and 38-42.

In another aspect, the instant disclosure provides an isolated antibody that specifically binds to human CTLA-4 protein, comprising a light chain variable region comprising an amino acid sequence selected from the group consisting of SEQ ID NOs: 8 and 43-47.

In another aspect, the instant disclosure provides an isolated antibody that specifically binds to human CTLA-4 protein, comprising a heavy chain variable region and a light chain variable region, wherein the heavy chain variable region and the light chain variable region, respectively, comprise the amino acid sequences set forth in SEQ ID NOs: 7 and 8; 7 and 44; 7 and 45; 38 and 8; 38 and 45; 39 and 43; 39 and 45; 39 and 46; 39 and 47; 40 and 43; 40 and 8; 40 and 44; 40 and 45; 41 and 8; 41 and 44; 41 and 45; 41 and 47; 42 and 43; or, 42 and 45. In certain embodiments, the antibody comprises a heavy chain variable region comprising the amino acid sequence of SEQ ID NO: 7; and a light chain variable region comprising the amino acid sequence of SEQ ID NO: 8. In certain embodiments, the antibody comprises a heavy chain comprising the amino acid sequence of SEQ ID NO: 12; and a light chain comprising the amino acid sequence of SEQ ID NO: 13. In certain embodiments, the antibody comprises a heavy chain comprising the amino acid sequence of SEQ ID NO: 93; and a light chain comprising the amino acid sequence of SEQ ID NO: 13. In certain embodiments, the antibody comprises a heavy chain comprising the amino acid sequence of SEQ ID NO: 14; and a light chain comprising the amino acid sequence of SEQ ID NO: 13. In certain embodiments, the antibody comprises a heavy chain comprising the amino acid sequence of SEQ ID NO: 94; and a light chain comprising the amino acid sequence of SEQ ID NO: 13. In certain embodiments, the antibody comprises a heavy chain comprising the amino acid sequence of SEQ ID NO: 76; and a light chain comprising the amino acid sequence of SEQ ID NO: 13. In certain embodiments, the antibody comprises a heavy chain comprising the amino acid sequence of SEQ ID NO: 97; and a light chain comprising the amino acid sequence of SEQ ID NO: 13.

In another aspect, the instant disclosure provides an isolated antibody that specifically binds to human CTLA-4 protein, comprising a heavy chain variable region having an amino acid sequence derived from a human IGHV3-21 germline sequence; and a light chain variable region having an amino acid sequence derived from a human IGKV3-20 germline sequence or a human IGKV3-11 germline sequence.

In another aspect, the instant disclosure provides an isolated antibody that cross-competes for binding to human CTLA-4 protein with an antibody comprising the heavy and light chain variable region amino acid sequences set forth in SEQ ID NOs: 7 and 8, respectively.

In another aspect, the instant disclosure provides an isolated antibody that binds to the same epitope on human CTLA-4 protein as an antibody comprising the heavy and light chain variable region amino acid sequences set forth in SEQ ID NOs: 7 and 8, respectively.

In another aspect, the instant disclosure provides an antibody that binds to an epitope of human CTLA-4. In certain embodiments, the antibody binds to an epitope of human CTLA-4 comprising, consisting essentially of, or consisting of residues 140-141 of SEQ ID NO: 77. In certain embodiments, the antibody binds to an epitope of human CTLA-4 consisting of residues 140-141 of SEQ ID NO: 77. In certain embodiments, the antibody binds to at least one residue of human CTLA-4 selected from the group consisting of residues 140 and 141 of SEQ ID NO: 77. In certain embodiments, the antibody binds to an epitope of human CTLA-4 comprising, consisting essentially of, or consisting of residues 140-143 of SEQ ID NO: 77. In certain embodiments, the antibody binds to an epitope of human CTLA-4 consisting of residues 140-143 of SEQ ID NO: 77. In certain embodiments, the antibody binds to an epitope of human CTLA-4 comprising, consisting essentially of, or consisting of residues 135-143 of SEQ ID NO: 77. In certain embodiments, the antibody binds to an epitope of human CTLA-4 consisting of residues 135-143 of SEQ ID NO: 77. In certain embodiments, the antibody binds to an epitope of human CTLA-4 comprising, consisting essentially of, or consisting of residues 140-149 of SEQ ID NO: 77. In certain embodiments, the antibody binds to an epitope of human CTLA-4 consisting of residues 140-149 of SEQ ID NO: 77. In certain embodiments, the antibody binds to an epitope of human CTLA-4 comprising, consisting essentially of, or consisting of residues 135-149 of SEQ ID NO: 77. In certain embodiments, the antibody binds to an epitope of human CTLA-4 consisting of residues 135-149 of SEQ ID NO: 77. In certain embodiments, the antibody binds to an epitope of human CTLA-4 comprising, consisting essentially of, or consisting of residues 80-82 of SEQ ID NO: 77. In certain embodiments, the antibody binds to an epitope of human CTLA-4 consisting of residues 80-82 of SEQ ID NO: 77.

In another aspect, the instant disclosure provides an antibody for which, upon binding of the antibody to human CTLA-4 protein followed by addition of deuterium, the exchange of hydrogen in the human CTLA-4 protein with deuterium in a region comprising residues 140-141 of SEQ ID NO: 77 is substantially reduced relative to the exchange of hydrogen in the human CTLA-4 protein with deuterium in the same region in the absence of the antibody, as determined by hydrogen/deuterium exchange. In certain embodiments, the region of human CTLA-4 comprises residues 140-143 of SEQ ID NO: 77. In certain embodiments, the region of human CTLA-4 comprises residues 135-143 of SEQ ID NO: 77. In certain embodiments, the region of human CTLA-4 comprises residues 140-149 of SEQ ID NO: 77. In certain embodiments, the region of human CTLA-4 comprises residues 135-149 of SEQ ID NO: 77. In certain embodiments, upon binding of the antibody to human CTLA-4 protein followed by addition of deuterium, the exchange of hydrogen in the human CTLA-4 protein with deuterium in a region comprising residues 80-82 of SEQ ID NO: 77 is substantially reduced relative to the exchange of hydrogen in the human CTLA-4 protein with deuterium in the same region in the absence of the antibody, as determined by hydrogen/deuterium exchange.

In certain embodiments, the antibody comprises a heavy chain constant region selected from the group consisting of human $IgG_1$, $IgG_2$, $IgG_3$, $IgG_4$, $IgA_1$, and $IgA_2$. In certain embodiments, the heavy chain constant region is $IgG_1$. In certain embodiments, the heavy chain constant region is $IgG_2$. In certain embodiments, the antibody comprises a light chain constant region selected from the group consisting of human IgGκ and IgGλ.

In certain embodiments, the antibody comprises a human IgG heavy chain constant region that is a variant of a wild type human IgG heavy chain constant region, wherein the variant human IgG heavy chain constant region binds to human Fc gamma receptors selected from the group consisting of FcγRIIB and FcγRIIA with higher affinity than the wild type human IgG heavy chain constant region binds to the human Fc gamma receptors. In certain embodiments, the antibody comprises a human IgG heavy chain constant region that is a variant of a wild type human IgG heavy chain constant region, wherein the variant human IgG heavy chain constant region binds to human FcγRIIB with higher affinity than the wild type human IgG heavy chain constant region binds to human FcγRIIB In certain embodiments, the variant human IgG heavy chain constant region is a variant human $IgG_1$, a variant human $IgG_2$, or a variant human $IgG_4$ heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of:

S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the variant human IgG heavy chain constant region further comprises one or more amino acid mutations that reduce the affinity of the IgG for human FcγRIIIA, human FcγRIIA, or human FcγRI. In certain embodiments, the FcγRIIB is expressed on a cell selected from the group consisting of macrophages, monocytes, B cells, dendritic cells, endothelial cells, and activated T cells.

In certain embodiments, the antibody comprises a human IgG heavy chain constant region that is a variant of a wild type human IgG heavy chain constant region, wherein the variant human IgG heavy chain constant region binds to human Fc gamma receptors with higher affinity than the wild type human IgG heavy chain constant region binds to the human Fc gamma receptors. In certain embodiments, the human Fc gamma receptor comprises immunoreceptor tyrosine-based activation motif (ITAM). In certain embodiments, the human Fc gamma receptor is selected from the group consisting of FcγRIIIA, FcγRIIA, and FcγRI. In certain embodiments, the human Fc gamma receptor is FcγRIIIA In certain embodiments, the variant human IgG heavy chain constant region comprises one or more of the following amino acid mutations, according to the EU numbering system: G236A, S239D, F243L, T256A, K290A, R292P, S298A, Y300L, V305I, A330L, I332E, E333A, K334A, A339T, and P396L. In certain embodiments, the variant human IgG heavy chain constant region comprises a set of amino acid mutations selected from the group consisting of: S239D; T256A; K290A; S298A; I332E; E333A; K334A; A339T; S239D and I332E; S239D, A330L, and I332E; S298A, E333A, and K334A; G236A, S239D, and I332E; and F243L, R292P, Y300L, V305I, and P396L, according to the EU numbering system. In certain embodiments, the variant human IgG heavy chain constant region comprises the following amino acid mutations, according to the EU numbering system: S239D, A330L, and I332E. In certain embodiments, the variant human IgG heavy chain constant region comprises the following amino acid mutations, according to the EU numbering system: S239D and I332E. In certain embodiments, the variant human IgG heavy chain constant region is a variant human $IgG_1$ heavy chain constant region comprising the following amino acid mutations, according to the EU numbering system: S239D and I332E. In certain embodiments, the antibody comprises an afucosylated Fc region. In certain embodiments, the antibody is formulated for intratumoral delivery. In certain embodiments, the antibody or pharmaceutical composition is administered intratumorally. In certain embodiments, the antibody is formulated for delivery into a tumor draining lymph node. In certain embodiments, the antibody or pharmaceutical composition is delivered to a tumor draining lymph node. In certain embodiments, the antibody is formulated for subcutaneous delivery. In certain embodiments, the antibody or pharmaceutical composition is delivered subcutaneously.

In certain embodiments, the human Fc gamma receptor is FcγRIIc. In certain embodiments, the human Fc gamma receptor is expressed on a cell selected from the group consisting of macrophages, monocytes, B cells, and dendritic cells. In certain embodiments, the antibody is a human antibody. In certain embodiments, the antibody is antagonistic to CTLA-4. In certain embodiments, the antibody inhibits binding of the human CTLA-4 protein to human CD80 or to human CD86.

In certain embodiments, the antibody is conjugated to a cytotoxic agent, cytostatic agent, toxin, radionuclide, or detectable label.

In one embodiment, the present invention relates to an antibody of the present invention for use as a medicament.

In one embodiment, the present invention relates to use of an antibody of the present invention for preparing pharmaceutical compositions or medicaments for immunotherapy. Preferably, the immunotherapy is for increasing T-cell activation in response to an antigen in a subject, optionally for treating cancer, or treating or preventing infectious diseases.

In one embodiment, the present invention relates to an antibody of the present invention for use as a diagnostic.

In one embodiment, the present invention relates to the use of an antibody of the present invention for in vitro detection of human CTLA-4 in a biological sample.

In another aspect, the instant disclosure provides a pharmaceutical composition comprising an anti-CTLA-4 antibody disclosed herein and a pharmaceutically acceptable carrier or excipient.

In another aspect, the instant disclosure provides an isolated polynucleotide encoding a heavy and/or light chain of an antibody disclosed herein. In another aspect, the instant disclosure provides a vector comprising the polynucleotide. In another aspect, the instant disclosure provides a recombinant host cell comprising the polynucleotide or the vector. In another aspect, the instant disclosure provides a method of producing an antibody that binds to human CTLA-4, the method comprising culturing the host cell so that the polynucleotide is expressed and the antibody is produced.

In another aspect, the instant disclosure provides a method of increasing T-cell activation in response to an antigen in a subject, the method comprising administering to the subject an effective amount of an anti-CTLA-4 antibody or pharmaceutical composition disclosed herein. In another aspect, the instant disclosure provides a method of treating cancer in a subject, the method comprising administering to the subject an effective amount of an anti-CTLA-4 antibody or pharmaceutical composition disclosed herein. In certain embodiments, the anti-CTLA-4 antibody or pharmaceutical composition disclosed herein is administered subcutaneously or intravenously. In certain embodiments, the anti-CTLA-4 antibody or pharmaceutical composition disclosed herein is administered intravenously at 0.1 mg/kg, 0.3 mg/kg, 1 mg/kg, 3 mg/kg, 6 mg/kg, or 10 mg/kg, optionally at an interval of once every three weeks. In certain embodiments, the anti-CTLA-4 antibody or pharmaceutical composition disclosed herein is administered intratumorally. In certain embodiments, the anti-CTLA-4 antibody or pharmaceutical composition disclosed herein is administered intratumorally at 0.01 mg/kg, 0.03 mg/kg, 0.1 mg/kg, 0.3 mg/kg, 1 mg/kg, or 3 mg/kg, optionally at an interval of once every three weeks. In certain embodiments, the anti-CTLA-4 antibody or pharmaceutical composition disclosed herein is administered intratumorally at 0.03 mg/kg, 0.1 mg/kg, or 0.3 mg/kg, optionally at an interval of once every three weeks. In certain embodiments, the anti-CTLA-4 antibody or pharmaceutical composition disclosed herein is administered intratumorally at a dose that is up to 5-fold, 10-fold, 20-fold, 30-fold, 40-fold, 50-fold, 60-fold, 70-fold, 80-fold, 90-fold, 100-fold, or 200-fold lower than a dose given by systemic administration. In certain embodiments, the anti-CTLA-4 antibody or pharmaceutical composition disclosed herein is administered intratumorally at a dose that is up to 10-fold lower than a dose given by systemic administration. In certain embodiments, the anti-CTLA-4 antibody or pharmaceutical composition disclosed herein is administered intratumorally at a dose that is up to 100-fold lower than a dose given by systemic administration. In certain embodiments, the anti-CTLA-4 antibody or pharmaceutical composition disclosed herein is administered intratumorally and the method further comprises administering an additional therapeutic agent to the subject. In certain embodiments, the additional therapeutic agent is administered systemically. In certain embodiments, the subject has a solid tumor and the additional therapeutic agent is an anti-PD-1 antibody. In certain embodiments, the anti-PD-1 antibody is pembrolizumab or nivolumab. In certain embodiments, the subject has head and neck squamous cell carcinoma and the additional therapeutic agent is an anti-EGFR antibody. In certain embodiments, the anti-EGFR antibody is cetuximab. In certain embodiments, the subject has HER2+ breast cancer and the additional therapeutic agent is an anti-HER2 antibody. In certain embodiments, the anti-HER2 antibody is trastuzumab. In certain embodiments, these methods further comprise administering a chemotherapeutic agent to the subject. In certain embodiments, the chemotherapeutic agent is administered systemically. In certain embodiments, the chemotherapeutic agent is gemcitabine. In certain embodiments, the anti-CTLA-4 antibody or pharmaceutical composition disclosed herein is administered intratumorally and the subject has an advanced or metastatic solid tumor. In certain embodiments, the anti-CTLA-4 antibody or pharmaceutical composition disclosed herein is administered intratumorally and the subject has head and neck cancer (e.g., relapsed/refractory head and neck squamous cell carcinoma). In certain embodiments, the anti-CTLA-4 antibody or pharmaceutical composition disclosed herein is administered intratumorally and the subject has breast cancer (e.g., relapsed/refractory HER2+ breast cancer). In certain embodiments, the anti-CTLA-4 antibody or pharmaceutical composition disclosed herein is delivered to a tumor draining lymph node. In certain embodiments, the anti-CTLA-4 antibody or pharmaceutical composition disclosed herein is delivered via a localized administration (e.g., subcutaneous administration). In certain embodiments, the anti-CTLA-4 antibody or pharmaceutical composition disclosed herein is delivered via a localized administration (e.g., subcutaneous administration) at 0.01 mg/kg, 0.03 mg/kg, 0.1 mg/kg, 0.3 mg/kg, 1 mg/kg, or 3 mg/kg. In certain embodiments, the anti-CTLA-4 antibody or pharmaceutical composition disclosed herein is delivered via a localized administration (e.g., subcutaneous administration) at a dose that is up to 5-fold, 10-fold, 20-fold, 30-fold, 40-fold, 50-fold, 60-fold, 70-fold, 80-fold, 90-fold, 100-fold, or 200-fold lower than a dose given by systemic administration. In certain embodiments, the anti-CTLA-4 antibody or pharmaceutical composition disclosed herein is delivered via a localized administration (e.g., subcutaneous administration) at a dose that is up to 10-fold lower than a dose given by systemic administration. In certain embodiments, the anti-CTLA-4 antibody or pharmaceutical composition disclosed herein is delivered via a localized administration (e.g., subcutaneous administration) at a dose that is up to 100-fold lower than a dose given by systemic administration. In certain embodiments, the anti-CTLA-4 antibody or pharmaceutical composition disclosed herein is delivered via a localized administration (e.g., subcutaneous administration) and the method further comprises administering an additional therapeutic agent to the subject. In certain embodiments, the additional therapeutic agent is a vaccine. In certain embodiments, the vaccine comprises a heat shock protein peptide complex (HSPPC) comprising a heat shock protein complexed with an antigenic peptide. In one embodiment, the heat shock protein is gp96 protein and is complexed with a tumor-associated antigenic peptide, wherein the HSPPC is derived from a tumor obtained from a subject. In certain embodiments, the heat shock protein is selected from the group consisting of hsc70, hsp70, hsp90, hsp110, grp170, gp96, calreticulin, a mutant thereof, and combinations of two or more thereof. In certain embodiments, the heat shock protein is hsc70. In certain embodiments, the heat shock protein is hsp70. In certain embodiments, the antigenic peptide is synthetic. In certain embodiments, the subject has cancer. In certain embodiments, the subject has an infectious disease. In certain embodiments, these methods further comprise administering an additional therapeutic agent to the subject. In certain embodiments, the additional therapeutic agent is a chemotherapeutic or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-OX40 antibody, and an agonist anti-CD137 antibody, an agonist anti-DR3 antibody, an agonist anti-TNFSF14 antibody, and an agonist anti-CD27 antibody. In certain embodiments, the additional therapeutic agent is radiotherapy. In certain embodiments, the additional therapeutic agent is an inhibitor of indoleamine-2,3-dioxygenase (IDO). Suitable IDO inhibitors include, without limitation, epacadostat, F001287, indoximod, and NLG919. In certain embodiments, the additional therapeutic agent is a vaccine. In certain embodiments, the vaccine comprises a heat shock protein peptide complex (HSPPC) comprising a heat shock protein complexed with an antigenic peptide. In one embodiment, the heat shock protein is gp96 protein and is complexed with a tumor-associated antigenic peptide, wherein the HSPPC is derived from a tumor obtained from a subject.

In one embodiment, the present invention relates to an antibody of the present invention, a polynucleotide of the invention, a vector of the invention, and/or a recombinant host cell of the invention, for use as a medicament.

In one embodiment, the present invention relates to an antibody of the present invention, a polynucleotide of the invention, a vector of the invention, and/or a recombinant host cell of the invention, for use as a diagnostic.

In one embodiment, the present invention relates to the use of an antibody of the present invention, a polynucleotide of the invention, a vector of the invention, and/or a recombinant host cell of the invention, for the in vitro detection of human CTLA-4 in a biological sample.

In one aspect, provided herein is a pharmaceutical composition comprising an anti-CTLA-4 antibody disclosed herein and a pharmaceutically acceptable carrier or excipient, for use as a medicament.

In one aspect, provided herein is a pharmaceutical composition comprising an anti-CTLA-4 antibody disclosed herein and a pharmaceutically acceptable carrier or excipient, for use as a diagnostic.

In one aspect, provided herein is a pharmaceutical composition comprising an anti-CTLA-4 antibody disclosed herein, a polynucleotide of the invention, a vector of the invention, and/or a recombinant host cell of the invention, and a pharmaceutically acceptable carrier or excipient. In one aspect, the pharmaceutical composition is for use as a medicament and/or diagnostic.

In one aspect, the present invention relates to an antibody, polynucleotide, vector, recombinant host cell, and/or pharmaceutical composition of the present invention, for use in a method for increasing T-cell activation in response to an antigen.

In one aspect, the present invention relates to an antibody, polynucleotide, vector, recombinant host cell, and/or pharmaceutical composition of the present invention, for use in a method for increasing T-cell activation in response to an antigen in a subject.

In one aspect, the present invention relates to an antibody, polynucleotide, vector, recombinant host cell, and/or pharmaceutical composition of the present invention, for use in a method for increasing T-cell activation in response to an antigen in a subject comprising administering to the subject an effective amount of an antibody, polynucleotide, vector, recombinant host cell, and/or pharmaceutical composition of the invention.

In one aspect, the present invention relates to an antibody, polynucleotide, vector, recombinant host cell, and/or pharmaceutical composition of the present invention, for use in a method for the treatment of cancer.

In one aspect, the present invention relates to an antibody, polynucleotide, vector, recombinant host cell, and/or pharmaceutical composition of the present invention, for use in a method for the treatment of cancer in a subject.

In one aspect, the present invention relates to an antibody, polynucleotide, vector, recombinant host cell, and/or pharmaceutical composition of the present invention, for use in a method for the treatment of cancer in a subject comprising administering to the subject an effective amount of an antibody, polynucleotide, vector, recombinant host cell, and/or pharmaceutical composition of the invention.

In one aspect, the present invention relates to (a) an antibody, polynucleotide, vector, recombinant host cell, and/or pharmaceutical composition of the present invention and (b) an additional therapeutic agent, preferably an anti-PD-1 antibody, for use as a medicament.

In one aspect, the present invention relates to (a) an antibody, polynucleotide, vector, recombinant host cell, and/or pharmaceutical composition of the present invention and (b) an additional therapeutic agent, preferably an anti-PD-1 antibody, for use in a method for the treatment of cancer. In a preferred embodiment, the cancer is a solid tumor. In another preferred embodiment, the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent, preferably an anti-PD-1 antibody.

In one aspect, the present invention relates to (a) an antibody, polynucleotide, vector, recombinant host cell, and/or pharmaceutical composition of the present invention and (b) an anti-EGFR antibody, and optionally (c) a chemotherapeutic agent, for use as a medicament.

In one aspect, the present invention relates to (a) an antibody, polynucleotide, vector, recombinant host cell, and/or pharmaceutical composition of the present invention and (b) an anti-EGFR antibody, and optionally (c) a chemotherapeutic agent, for use in a method for the treatment of cancer. In a preferred embodiment, the cancer is head and neck squamous cell carcinoma. In another preferred embodiment, the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to a pharmaceutical composition, kit or kit-of-parts comprising (a) an antibody, polynucleotide, vector, recombinant host cell, and/or pharmaceutical composition of the present invention and (b) an anti-EGFR antibody, and optionally (c) a chemotherapeutic agent.

In one aspect, the present invention relates to (a) an antibody, polynucleotide, vector, recombinant host cell, and/or pharmaceutical composition of the present invention and (b) an anti-HER2 antibody, and optionally (c) a chemotherapeutic agent, for use as a medicament.

In one aspect, the present invention relates to (a) an antibody, polynucleotide, vector, recombinant host cell, and/or pharmaceutical composition of the present invention and (b) an anti-HER2 antibody, and optionally (c) a chemotherapeutic agent, for use in a method for the treatment of HER2+ breast cancer. In another preferred embodiment, the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to a pharmaceutical composition, kit or kit-of-parts comprising (a) an antibody, polynucleotide, vector, recombinant host cell, and/or pharmaceutical composition of the present invention and (b) an anti-HER2 antibody, and optionally (c) a chemotherapeutic agent.

In one aspect, the present invention relates to an antibody, polynucleotide, vector, recombinant host cell, and/or pharmaceutical composition of the present invention, for use in a method for the treatment of cancer, wherein the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to an antibody, polynucleotide, vector, recombinant host cell, and/or pharmaceutical composition of the present invention, for use in a method for the treatment of cancer, wherein the antibody, polynucleotide, vector, recombinant host cell, and/or pharmaceutical composition of the present invention is administered subcutaneously or intravenously to the subject, preferably administered intravenously to the subject at 0.1 mg/kg, 0.3 mg/kg, 1 mg/kg, 3 mg/kg, 6 mg/kg, or 10 mg/kg, optionally at an interval of once every three weeks.

In one aspect, the present invention relates to (a) an antibody, polynucleotide, vector, recombinant host cell, and/or pharmaceutical composition of the present invention and (b) an additional therapeutic agent, for use as a medicament. In a preferred embodiment, the additional therapeutic agent is a chemotherapeutic agent or a checkpoint targeting agent or an inhibitor of indoleamine-2,3-dioxygenase (IDO) or a vaccine.

In one aspect, the present invention relates to (a) an antibody, polynucleotide, vector, recombinant host cell, and/or pharmaceutical composition of the present invention and (b) an additional therapeutic agent, for use in a method for the treatment of cancer. In a preferred embodiment, the additional therapeutic agent is a chemotherapeutic agent or a checkpoint targeting agent or an inhibitor of indoleamine-2,3-dioxygenase (IDO) or a vaccine.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent. In a preferred embodiment, the additional therapeutic agent is a chemotherapeutic agent or a checkpoint targeting agent or an inhibitor of indoleamine-2,3-dioxygenase (IDO) or a vaccine.

In one aspect, the present invention relates to an antibody, polynucleotide, vector, recombinant host cell, and/or pharmaceutical composition of the present invention, for use in a method for the treatment of cancer, and/or for use in a method for increasing T-cell activation in response to an antigen, wherein the antibody, polynucleotide, vector, recombinant host cell, and/or pharmaceutical composition of the present invention is delivered to a tumor draining lymph node.

In one aspect, the present invention relates to the use of an antibody, polynucleotide, vector, recombinant host cell, and/or pharmaceutical composition of the present invention in a method for the treatment of cancer, and/or in a method for increasing T-cell activation in response to an antigen in a subject, wherein the antibody, polynucleotide, vector, recombinant host cell, and/or pharmaceutical composition of the present invention is delivered to a tumor draining lymph node.

In one aspect, the present invention relates to the use of an antibody, polynucleotide, vector, recombinant host cell, and/or pharmaceutical composition of the present invention, for preparing medicaments for immunotherapy, for example, for increasing T-cell activation in response to an antigen in a subject, treating cancer, or treating or preventing infectious diseases.

In one aspect, the present invention relates to the use of an antibody, polynucleotide, vector, recombinant host cell, and/or pharmaceutical composition of the present invention, for preparing medicaments for immunotherapy, for example, for increasing T-cell activation in response to an antigen in a subject, treating cancer, or treating or preventing infectious diseases, wherein the antibody, polynucleotide, vector, recombinant host cell, and/or pharmaceutical composition of the present invention is delivered to a tumor draining lymph node.

In one aspect, the present invention relates to the use of (a) an antibody, polynucleotide, vector, recombinant host cell, and/or pharmaceutical composition of the present invention and (b) an anti-HER2 antibody, and optionally (c) a chemotherapeutic agent, to prepare a medicament for immunotherapy, for example, for increasing T-cell activation in response to an antigen in a subject, treating cancer, or treating or preventing infectious diseases.

In one aspect, the present invention relates to the use of (a) an antibody, polynucleotide, vector, recombinant host cell, and/or pharmaceutical composition of the present invention and (b) an anti-HER2 antibody, and optionally (c) a chemotherapeutic agent, to prepare a medicament for immunotherapy, for example, for increasing T-cell activation in response to an antigen in a subject, treating cancer, or treating or preventing infectious diseases, wherein the antibody, polynucleotide, vector, recombinant host cell, and/or pharmaceutical composition of the present invention is delivered to a tumor draining lymph node.

4. BRIEF DESCRIPTION OF THE DRAWINGS

FIG. 1A is a table showing the binding affinities ($K_D$) of the anti-CTLA-4 antibody AGEN1884 and a reference anti-CTLA-4 $IgG_1$ antibody to dimeric and monomeric recombinant human, cynomolgus, mouse, and rat CTLA-4 as measured by surface plasmon resonance. FIG. 1B is a graph showing the binding of AGEN1884w, a reference anti-CTLA-4 $IgG_1$ antibody, and an $IgG_1$ isotype control to CTLA-4-expressing cells, as measured by flow cytometry. The mean fluorescence intensity (MFI) was calculated and plotted against a range of antibody concentrations. FIGS. 1C and 1D show the selectivity of AGEN1884 and a reference anti-CTLA-4 IgG1 antibody binding to recombinant human (rh) and cynomolgus (rc) CTLA-4, as compared with related family members (recombinant human CD28, ICOS, BTLA, and PD-1, and recombinant cynomolgus PD-1), shown relative to an isotype control $IgG_1$ antibody. The binding was measured by suspension array technology and the mean fluorescence intensity (MFI) at three different antibody concentrations (10, 100, and 1000 ng/ml) is shown in FIG. 1C. FIG. 1D is a summary table of relative binding affinity based on the data shown in FIG. 1C.

FIG. 2A shows binding of AGEN1884w, an anti-CTLA-4 reference antibody, and an $IgG_1$ isotype control antibody to activated primary human CD4+ T cells. Briefly, freshly isolated CD4+ T cells were stimulated using plate-bound anti-CD3 and anti-CD28 antibodies for five days prior to antibody binding analysis by flow cytometry. The mean fluorescence intensity (MFI) was calculated across a range of antibody concentrations. FIG. 2B shows intracellular binding of AGEN1884 and an anti-CTLA-4 reference antibody as compared with an $IgG_1$ isotype control antibody across a concentration titration using activated (anti-CD3 and anti-CD28 with recombinant IL-2 for three days) primary cynomolgus CD8+ T cells. Data were generated by flow cytometry and are shown as the percent of CTLA-4+ T cells as a proportion of the total CD8+ T cell population. FIG. 2C shows results from a flow cytometry analysis testing the binding of AGEN1884w and an $IgG_1$ isotype control antibody to phytohemagglutinin-stimulated CD4+ human, cynomolgus, rat, or mouse T cells.

FIG. 3A is a schematic of the ligand blocking assay using suspension array technology. FIGS. 3B and 3C show the percent of recombinant CD80-Fc (FIG. 3B) and CD86-Fc proteins (FIG. 3C) binding to CTLA-4 conjugated beads in the absence (100%) or presence of a dose titration of AGEN1884, a reference anti-CTLA-4 $IgG_1$ antibody, or an isotype control ($IgG_1$) antibody. FIG. 3D shows the percent of recombinant CD80-Fc and CD86-Fc binding to CTLA-4 expressing T cells (Jurkat) in the presence of increasing concentrations of AGEN1884w, a reference anti-CTLA-4 $IgG_1$ antibody, or an isotype control ($IgG_1$) antibody. FIG. 3E shows results of an assay in which CTLA-4 expressing T cells (Jurkat) were incubated with a titrated dose of CD80-Fc or CD86-Fc before a fixed concentration of directly fluorochrome-conjugated AGEN1884w or a reference anti-CTLA-4 $IgG_1$ antibody was added. The mean fluorescence intensity (MFI) was calculated and plotted against a range of CD80-Fc or CD86-Fc concentrations.

FIG. 4A depicts the functional activity of anti-CTLA-4 antibodies on cultures of primary human PBMCs upon *Staphylococcus* Enterotoxin A (SEA) stimulation. Specifically, FIG. 4A shows the fold change in IL-2 production in response to a dose-response of AGEN1884w and a reference anti-CTLA-4 $IgG_1$ antibody, as compared with an $IgG_1$ isotype control. Error bars represent the standard deviation from triplicate wells. FIGS. 4B and 4C are results from an IL-2-luciferase reporter assay showing that blockade of CTLA-4 leads to T cell activation. A CD3 and CD28 co-expressing human T cell line (Jurkat), engineered to constitutively express cell surface CTLA-4 in addition to a luciferase reporter gene under the control of an IL-2 promoter, was co-cultured with an antigen presenting cell line (Raji) that expressed CD80 and CD86. FIG. 4B is a pair of histograms showing the expression of CD80 and CD86 on Raji cells as measured by flow cytometry. TCR signaling was triggered using an anti-CD3 antibody in the presence of increasing concentrations of AGEN1884w or an $IgG_1$ isotype control antibody. FIG. 4C shows fold-increase of luciferase expression, a surrogate marker for IL-2 gene activation, in response to increasing concentrations of AGEN1884w relative to the isotype control antibody. FIGS. 4D and 4E are results from an assay testing the ability of the anti-CTLA-4 antibody AGEN1884w to decrease IFNγ production from primary CD8+ T cells in the presence of high concentrations of anti-CD3 antibody. Primary human T cells were stimulated with an anti-CD3 antibody (10 μg/ml) in the presence of increasing concentrations of either soluble (FIG. 4D) or plate-bound (FIG. 4E) AGEN1884w or an $IgG_1$ isotype control antibody. The percentage of CD8+ IFNγ+ T cells is plotted against antibody concentrations tested. The dotted line depicts the frequency of CD8+ IFNγ+ T cells in the absence of anti-CD3 antibody stimulation. FIG. 4F is a graph showing the functional activity of the anti-CTLA-4 antibody AGEN1884w, either alone or in combination with an anti-LAG-3 antibody AGEN1746, an anti-PD-1 antibody Nivolumab, or an anti-PD-1 antibody Pembrolizumab, on cultures of primary human PBMCs upon *Staphylococcus* Enterotoxin A (SEA) stimulation. Mean and standard deviation of IL-2 concentration are shown. IC stands for isotype control.

FIG. 5A shows the binding affinities ($K_D$) of AGEN2041w, a reference anti-CTLA-4 $IgG_1$ antibody, and a reference anti-CTLA-4 $IgG_2$ antibody to dimeric and monomeric recombinant human and cynomolgus CTLA-4 as measured by surface plasmon resonance. FIG. 5B is a graph showing the binding of AGEN2041w, a reference anti-CTLA-4 $IgG_2$ antibody, and an $IgG_2$ isotype control to CTLA-4-expressing cells as measured in a flow cytometry analysis. The mean fluorescence intensity (MFI) was calculated and plotted against different antibody concentrations tested. FIG. 5C is a graph showing the percentage of CD80 and CD86 binding to CTLA-4 in the presence of increasing concentrations of AGEN2041w or a reference anti-CTLA-4 $IgG_2$ antibody (12, 37, 111, 333, 1000, 3000, and 9000 ng/ml before adding beads) as measured by suspension array technology. FIGS. 5D and 5E are similar tables to those shown in FIGS. 1C and 1D, respectively, where the selectivity of AGEN2041w and a reference anti-CTLA-4 $IgG_2$ antibody binding to recombinant human (rh) and cynomolgus (rc) CTLA-4, as compared with related family members (recombinant human CD28, ICOS, BTLA, and PD-1; and recombinant cynomolgus PD-1), was tested relative to an isotype control $IgG_2$ antibody. FIG. 5D shows MFI values as measured by suspension array technology and FIG. 5E is a summary table based on the data shown in FIG. 5D.

FIG. 6A depicts the functional activity of anti-CTLA-4 antibodies on cultures of primary human PBMCs upon *Staphylococcus* Enterotoxin A (SEA) stimulation. FIG. 6A shows the fold change in IL-2 production in response to a dose-response of AGEN1884w and AGEN2041w, as compared with $IgG_1$ and $IgG_2$ isotype control antibodies. Error bars represent the standard deviation from triplicate wells. FIG. 6B is a graph showing results from an IL-2-luciferase reporter assay testing AGEN2041w and an $IgG_2$ isotype control antibody. Fold-increase of luciferase expression, a surrogate marker for IL-2 gene activation, is shown for increasing doses of AGEN2041w and the isotype control antibody.

FIG. 7A is a graph showing the binding of AGEN1884w-105 (AGEN1884w produced by a stable clone 105), a reference anti-CTLA-4 $IgG_1$ antibody, and an $IgG_1$ isotype control to CTLA-4-expressing cells as measured in a flow cytometry analysis. The mean fluorescence intensity (MFI) was calculated and plotted against an antibody titration. FIG. 7B is the result of an assay examining IL-2 production enhanced by AGEN1884w-105, a reference anti-CTLA-4 $IgG_1$ antibody, and an $IgG_1$ isotype control following *Staphylococcus* Enterotoxin A (SEA) stimulation. In FIG. 7B, six biological replicates and mean values (bar) of fold change of IL-2 are shown.

FIGS. 8A, 8B, and 8C are binding curves of a dose titration of antibodies to CHO cells expressing FcγRIIA$^{H131}$ (FIG. 8A), FcγRIIB (FIG. 8B), and FcγRIIIA$^{V158}$ (FIG. 8C), respectively. The mean fluorescence intensity (MFI) of the secondary detection antibody is plotted. Error bars represent the standard deviation from triplicates. The antibodies tested were AGEN1884w-FortiCHO, AGEN1884w-PowerCHO, AGEN2041w, a reference anti-CTLA-4 $IgG_1$ antibody, and an $IgG_1$ isotype control antibody.

FIGS. 9A and 9B are graphs showing the mean response (response units, RU) of triplicate samples at a range of antibody concentrations of AGEN1884w-FortiCHO, AGEN1884w-PowerCHO, AGEN2041w, and a reference anti-CTLA-4 $IgG_1$ antibody bound to human FcγRIIA (FIG. 9A) or human FcγRIIIA (FIG. 9B) as determined by surface plasmon resonance.

FIG. 10A is a schematic of an Fc gamma receptor IIIA (FcγRIIIA) gene reporter assay. FIGS. 10B-10G are results from a reporter assay where the ability of AGEN1884w-105 or AGEN1884w (AGEN1884w-105 in FIGS. 10B, 10C, 10F, and 10G; AGEN1884w in FIGS. 10D and 10E) to activate a reporter cell line expressing either the FcγRIIIA V158 variant or the FcγRIIIA F158 variant was compared with that of a reference anti-CTLA-4 $IgG_1$ antibody (FIGS. 10B and 10C), AGEN2041w (FIGS. 10D and 10E), and an AGEN1884w N297A variant (FIGS. 10F and 10G). The relative light units (RLU) are plotted against a range of antibody concentrations.

FIG. 11 is the result of a reporter assay where AGEN2041w, a reference anti-CTLA-4 IgG2 antibody, and an IgG2 isotype control antibody were tested for their ability to activate a reporter cell line expressing the FcγRIIA$^{H131}$ variant when the antibodies were bound to CTLA-4-expressing target cells. The relative light units (RLU) are plotted against a range of antibody concentrations.

FIG. 12A is a graph showing the binding of AGEN1884w-105, an AGEN1884w-N297A variant, and an $IgG_1$ isotype control to CTLA-4-expressing cells as measured in a flow cytometry analysis. The mean fluorescence intensity (MFI) was calculated and plotted against different antibody concentrations tested. FIG. 12B is the result of an assay examining IL-2 production induced by AGEN1884w-105, AGEN1884w-N297A, and an $IgG_1$ isotype control following *Staphylococcus* Enterotoxin A (SEA) stimulation. In FIG. 12B, six biological replicates and mean values (bar) of fold change of IL-2 are shown.

FIGS. 13A and 13B are results from an assay examining the impact of blocking FcR engagement on the antagonistic activity of anti-CTLA-4 antibodies. In FIG. 13A, seven biological replicates and mean values (bar) of fold change of IL-2 are shown. In FIG. 13B, seven biological replicates of IL-2 production (pg/ml) are shown.

Figure 16:
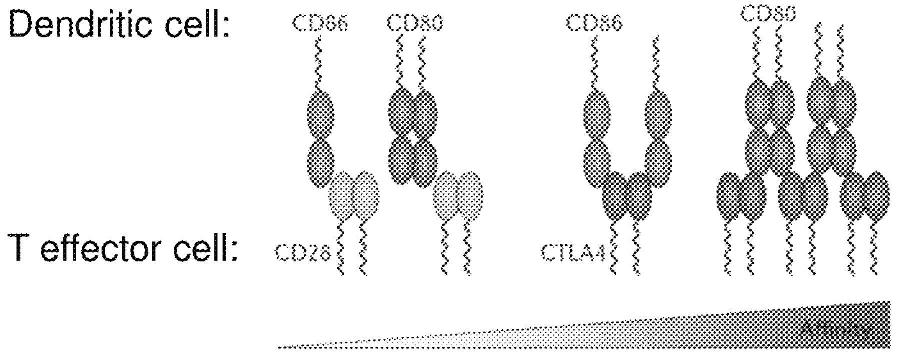

FIG. 16 compares the binding affinities ($K_D$) of CD80-Fc-His, CD86-Fc-His, a reference anti-CTLA-4 $IgG_1$ antibody, and AGEN1884 for CTLA-4. Walker and Sansom Nat. Rev. Immunology 2011 refers to Walker and Sansom Nat. Rev. Immunol. (2011) 11(12):852-63. Xu et al., JI 2012 refers to Xu et al., J Immunol. (2012) 189(9):4470-7.

Figure 17D:
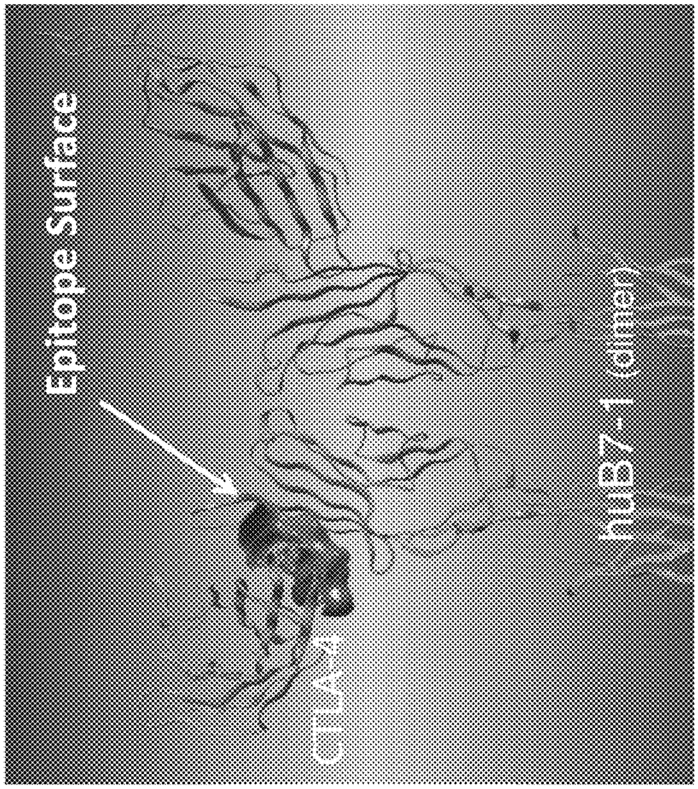
Figure 17E:
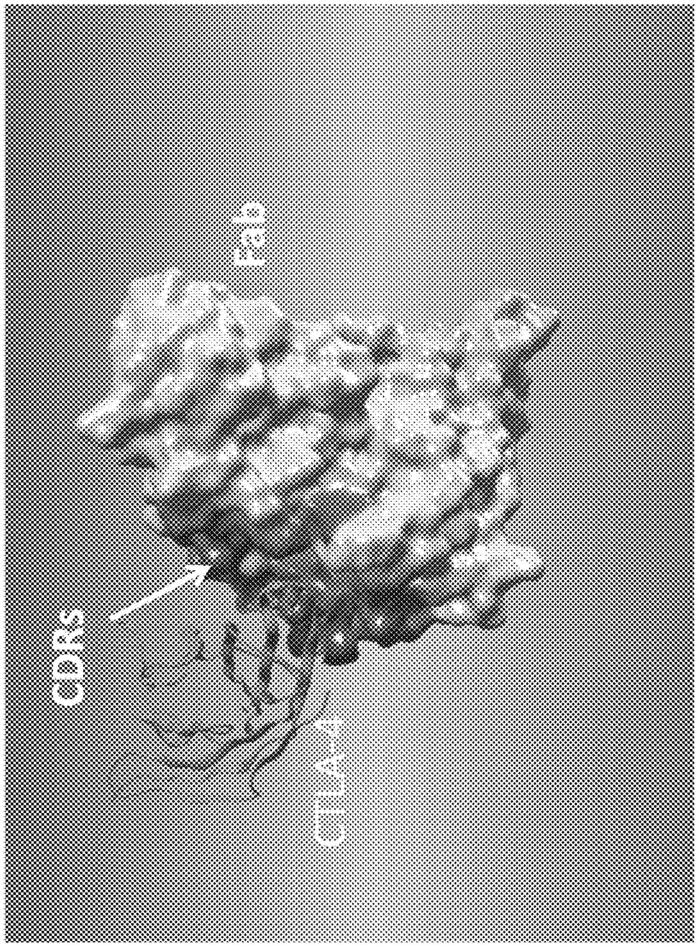

FIG. 17A is a sequence alignment for human CTLA-4 (SEQ ID NO: 77), cynomolgus monkey CTLA-4 (SEQ ID NO: 84), mouse CTLA-4 (SEQ ID NO: 85), and rat CTLA-4 (SEQ ID NO: 86). Dots represent residues identical to corresponding human residues. An * (asterisk) indicates positions which have a single, fully conserved residue. A : (colon) indicates conservation between groups of strongly similar properties. A . (period) indicates conservation between groups of weakly similar properties. FIGS. 17B and 17C are sequence alignments for human CTLA-4 (SEQ ID NO: 77), cynomolgus monkey CTLA-4 (SEQ ID NO: 84), human CD28 (SEQ ID NO: 87), human ICOS (SEQ ID NO: 88), human BTLA (SEQ ID NO: 89), and human PD-1 (SEQ ID NO: 90). The two regions showing strong decrease in deuterium uptake when human CTLA-4 was bound to AGEN1884w-Fab were underlined in FIGS. 17A-C: $Q^{80}VT^{82}$ and $Y^{135}PPPYYLGIGNGTQI^{149}$. FIG. 17D is a composite assembly of the X-ray coordinates in the Protein Data Bank files 3osk and 1i8l. This composite structural analysis indicates a daisy-chain clustering of CTLA-4 and B7-1 clusters. This provides a model of the human B7-1 dimer along with the human CTLA-4 dimer which is believed to be the simplest oligomeric form of the signaling competent immune complex. The site of contact between CTLA-4 and B7-1 includes the $M^{134}YPPPYY^{140}$ region but not limited to this particular motif. FIG. 17E is a model of the binding of AGEN1884w-Fab to human CTLA-4. All the residues of CTLA-4 recited in the preceding description of FIGS. 17A-17E are numbered according to SEQ ID NO: 77.

Figure 18A:
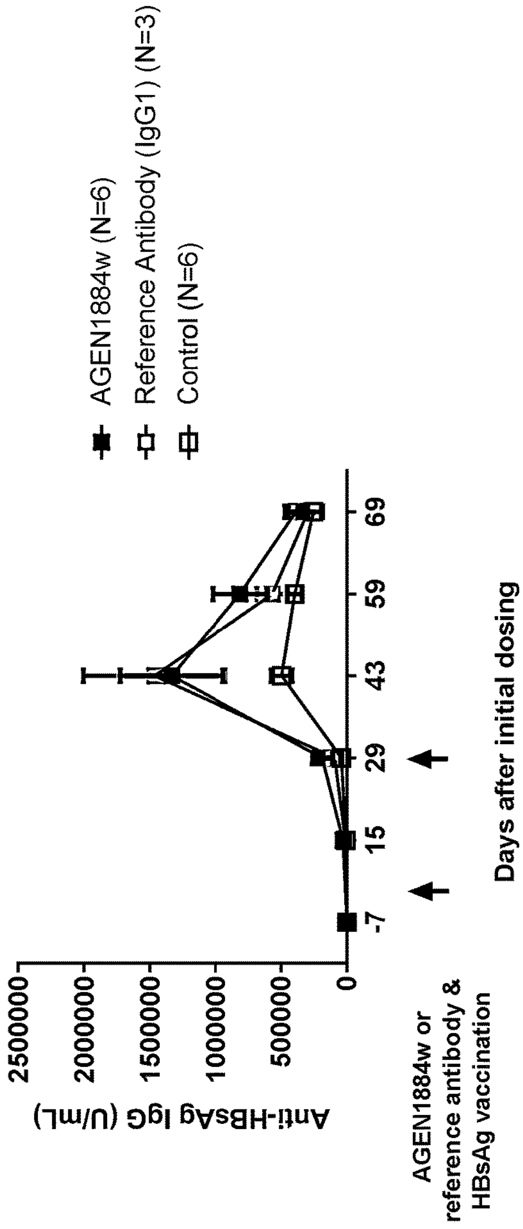
Figure 18B:
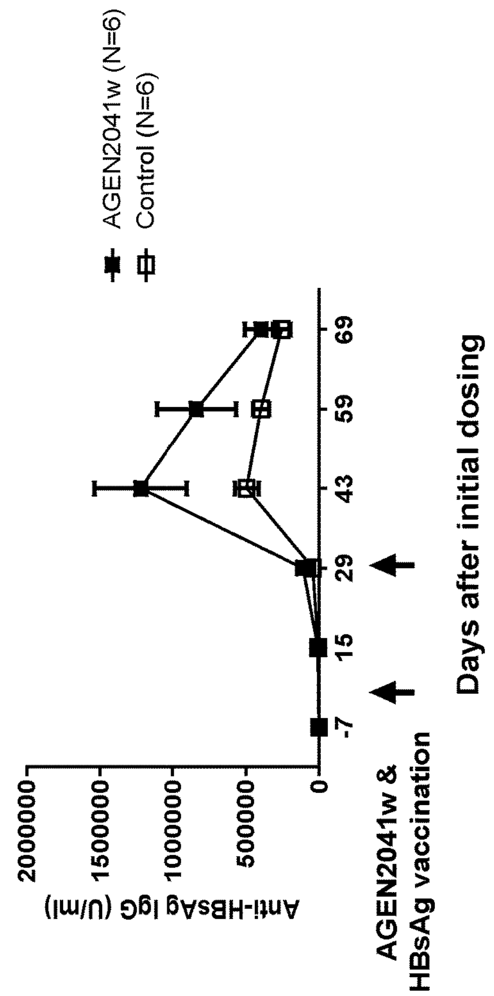
Figure 20A:
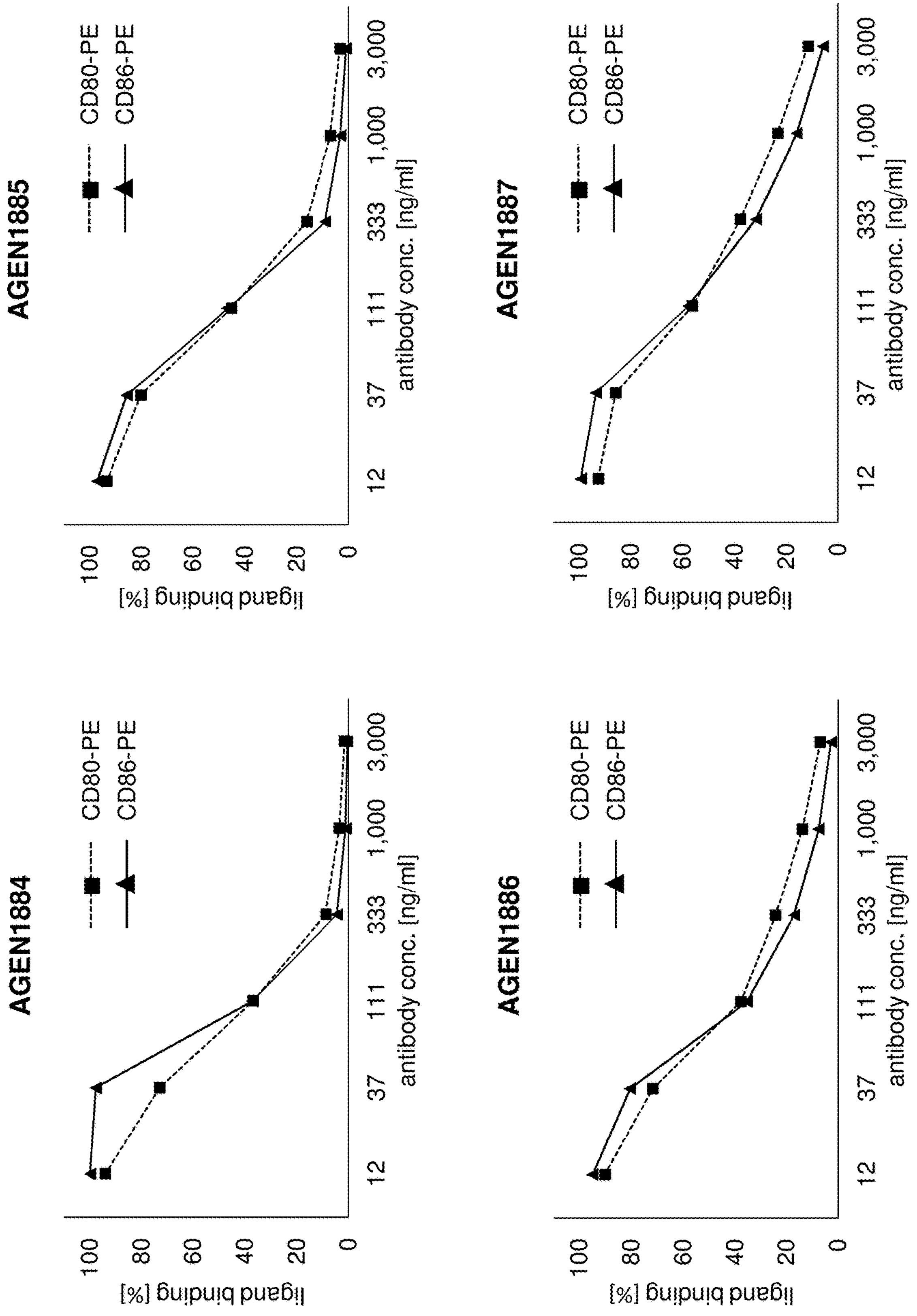
Figure 20B:
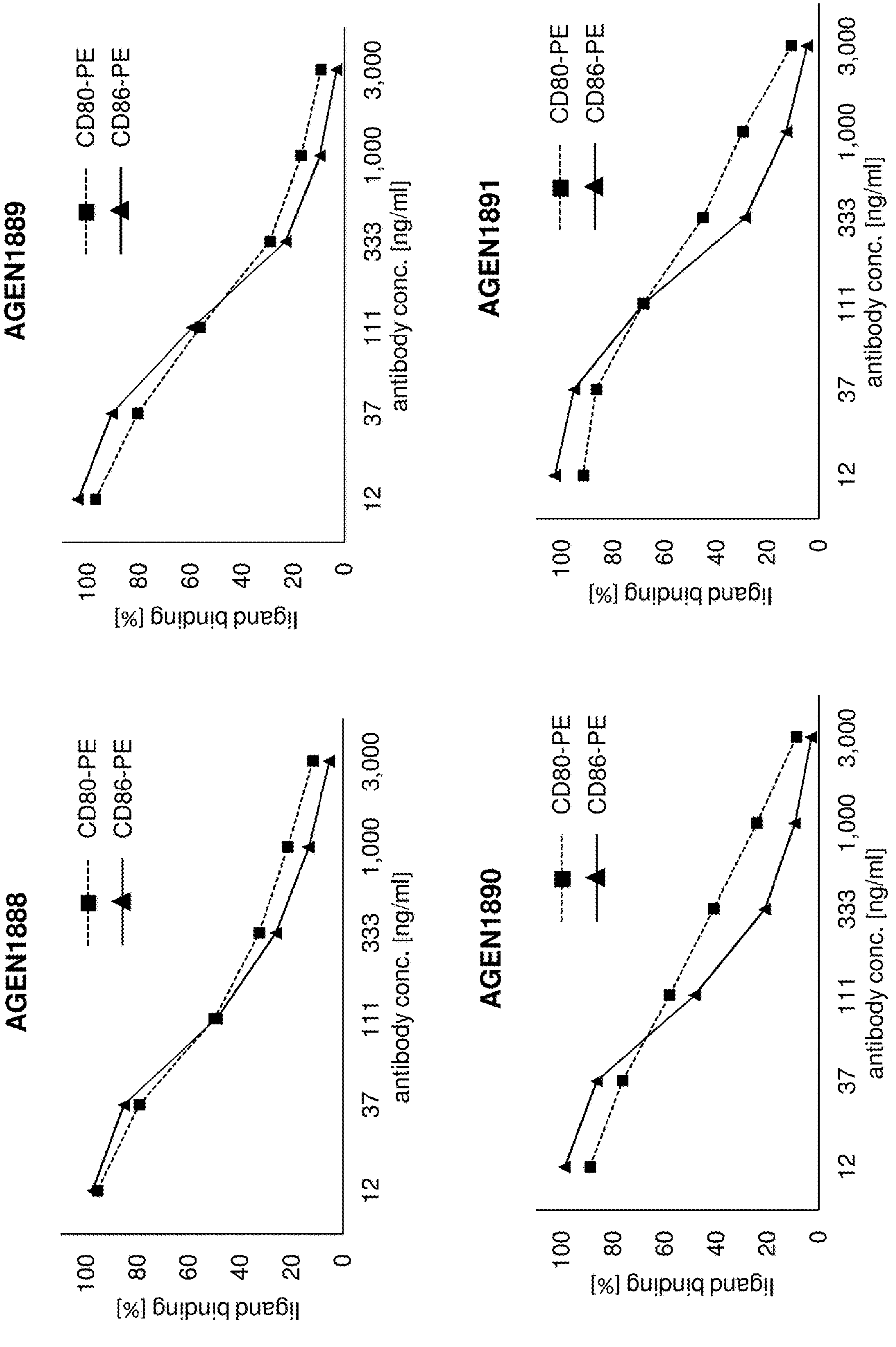
Figure 20C:
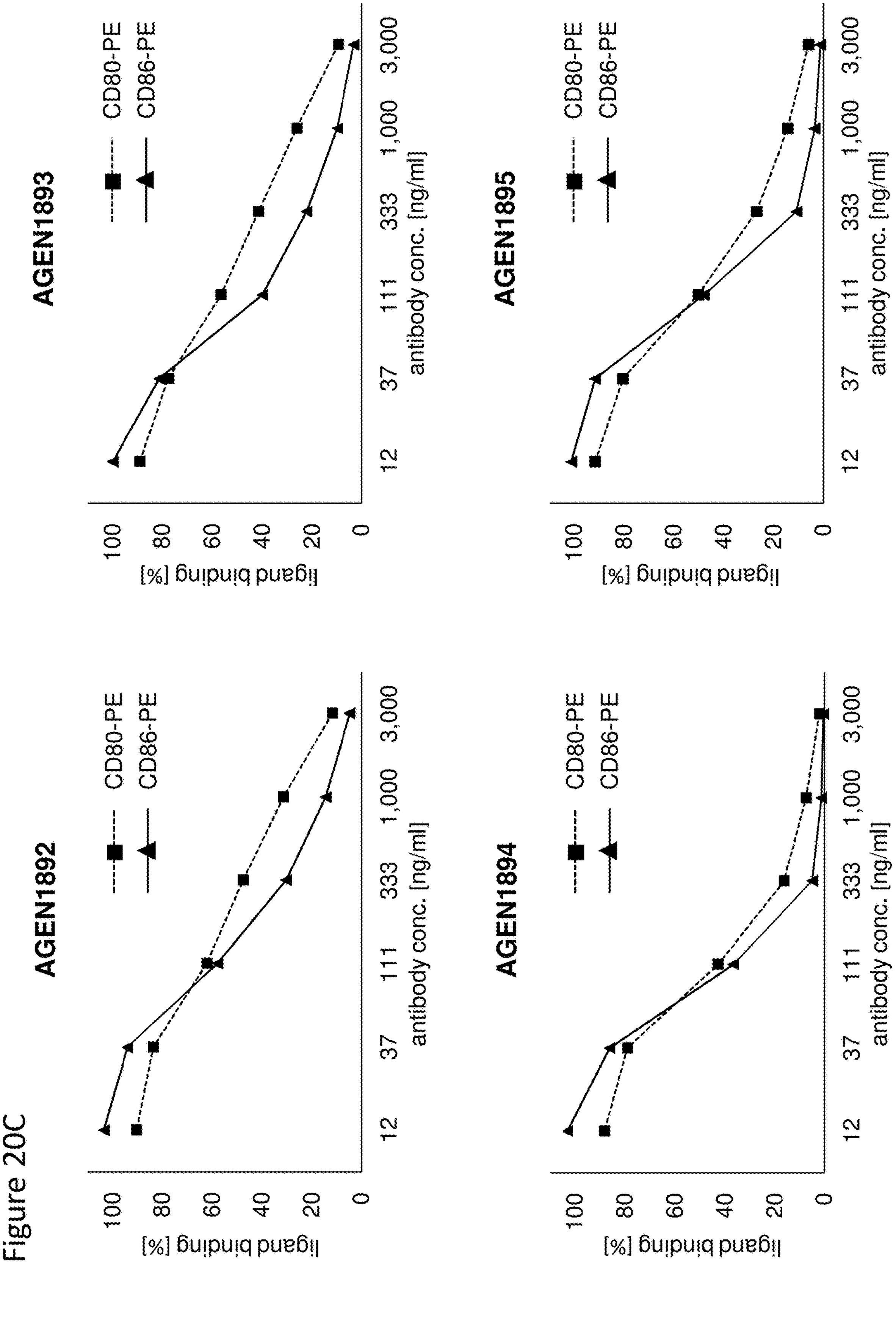
Figure 20D:
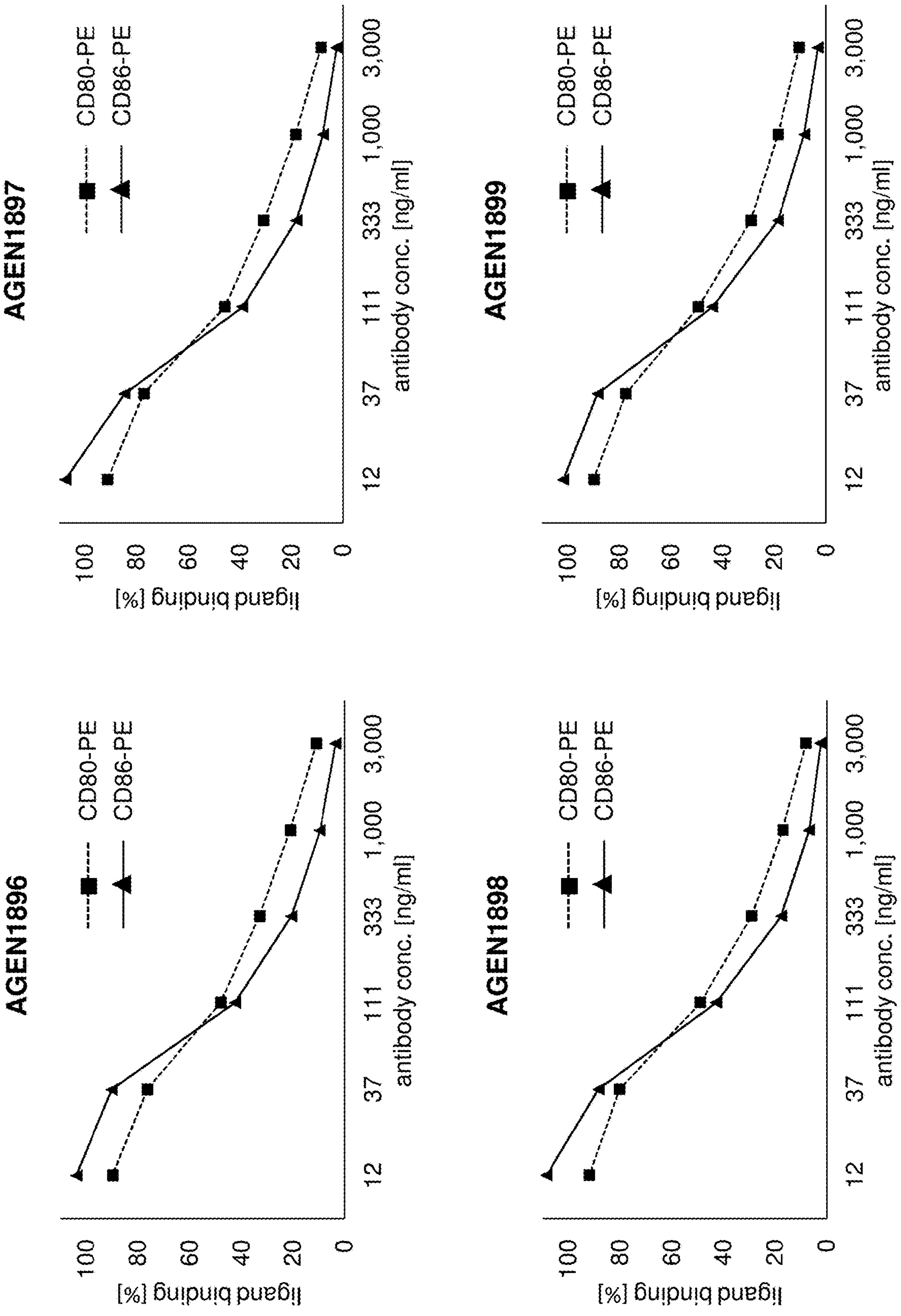
Figure 20E:
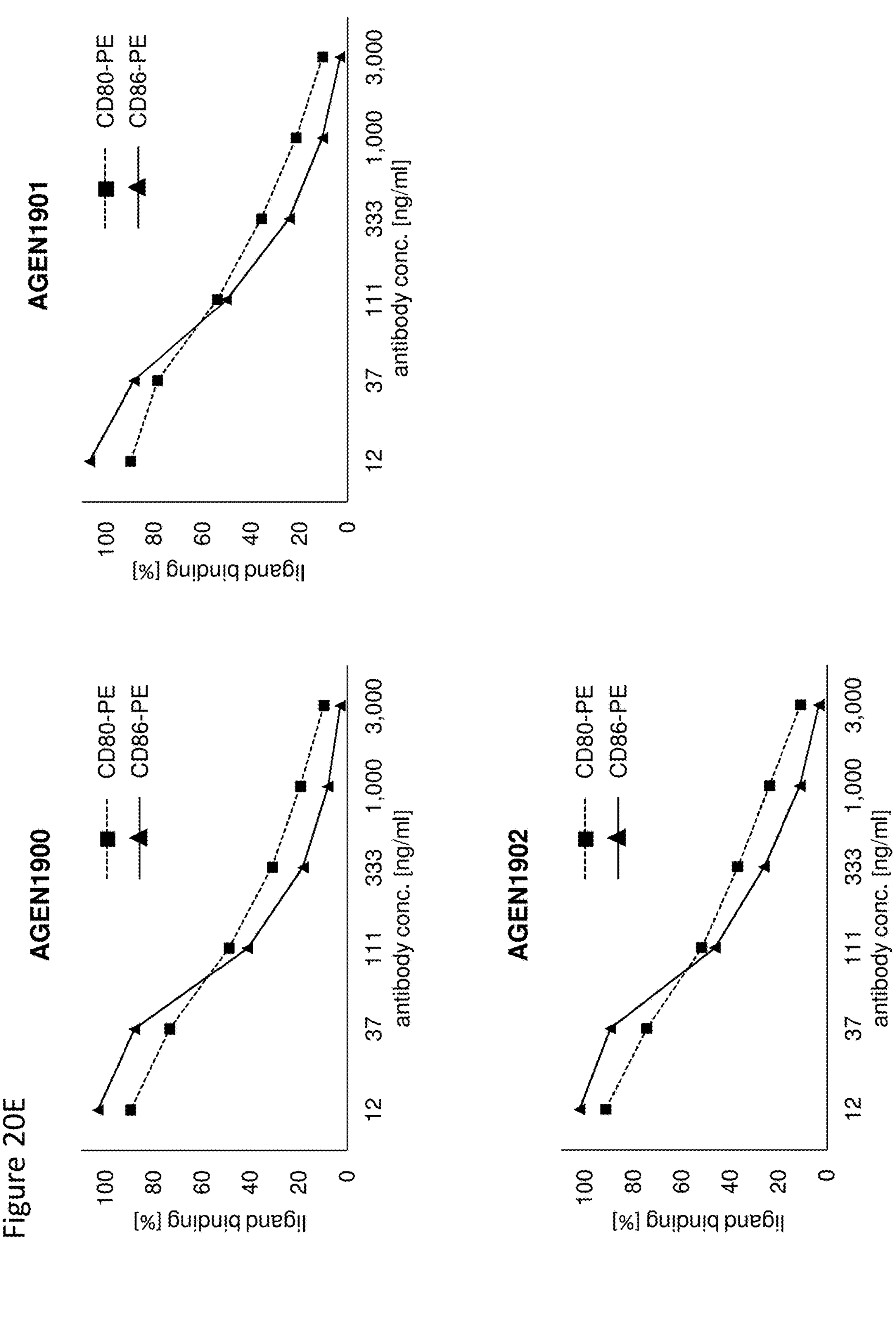

FIGS. 18A and 18B are results from a T cell dependent antigen response (TDAR) study in cynomolgus monkeys. AGEN1884w (10 mg/kg), a reference anti-CTLA-4 $IgG_1$ antibody (3 mg/kg) (FIG. 18A), AGEN2041w (10 mg/kg) (FIG. 18B), or control article (FIGS. 18A and 18B) was given via intravenous administration (slow bolus) together with HBsAg vaccines (30 μg in the hind leg) on Days 1 and 29. Duplicate samples were analyzed for anti-HBsAg (IgG) serum titers using ELISA. Data points represent mean±SEM in each treatment group.

FIGS. 19A and 19B are sequence alignments of variable heavy chains BADD411-2354 (SEQ ID NO: 7), BADD412-2356 (SEQ ID NO: 38), BADD412-2357 (SEQ ID NO: 39), BADD412-2358 (SEQ ID NO: 40), BADD412-2359 (SEQ ID NO: 41), and BADD412-2360 (SEQ ID NO: 42), and variable light chains BADD412-2367 (SEQ ID NO: 43), BADD412-2376 (SEQ ID NO: 8), BADD412-2382 (SEQ ID NO: 44), BADD412-2384 (SEQ ID NO: 45), BADD412-2390 (SEQ ID NO: 46), and BADD412-2393 (SEQ ID NO: 47), respectively. Heavy and light chain CDRs shown are determined according to Kabat.

FIGS. 20A-20E are graphs showing the percentage of recombinant CD80-PE or CD86-PE binding to CTLA-4 coupled beads in the presence of a dose titration of 19 anti-CTLA-4 antibodies (AGEN1884-AGEN1902) as measured by suspension array technology.

5. DETAILED DESCRIPTION

The instant disclosure provides antibodies that specifically bind to human CTLA-4 and antagonize CTLA-4 function, e.g., CTLA-4-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T-cell activation in response to an antigen (e.g., a tumor antigen), and hence for treating cancer, or preventing or treating infectious diseases in a subject. The antibodies disclosed herein are also useful for use in pharmaceutical compositions for, or in the manufacture of medicaments for, treating cancer, or preventing or treating infectious diseases.

5.1 Definitions

As used herein, the terms "about" and "approximately," when used to modify a numeric value or numeric range, indicate that deviations of 5% to 10% above and 5% to 10% below the value or range remain within the intended meaning of the recited value or range.

As used herein, the term "CTLA-4" refers to cytotoxic T-lymphocyte-associated protein 4. CTLA-4 nucleotide and polypeptide sequences are well known in the art. An exemplary human CTLA-4 amino sequence is set forth in GenBank deposit GI: 15778585 and an exemplary mouse CTLA-4 amino sequence is set forth in GenBank deposit GI: 15778586.

As used herein, the terms "antibody" and "antibodies" include full length antibodies, antigen-binding fragments of antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain—antibody heavy chain pair, intrabodies, heteroconjugate antibodies, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$ or $IgG_4$) or subclass thereof. In a specific embodiment, the antibody is a humanized monoclonal antibody. In another specific embodiment, the antibody is a human monoclonal antibody. In certain embodiments, an antibody described herein is an $IgG_1$ or $IgG_2$ antibody.

As used herein, the terms "VH region" and "VL region" refer to single antibody heavy and light chain variable regions, respectively, comprising FR (Framework Regions) 1, 2, 3 and 4 and CDR (Complementarity Determining Regions) 1, 2 and 3 (see Kabat et al. (1991) Sequences of Proteins of Immunological Interest. (NIH Publication No. 91-3242, Bethesda).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons. CDRH1, CDRH2 and CDRH3 denote the heavy chain CDRs, and CDRL1, CDRL2 and CDRL3 denote the light chain CDRs.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, in "Sequences of Proteins of Immunological Interest", U.S. Dept. Health and Human Services, 5th edition, 1991.

As used herein the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat definition of CDRs).

As used herein, the term "afucosylation" or "afucosylated" in the context of an Fc refers to a substantial lack of a fucose covalently attached, directly or indirectly, to residue 297 of the human IgG1 Fc region, numbered according to the EU index (Kabat et al., Sequences of Proteins of Immunological Interest, 5th Ed. Public Health Service, National Institutes of Health, Bethesda, Md. (1991)), or the corresponding residue in non-IgG1 or non-human IgG1 immunoglobulins. Thus, in a composition comprising a plurality of afucosylated antibodies, at least 70% of the antibodies will not be fucosylated, directly or indirectly (e.g., via intervening sugars) at residue 297 of the Fc region of the antibodies, and in some embodiments at least 80%, 85%, 90%, 95%, or 99% will not be fucosylated, directly or indirectly, at residue 297 of the Fc region.

As used herein, the term "specifically binds to" refers to the ability of an antibody to bind to an antigen with an dissociation constant (Kd) of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or less, and/or bind to an antigen with an affinity that is at least two-fold greater than its affinity for a nonspecific antigen.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques. In a specific embodiment, the epitope of an antibody or antigen-binding fragment thereof is determined using alanine scanning mutagenesis studies.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal.

Hydrogen-deuterium exchange is evaluated using an assay comprising the following steps: (a) taking a solution of CTLA-4 alone or CTLA-4 in combination with an antibody in aqueous buffer and diluting this solution into an approximately 90% volume/volume excess of deuterium oxide labeling buffer for, e.g., 0, 60, 300, 1800, and 7200 seconds; (b) quenching the exchange of hydrogen with deuterium by lowering the pH; (c) subjecting the samples to protease digestion and mass spectrometric analysis; and (d) calculating deuterium incorporation in CTLA-4 proteolytic peptides and comparing deuterium incorporation in the presence or absence of the antibody. The exchange of hydrogen with deuterium in a CTLA-4 proteolytic peptide is "reduced" if the hydrogen/deuterium exchange in the presence of an anti-CTLA-4 antibody is reduced by at least 10% relative to the hydrogen/deuterium exchange in the absence of the antibody, as assessed by the foregoing assay.

5.2 Anti-CTLA-4 Antibodies

In one aspect the instant disclosure provides antibodies that specifically bind to human CTLA-4 and antagonize CTLA-4 function. The amino acid sequences of exemplary antibodies are set forth in Tables 1-6, herein.

TABLE 1

Sequences of variable regions, CDRs, and frameworks (FRs) of exemplary anti-CTLA-4 antibodies

| SEQ ID NO: | Description | Amino acid Sequence |
|---|---|---|
| 1 | Kabat CDRH1 (AGEN1884w) | SYSMN |
| 2 | Kabat CDRH2 (AGEN1884w) | SISSSSSYIYYADSVKG |
| 3 | Kabat CDRH3 (AGEN1884w) | VGLMGPFDI |
| 4 | Kabat CDRL1 (AGEN1884w) | RASQSVSRYLG |
| 5 | Kabat CDRL2 (AGEN1884w) | GASTRAT |
| 6 | Kabat CDRL3 (AGEN1884w) | QQYGSSPWT |
| 7 | VH (AGEN1884w) | EVQLVESGGGLVKPGGSLRLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS |
| 8 | VL (AGEN1884w) | EIVLTQSPGTLSLSPGERATLSCRASQSVSRYLGWYQQKP GQAPRLLIYGASTRATGIPDRFSGSGSGTDFTLTITRLEPED FAVYYCQQYGSSPWTFGQGTKVEIK |
| 9 | Germline sequence: IGHV3-21*01 | EVQLVESGGGLVKPGGSLRLSCAASGFTFSSYSMNWVRQ APGKGLEWVSSISSSSSYIYYADSVKGRFTISRDNAKNSLY LQMNSLRAEDTAVYYCAR |
| 10 | Germline sequence: IGKV3-20*01 | EIVLTQSPGTLSLSPGERATLSCRASQSVSSSYLAWYQQKP GQAPRLLIYGASSRATGIPDRFSGSGSGTDFTLTISRLEPED FAVYYCQQYGSSP |
| 11 | Germline sequence: IGKV3-11*01 | EIVLTQSPATLSLSPGERATLSCRASQSVSSYLAWYQQKP GQAPRLLIYDASNRATGIPARFSGSGSGTDFTLTISSLEPED FAVYYCQQRSNWPP |
| 12 | AGEN1884w full length heavy chain (with C-terminal lysine) | EVQLVESGGGLVKPGGSLRLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 93 | AGEN1884w full length heavy chain (without C-terminal lysine) | EVQLVESGGGLVKPGGSLRLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPG |

TABLE 1-continued

Sequences of variable regions, CDRs, and frameworks (FRs) of exemplary anti-CTLA-4 antibodies

| SEQ ID NO: | Description | Amino acid Sequence |
|---|---|---|
| 13 | AGEN1884w full length light chain sequence | EIVLTQSPGTLSLSPGERATLSCRASQSVSRYLGWYQQKP GQAPRLLIYGASTRATGIPDRFSGSGSGTDFTLTITRLEPED FAVYYCQQYGSSPWTFGQGTKVEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQ GLSSPVTKSFNRGEC |
| 14 | AGEN2041w full length heavy chain sequence (with C-terminal lysine) | EVQLVESGGGLVKPGGSLRLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS ASTKGPSVFPLAPCSRSTSESTAALGCLVKDYFPEPVTVS WNSGALTSGVHTFPAVLQSSGLYSLSSVVTVPSSNFGTQT YTCNVDHKPSNTKVDKTVERKCCVECPPCPAPPVAGPSV FLFPPKPKDTLMISRTPEVTCVVVDVSHEDPEVQFNWYV DGVEVHNAKTKPREEQFNSTFRVVSVLTVVHQDWLNGK EYKCKVSNKGLPAPIEKTISKTKGQPREPQVYTLPPSREE MTKNQVSLTCLVKGFYPSDIAVEWESNGQPENNYKTTPP MLDSDGSFFLYSKLTVDKSRWQQGNVFSCSVMHEALHN HYTQKSLSLSPGK |
| 94 | AGEN2041w full length heavy chain sequence (without C-terminal lysine) | EVQLVESGGGLVKPGGSLRLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS ASTKGPSVFPLAPCSRSTSESTAALGCLVKDYFPEPVTVS WNSGALTSGVHTFPAVLQSSGLYSLSSVVTVPSSNFGTQT YTCNVDHKPSNTKVDKTVERKCCVECPPCPAPPVAGPSV FLFPPKPKDTLMISRTPEVTCVVVDVSHEDPEVQFNWYV DGVEVHNAKTKPREEQFNSTFRVVSVLTVVHQDWLNGK EYKCKVSNKGLPAPIEKTISKTKGQPREPQVYTLPPSREE MTKNQVSLTCLVKGFYPSDIAVEWESNGQPENNYKTTPP MLDSDGSFFLYSKLTVDKSRWQQGNVFSCSVMHEALHN HYTQKSLSLSPG |
| 15 | AGEN1884 full length light chain sequence | EIVLTQSPGTLSLSPGERATLSCRASQSVSRYLGWYQQKP GQAPRLLIYGASTRATGIPDRFSGSGSGTDFTLTITRLEPED FAVYYCQQYGSSPWTFGQGTKVEIKRSVAAPSVFIFPPSD EQLKSGTASVVCLLNNFYPREAKVQWKVDNALQSGNSQ ESVTEQDSKDSTYSLSSTLTLSKADYEKHKVYACEVTHQ GLSSPVTKSFNRGEC |
| 16 | IMGT CDRH1 (AGEN1884w) | GFTFSSYS |
| 17 | IMGT CDRH2 (AGEN1884w) | ISSSSSYI |
| 18 | IMGT CDRH3 (AGEN1884w) | ARVGLMGPFDI |
| 19 | IMGT CDRL1 (AGEN1884w) | QSVSRY |
| 20 | IMGT CDRL2 (AGEN1884w) | GAS |
| 21 | IMGT CDRL3 (AGEN1884w) | QQYGSSPWT |
| 22 | CDRH1 consensus sequence | $SYX_1MX_2$, wherein $X_1$ is S or A; and $X_2$ is N or S |
| 23 | CDRH3 consensus sequence | VGLMGPFXI, wherein X is D or N |
| 24 | CDRL1 consensus sequence | $RASQSVX_1X_2YLX_3$, wherein $X_1$ is S or G; $X_2$ is R, S, or T; and $X_3$ is G or A |
| 25 | CDRL2 consensus sequence | $X_1X_2SX_3RAT$, wherein $X_1$ is G or A; $X_2$ is A or T; and $X_3$ is T, S, R, or N |

TABLE 1-continued

Sequences of variable regions, CDRs, and frameworks (FRs) of exemplary anti-CTLA-4 antibodies

| SEQ ID NO: | Description | Amino acid Sequence |
|---|---|---|
| 26 | CDRL3 consensus sequence | QQYG$X_1$SP$X_2$T, wherein $X_1$ is S or T; and $X_2$ is W or F |
| 27 | CDRH1 | SYAMS |
| 28 | CDRH3 | VGLMGPFNI |
| 29 | CDRL1 | RASQSVSSYLA |
| 30 | CDRL1 | RASQSVGTYLA |
| 31 | CDRL2 | GASRRAT |
| 32 | CDRL2 | ATSSRAT |
| 33 | CDRL2 | GASSRAT |
| 34 | CDRL2 | AASTRAT |
| 35 | CDRL2 | GASNRAT |
| 36 | CDRL3 | QQYGTSPWT |
| 37 | CDRL3 | QQYGSSPFT |
| 38 | VH | EVQLLESGGGLVQPGGSLRLSCAASGFTFSSYAMSWVRQ APGKGLVWVSSISSSSSYIYYADSVKGRFTISRDNAKNSL YLQMNSLRAEDTAVYYCARVGLMGPFDIWGQGTMVTVS S |
| 39 | VH | EVQLVESGGGLVKPGGSLRLSCAASGFTFSSYSMNWVRQ APGKGLEWVSSISSSSSYIYYADSVKGRFTISRDNAKNTLY LQMNSLRAEDTAVYYCARVGLMGPFDIWGQGTMVTVSS |
| 40 | VH | EVQLLESGGGLVKPGGSLRLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS |
| 41 | VH | EVQLLESGGGLVQPGGSLRLSCAASGFTFSSYAMSWVRQ APGKGLVWVSSISSSSSYIYYADSVKGRFTISRDNAKNSL YLQMNSLRAEDTAVYYCARVGLMGPFNIWGQGTMVTVS S |
| 42 | VH | EVQLVESGGGLVQPGGSLTLSCAASGFTFSSYSMNWVRQ APGKGLEWVSSISSSSSYIYYADSVKGRFTISRDNAKNSLY LQMNSLRAEDTAVYYCARVGLMGPFDIWGQGTMVTVSS |
| 43 | VL | EIVLTQSPATLSLSPGERATLSCRASQSVGTYLAWYQHKV GQAPRLLIYGASRRATGIPDRFSGSGSGTDFTLTISRLEPED FAVYYCQQYGSSPWTFGQGTKVEIK |
| 44 | VL | EIVLTQSPATLSLSPGERATLSCRASQSVSSYLAWYQQKP GQAPSLLIYATSSRATGIPDRFSGSVSGTDFTLTISRLEPED FAVYYCQQYGTSPWTFGQGTKVEIK |
| 45 | VL | EIVLTQSPATLSFSPGERATLSCRASQSVSSYLAWYQQKP GQAPRLLIYGASSRATGIPDRFSGSGSGTDFTFTISRLEPED FAVYYCQQYGSSPFTFGPGTKVDIK |
| 46 | VL | EIVLTQSPATLSVSPGERATLSCRASQSVSSYLAWYQQKP GQAPRLLIYAASTRATGIPDRFSGSASGTDFTLTISRLEPED FAVYYCQQYGSSPWTFGQGTKVEIK |
| 47 | VL | EIVLTQSPATLSLSPGERATLSCRASQSVSSYLAWYQQKP GQAPRLLIYGASNRATGIPARFSGSGSGTDFTLTISSLEPED FAVYYCQQYGSSPFTFGPGTKVDIK |
| 48 | VH FR1 | EVQLVESGGGLVKPGGSLRLSCAASGFTFS |
| 49 | VH FR2 | WVRQAPGKGLEWVS |
| 50 | VH FR3 | RFTISRDNAKNSLYLQMNSLRAEDTAVYYCAR |

TABLE 1-continued

Sequences of variable regions, CDRs, and frameworks (FRs) of exemplary anti-CTLA-4 antibodies

| SEQ ID NO: | Description | Amino acid Sequence |
|---|---|---|
| 51 | VH FR4 | WGQGTMVTVSS |
| 52 | VH FR1 | EVQLLESGGGLVQPGGSLRLSCAASGFTFS |
| 53 | VH FR2 | WVRQAPGKGLVWVS |
| 54 | VH FR3 | RFTISRDNAKNTLYLQMNSLRAEDTAVYYCAR |
| 55 | VH FR1 | EVQLLESGGGLVKPGGSLRLSCAASGFTFS |
| 56 | VH FR1 | EVQLVESGGGLVQPGGSLTLSCAASGFTFS |
| 57 | VL FR1 | EIVLTQSPGTLSLSPGERATLSC |
| 58 | VL FR2 | WYQQKPGQAPRLLIY |
| 59 | VL FR3 | GIPDRFSGSGSGTDFTLTITRLEPEDFAVYYC |
| 60 | VL FR4 | FGQGTKVEIK |
| 61 | VL FR1 | EIVLTQSPATLSLSPGERATLSC |
| 62 | VL FR2 | WYQHKVGQAPRLLIY |
| 63 | VL FR3 | GIPDRFSGSGSGTDFTLTISRLEPEDFAVYYC |
| 64 | VL FR2 | WYQQKPGQAPSLLIY |
| 65 | VL FR3 | GIPDRFSGSVSGTDFTLTISRLEPEDFAVYYC |
| 66 | VL FR1 | EIVLTQSPATLSFSPGERATLSC |
| 67 | VL FR3 | GIPDRFSGSGSGTDFTFTISRLEPEDFAVYYC |
| 68 | VL FR4 | FGPGTKVDIK |
| 69 | VL FR1 | EIVLTQSPATLSVSPGERATLSC |
| 70 | VL FR3 | GIPDRFSGSASGTDFTLTISRLEPEDFAVYYC |
| 71 | VL FR3 | GIPARFSGSGSGTDFTLTISSLEPEDFAVYYC |
| 72 | VH consensus sequence | EVQLX$_1$ESGGGLVX$_2$PGGSLX$_3$LSCAASGFTFSSYX$_4$MX$_5$W VRQAPGKGLX$_6$WVSSISSSSSYIYYADSVKGRFTISRDNAK NX$_7$LYLQMNSLRAEDTAVYYCARVGLMGPFX$_8$IWGQGT MVTVS S, wherein<br>$X_1$ is V or L;<br>$X_2$ is K or Q;<br>$X_3$ is R or T;<br>$X_4$ is S or A;<br>$X_5$ is N or S;<br>$X_6$ is E or V;<br>$X_7$ is S or T; and<br>$X_8$ is D or N |
| 73 | VL consensus sequence | EIVLTQSPX$_1$TLSX$_2$SPGERATLSCRASQSVX$_3$X$_4$YLX$_5$WYQ X$_6$KX$_7$GQAPX$_8$LLIYX$_9$X$_{10}$SX$_{11}$RATGIPX$_{12}$RFSGSX$_{13}$SGTDF TX$_{14}$TIX$_{15}$X$_{16}$LEPEDFAVYYCQQYGX$_{17}$SPX$_{18}$TFGX$_{19}$GTKV X$_{20}$IK, wherein<br>$X_1$ is G or A;<br>$X_2$ is L, V, or F;<br>$X_3$ is S or G;<br>$X_4$ is R, T, or S;<br>$X_5$ is G or A;<br>$X_6$ is Q or H;<br>$X_7$ is P or V;<br>$X_8$ is R or S;<br>$X_9$ is G or A;<br>$X_{10}$ is A or T;<br>$X_{11}$ is T, R, S, or N;<br>$X_{12}$ is D or A;<br>$X_{13}$ is G, V, or A;<br>$X_{14}$ is L or F; |

TABLE 1-continued

Sequences of variable regions, CDRs, and frameworks (FRs) of exemplary anti-CTLA-4 antibodies

| SEQ ID NO: | Description | Amino acid Sequence |
|---|---|---|
| | | $X_{15}$ is T or S;<br>$X_{16}$ is R or S;<br>$X_{17}$ is S or T;<br>$X_{18}$ is W or F;<br>$X_{19}$ is Q or P; and<br>$X_{20}$ is E or D |
| 74 | AGEN1884w N297A full length heavy chain (with C-terminal lysine) | EVQLVESGGGLVKPGGSLRLSCAASGFTFSSYSMNWVRQ<br>APGKGLEWVSSISSSSSYIYYADSVKGRFTISRDNAKNSLY<br>LQMNSLRAEDTAVYYCARVGLMGPFDIWGQGTMVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVDVSHEDPEVKFNW<br>YVDGVEVHNAKTKPREEQYASTYRVVSVLTVLHQDWLN<br>GKEYKCKVSNKALPAPIEKTISKAKGQPREPQVYTLPPSR<br>EEMTKNQVSLTCLVKGFYPSDIAVEWESNGQPENNYKTT<br>PPVLDSDGSFFLYSKLTVDKSRWQQGNVFSCSVMHEALH<br>NHYTQKSLSLSPGK |
| 95 | AGEN1884w N297A full length heavy chain (without C-terminal lysine) | EVQLVESGGGLVKPGGSLRLSCAASGFTFSSYSMNWVRQ<br>APGKGLEWVSSISSSSSYIYYADSVKGRFTISRDNAKNSLY<br>LQMNSLRAEDTAVYYCARVGLMGPFDIWGQGTMVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVDVSHEDPEVKFNW<br>YVDGVEVHNAKTKPREEQYASTYRVVSVLTVLHQDWLN<br>GKEYKCKVSNKALPAPIEKTISKAKGQPREPQVYTLPPSR<br>EEMTKNQVSLTCLVKGFYPSDIAVEWESNGQPENNYKTT<br>PPVLDSDGSFFLYSKLTVDKSRWQQGNVFSCSVMHEALH<br>NHYTQKSLSLSPG |
| 75 | AGEN1884w S267E/L328F full length heavy chain (with C-terminal lysine) | EVQLVESGGGLVKPGGSLRLSCAASGFTFSSYSMNWVRQ<br>APGKGLEWVSSISSSSSYIYYADSVKGRFTISRDNAKNSLY<br>LQMNSLRAEDTAVYYCARVGLMGPFDIWGQGTMVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVDVEHEDPEVKFNW<br>YVDGVEVHNAKTKPREEQYNSTYRVVSVLTVLHQDWLN<br>GKEYKCKVSNKAFPAPIEKTISKAKGQPREPQVYTLPPSR<br>EEMTKNQVSLTCLVKGFYPSDIAVEWESNGQPENNYKTT<br>PPVLDSDGSFFLYSKLTVDKSRWQQGNVFSCSVMHEALH<br>NHYTQKSLSLSPGK |
| 96 | AGEN1884w S267E/L328F full length heavy chain (without C-terminal lysine) | EVQLVESGGGLVKPGGSLRLSCAASGFTFSSYSMNWVRQ<br>APGKGLEWVSSISSSSSYIYYADSVKGRFTISRDNAKNSLY<br>LQMNSLRAEDTAVYYCARVGLMGPFDIWGQGTMVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVDVEHEDPEVKFNW<br>YVDGVEVHNAKTKPREEQYNSTYRVVSVLTVLHQDWLN<br>GKEYKCKVSNKAFPAPIEKTISKAKGQPREPQVYTLPPSR<br>EEMTKNQVSLTCLVKGFYPSDIAVEWESNGQPENNYKTT<br>PPVLDSDGSFFLYSKLTVDKSRWQQGNVFSCSVMHEALH<br>NHYTQKSLSLSPG |
| 76 | AGEN1884w S239D/A330L/I332E full length heavy chain (with C-terminal lysine) | EVQLVESGGGLVKPGGSLRLSCAASGFTFSSYSMNWVRQ<br>APGKGLEWVSSISSSSSYIYYADSVKGRFTISRDNAKNSLY<br>LQMNSLRAEDTAVYYCARVGLMGPFDIWGQGTMVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PDVFLFPPKPKDTLMISRTPEVTCVVVDVSHEDPEVKFNW<br>YVDGVEVHNAKTKPREEQYNSTYRVVSVLTVLHQDWLN<br>GKEYKCKVSNKALPLPEEKTISKAKGQPREPQVYTLPPSR<br>EEMTKNQVSLTCLVKGFYPSDIAVEWESNGQPENNYKTT<br>PPVLDSDGSFFLYSKLTVDKSRWQQGNVFSCSVMHEALH<br>NHYTQKSLSLSPGK |

TABLE 1-continued

Sequences of variable regions, CDRs, and frameworks (FRs) of exemplary anti-CTLA-4 antibodies

| SEQ ID NO: | Description | Amino acid Sequence |
|---|---|---|
| 97 | AGEN1884w S239D/A330L/I332E full length heavy chain (without C-terminal lysine) | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARVGLMGPFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPDVFLFPPKPKDTLMISRTPEVTCVVVDVSHEDPEVKFNWYVDGVEVHNAKTKPREEQYNSTYRVVSVLTVLHQDWLNGKEYKCKVSNKALPLPEEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |

TABLE 2

Heavy chain CDR sequences of exemplary anti-CTLA-4 antibodies[1]

| Antibody | CDRH1 (SEQ ID NO:) | CDRH2 (SEQ ID NO:) | CDRH3 (SEQ ID NO:) |
|---|---|---|---|
| AGEN1884w | SYSMN (1) | SISSSSSYIYYADSVKG (2) | VGLMGPFDI (3) |
| AGEN1885 | SYSMN (1) | SISSSSSYIYYADSVKG (2) | VGLMGPFDI (3) |
| AGEN1886 | SYSMN (1) | SISSSSSYIYYADSVKG (2) | VGLMGPFDI (3) |
| AGEN1887 | SYAMS (27) | SISSSSSYIYYADSVKG (2) | VGLMGPFDI (3) |
| AGEN1888 | SYAMS (27) | SISSSSSYIYYADSVKG (2) | VGLMGPFDI (3) |
| AGEN1889 | SYSMN (1) | SISSSSSYIYYADSVKG (2) | VGLMGPFDI (3) |
| AGEN1890 | SYSMN (1) | SISSSSSYIYYADSVKG (2) | VGLMGPFDI (3) |
| AGEN1891 | SYSMN (1) | SISSSSSYIYYADSVKG (2) | VGLMGPFDI (3) |
| AGEN1892 | SYSMN (1) | SISSSSSYIYYADSVKG (2) | VGLMGPFDI (3) |
| AGEN1893 | SYSMN (1) | SISSSSSYIYYADSVKG (2) | VGLMGPFDI (3) |
| AGEN1894 | SYSMN (1) | SISSSSSYIYYADSVKG (2) | VGLMGPFDI (3) |
| AGEN1895 | SYSMN (1) | SISSSSSYIYYADSVKG (2) | VGLMGPFDI (3) |
| AGEN1896 | SYSMN (1) | SISSSSSYIYYADSVKG (2) | VGLMGPFDI (3) |
| AGEN1897 | SYAMS (27) | SISSSSSYIYYADSVKG (2) | VGLMGPFNI (28) |
| AGEN1898 | SYAMS (27) | SISSSSSYIYYADSVKG (2) | VGLMGPFNI (28) |
| AGEN1899 | SYAMS (27) | SISSSSSYIYYADSVKG (2) | VGLMGPFNI (28) |
| AGEN1900 | SYAMS (27) | SISSSSSYIYYADSVKG (2) | VGLMGPFNI (28) |
| AGEN1901 | SYSMN (1) | SISSSSSYIYYADSVKG (2) | VGLMGPFDI (3) |
| AGEN1902 | SYSMN (1) | SISSSSSYIYYADSVKG (2) | VGLMGPFDI (3) |

[1]The VH CDRs in Table 2 are determined according to Kabat.

TABLE 3

Light chain CDR sequences of exemplary anti-CTLA-4 antibodies[2]

| Antibody | CDRL1 (SEQ ID NO:) | CDRL2 (SEQ ID NO:) | CDRL3 (SEQ ID NO:) |
|---|---|---|---|
| AGEN1884w | RASQSVSRYLG (4) | GASTRAT (5) | QQYGSSPWT (6) |
| AGEN1885 | RASQSVSSYLA (29) | ATSSRAT (32) | QQYGTSPWT (36) |
| AGEN1886 | RASQSVSSYLA (29) | GASSRAT (33) | QQYGSSPFT (37) |
| AGEN1887 | RASQSVSRYLG (4) | GASTRAT (5) | QQYGSSPWT (6) |
| AGEN1888 | RASQSVSSYLA (29) | GASSRAT (33) | QQYGSSPFT (37) |
| AGEN1889 | RASQSVGTYLA (30) | GASRRAT (31) | QQYGSSPWT (6) |
| AGEN1890 | RASQSVSSYLA (29) | GASSRAT (33) | QQYGSSPFT (37) |
| AGEN1891 | RASQSVSSYLA (29) | AASTRAT (34) | QQYGSSPWT (6) |
| AGEN1892 | RASQSVSSYLA (29) | GASNRAT (35) | QQYGSSPFT (37) |
| AGEN1893 | RASQSVGTYLA (30) | GASRRAT (31) | QQYGSSPWT (6) |
| AGEN1894 | RASQSVSRYLG (4) | GASTRAT (5) | QQYGSSPWT (6) |
| AGEN1895 | RASQSVSSYLA (29) | ATSSRAT (32) | QQYGTSPWT (36) |
| AGEN1896 | RASQSVSSYLA (29) | GASSRAT (33) | QQYGSSPFT (37) |
| AGEN1897 | RASQSVSRYLG (4) | GASTRAT (5) | QQYGSSPWT (6) |
| AGEN1898 | RASQSVSSYLA (29) | ATSSRAT (32) | QQYGTSPWT (36) |
| AGEN1899 | RASQSVSSYLA (29) | GASSRAT (33) | QQYGSSPFT (37) |
| AGEN1900 | RASQSVSSYLA (29) | GASNRAT (35) | QQYGSSPFT (37) |
| AGEN1901 | RASQSVGTYLA (30) | GASRRAT (31) | QQYGSSPWT (6) |
| AGEN1902 | RASQSVSSYLA (29) | GASSRAT (33) | QQYGSSPFT (37) |

[2]The VL CDRs in Table 3 are determined according to Kabat.

TABLE 4

VH framework (FR) sequences of exemplary anti-CTLA-4 antibodies[3]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| AGEN1884w | EVQLVESGGGLVKPGGSLR LSCAASGFTFS (48) | WVRQAPGKG LEWVS (49) | RFTISRDNAKNSLYLQMN SLRAEDTAVYYCAR (50) | WGQGTMVT VSS (51) |
| AGEN1885 | EVQLVESGGGLVKPGGSLR LSCAASGFTFS (48) | WVRQAPGKG LEWVS (49) | RFTISRDNAKNSLYLQMN SLRAEDTAVYYCAR (50) | WGQGTMVT VSS (51) |
| AGEN1886 | EVQLVESGGGLVKPGGSLR LSCAASGFTFS (48) | WVRQAPGKG LEWVS (49) | RFTISRDNAKNSLYLQMN SLRAEDTAVYYCAR (50) | WGQGTMVT VSS (51) |
| AGEN1887 | EVQLLESGGGLVQPGGSLR LSCAASGFTFS (52) | WVRQAPGKG LVWVS (53) | RFTISRDNAKNSLYLQMN SLRAEDTAVYYCAR (50) | WGQGTMVT VSS (51) |
| AGEN1888 | EVQLLESGGGLVQPGGSLR LSCAASGFTFS (52) | WVRQAPGKG LVWVS (53) | RFTISRDNAKNSLYLQMN SLRAEDTAVYYCAR (50) | WGQGTMVT VSS (51) |
| AGEN1889 | EVQLVESGGGLVKPGGSLR LSCAASGFTFS (48) | WVRQAPGKG LEWVS (49) | RFTISRDNAKNTLYLQMN SLRAEDTAVYYCAR (54) | WGQGTMVT VSS (51) |
| AGEN1890 | EVQLVESGGGLVKPGGSLR LSCAASGFTFS (48) | WVRQAPGKG LEWVS (49) | RFTISRDNAKNTLYLQMN SLRAEDTAVYYCAR (54) | WGQGTMVT VSS (51) |
| AGEN1891 | EVQLVESGGGLVKPGGSLR LSCAASGFTFS (48) | WVRQAPGKG LEWVS (49) | RFTISRDNAKNTLYLQMN SLRAEDTAVYYCAR (54) | WGQGTMVT VSS (51) |
| AGEN1892 | EVQLVESGGGLVKPGGSLR LSCAASGFTFS (48) | WVRQAPGKG LEWVS (49) | RFTISRDNAKNTLYLQMN SLRAEDTAVYYCAR (54) | WGQGTMVT VSS (51) |

TABLE 4-continued

VH framework (FR) sequences of exemplary anti-CTLA-4 antibodies[3]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| AGEN1893 | EVQLLESGGGLVKPGGSLR LSCAASGFTFS (55) | WVRQAPGKG LEWVS (49) | RFTISRDNAKNSLYLQMN SLRAEDTAVYYCAR (50) | WGQGTMVT VSS (51) |
| AGEN1894 | EVQLLESGGGLVKPGGSLR LSCAASGFTFS (55) | WVRQAPGKG LEWVS (49) | RFTISRDNAKNSLYLQMN SLRAEDTAVYYCAR (50) | WGQGTMVT VSS (51) |
| AGEN1895 | EVQLLESGGGLVKPGGSLR LSCAASGFTFS (55) | WVRQAPGKG LEWVS (49) | RFTISRDNAKNSLYLQMN SLRAEDTAVYYCAR (50) | WGQGTMVT VSS (51) |
| AGEN1896 | EVQLLESGGGLVKPGGSLR LSCAASGFTFS (55) | WVRQAPGKG LEWVS (49) | RFTISRDNAKNSLYLQMN SLRAEDTAVYYCAR (50) | WGQGTMVT VSS (51) |
| AGEN1897 | EVQLLESGGGLVQPGGSLR LSCAASGFTFS (52) | WVRQAPGKG LVWVS (53) | RFTISRDNAKNSLYLQMN SLRAEDTAVYYCAR (50) | WGQGTMVT VSS (51) |
| AGEN1898 | EVQLLESGGGLVQPGGSLR LSCAASGFTFS (52) | WVRQAPGKG LVWVS (53) | RFTISRDNAKNSLYLQMN SLRAEDTAVYYCAR (50) | WGQGTMVT VSS (51) |
| AGEN1899 | EVQLLESGGGLVQPGGSLR LSCAASGFTFS (52) | WVRQAPGKG LVWVS (53) | RFTISRDNAKNSLYLQMN SLRAEDTAVYYCAR (50) | WGQGTMVT VSS (51) |
| AGEN1900 | EVQLLESGGGLVQPGGSLR LSCAASGFTFS (52) | WVRQAPGKG LVWVS (53) | RFTISRDNAKNSLYLQMN SLRAEDTAVYYCAR (50) | WGQGTMVT VSS (51) |
| AGEN1901 | EVQLVESGGGLVQPGGSLT LSCAASGFTFS (56) | WVRQAPGKG LEWVS (49) | RFTISRDNAKNSLYLQMN SLRAEDTAVYYCAR (50) | WGQGTMVT VSS (51) |
| AGEN1902 | EVQLVESGGGLVQPGGSLT LSCAASGFTFS (56) | WVRQAPGKG LEWVS (49) | RFTISRDNAKNSLYLQMN SLRAEDTAVYYCAR (50) | WGQGTMVT VSS (51) |

[3]The VH framework regions described in Table 4 are determined based upon the boundaries of the Kabat numbering system for CDRs. In other words, the VH CDRs are determined by Kabat and the framework regions are the amino acid residues surrounding the CDRs in the variable region in the format FR1, CDRH1, FR2, CDRH2, FR3, CDRH3, and FR4.

TABLE 5

VL framework (FR) sequences of exemplary anti-CTLA-4 antibodies[4]

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| AGEN1884w | EIVLTQSPGTLSLSPG ERATLSC (57) | WYQQKPGQA PRLLIY (58) | GIPDRFSGSGSGTDFTLTI TRLEPEDFAVYYC (59) | FGQGTKVEIK (60) |
| AGEN1885 | EIVLTQSPATLSLSPG ERATLSC (61) | WYQQKPGQA PSLLIY (64) | GIPDRFSGSVSGTDFTLTI SRLEPEDFAVYYC (63) | FGQGTKVEIK (60) |
| AGEN1886 | EIVLTQSPATLSFSPG ERATLSC (66) | WYQQKPGQA PRLLIY (58) | GIPDRFSGSGSGTDFTFTIS RLEPEDFAVYYC (67) | FGPGTKVDIK (68) |
| AGEN1887 | EIVLTQSPGTLSLSPG ERATLSC (57) | WYQQKPGQA PRLLIY (58) | GIPDRFSGSGSGTDFTLTI TRLEPEDFAVYYC (59) | FGQGTKVEIK (60) |
| AGEN1888 | EIVLTQSPATLSFSPG ERATLSC (66) | WYQQKPGQA PRLLIY (58) | GIPDRFSGSGSGTDFTFTIS RLEPEDFAVYYC (67) | FGPGTKVDIK (68) |
| AGEN1889 | EIVLTQSPATLSLSPG ERATLSC (61) | WYQHKVGQA PRLLIY (62) | GIPDRFSGSGSGTDFTLTI SRLEPEDFAVYYC (63) | FGQGTKVEIK (60) |
| AGEN1890 | EIVLTQSPATLSFSPG ERATLSC (66) | WYQQKPGQA PRLLIY (58) | GIPDRFSGSGSGTDFTFTIS RLEPEDFAVYYC (67) | FGPGTKVDIK (68) |
| AGEN1891 | EIVLTQSPATLSVSP GERATLSC (69) | WYQQKPGQA PRLLIY (58) | GIPDRFSGSASGTDFTLTI SRLEPEDFAVYYC (70) | FGQGTKVEIK (60) |
| AGEN1892 | EIVLTQSPATLSLSPG ERATLSC (61) | WYQQKPGQA PRLLIY (58) | GIPARFSGSGSGTDFTLTI SSLEPEDFAVYYC (71) | FGPGTKVDIK (68) |
| AGEN1893 | EIVLTQSPATLSLSPG ERATLSC (61) | WYQHKVGQA PRLLIY (62) | GIPDRFSGSGSGTDFTLTI SRLEPEDFAVYYC (63) | FGQGTKVEIK (60) |

TABLE 5-continued

VL framework (FR) sequences of exemplary anti-CTLA-4 antibodies[4]

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| AGEN1894 | EIVLTQSPGTLSLSPG ERATLSC (57) | WYQQKPGQA PRLLIY (58) | GIPDRFSGSGSGTDFTLTI TRLEPEDFAVYYC (59) | FGQGTKVEIK (60) |
| AGEN1895 | EIVLTQSPATLSLSPG ERATLSC (61) | WYQQKPGQA PSLLIY (64) | GIPDRFSGSVSGTDFTLTI SRLEPEDFAVYYC (63) | FGQGTKVEIK (60) |
| AGEN1896 | EIVLTQSPATLSFSPG ERATLSC (66) | WYQQKPGQA PRLLIY (58) | GIPDRFSGSGSGTDFTFTIS RLEPEDFAVYYC (67) | FGPGTKVDIK (68) |
| AGEN1897 | EIVLTQSPGTLSLSPG ERATLSC (57) | WYQQKPGQA PRLLIY (58) | GIPDRFSGSGSGTDFTLTI TRLEPEDFAVYYC (59) | FGQGTKVEIK (60) |
| AGEN1898 | EIVLTQSPATLSLSPG ERATLSC (61) | WYQQKPGQA PSLLIY (64) | GIPDRFSGSVSGTDFTLTI SRLEPEDFAVYYC (63) | FGQGTKVEIK (60) |
| AGEN1899 | EIVLTQSPATLSFSPG ERATLSC (66) | WYQQKPGQA PRLLIY (58) | GIPDRFSGSGSGTDFTFTIS RLEPEDFAVYYC (67) | FGPGTKVDIK (68) |
| AGEN1900 | EIVLTQSPATLSLSPG ERATLSC (61) | WYQQKPGQA PRLLIY (58) | GIPARFSGSGSGTDFTLTI SSLEPEDFAVYYC (71) | FGPGTKVDIK (68) |
| AGEN1901 | EIVLTQSPATLSLSPG ERATLSC (61) | WYQHKVGQA PRLLIY (62) | GIPDRFSGSGSGTDFTLTI SRLEPEDFAVYYC (63) | FGQGTKVEIK (60) |
| AGEN1902 | EIVLTQSPATLSFSPG ERATLSC (66) | WYQQKPGQA PRLLIY (58) | GIPDRFSGSGSGTDFTFTIS RLEPEDFAVYYC (67) | FGPGTKVDIK (68) |

[4]The VL framework regions described in Table 5 are determined based upon the boundaries of the Kabat numbering system for CDRs. In other words, the VL CDRs are determined by Kabat and the framework regions are the amino acid residues surrounding the CDRs in the variable region in the format FR1, CDRL1, FR2, CDRL2, FR3, CDRL3, and FR4.

TABLE 6

VH and VL sequences of exemplary anti-CTLA-4 antibodies

| Antibody | Heavy chain variable region | SEQ ID NO: | Light chain variable region | SEQ ID NO: |
|---|---|---|---|---|
| AGEN1884w | BADD411-2354 | 7 | BADD412-2376 | 8 |
| AGEN1885 | BADD411-2354 | 7 | BADD412-2382 | 44 |
| AGEN1886 | BADD411-2354 | 7 | BADD412-2384 | 45 |
| AGEN1887 | BADD412-2356 | 38 | BADD412-2376 | 8 |
| AGEN1888 | BADD412-2356 | 38 | BADD412-2384 | 45 |
| AGEN1889 | BADD412-2357 | 39 | BADD412-2367 | 43 |
| AGEN1890 | BADD412-2357 | 39 | BADD412-2384 | 45 |
| AGEN1891 | BADD412-2357 | 39 | BADD412-2390 | 46 |
| AGEN1892 | BADD412-2357 | 39 | BADD412-2393 | 47 |
| AGEN1893 | BADD412-2358 | 40 | BADD412-2367 | 43 |
| AGEN1894 | BADD412-2358 | 40 | BADD412-2376 | 8 |
| AGEN1895 | BADD412-2358 | 40 | BADD412-2382 | 44 |
| AGEN1896 | BADD412-2358 | 40 | BADD412-2384 | 45 |
| AGEN1897 | BADD412-2359 | 41 | BADD412-2376 | 8 |
| AGEN1898 | BADD412-2359 | 41 | BADD412-2382 | 44 |
| AGEN1899 | BADD412-2359 | 41 | BADD412-2384 | 45 |
| AGEN1900 | BADD412-2359 | 41 | BADD412-2393 | 47 |

TABLE 6-continued

| VH and VL sequences of exemplary anti-CTLA-4 antibodies | | | | |
|---|---|---|---|---|
| Antibody | Heavy chain variable region | SEQ ID NO: | Light chain variable region | SEQ ID NO: |
| AGEN1901 | BADD412-2360 | 42 | BADD412-2367 | 43 |
| AGEN1902 | BADD412-2360 | 42 | BADD412-2384 | 45 |

TABLE 7

| Exemplary sequences of CTLA-4 and family members | | |
|---|---|---|
| SEQ ID NO: | Description | Amino acid Sequence |
| 77 | Human CTLA-4 (P16410) | MACLGFQRHKAQLNLATRTWPCTLLFFLLFIPVFCKAMH VAQPAVVLASSRGIASFVCEYASPGKATEVRVTVLRQAD SQVTEVCAATYMMGNELTFLDDSICTGTSSGNQVNLTIQ GLRAMDTGLYICKVELMYPPPYYLGIGNGTQIYVIDPEPC PDSDFLLWILAAVSSGLFFYSFLLTAVSLSKMLKKRSPLTT GVYVKMPPTEPECEKQFQPYFIPIN |
| 78 | CTLA-4 epitope | QVT |
| 79 | CTLA-4 epitope | YPPPYYLGIGNGTQI |
| 80 | CTLA-4 epitope | YLGI |
| 81 | CTLA-4 epitope | MYPPPYY |
| 82 | CTLA-4 epitope | YPPPYYLGI |
| 83 | CTLA-4 epitope | YLGIGNGTQI |
| 84 | MACFA CTLA-4 (G7PL88) | MACLGFQRHKARLNLATRTRPYTLLFSLLFIPVFSKAMHV AQPAVVLANSRGIASFVCEYASPGKATEVRVTVLRQADS QVTEVCAATYMMGNELTFLDDSICTGTSSGNQVNLTIQG LRAMDTGLYICKVELMYPPPYYMGIGNGTQIYVIDPEPCP DSDFLLWILAAVSSGLFFYSFLLTAVSLSKMLKKRSPLTT GVYVKMPPTEPECEKQFQPYFIPIN |
| 85 | Mouse CTLA-4 (P09793) | MACLGLRRYKAQLQLPSRTWPFVALLTLLFIPVFSEAIQV TQPSVVLASSHGVASFPCEYSPSHNTDEVRVTVLRQTNDQ MTEVCATTFTEKNTVGFLDYPFCSGTFNESRVNLTIQGLR AVDTGLYLCKVELMYPPPYFVGMGNGTQIYVIDPEPCPD SDFLLWILVAVSLGLFFYSFLVSAVSLSKMLKKRSPLTTG VYVKMPPTEPECEKQFQPYFIPIN |
| 86 | Rat CTLA-4 (Q62859) | MACLGLQRYKTHLQLPSRTWPFGVLLSLLFIPIFSEAIQVT QPSVVLASSHGVASFPCEYASSHNTDEVRVTVLRQTNDQ VTEVCATTFTVKNTLGFLDDPFCSGTFNESRVNLTIQGLR AADTGLYFCKVELMYPPPYFVGMGNGTQIYVIDPEPCPDS DFLLWILAAVSSGLFFYSFLVTAVSLNRTLKKRSPLTTGV YVKMPPTEPECEKQFQPYFIPIN |
| 87 | Human CD28 (P10747) | MLRLLLALNLFPSIQVTGNKILVKQSPMLVAYDNAVNLS CKYSYNLFSREFRASLHKGLDSAVEVCVVYGNYSQQLQV YSKTGFNCDGKLGNESVTFYLQNLYVNQTDIYFCKIEVM YPPPYLDNEKSNGTIIHVKGKHLCPSPLFPGPSKPFWVLVV VGGVLACYSLLVTVAFBFWVRSKRSRLLHSDYMNMTPR RPGPTRKHYQPYAPPRDFAAYRS |
| 88 | Human ICOS (Q9Y6W8) | MKSGLWYFFLFCLRIKVLTGEINGSANYEMFIFHNGGVQI LCKYPDIVQQFKMQLLKGGQILCDLTKTKGSGNTVSIKSL KFCHSQLSNNSVSFFLYNLDHSHANYYFCNLSIFDPPPFKV TLTGGYLHIYESQLCCQLKFWLPIGCAAFVVVCILGCILIC WLTKKKYSSSVHDPNGEYMFMRAVNTAKKSRLTDVTL |
| 89 | Human BTLA (Q7Z6A9) | MKTLPAMLGTGKLFWVFFLIPYLDIWNIHGKESCDVQLYI KRQSEHSILAGDPFELECPVKYCANRPHVTWCKLNGTTC VKLEDRQTSWKEEKNISFFILHFEPVLPNDNGSYRCSANF QSNLIESHSTTLYVTDVKSASERPSKDEMASRPWLLYRLL PLGGLPLLITTCFCLFCCLRRHQGKQNELSDTAGREINLVD AHLKSEQTEASTRQNSQVLLSETGIYDNDPDLCFRMQEGS EVYSNPCLEENKPGIVYASLNHSVIGPNSRLARNVKEAPT EYASICVRS |

TABLE 7-continued

| Exemplary sequences of CTLA-4 and family members | | |
|---|---|---|
| SEQ ID NO: | Description | Amino acid Sequence |
| 90 | Human PD-1 (Q15116) | MQIPQAPWPVVWAVLQLGWRPGWELDSPDRPWNPPTFS PALLVVTEGDNATFTCSFSNTSESFVLNWYRMSPSNQTD KLAAFPEDRSQPGQDCRFRVTQLPNGRDFHMSVVRARRN DSGTYLCGAISLAPKAQIKESLRAELRVTERRAEVPTAHPS PSPRPAGQFQTLVVGVVGGLLGSLVLLVWVLAVICSRAA RGTIGARRTGQPLKEDPSAVPVFSVDYGELDFQWREKTPE PPVPCVPEQTEYATIVFPSGMGTSSPARRGSADGPRSAQPL RPEDGHCSWPL |

In certain embodiments, the instant disclosure provides an isolated antibody that specifically binds to human CTLA-4 protein, comprising:

(a) a CDRH1 comprising the amino acid sequence of $SYX_1MX_2$ (SEQ ID NO: 22), wherein $X_1$ is S or A; and $X_2$ is N or S; and/or
(b) a CDRH2 comprising the amino acid sequence of SISSSSSYIYYADSVKG (SEQ ID NO: 2); and/or
(c) a CDRH3 comprising the amino acid sequence of VGLMGPFXI (SEQ ID NO: 23), wherein X is D or N; and/or
(d) a CDRL1 comprising the amino acid sequence of $RASQSVX_1X_2YLX_3$ (SEQ ID NO: 24), wherein $X_1$ is S or G; $X_2$ is R, S, or T; and $X_3$ is G or A; and/or
(e) a CDRL2 comprising the amino acid sequence of $X_1X_2SX_3RAT$ (SEQ ID NO: 25), wherein: $X_1$ is G or A; $X_2$ is A or T; and $X_3$ is T, S, R or N; and/or
(f) a CDRL3 comprising the amino acid sequence of $QQYGX_1SPX_2T$ (SEQ ID NO: 26), wherein: $X_1$ is S or T; and $X_2$ is W or F.

In certain embodiments, the antibody comprises one, two, or all three of the VH CDRs above. In certain embodiments, the antibody comprises the CDRH1 of one of the antibodies in Table 2. In certain embodiments, the antibody comprises the CDRH2 of one of the antibodies in Table 2. In certain embodiments, the antibody comprises the CDRH3 of one of the antibodies in Table 2. In certain embodiments, the antibody comprises one, two, or all three of VH CDRs of one of the antibodies in Table 2 (e.g., the VH CDRs in one row of Table 2, for example, all of the VH CDRs are from the antibody AGEN1884w). In certain embodiments, the antibody comprises the VH frameworks described herein. In certain embodiments, the antibody comprises the VH framework regions of an antibody set forth in Table 4 (e.g., one, two, three, or four of the framework regions in one row of Table 4).

In certain embodiments, the antibody comprises one, two, or all three of the VL CDRs above. In certain embodiments, the antibody comprises the CDRL1 of one of the antibodies in Table 3. In certain embodiments, the antibody comprises the CDRL2 of one of the antibodies in Table 3. In certain embodiments, the antibody comprises the CDRL3 of one of the antibodies in Table 3. In certain embodiments, the antibody comprises one, two, or all three of the VL CDRs of one of the antibodies in Table 3 (e.g., the VL CDRs in one row of Table 3, for example, all of the VL CDRs are from antibody AGEN1884w). In certain embodiments, the antibody comprises the VL framework regions described herein. In certain embodiments, the antibody comprises the VL framework regions (FRs) of an antibody set forth in Table 5 (e.g., one, two, three, or four of the framework regions in one row of Table 5).

In certain embodiments, the instant disclosure provides an isolated antibody that specifically binds to human CTLA-4 protein, comprising a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of $SYX_1MX_2$ (SEQ ID NO: 22), wherein $X_1$ is S or A; and $X_2$ is N or S;
(b) CDRH2 comprises the amino acid sequence of SISSSSSYIYYADSVKG (SEQ ID NO: 2);
(c) CDRH3 comprises the amino acid sequence of VGLMGPFXI (SEQ ID NO: 23), wherein X is D or N;
(d) CDRL1 comprises the amino acid sequence of $RASQSVX_1X_2YLX_3$ (SEQ ID NO: 24), wherein $X_1$ is S or G; $X_2$ is R, S, or T; and $X_3$ is G or A;
(e) CDRL2 comprises the amino acid sequence of $X_1X_2SX_3RAT$ (SEQ ID NO: 25), wherein $X_1$ is G or A; $X_2$ is A or T; and $X_3$ is T, S, R, or N; and
(f) CDRL3 comprises the amino acid sequence of $QQYGX_1SPX_2T$ (SEQ ID NO: 26), wherein $X_1$ is S or T; and $X_2$ is W or F.

In certain embodiments, the CDRH1 comprises an amino acid sequence selected from the group consisting of SEQ ID NOs: 1 and 27. In certain embodiments, the CDRH3 comprises an amino acid sequence selected from the group consisting of SEQ ID NOs: 3 and 28. In certain embodiments, CDRL1 comprises an amino acid sequence selected from the group consisting of SEQ ID NOs: 4, 29, and 30. In certain embodiments, CDRL2 comprises an amino acid sequence selected from the group consisting of SEQ ID NOs: 5 and 31-35. In certain embodiments, CDRL3 comprises an amino acid sequence selected from the group consisting of SEQ ID NOs: 6, 36, and 37. In certain embodiments, CDRH1, CDRH2, and CDRH3 comprise the CDRH1, CDRH2, and CDRH3 amino acid sequences, respectively, of an antibody in Table 2. In certain embodiments, CDRL1, CDRL2, and CDRL3 comprise the CDRL1, CDRL2, and CDRL3 amino acid sequences, respectively, of an antibody in Table 3.

In certain embodiments, the instant disclosure provides an isolated antibody that specifically binds to human CTLA-4 protein, comprising a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences, respectively, set forth in SEQ ID NOs: 1, 2, and 3; 27, 2, and 3; or, 27, 2, and 28.

In certain embodiments, the instant disclosure provides an isolated antibody that specifically binds to human CTLA-4 protein, comprising a light chain variable region comprising complementarity determining regions CDRL1, CDRL2 and CDRL3, wherein the CDRL1, CDRL2 and CDRL3 comprise the CDRL1, CDRL2 and CDRL3 amino acid sequences, respectively, set forth in SEQ ID NOs: 4, 5, and 6; 29, 32, and 36; 29, 33, and 37; 30, 31, and 6; 29, 34, and 6; or, 29, 35, and 37.

In certain embodiments, the instant disclosure provides an isolated antibody that specifically binds to human CTLA-4 protein, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2 and CDRL3 comprise the CDRH1, CDRH2, CDRH3, CDRL1, CDRL2 and CDRL3 amino acid sequences, respectively, set forth in SEQ ID NOs: 1, 2, 3, 4, 5, and 6; 1, 2, 3, 29, 32, and 36; 1, 2, 3, 29, 33, and 37; 27, 2, 3, 4, 5, and 6; 27, 2, 3, 29, 33, and 37; 1, 2, 3, 30, 31, and 6; 1, 2, 3, 29, 34, and 6; 1, 2, 3, 29, 35, and 37; 27, 2, 28, 4, 5, and 6; 27, 2, 28, 29, 32, and 36; 27, 2, 28, 29, 33, and 37; or, 27, 2, 28, 29, 35, and 37, respectively.

In certain embodiments, the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to human CTLA-4 protein, the antibody comprising the *Chothia* VL CDRs of a VL of an antibody disclosed in Table 6 herein (e.g., AGEN1884w or AGEN2041w). In certain embodiments, the instant disclosure provides an isolated antibody that specifically binds to human CTLA-4 protein, the antibody comprising the Chothia VH CDRs of an antibody disclosed in Table 6 herein (e.g., AGEN1884w or AGEN2041w). In certain embodiments, the instant disclosure provides an isolated antibody that specifically binds to human CTLA-4 protein, the antibody comprising the Chothia VH CDRs and Chothia VL CDRs of an antibody disclosed in Table 6 herein (e.g., AGEN1884w or AGEN2041w). In certain embodiments, antibodies that specifically bind to human CTLA-4 protein comprise one or more CDRs, in which the Chothia and Kabat CDRs have the same amino acid sequence. In certain embodiments, the instant disclosure provides an isolated antibody that specifically binds to human CTLA-4 protein and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97. In a particular embodiment, the instant disclosure provides antibodies that specifically bind to human CTLA-4 protein and comprise CDRs of an antibody disclosed in Table 6 herein (e.g., AGEN1884w or AGEN2041w) as determined by the IMGT numbering system, for example, as described in Lefranc M-P (1999) supra and Lefranc M-P et al., (1999) supra.

In certain embodiments, the CDRs of an antibody can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular embodiment, the instant disclosure provides antibodies that specifically bind to human CTLA-4 protein and comprise CDRs of an antibody disclosed in Table 6 herein (e.g., AGEN1884w or AGEN2041w) as determined by the method in MacCallum R M et al.

In certain embodiments, the CDRs of an antibody can be determined according to the AbM numbering scheme, which refers AbM hypervariable regions, which represent a compromise between the Kabat CDRs and Chothia structural loops, and are used by Oxford Molecular's AbM antibody modeling software (Oxford Molecular Group, Inc.). In a particular embodiment, the instant disclosure provides antibodies that specifically bind to human CTLA-4 protein and comprise CDRs of an antibody disclosed in Table 6 herein (e.g., AGEN1884w or AGEN2041w) as determined by the AbM numbering scheme.

Accordingly, in certain embodiments, the instant disclosure provides an isolated antibody that specifically binds to human CTLA-4 protein, wherein the antibody comprises a heavy chain variable region comprising the CDRH1, CDRH2, and CDRH3 region amino acid sequences set forth in SEQ ID NO: 7, and the CDRL1, CDRL2, and CDRL3 region amino acid sequences set forth in SEQ ID NO: 8, wherein each CDR is defined in accordance with the Kabat definition, the Chothia definition, the combination of the Kabat definition and the Chothia definition, the IMGT numbering system, the AbM definition, or the contact definition of CDR.

In certain embodiments, the instant disclosure provides an isolated antibody that specifically binds to human CTLA-4 protein, the antibody comprising a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 16, 17, 18, 19, 20, and 21, respectively.

In certain embodiments, the instant disclosure provides an isolated antibody that specifically binds to human CTLA-4 protein, comprising a heavy chain variable region comprising the amino acid sequence of SEQ ID NO: 72.

In certain embodiments, the instant disclosure provides an isolated antibody that specifically binds to human CTLA-4 protein, comprising a heavy chain variable region having an amino acid sequence derived from a human IGHV3-21 germline sequence. One or more regions selected from framework 1, framework 2, framework 3, CDRH1, and CDRH2 (e.g., two, three, four or five of these regions) can be derived from a human IGHV3-21 germline sequence. In one embodiment, framework 1, framework 2, framework 3, CDRH1, and CDRH2 are all derived from a human IGHV3-21 germline sequence.

In certain embodiments, the instant disclosure provides an isolated antibody that specifically binds to human CTLA-4 protein, comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 7 and 38-42. In certain embodiments, the antibody comprises a heavy chain variable region having an amino acid sequence selected from the group consisting of SEQ ID NO: 7 and 38-42. In certain embodiments, the antibody comprises a heavy chain variable region having the amino acid sequence set forth in SEQ ID NO: 7. In certain embodiments, the antibody comprises a heavy chain having the amino acid sequence set forth in SEQ ID NO: 12. In certain embodiments, the antibody comprises a heavy chain having the amino acid sequence set forth in SEQ ID NO: 93. In certain embodiments, the antibody comprises a heavy chain having the amino acid sequence set forth in SEQ ID NO: 14. In certain embodiments, the antibody comprises a heavy chain having the amino acid sequence set forth in SEQ ID NO: 94. In certain embodiments, the antibody comprises a heavy chain having the amino acid sequence set forth in SEQ ID NO: 76. In certain embodiments, the antibody comprises a heavy chain having the amino acid sequence set forth in SEQ ID NO: 97.

In certain embodiments, the instant disclosure provides an isolated antibody that specifically binds to human CTLA-4 protein, comprising a light chain variable region comprising the amino acid sequence of SEQ ID NO: 73.

In certain embodiments, the instant disclosure provides an isolated antibody that specifically binds to human CTLA-4 protein, comprising a light chain variable region having an amino acid sequence derived from a human IGKV3-20 or IGKV3-11 germline sequence. One or more regions selected from framework 1, framework 2, framework 3, CDRL1, and CDRL2 (e.g., two, three, four or five of these regions) can be derived from a human IGKV3-20 or IGKV3-11 germline sequence. In one embodiment, framework 1, framework 2, framework 3, CDRL1, and CDRL2 are all derived from a human IGKV3-20 or IGKV3-11 germline sequence.

In certain embodiments, the instant disclosure provides an isolated antibody that specifically binds to human CTLA-4 protein, comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 8 and 43-47. In certain embodiments, the antibody comprises a light chain variable region having an amino acid sequence selected from the group consisting of SEQ ID NO: 8 and 43-47. In certain embodiments, the antibody comprises a light chain variable region having the amino acid sequence set forth in SEQ ID NO: 8. In certain embodiments, the antibody comprises a light chain having the amino acid sequence set forth in SEQ ID NO: 13. In certain embodiments, the antibody comprises a light chain having the amino acid sequence set forth in SEQ ID NO: 15.

In certain embodiments, the instant disclosure provides an isolated antibody that specifically binds to human CTLA-4 protein, comprising a heavy chain variable region having an amino acid sequence derived from a human IGHV3-21 germline sequence, and a light chain variable region having an amino acid sequence derived from a human IGKV3-20 or IGKV3-11 germline sequence. One or more regions selected from framework 1, framework 2, framework 3, CDRH1, and CDRH2 (e.g., two, three, four or five of these regions) can be derived from human IGHV3-21 germline sequence. In one embodiment, framework 1, framework 2, framework 3, CDRH1, and CDRH2 are all derived from human IGHV3-21 germline sequence. One or more regions selected from framework 1, framework 2, framework 3, CDRL1, and CDRL2 (e.g., two, three, four or five of these regions) can be derived from a human IGKV3-20 or IGKV3-11 germline sequence. In one embodiment, framework 1, framework 2, framework 3, CDRL1, and CDRL2 are all derived from a human IGKV3-20 or IGKV3-11 germline sequence.

In certain embodiments, the instant disclosure provides an isolated antibody that specifically binds to human CTLA-4 protein, comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NO: 7 and 38-42, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 8 and 43-47. In certain embodiments, the antibody comprises a heavy chain variable region having an amino acid sequence selected from the group consisting of SEQ ID NO: 7 and 38-42, and a light chain variable region having an amino acid sequence selected from the group consisting of SEQ ID NO: 8 and 43-47. In certain embodiments, the antibody comprises the heavy chain variable region and light chain variable region amino acid sequences set forth in SEQ ID NOs: 7 and 8; 7 and 44; 7 and 45; 38 and 8; 38 and 45; 39 and 43; 39 and 45; 39 and 46; 39 and 47; 40 and 43; 40 and 8; 40 and 44; 40 and 45; 41 and 8; 41 and 44; 41 and 45; 41 and 47; 42 and 43; or, 42 and 45, respectively. In certain embodiments, the antibody comprises a heavy chain variable region comprising the amino acid sequence of SEQ ID NO: 7; and a light chain variable region comprising the amino acid sequence of SEQ ID NO: 8. In certain embodiments, the antibody comprises a heavy chain comprising the amino acid sequence of SEQ ID NO: 12; and a light chain comprising the amino acid sequence of SEQ ID NO: 13. In certain embodiments, the antibody comprises a heavy chain comprising the amino acid sequence of SEQ ID NO: 93; and a light chain comprising the amino acid sequence of SEQ ID NO: 13. In certain embodiments, the antibody comprises a heavy chain comprising the amino acid sequence of SEQ ID NO: 14; and a light chain comprising the amino acid sequence of SEQ ID NO: 13. In certain embodiments, the antibody comprises a heavy chain comprising the amino acid sequence of SEQ ID NO: 94; and a light chain comprising the amino acid sequence of SEQ ID NO: 13. In certain embodiments, the antibody comprises a heavy chain comprising the amino acid sequence of SEQ ID NO: 76; and a light chain comprising the amino acid sequence of SEQ ID NO: 13. In certain embodiments, the antibody comprises a heavy chain comprising the amino acid sequence of SEQ ID NO: 97; and a light chain comprising the amino acid sequence of SEQ ID NO: 13.

In certain embodiments, the instant disclosure provides an isolated antibody that cross-competes for binding to human CTLA-4 protein with an antibody comprising the heavy and light chain variable region amino acid sequences set forth in SEQ ID NOs: 7 and 8, respectively.

In certain embodiments, the instant disclosure provides an isolated antibody that binds to the same epitope on human CTLA-4 protein as an antibody comprising the heavy and light chain variable region amino acid sequences set forth in SEQ ID NOs: 7 and 8, respectively.

Any Ig constant region can be used in the antibodies disclosed herein. In certain embodiments, the Ig region is a human $IgG_1$ or human $IgG_2$ heavy chain constant region.

In certain embodiments, the IgG regions of the antibodies described herein have an increased affinity for CD32B (also known as FcγRIIB or FCGR2B), e.g., as compared with an antibody with a wild-type Fc region, e.g., an $IgG_1$ Fc. In certain embodiments, antibodies described herein have a selectively increased affinity for CD32B (FcγRIIB) over both CD32A (FcγRIIA) and CD16 (FcγRIIIA) Sequence alterations that result in increased affinity for CD32B are known in the art, for example, in Mimoto et al., *Protein Engineering, Design & Selection* 10: 589-598 (2013), Chu et al., *Molecular Immunology* 45: 3926-3933 (2008), and Strohl, *Current Opinion in Biology* 20: 685-691 (2009), each of which is herein incorporated by reference in its entirety. In certain embodiments, the antibody comprises a heavy chain constant region, e.g., an $IgG_1$ constant region, or fragment thereof comprising a mutation selected from the group consisting of: G236D, P238D, S239D, S267E, L328F, and L328E, and combinations thereof, numbered according to EU index (Kabat et al., *Sequences of Proteins of Immunological Interest*, U.S. Department of Health and Human Services, Bethesda (1991)). In certain embodiments, the antibody comprises a heavy chain constant region, e.g., an IgG1 constant region, or fragment thereof comprising S267E and L328F substitutions. In certain embodiments, the antibody comprises a heavy chain constant region, e.g., an $IgG_1$ constant region, or fragment thereof comprising P238D and L328E substitutions. In certain embodiments, the antibody comprises a heavy chain constant region, e.g., an $IgG_1$ constant region, or fragment thereof comprising a P238D substitution and substitution selected from the group consisting of E233D, G237D, H268D, P271G, A330R, and combinations thereof. In certain embodiments, the antibody comprises a heavy chain constant region, e.g., an $IgG_1$ constant region, or fragment thereof comprising P238D, E233D, G237D, H268D, P271G, and A330R substitutions. In certain embodiments, the antibody comprises a heavy chain constant region, e.g., an $IgG_1$ constant region, or fragment thereof comprising G236D and S267E. In certain embodiments, the antibody comprises a heavy chain constant region, e.g., an $IgG_1$ constant region, or fragment thereof comprising S239D and S267E. In certain embodiments, the antibody comprises a heavy chain constant region, e.g., an $IgG_1$ constant region, or fragment thereof comprising V262E, S267E, and L328F. In certain embodiments, the antibody comprises a heavy chain constant region, e.g., an $IgG_1$ constant region, or fragment thereof comprising V264E, S267E, and L328F.

In certain embodiments, the IgG regions of the antibodies described herein have an increased affinity for FcγRIIIA, e.g., as compared with an antibody with a wild-type Fc region, e.g., an $IgG_1$ Fc. Sequence alterations that result in increased affinity for FcγRIIIA are known in the art, for example, in Kellner et al., *Methods* 65: 105-113 (2014), Lazar et al., *Proc Natl Acad Sci* 103: 4005-4010 (2006), Shields et al., *J Biol Chem.* 276(9):6591-6604 (2001), each of which is herein incorporated by reference in its entirety. In certain embodiments, the antibody comprises a heavy chain constant region, e.g., an $IgG_1$ constant region, or fragment thereof comprising a mutation selected from the group consisting of: G236A, S239D, F243L, T256A, K290A, R292P, S298A, Y300L, V305I, A330L, I332E, E333A, K334A, A339T, and P396L, and combinations thereof, numbered according to EU index (Kabat et al., *Sequences of Proteins of Immunological Interest*, U.S. Department of Health and Human Services, Bethesda (1991)). In certain embodiments, the antibody comprises a heavy chain constant region, e.g., an IgG1 constant region, or fragment thereof comprising S239D. In certain embodiments, the antibody comprises a heavy chain constant region, e.g., an IgG1 constant region, or fragment thereof comprising T256A. In certain embodiments, the antibody comprises a heavy chain constant region, e.g., an IgG1 constant region, or fragment thereof comprising K290A. In certain embodiments, the antibody comprises a heavy chain constant region, e.g., an IgG1 constant region, or fragment thereof comprising S298A. In certain embodiments, the antibody comprises a heavy chain constant region, e.g., an IgG1 constant region, or fragment thereof comprising I332E. In certain embodiments, the antibody comprises a heavy chain constant region, e.g., an IgG1 constant region, or fragment thereof comprising E333A. In certain embodiments, the antibody comprises a heavy chain constant region, e.g., an IgG1 constant region, or fragment thereof comprising K334A. In certain embodiments, the antibody comprises a heavy chain constant region, e.g., an IgG1 constant region, or fragment thereof comprising A339T. In certain embodiments, the antibody comprises a heavy chain constant region, e.g., an IgG1 constant region, or fragment thereof comprising S239D and I332E. In certain embodiments, the antibody comprises a heavy chain constant region, e.g., an IgG1 constant region, or fragment thereof comprising S239D, A330L, and I332E. In certain embodiments, the antibody comprises a heavy chain constant region, e.g., an IgG1 constant region, or fragment thereof comprising S298A, E333A, and K334A. In certain embodiments, the antibody comprises a heavy chain constant region, e.g., an IgG1 constant region, or fragment thereof comprising G236A, S239D, and I332E. In certain embodiments, the antibody comprises a heavy chain constant region, e.g., an IgG1 constant region, or fragment thereof comprising F243L, R292P, Y300L, V305I, and P396L.

In certain embodiments, the antibodies described herein exhibit antibody-dependent cellular cytotoxicity (ADCC) activity. In certain embodiments, the antibodies described herein initiate natural killer cell mediated cell depletion. In certain embodiments, the antibodies described herein are used for treating tumor infiltrated with natural killer cells. In certain embodiments, the antibodies described herein exhibit antibody-dependent cellular phagocytosis (ADCP) activity. In certain embodiments, the antibodies described herein initiate macrophage mediated cell depletion. In certain embodiments, the antibodies described herein are used for treating tumor infiltrated with macrophages. In certain embodiments, the antibodies described herein selectively deplete intratumoral regulatory T cells.

In certain embodiments, an antibody disclosed herein is an activatable antibody that in an activated state binds human CTLA-4 protein. In certain embodiments, the activatable antibody comprises a masking moiety that inhibits the binding of the antibody in an uncleaved state to human CTLA-4 protein, and at least one cleavable moiety coupled to the antibody, e.g., wherein the cleavable moiety is a polypeptide that functions as a substrate for a protease that is enriched in the tumor microenvironment. Exemplary activatable antibodies are described, e.g., in U.S. Pat. Nos. 8,513,390 and 8,518,404, and U.S. Patent Application Publication Nos. US 2014/0255313, US 2014/0010810, US 2014/0023664, which are incorporated herein by reference. In certain embodiments, the activatable antibody comprises a human IgG heavy chain constant region that is a variant of a wild type human IgG heavy chain constant region, wherein the variant human IgG heavy chain constant region binds to human FcγRIIIA with higher affinity than the wild type human IgG heavy chain constant region binds to human FcγRIIIA.

5.3 Pharmaceutical Compositions

Provided herein are compositions comprising an anti-CTLA-4 antibody described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-CTLA-4 antibody described herein, and optionally one or more additional prophylactic or therapeutic agents, in a pharmaceutically acceptable carrier. In a specific embodiment, pharmaceutical compositions comprise an effective amount of an antibody or antigen-binding fragment thereof described herein, and optionally one or more additional prophylactic or therapeutic agents, in a pharmaceutically acceptable carrier. In some embodiments, the antibody is the only active ingredient included in the pharmaceutical composition. Pharmaceutical compositions described herein can be useful in inhibiting, CTLA-4 activity and treating a condition, such as cancer or an infectious disease.

In one aspect, provided herein is a pharmaceutical composition comprising an anti-CTLA-4 antibody of the invention and a pharmaceutically acceptable carrier or excipient, for use as a medicament.

In one aspect, provided herein is a pharmaceutical composition comprising an anti-CTLA-4 antibody of the invention and a pharmaceutically acceptable carrier or excipient, for use in a method for the treatment of cancer.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-CTLA-4 antibody described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-CTLA-4 antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody or antigen-binding fragment thereof described herein is a lyophilized powder, which can be reconstituted for administration as solutions, emulsions and other mixtures. It may also be reconstituted and formulated as solids or gels. The lyophilized powder is prepared by dissolving an antibody or antigen-binding fragment thereof described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-CTLA-4 antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In a specific embodiment, an antibody or antigen-binding fragment thereof described herein is targeted to a tumor.

The compositions to be used for in vivo administration can be sterile. This is readily accomplished by filtration through, e.g., sterile filtration membranes.

5.4 Methods of Use

In another aspect, the instant disclosure provides a method of treating a subject using the anti-CTLA-4 antibodies disclosed herein. Any disease or disorder in a subject that would benefit from inhibition of CTLA-4 function can be treated using the anti-CTLA-4 antibodies disclosed herein. The anti-CTLA-4 antibodies disclosed herein are particularly useful for inhibiting immune system tolerance to tumors, and accordingly can be used as an immunotherapy for subjects with cancer. For example, in certain embodiments, the instant disclosure provides a method of increasing T-cell activation in response to an antigen in a subject, the method comprising administering to the subject an effective amount of an anti-CTLA-4 antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein. In certain embodiments, the subject has previously received an immunotherapy. In certain embodiments, the subject has not previously received any immunotherapy. In certain embodiments, the cancer is an advanced or metastatic cancer. Cancers that can be treated with the anti-CTLA-4 antibodies or pharmaceutical compositions disclosed herein include, without limitation, solid cancer (e.g., relapsed or refractory solid cancer, and advanced or metastatic solid cancer), carcinoma, sarcoma, melanoma (e.g., stage III or stage IV melanoma), small cell lung cancer, non-small cell lung cancer, urothelial cancer, ovarian cancer, prostate cancer (e.g., metastatic hormone-refractory prostate cancer and progressive metastatic prostate cancer), pancreatic cancer, breast cancer (e.g., $HER2^+$ breast cancer (e.g., relapsed/refractory $HER2^+$ breast cancer)), head and neck cancer (e.g., relapsed/refractory head and neck squamous cell carcinoma (HNSCC)), glioma, malignant glioma, glioblastoma multiforme, brain metastasis, merkel cancer, gastric cancer, gastroesophageal cancer, renal cell carcinoma, uveal melanoma, colon cancer, cervical cancer, lymphoma (e.g., relapsed or refractory lymphoma), non-Hodgkin's lymphoma, Hodgkin's lymphoma, leukemia, and multiple myeloma. In certain embodiments, the cancer is treated with intratumoral administration of the anti-CTLA-4 antibodies or pharmaceutical compositions disclosed herein. Cancers that can be treated with intratumoral administration of the anti-CTLA-4 antibodies or pharmaceutical compositions disclosed herein include, without limitation, solid tumors (e.g., advanced or metastatic solid tumors), head and neck cancer (e.g., relapsed/refractory head and neck squamous cell carcinoma (HNSCC)), and breast cancer (e.g., $HER1^+$ breast cancer (e.g., relapsed/refractory $HER2^+$ breast cancer)).

Additional cancers that can be treated with the anti-CTLA-4 antibodies or pharmaceutical compositions disclosed herein include, without limitation, B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In some embodiments, the cancer treated in accordance with the methods described herein is a human sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (e.g., metastatic), hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma. In certain embodiments, the cancer treated in accordance with the methods described herein is an acute lymphocytic leukemia or acute myelocytic leukemia (e.g., myeloblastic, promyelocytic, myelomonocytic, monocytic and erythroleukemia); chronic leukemia (chronic myelocytic (granulocytic) leukemia or chronic lymphocytic leukemia); Hodgkin's disease; non-Hodgkin's disease; acute myeloid leukemia; B-cell lymphoma; T-cell lymphoma; anaplastic large cell lymphoma; intraocular lymphoma; follicular lymphoma; small intestine lymphoma; or orsplenic marginal zone lymphoma. In certain embodiments, the cancer treated in accordance with the methods described herein is multiple myeloma, Waldenstrom's macroglobulinemia, heavy chain disease, gastrointestinal stromal tumors, head and/or neck cancer (e.g., squamous cell carcinoma of the hypopharynx, squamous cell carcinoma of the larynx, cell carcinoma of the oropharynx, or verrucous carcinoma of the larynx), endometrial stromal sarcoma, mast cell sarcoma, adult soft tissue sarcoma, uterine sarcoma, merkel cell carcinoma, urothelial carcinoma, melanoma with brain metastases, uveal melanoma, uveal melanoma with liver metastases, non-small cell lung cancer, rectal cancer, or myelodysplastic syndrome. In some embodiments, the cancer treated in accordance with the methods is metastatic.

In certain embodiments, the cancer treated in accordance with the methods described herein includes prostate cancer, breast cancer, lung cancer, colorectal cancer, melanoma, bronchial cancer, bladder cancer, brain or central nervous system cancer, peripheral nervous system cancer, uterine or endometrial cancer, cancer of the oral cavity or pharynx, non-Hodgkin's lymphoma, thyroid cancer, kidney cancer, biliary tract cancer, small bowel or appendix cancer, salivary gland cancer, thyroid gland cancer, adrenal gland cancer, squamous cell cancer, mesothelioma, osteocarcinoma, thyoma/thymic carcinoma, glioblastoma, myelodysplastic syndrome, soft tissue sarcoma, DIPG, adenocarcinoma, osteosarcoma, chondrosarcoma, leukemia, or pancreatic cancer. In some embodiments, the cancer treated in accordance with the methods described herein includes a carcinoma (e.g., an adenocarcinoma), lymphoma, blastoma, melanoma, sarcoma, or leukemia. In certain embodiments, the cancer treated in accordance with the methods described herein includes squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer (e.g., hepatic carcinoma and hepatoma), bladder cancer, breast cancer, inflammatory breast cancer, Merkel cell carcinoma, colon cancer, colorectal cancer, stomach cancer, urinary bladder cancer, endometrial carcinoma, myeloma (e.g., multiple myeloma), salivary gland, carcinoma, kidney cancer (e.g., renal cell carcinoma and Wilms' tumors), basal cell carcinoma, melanoma, prostate cancer, vulval cancer, thyroid cancer, testicular cancer, esophageal cancer, serous adenocarcinoma or various types of head and neck cancer. In certain embodiments, the cancer treated in accordance with the methods described herein includes desmoplastic melanoma, inflammatory breast cancer, thymoma, rectal cancer, anal cancer, or surgically treatable or non-surgically treatable brain stem glioma. In a specific embodiment, the cancer is a solid tumor. In another specific embodiment, the cancer is glioblastoma multiforme. In some embodiments, the glioblastoma multiforme is recurrent. In some embodiments, the glioblastoma multiforme is newly diagnosed. In some embodiments, the glioblastoma multiforme is in a subject having non-methylated MGMT promoters. In some embodiments, the glioblastoma multiforme is refractory to Bevacizumab therapy. In some embodiments, the glioblastoma multiforme is in a subject that has not received Bevacizumab therapy.

In some embodiments, the cancer treated in accordance with the methods described herein is metastatic melanoma (e.g., resistant metastatic melanoma), metastatic ovarian cancer, or metastatic renal cell carcinoma. In certain embodiments, the cancer treated in accordance with the methods described herein is melanoma that is resistant to Ipilimumab. In some embodiments, the cancer treated in accordance with the methods described herein is melanoma that is resistant to Nivolumab or Pembrolizumab. In some embodiments, the cancer treated in accordance with the methods described herein is melanoma that is resistant to Ipilimumab and Nivolumab or Pembrolizumab.

In certain embodiments, the instant disclosure provides a method of preventing or treating an infectious disease in a subject, the method comprising administering to the subject an effective amount of an anti-CTLA-4 antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-CTLA-4 antibody described herein or a composition thereof is the only active agent administered to a subject. In some embodiments, an anti-CTLA-4 antibody described herein or a composition thereof is used in combination with anti-infective interventions (e.g., antivirals, antibacterials, antifungals, or anti-helminthics) for the treatment of infectious diseases.

Infectious diseases that can be treated and/or prevented by anti-CTLA-4 antibodies or pharmaceutical compositions disclosed herein are caused by infectious agents including but not limited to bacteria, parasites, fungi, protozae, and viruses. In a specific embodiment, the infectious disease treated and/or prevented by anti-CTLA-4 antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, *Mycobacteria rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertissus, cholera, plague, diptheria, chlamydia, *S. aureus* and *legionella.*

Protozoal diseases or protozoal infections caused by protozoa that can be prevented and/or treated in accordance with the methods described herein include, but are not limited to, leishmania, coccidiosis, trypanosoma schistosoma or malaria. Parasitic diseases or parasitic infections caused by parasites that can be prevented and/or treated in accordance with the methods described herein include, but are not limited to, chlamydia and rickettsia.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, the infectious disease is acute. In certain embodiments, the infectious disease is chronic. In certain embodiments, the infectious disease is caused by flavivirus, e.g., West Nile virus, Saint Louis encephalitis virus, Powassan virus, tick-borne encephalitis virus, dengue virus, zika virus, Kyasanur Forest disease virus, yellow fever virus, and chikungunya virus. In certain embodiments, the infectious disease is caused by Ebola virus. In certain embodiments, the infectious disease is caused by influenza virus. In certain embodiments, the infectious disease is caused by Human Immunodeficiency Virus (HIV), Hepatitis B virus (HBV) or Hepatitis C virus (HCV). In certain embodiments, the anti-CTLA-4 antibody or pharmaceutical composition thereof, as disclosed herein, promotes viral control. In certain embodiments, the anti-CTLA-4 antibody or pharmaceutical composition thereof, as disclosed herein, eliminates viral reservoirs.

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use as a medicament.

The present invention relates, in one aspect, to an anti-CTLA-4 antibody of the invention, and/or its use in combination with pharmaceutically acceptable carriers or excipients, for preparing pharmaceutical compositions or medicaments for immunotherapy (e.g., an immunotherapy for increasing T-cell activation in response to an antigen in a subject, treating cancer, or treating or preventing infectious diseases).

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use in a method for the treatment of cancer.

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use in a method for inhibiting immune system tolerance to tumors and/or for immunotherapy for subjects with cancer.

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use in a method for the treatment of an infectious disease.

In certain embodiments, these methods further comprise administering an additional therapeutic agent to the subject. In certain embodiments, the additional therapeutic agent is a chemotherapeutic or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-OX40 antibody, an agonist anti-CD137 antibody, an agonist anti-DR3 antibody, an agonist anti-TNFSF14 antibody, and an agonist anti-CD27 antibody. In certain embodiments, the checkpoint targeting agent is an antagonist anti-PD-1 antibody. In certain embodiments, the checkpoint targeting agent is an antagonist anti-PD-L1 antibody. In certain embodiments, the checkpoint targeting agent is an antagonist anti-LAG-3 antibody. In certain embodiments, the additional therapeutic agent is an agonist to a tumor necrosis factor receptor superfamily member or a tumor necrosis factor superfamily member.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) an additional therapeutic agent, for use as a medicament. In a preferred embodiment, the additional therapeutic agent is a chemotherapeutic or a checkpoint targeting agent.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) an additional therapeutic agent, for use in a method for the treatment of cancer.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) an additional therapeutic agent, for use in a method for the treatment of an infectious disease.

In certain embodiments, an anti-CTLA-4 antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., WO 2010/005958 which is incorporated by reference herein in its entirety), F001287 (Flexus Biosciences), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a compound that targets an immunomodulatory enzyme, for use as a medicament. In a preferred embodiment, the compound targets IDO and/or TDO.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a compound that targets an immunomodulatory enzyme, for use in a method for the treatment of cancer. In a preferred embodiment, the compound targets IDO and/or TDO.

In certain embodiments, an anti-CTLA-4 antibody disclosed herein is administered to a subject in combination with a vaccine. In certain embodiments, the vaccine is a heat shock protein based tumor vaccine or a heat shock protein based pathogen vaccine. In a specific embodiment, an anti-CTLA-4 antibody disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, an anti-CTLA-4 antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference herein in their entireties, U.S. Pat. Nos. 6,391,306, 6,383,492, 6,403,095, 6,410,026, 6,436,404, 6,447,780, 6,447,781 and 6,610,659.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a vaccine, for use as a medicament. In a preferred embodiment, the vaccine is a heat shock protein based tumor vaccine or a heat shock protein based pathogen vaccine. In a preferred embodiment, the vaccine is a heat shock protein based viral vaccine.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a vaccine, for use in a method for the treatment of cancer. In a preferred embodiment, the vaccine is a heat shock protein based tumor vaccine.

The anti-CTLA-4 antibody and the additional therapeutic agent (e.g., chemotherapeutic, checkpoint targeting agent, IDO inhibitor, and/or vaccine) can be administered separately, sequentially or concurrently as separate dosage forms. In one embodiment, an anti-CTLA-4 antibody is administered parenterally, and an IDO inhibitor is administered orally.

In certain embodiments, an anti-CTLA-4 antibody disclosed herein is administered to a subject intratumorally. In certain embodiments, an anti-CTLA-4 antibody disclosed herein is administered to a subject intratumorally in combination with an additional therapeutic agent. In certain embodiments, the additional therapeutic agent is administered systemically. In certain embodiments, the subject has solid tumors. In certain embodiments, the subject has head and neck squamous cell carcinoma (HNSCC). In certain embodiments, the subject has $HER2^+$ breast cancer. In certain embodiments, the additional therapeutic agent that is administered systemically is an anti-PD-1 antibody (e.g., pembrolizumab or nivolumab). In certain embodiments, the additional therapeutic agent that is administered systemically is an anti-EGFR antibody (e.g., cetuximab). In certain embodiments, the additional therapeutic agent that is administered systemically is an anti-HER2 antibody (e.g., trastuzumab). In certain embodiments, the additional therapeutic agent that is administered systemically is a chemotherapeutic agent (e.g., gemcitabine). In certain embodiments, the subject has solid tumors and the additional therapeutic agent that is administered systemically is an anti-PD-1 antibody (e.g., pembrolizumab or nivolumab). In certain embodiments, the subject has head and neck squamous cell carcinoma (HNSCC) and the additional therapeutic agent that is administered systemically is an anti-EGFR antibody (e.g., cetuximab). In certain embodiments, the subject has $HER2^+$ breast cancer and the additional therapeutic agent that is administered systemically is an anti-HER2 antibody (e.g., trastuzumab). In certain embodiments, the subject further received a chemotherapeutic agent (e.g., gemcitabine). In one aspect, the present invention relates to an anti-CTLA-4 antibody and/or pharmaceutical composition of the present invention, and optionally an additional therapeutic agent, for use in a method for the treatment of cancer, wherein the anti-CTLA-4 antibody and/or pharmaceutical composition of the present invention is administered intratumorally to the subject. In one preferred embodiment, an additional therapeutic agent is administered to the subject, more preferably, an additional therapeutic agent is administered systemically to the subject.

In certain embodiments, an anti-PD-1 antibody is used in methods disclosed herein. In certain embodiments, the anti-PD-1 antibody is Nivolumab, also known as BMS-936558 or MDX1106, developed by Bristol-Myers Squibb. In certain embodiments, the anti-PD-1 antibody is Pembrolizumab, also known as Lambrolizumab or MK-3475, developed by Merck & Co. In certain embodiments, the anti-PD-1 antibody is Pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-LAG-3 antibody is used in methods disclosed herein. In certain embodiments, the anti-LAG-3 antibody is BMS-986016 developed by Bristol-Myers Squibb. In certain embodiments, the anti-LAG-3 antibody is LAG525 developed by Novartis. In certain embodiments, the anti-LAG-3 antibody is GSK2831781 developed by GSK.

Non-limiting examples of anti-LAG-3 antibodies that may be used in treatment methods disclosed herein are disclosed in the following patents and patent applications, which are incorporated herein by reference in their entireties for all purposes: U.S. Pat. No. 9,244,059; U.S. Publication No. US 2011/0150892 A1; U.S. Publication No. US 2014/0093511 A1; U.S. Publication No. US 2014/0286935 A1; U.S. Publication No. US 2015/0259420 A1; and PCT Publication No. WO 2015/042246 A1; PCT Publication No. WO 2015/116539 A1; PCT Publication No. WO 2015/200119 A1; and PCT Publication No. WO 2016/028672 A1.

In certain embodiments, an anti-EGFR antibody is used in methods disclosed herein. In certain embodiments, the anti-EGFR antibody is cetuximab developed by Bristol-Myers Squibb and ImClone, panitumumab developed by Abgenix and Amgen, nimotuzumab developed by CMI Cuba and YM BioSciences, necitumumab developed by ImClone, zalutumumab developed by Genmab, matuzumab developed by Takeda, Sym004 developed by Merck Serono and Symphogen, imgatuzumab developed by Glycart and Roche, duligotumab developed by Genentech and Roche, depatuxizumab developed by Abbott, depatuxizumab mafodotin developed by Abbvie, MM-151 developed by Adimab and Merrimack, GC1118 developed by Green Cross, AMG 595 developed by Amgen and ImmunoGen, CetuGEX developed by Glycotope, laprituximab emtansine developed by ImmunoGen, JNJ-61186372 developed by Genmab and Janssen Biotech, SCT200 developed by Sinocelltech, LY3164530 developed by Lilly, HLX07 developed by Shanghai Henlius, or SYN004 developed by Synermore.

In certain embodiments, an anti-HER2 antibody is used in methods disclosed herein. In certain embodiments, the anti-HER2 antibody is trastuzumab developed by Genentech and Roche, trastuzumab emtansine developed by Genentech and Roche, pertuzumab developed by Genentech, ertumaxomab developed by Fresenius, margetuximab developed by MacroGenics, MM-111 developed by Merrimack, CT-P06 developed by Celltrion, PF-05280014 developed by Pfizer, MM-302 developed by Merrimack, SB3 developed by Merck & Co, CMAB302 developed by Shanghai CP Guojian, TrasGEX developed by Glycotope, ARX788 developed by Ambrx and Zhejiang Medicine, SYD985 developed by Synthon, FS102 developed by Bristol-Myers Squibb and f-star, BCD-022 developed by Biocad, ABP 980 developed by Amgen, DS-8201a developed by Daiichi Sankyo, HLX02 developed by Shanghai Henlius, or CANMAb developed by Biocon and Mylan.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intratumorally. In certain embodiments, the anti-CTLA-4 antibody or pharmaceutical composition disclosed herein is delivered to a tumor draining lymph node. In certain embodiments, the antibody or pharmaceutical composition described herein is delivered via a localized administration (e.g., subcutaneous administration). In certain embodiments, the anti-CTLA-4 antibody or pharmaceutical composition disclosed herein is delivered systemically. In certain embodiments, the anti-CTLA-4 antibody or pharmaceutical composition disclosed herein is delivered locally.

In one aspect, the present invention relates to an anti-CTLA-4 antibody and/or pharmaceutical composition of the present invention, and optionally an additional therapeutic agent, for use in a method for the treatment of cancer, wherein the anti-CTLA-4 antibody and/or pharmaceutical composition of the present invention is delivered intratumorally to the subject, is delivered to a tumor draining lymph node of a subject, or is delivered via a localized administration (e.g., subcutaneous administration) to a subject.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an anti-CTLA-4 antibody or pharmaceutical composition described herein is administered to a subject (e.g., via intravenous injection) at 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg. In certain embodiments, an anti-CTLA-4 antibody or pharmaceutical composition described herein is administered to a subject (e.g., via intravenous injection) every three weeks at the doses described above.

In one aspect, the present invention relates to an anti-CTLA-4 antibody and/or pharmaceutical composition of the present invention, and optionally an additional therapeutic agent, for use in a method for the treatment of cancer, wherein the anti-CTLA-4 antibody and/or pharmaceutical composition of the present invention is administered to a subject at 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, more preferably every three weeks.

In certain embodiments, an anti-CTLA-4 antibody or pharmaceutical composition described herein is administered to a subject (e.g., via intravenous injection) at 0.1 mg/kg or about 0.1 mg/kg every three weeks. In certain embodiments, an anti-CTLA-4 antibody or pharmaceutical composition described herein is administered to a subject (e.g., via intravenous injection) at 0.3 mg/kg or about 0.3 mg/kg every three weeks. In certain embodiments, an anti-CTLA-4 antibody or pharmaceutical composition described herein is administered to a subject (e.g., via intravenous injection) at 1 mg/kg or about 1 mg/kg every three weeks. In certain embodiments, an anti-CTLA-4 antibody or pharmaceutical composition described herein is administered to a subject (e.g., via intravenous injection) at 3 mg/kg or about 3 mg/kg every three weeks. In certain embodiments, an anti-CTLA-4 antibody or pharmaceutical composition described herein is administered to a subject (e.g., via intravenous injection) at 6 mg/kg or about 6 mg/kg every three weeks. In certain embodiments, an anti-CTLA-4 antibody or pharmaceutical composition described herein is administered to a subject (e.g., via intravenous injection) at 10 mg/kg or about 10 mg/kg every three weeks.

In certain embodiments, an anti-CTLA-4 antibody or pharmaceutical composition described herein is administered to a subject via intratumoral injection at 0.01 mg/kg, 0.03 mg/kg, 0.1 mg/kg, 0.3 mg/kg, 1 mg/kg, 3 mg/kg, about 0.01 mg/kg, about 0.03 mg/kg, about 0.1 mg/kg, about 0.3 mg/kg, about 1 mg/kg, or about 3 mg/kg. In certain embodiments, an anti-CTLA-4 antibody or pharmaceutical composition described herein is administered to a subject via intratumoral injection every three weeks at the doses described above.

In certain embodiments, an anti-CTLA-4 antibody or pharmaceutical composition described herein is administered to a subject via intratumoral injection at 0.01 mg/kg or about 0.01 mg/kg every three weeks. In certain embodiments, an anti-CTLA-4 antibody or pharmaceutical composition described herein is administered to a subject via intratumoral injection at 0.03 mg/kg or about 0.03 mg/kg every three weeks. In certain embodiments, an anti-CTLA-4 antibody or pharmaceutical composition described herein is administered to a subject via intratumoral injection at 0.1 mg/kg or about 0.1 mg/kg every three weeks. In certain embodiments, an anti-CTLA-4 antibody or pharmaceutical composition described herein is administered to a subject via intratumoral injection at 0.3 mg/kg or about 0.3 mg/kg every three weeks. In certain embodiments, an anti-CTLA-4 antibody or pharmaceutical composition described herein is administered to a subject via intratumoral injection at 1 mg/kg or about 1 mg/kg every three weeks. In certain embodiments, an anti-CTLA-4 antibody or pharmaceutical composition described herein is administered to a subject via intratumoral injection at 3 mg/kg or about 3 mg/kg every three weeks.

In certain embodiments, an anti-CTLA-4 antibody or pharmaceutical composition described herein is administered to a subject via a localized administration (e.g., subcutaneous administration) at 0.01 mg/kg, 0.03 mg/kg, 0.1 mg/kg, 0.3 mg/kg, 1 mg/kg, 3 mg/kg, about 0.01 mg/kg, about 0.03 mg/kg, about 0.1 mg/kg, about 0.3 mg/kg, about 1 mg/kg, or about 3 mg/kg.

An anti-CTLA-4 antibody described herein can also be used to assay CTLA-4 protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}I$, $^{121}I$) carbon ($^{14}C$), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin. Such labels can be used to label an antibody or an antigen-binding fragment thereof described herein. Alternatively, a second antibody that recognizes an anti-CTLA-4 antibody or antigen-binding fragment thereof described herein can be labeled and used in combination with an anti-CTLA-4 antibody or antigen-binding fragment thereof to detect CTLA-4 protein levels. In one embodiment, the present invention relates to the use of an anti-CTLA-4 antibody of the invention, for assaying and/or detecting CTLA-4 protein levels in a biological sample in vitro.

Assaying for the expression level of CTLA-4 protein is intended to include qualitatively or quantitatively measuring or estimating the level of a CTLA-4 protein in a first biological sample either directly (e.g., by determining or estimating absolute protein level) or relatively (e.g., by comparing to the disease associated protein level in a second biological sample). CTLA-4 polypeptide expression level in the first biological sample can be measured or estimated and compared to a standard CTLA-4 protein level, the standard being taken from a second biological sample obtained from an individual not having the disorder or being determined by averaging levels from a population of individuals not having the disorder. As will be appreciated in the art, once the "standard" CTLA-4 polypeptide level is known, it can be used repeatedly as a standard for comparison.

As used herein, the term "biological sample" refers to any biological sample obtained from a subj ect, cell line, tissue, or other source of cells potentially expressing CTLA-4. Methods for obtaining tissue biopsies and body fluids from animals (e.g., humans) are well known in the art. Biological samples include peripheral mononuclear blood cells.

An anti-CTLA-4 antibody or antigen-binding fragment thereof described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent or an antibody or antigen-binding fragment thereof, including combinations thereof, versus a different agent or antibody or antigen-binding fragment thereof. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one aspect, the present invention relates to an anti-CTLA-4 antibody and/or pharmaceutical composition of the present invention for use as a diagnostic.

In one aspect, the present invention relates to an anti-CTLA-4 antibody and/or pharmaceutical composition of the present invention for use in a method for the prediction, diagnosis and/or monitoring of an immune system-dysfunction and/or cancer.

In one embodiment, the present invention relates to the use of an anti-CTLA-4 antibody of the invention, for predicting, diagnosing and/or monitoring an immune system-dysfunction and/or cancer in a subject by assaying and/or detecting CTLA-4 protein levels in a biological sample of the subject of in vitro.

In one embodiment, an anti-CTLA-4 antibody or antigen-binding fragment thereof can be used in immunohistochemistry of biopsy samples. In another embodiment, an anti-CTLA-4 antibody or antigen-binding fragment thereof can be used to detect levels of CTLA-4, or levels of cells which contain CTLA-4 on their membrane surface, which levels can then be linked to certain disease symptoms. Anti-CTLA-4 antibodies or antigen-binding fragments thereof described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-CTLA-4 antibodies or antigen-binding fragments thereof described herein may carry a fluorescence label. Exemplary fluorescence labels include, for example, reactive and conjugated probes e.g. Aminocoumarin, Fluorescein and Texas red, Alexa Fluor dyes, Cy dyes and DyLight dyes. An anti-CTLA-4 antibody or antigen-binding fragment thereof may carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of anti-CTLA-4 antibody or antigen-binding fragment thereof to CTLA-4 (e.g., human CTLA-4). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-CTLA-4 antibody or antigen-binding fragment thereof under conditions that allow for the formation of a complex between the antibody or antigen-binding fragment thereof and CTLA-4. Any complexes formed between the antibody or antigen-binding fragment thereof and CTLA-4 are detected and compared in the sample and the control. In light of the specific binding of the antibodies described herein for CTLA-4, the antibodies or antigen-binding fragments thereof can be used to specifically detect CTLA-4 expression on the surface of cells. The antibodies or antigen-binding fragments thereof described herein can also be used to purify CTLA-4 via immunoaffinity purification. Also included herein is an assay system which may be prepared in the form of a test kit for the quantitative analysis of the extent of the presence of, for instance, CTLA-4 or CTLA-4/CTLA-4 ligand complexes. The system or test kit may comprise a labeled component, e.g., a labeled antibody, and one or more additional immunochemical reagents.

In one embodiment, the present invention relates to an in vitro method for assaying and/or detecting CTLA-4 protein levels in a biological sample comprising (1) contacting a sample and optionally a control sample with an anti-CTLA-4 antibody or antigen-binding fragment thereof of the invention under conditions that allow for the formation of a complex between the antibody or antigen-binding fragment thereof and CTLA-4, and (2) detecting and comparing the complexes formed in the sample and optionally the control.

5.5 Polynucleotides, Vectors and Methods of Producing Anti-CTLA-4 Antibodies

In another aspect, provided herein are polynucleotides comprising a nucleotide sequence encoding an antibody described herein or a fragment thereof (e.g., a light chain variable region and/or heavy chain variable region) that specifically binds to a CTLA-4 (e.g., human CTLA-4) antigen, and vectors, e.g., vectors comprising such polynucleotides for recombinant expression in host cells (e.g., *E. coli* and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies or antigen-binding fragments thereof, which specifically bind to a CTLA-4 polypeptide (e.g., human CTLA-4) and comprises an amino acid sequence as described herein, as well as antibodies which compete with such antibodies for binding to a CTLA-4 polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Table 1).

Also provided herein are polynucleotides encoding an anti-CTLA-4 antibody that are optimized, e.g., by codon/RNA optimization, replacement with heterologous signal sequences, and elimination of mRNA instability elements. Methods to generate optimized nucleic acids encoding an anti-CTLA-4 antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-CTLA-4 antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-CTLA-4 antibody encoded by polynucleotides that have not been optimized.

In certain embodiments, an optimized polynucleotide sequence encoding an anti-CTLA-4 antibody described herein or a fragment thereof (e.g., VL domain and/or VH domain) can hybridize to an antisense (e.g., complementary) polynucleotide of an unoptimized polynucleotide sequence encoding an anti-CTLA-4 antibody described herein or a fragment thereof (e.g., VL domain and/or VH domain). In specific embodiments, an optimized nucleotide sequence encoding an anti-CTLA-4 antibody described herein or a fragment hybridizes under high stringency conditions to antisense polynucleotide of an unoptimized polynucleotide sequence encoding an anti-CTLA-4 antibody described herein or a fragment thereof. In a specific embodiment, an optimized nucleotide sequence encoding an anti-CTLA-4 antibody described herein or a fragment thereof hybridizes under high stringency, intermediate or lower stringency hybridization conditions to an antisense polynucleotide of an unoptimized nucleotide sequence encoding an anti-CTLA-4 antibody described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-CTLA-4 antibodies described herein can be readily isolated and sequenced using conventional procedures (e.g., by using oligonucleotide probes that are capable of binding specifically to genes encoding the heavy and light chains of the anti-CTLA-4 antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-CTLA-4 antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

In certain aspects, provided herein are cells (e.g., host cells) expressing (e.g., recombinantly) antibodies described herein (or an antigen-binding fragment thereof) which specifically bind to CTLA-4 (e.g., human CTLA-4) and related polynucleotides and expression vectors. Provided herein are vectors (e.g., expression vectors) comprising polynucleotides comprising nucleotide sequences encoding anti-CTLA-4 antibodies or a fragment for recombinant expression in host cells, preferably in mammalian cells. Also provided herein are host cells comprising such vectors for recombinantly expressing anti-CTLA-4 antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to CTLA-4 (e.g., human CTLA-4) involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-CTLA-4 antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-CTLA-4 antibody described herein, and a second vector comprising a polynucleotide encoding a heavy chain/heavy chain variable region of an anti-CTLA-4 antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7). In certain embodiments, antibodies described herein are produced by CHO cells or NS0 cells. In a specific embodiment, the expression of nucleotide sequences encoding antibodies described herein which specifically bind CTLA-4 (e.g., human CTLA-4) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-CTLA-4 antibodies described herein are produced in mammalian cells, such as CHO cells.

In a specific embodiment, the antibodies described herein or antigen-binding fragments thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies or antigen-binding fragments thereof with reduced fucose content. The Potelligent® system (Lonza) is an example of such a system that can be used to produce antibodies or antigen-binding fragments thereof with reduced fucose content.

For long-term, high-yield production of recombinant proteins, stable expression cells can be generated. For example, cell lines which stably express an anti-CTLA-4 antibody described herein or an antigen-binding fragment thereof can be engineered. In specific embodiments, a cell provided herein stably expresses a light chain/light chain variable region and a heavy chain/heavy chain variable region which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CTLA-4 antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, NY (1993); Kriegler M, Gene Transfer and Expression, A Laboratory Manual, Stockton Press, NY (1990); and in Chapters 12 and 13, Dracopoli N C et al., (eds.), Current Protocols in Human Genetics, John Wiley & Sons, NY (1994); Colbere-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or an antigen-binding fragment thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to CTLA-4 (e.g., human CTLA-4) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody or an antigen-binding fragment thereof which specifically binds to CTLA-4 (e.g., human CTLA-4) comprising culturing a cell or host cell described herein. In a certain aspect, provided herein is a method of making an antibody or an antigen-binding fragment thereof which specifically binds to CTLA-4 (e.g., human CTLA-4) comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell. Preferably, the method is performed in vitro.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to CTLA-4 (e.g., human CTLA-4) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., CTLA-4 (e.g., human CTLA-4)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., CTLA-4 (e.g., human CTLA-4)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against CTLA-4 (e.g., human CTLA-4). The binding specificity of monoclonal antibodies produced by hybridoma cells is determined by methods known in the art, for example, immunoprecipitation or by an in vitro binding assay, such as radioimmunoassay (MA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific CTLA-4 (e.g., human CTLA-4) and can be generated by any technique known to those of skill in the art. For example, Fab and $F(ab')_2$ fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of an antibody molecule and contains the complete light chain paired with the VH and CH1 domains of the heavy chain. A $F(ab')_2$ fragment contains the two antigen-binding arms of an antibody molecule linked by disulfide bonds in the hinge region.

Further, the antibodies described herein or antigen-binding fragments thereof can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and $F(ab')_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan EA (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989, 830; 5,869,620; 6,132,992 and 8,586,713.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that specifically bind to a CTLA-4 antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody described herein, which binds to the same epitope of CTLA-4 (e.g., human CTLA-4) as an anti-CTLA-4 antibody described herein, is a human antibody or an antigen-binding fragment thereof. In particular embodiments, an antibody described herein, which competitively blocks (e.g., in a dose-dependent manner) any one of the antibodies described herein, from binding to CTLA-4 (e.g., human CTLA-4), is a human antibody or an antigen-binding fragment thereof. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., CTLA-4). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569, 825), the Trans Chromo Mouse™ (Kirin) and the KM Mouse™ (Medarex/Kirin).

Human antibodies which specifically bind to CTLA-4 (e.g., human CTLA-4) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., CTLA-4 (e.g., human CTLA-4)). Such methods are known and are described in the art, see, e.g., Shinmoto H et al., (2004) Cytotechnology 46: 19-23; Naganawa Y et al., (2005) Human Antibodies 14: 27-31.

5.6 Kits

Also provided, are kits comprising one or more antibodies described herein, or pharmaceutical composition or conjugates thereof. In a specific embodiment, provided herein is a pharmaceutical pack or kit comprising one or more containers filled with one or more of the ingredients of the pharmaceutical compositions described herein, such as one or more antibodies provided herein or an antigen-binding fragment thereof. In some embodiments, the kits contain a pharmaceutical composition described herein and any prophylactic or therapeutic agent, such as those described herein. In certain embodiments, the kits may contain a T-cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated CTLA-4 antigen (e.g., human CTLA-4) as a control. In another specific embodiment, the kits described herein further comprise a control antibody which does not react with a CTLA-4 antigen. In another specific embodiment, kits described herein contain one or more elements for detecting the binding of an antibody to a CTLA-4 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CTLA-4 antigen. The CTLA-4 antigen provided in the kit can also be attached to a solid support. In a more specific embodiment, the detecting means of the above described kit includes a solid support to which a CTLA-4 antigen is attached. Such a kit can also include a non-attached reporter-labeled anti-human antibody or anti-mouse/rat antibody. In this embodiment, binding of the antibody to the CTLA-4 antigen can be detected by binding of the said reporter-labeled antibody.

In one embodiment, the present invention relates to the use of a kit of the present invention for in vitro assaying and/or detection of human CTLA-4 in a biological sample.

6. EXAMPLES

The examples in this Section (i.e., Section 6) are offered by way of illustration, and not by way of limitation.

6.1 Example 1

Characterization of Anti-CTLA-4 Antibody

This example describes the characterization of antibodies that bind to human CTLA-4. In particular, an antibody designated AGEN1884 was characterized in a number of assays described below. The anti-CTLA-4 antibody AGEN1884 comprises a heavy chain comprising the amino acid sequence of SEQ ID NO: 93 and a light chain comprising the amino acid sequence of SEQ ID NO: 15. The antibody AGEN1884 is a human $IgG_1$ antibody containing a T109S substitution (i.e., substitution of threonine with serine at position 109 relative to the wild type Fc sequence), numbered according to Kabat, in the light chain constant domain, which facilitates the cloning of the variable region in frame to the constant region. This mutation is a conservative modification that does not affect antibody binding or function. The wild type counterpart, named AGEN1884w, which contains a threonine at position 109, numbered according to Kabat, was also generated. The antibody AGEN1884w is a human $IgG_1$ antibody comprising a heavy chain of SEQ ID NO: 93 and a light chain of SEQ ID NO: 13.

6.1.1 Kinetic Analysis by Surface Plasmon Resonance

Surface plasmon resonance was used to determine the affinity of the anti-CTLA-4 antibody AGEN1884 and a reference anti-CTLA-4 $IgG_1$ antibody (BIAcore® T100/T200 sensitivity enhanced system (GE Healthcare) and a Fab-capture assay). All interactions were analyzed at 25° C. using 1×DPBS (PAA, H15-002) plus P20 (0.05%, Pierce, 28320) as running buffer. The anti-CTLA-4 antibodies (8 μg/ml in running buffer) were captured to the chip surface of a CM5 sensor chip (GE Healthcare, Series S CM5, BR-1005-30) via an immobilized anti-human Fab antibody (GE Healthcare, Fab Capture Kit, 28958325). To detect nonspecific interactions of the CTLA-4 antigen, antibody capture was only performed in flow cell 2, whereas in flow cell 1 only the capturing antibody was immobilized. After capture of the anti-CTLA-4 antibodies, the CTLA-4 antigens were run through both flow cells in different amounts. Specifically, recombinant human CTLA-4-Fc (R&D Systems, #7268-CT), recombinant human CTLA-4 (Sino Biological, #11159-H08H), recombinant cynomolgus CTLA-4-Fc (Sino Biological, #90213-C02H), and recombinant cynomolgus CTLA-4 (Sino Biological, #90213-C08H) were run at 100 nM, 25 nM, and 6.25 nM; and recombinant mouse CTLA-4-Fc (R&D, # 434-CT), recombinant rat CTLA-4-Fc (Sino Biological, #81069-RO2H), and recombinant rat CTLA-4 (Sino Biological, #81069-R08H) were run at 400 nM, 100 nM, and 25 nM. A blank curve (running buffer only) was also included in each run. Association was run for 90 seconds and dissociation for 600 seconds with a flow rate of 10 μl/min. After each run a regeneration step was performed with 10 mM Glycine pH 2.0 (GE Healthcare, BR-1003-55) for 60 seconds with 30 μl/min. Binding curves were evaluated using BIAcore® T200 evaluation software version 2.0.1 applying a Langmuir 1:1 model with global fit of Rmax. From these values the affinities ($K_D$) of AGEN1884 and the reference anti-CTLA-4 antibody for various antigens were calculated and shown in FIG. 1A. The recombinant monomeric cynomolgus CTLA-4, mouse CTLA-4-Fc, and monomeric rat CTLA-4 used in this study failed quality control assessment. The binding of anti-CTLA-4 antibodies to recombinant mouse CTLA-4-Fc protein, which showed 50% aggregation, was likely due to nonspecific interactions. The surface plasmon resonance analysis was later repeated twice using recombinant mouse CTLA-4-Fc (Sino Biological, #81069-R02H) that passed a quality control assessment at 360 nM, 120 nM, 40 nM, and 13.3 nM for AGEN1884w. AGEN1884w did not show any detectable binding to mouse CTLA-4.

6.1.2 Antibody Binding to Cells Over-Expressing CTLA-4

Figures 1A, 1B:
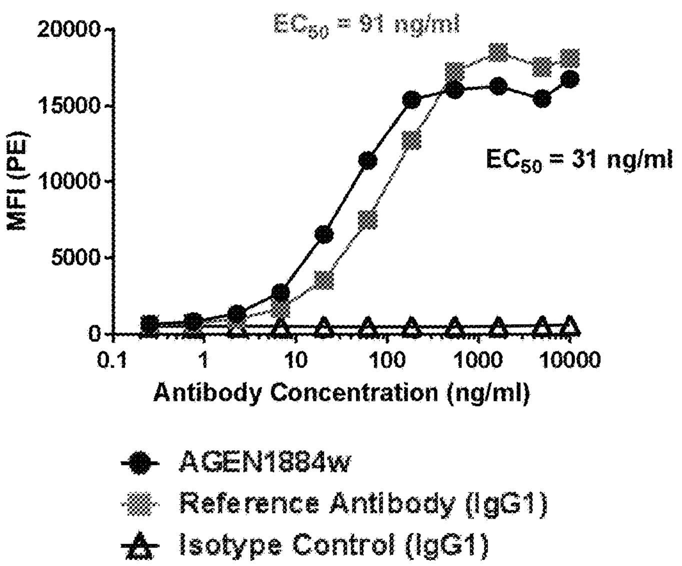

Jurkat cells over-expressing human CTLA-4 (Promega) were maintained in RPMI1640 (Life Technologies) containing 10% FBS (Gemini Bio Products), 100 μg/ml Hygromycin B (Gibco), and 500 μg/ml G418 (Promega). Before staining with antibodies, the cells were washed once in FACS buffer (PBS with 2% FBS). Serial dilutions of AGEN1884w, a reference anti-CTLA-4 $IgG_1$ antibody, and an $IgG_1$ isotype control starting at 10 μg/ml were added to duplicate wells on 96-well round bottom plates in a volume of 100 μl and incubated for 30 minutes at 4° C. The cells were washed three times with 150 μl FACS buffer and were stained with 100 μl FACS buffer containing 0.25 μl PE conjugated mouse anti-human kappa antibody (Invitrogen) for 30 minutes at 4° C. The cells were then washed twice and re-suspended in 100 μl FACS buffer. The samples were acquired on an LSRFortessa (BD Biosciences). Mean fluorescence intensities (1W I) were analyzed using FlowJo software (FlowJo, LLC) and plotted using Prism 6 (GraphPad Software). As shown in FIG. 1B, the antibody AGEN1884w bound to human CTLA-4 expressed on the surface of Jurkat cells.

6.1.3 CTLA-4 Antibody Selectivity Assay

The selectivity of AGEN1884 for CTLA-4 was assessed against other members of the immunoglobulin superfamily using suspension array technology as a multiplex assay. A number of immunoglobulin superfamily members were chemically coupled to Luminex® microspheres using standard NHS-ester chemistry. Purified materials of AGEN1884, a reference anti-CTLA-4 $IgG_1$ antibody, and an $IgG_1$ isotype control were diluted in assay buffer (Roche 11112589001) to 10 ng/ml, 100 ng/ml, and 1000 ng/ml. Briefly, 25 μl of each dilution was incubated in the dark (20° C., 650 rpm) with 1500 Luminex® microspheres in 5 μl assay buffer for 1 hour in 96 half-well filter plates (Millipore, MABVN1250). Luminex® microspheres were coupled with recombinant human CTLA-4-Fc (R&D Systems, #7268-CT), recombinant cynomolgus CTLA-4-Fc (Sino Biological, #90213-C02H), rhCD28-Fc (R&D, #342-CD-200), rhICOS-Fc (R&D, #169-CS-050), rhBTLA-Fc (Sino Biological, #11896-H02H), rhPD-1-Fc (R&D Systems, #1086-PD), or recombinant cynomolgus PD-1-Fc (produced in-house) via amine coupling with the COOH bead surface. Standard curves were generated using duplicates of 25 μl of a human $IgG_1$ standard (Sigma, 15154) with 1:3 dilution series (0.08-540 ng/ml). Detection was carried out using 60 μl of goat anti-human IgG $F(ab)_2$ labeled with R-PE (2.5 μg/ml; JIR 109-116-098, AbDSerotec Rapid RPE Antibody Conjugation Kit, LNK022RPE) and another hour of incubation time (20° C., 650 rpm). Plates were analyzed using a Luminex® 200 system (Millipore). A total of 100 beads were counted per well in a 48 μl sample volume. PE MFI values were used to determine specific or nonspecific binding to the recombinant proteins mentioned above.

As shown in FIGS. 1C and 1D, the antibody AGEN1884 demonstrated specific binding to human and cynomolgus CTLA-4. No significant binding to other listed immunoglobulin superfamily members was observed at tested concentrations.

6.1.4 Antibody Binding to CTLA-4 Expressed by Activated T Cells

Figure 2A:
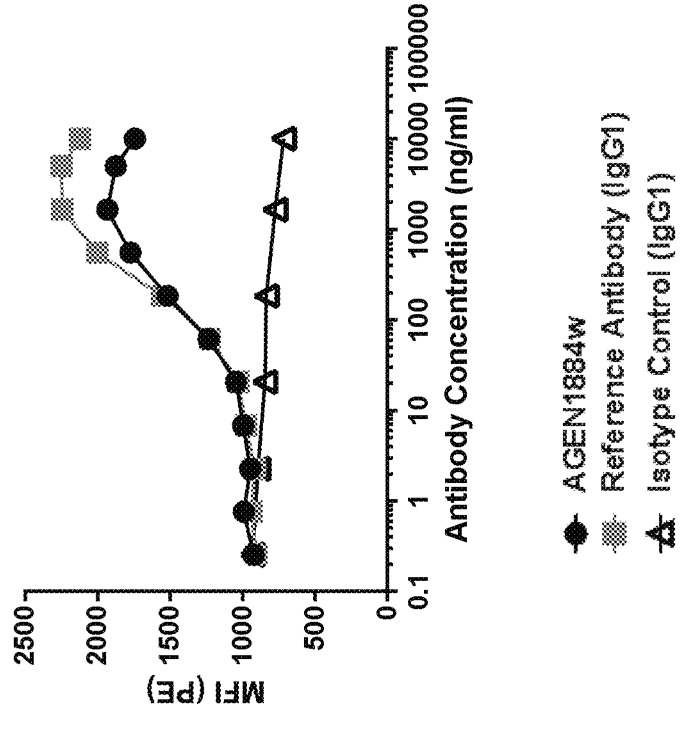

Next, the binding of AGEN1884w to CTLA-4 expressed on the surface of activated human T cells was examined. Human PBMCs isolated via Ficoll gradient density separation from healthy donor buffy coats (Research Blood Components, LLC) were enriched for untouched CD4+ T cells using magnetic beads (Stemcell Technologies). The enriched population of CD4+ T cells was then re-suspended in RPMI1640 media supplemented with 10% human AB serum (Sigma) at $1\times10^6$/ml. $1\times10^5$ cells in 100 μl were seeded into each well of flat bottom 96 well plates pre-coated with an anti-CD3 antibody (3 μg/ml, BD Biosciences) and an anti-CD28 antibody (10 μg/ml, BD Biosciences) and cultured at 37° C. and 5% $CO_2$. On day 5, the cells were pooled and counted using Muse Cell Analyzer (EMD Millipore). 50,000 cells were stained with 100 μl of AGEN1884w, a reference anti-CTLA-4 $IgG_1$ antibody and an $IgG_1$ isotype control serially diluted starting at 10 μg/ml on 96-well round bottom plates for 30 minutes at 4° C. The cells were washed three times with 150 μl FACS buffer and stained with 100 μl FACS buffer containing 0.25 μl PE labeled mouse anti-human kappa antibody (Invitrogen) and 1 μl of APC-CD4 (BD Bioscience) for 30 minutes at 4° C. The cells were then washed twice and re-suspended in 100 μl of FACS buffer. The samples were acquired on a FACSCanto II System (BD Biosciences). Mean fluorescence intensities (MFI) of PE in CD4+ T cells were analyzed using FlowJo software (FlowJo, LLC). As shown in FIG. 2A, AGEN1884w bound to CTLA-4 expressed on the surface of activated human CD4+ T cells.

Figure 2B:
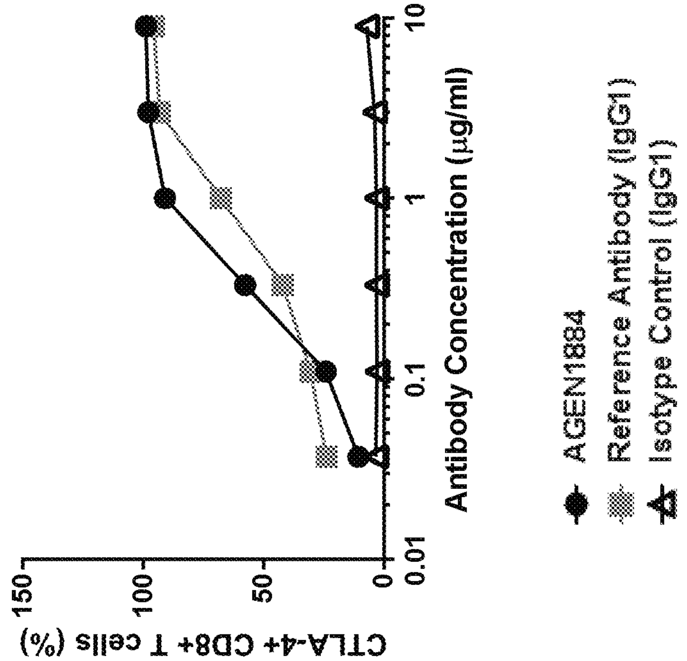

The binding characteristics of the antibody AGEN1884 to cynomolgus (*Macaca fascicularis*) CTLA-4 was analyzed by a flow cytometry analysis. Cynomolgus PBMCs (Biomedical Primate Research Centre, Netherlands) isolated via ficoll gradient were activated using plate-bound 8 μg/ml anti-CD3 (BD, 557052) and 0.1 μg/ml anti-CD28 antibodies (eBioscience, Cat. 16-0289-85) in the presence of 50 U/ml IL-2 (BioLegend, 589106) for 3 days in RPMI-1640 media supplemented with 10% fetal bovine serum, 10 mM HEPES and 1× Pen/Strep-Glutamine at 37° C. and 5% $CO_2$. Following activation, the cells were incubated with an anti-CD8a antibody (eBioscience, 9043-0087-120) diluted 1:100 in FACS buffer (PBS with 2% FBS) for 30 minutes at 4° C. The cells were then washed with FACS buffer twice and applied to the Cytofix/Cytoperm procedure of the BD Bioscience Kit (51-2090KZ) according to the manufacturer's protocol. Serial dilutions of 1:3 from 9 to 0.037 μg/ml of AGEN1884, a reference anti-CTLA-4 $IgG_1$ antibody, and an $IgG_1$ isotype control were applied to the cells. The samples were suspended in 200 μl of FACS buffer and analyzed using the FACS Diva flow cytometer (BD Biosciences). When used for intracellular staining, the anti-CTLA-4 antibody AGEN1884 showed binding to activated cynomolgus CD8+ T cells (FIG. 2B).

Figure 2C:
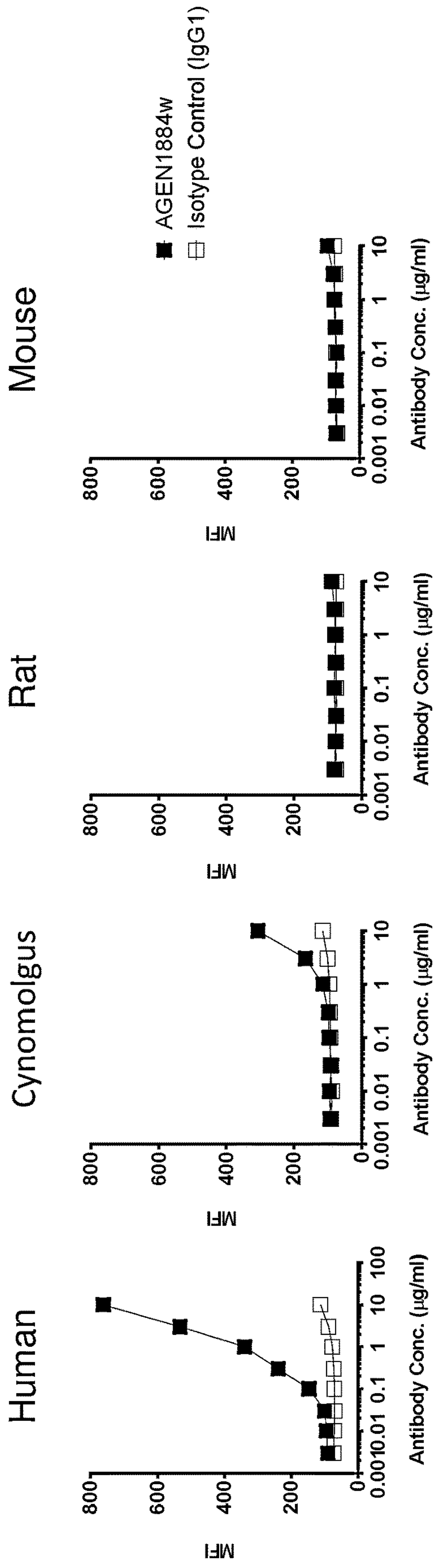

Further, peripheral blood mononuclear cells (PBMCs) from human, cynomolgus monkey (Indochinese), rat, or mouse were aliquoted into wells of a 96-well round bottom tissue culture plate ($1\times10^5$ cells/well) and stimulated for 4 days in RPMI-1640 supplemented with 10% fetal bovine serum, 15 mM HEPES, 100 IU/ml penicillin, 100 mg/ml streptomycin, 2 mM L-glutamine, 100 IU/ml IL-2 (Peprotech), and 1 μg/ml phytohemagglutinin (PHA) (Roche) at 37° C. and 5% $CO_2$. After stimulation, cells were washed and 5% heat-inactivated human AB serum (Sigma-Aldrich) was added to block Fc receptors and prevent non-specific binding of antibodies. Cells were washed again and re-suspended in 100 μl of a diluted APC-conjugated anti-CD4 antibody (clone OKT4, GK15, or W3/25; Biolegend). After incubating for 45 minutes in the dark, cells were washed three times and permeabilized using a FoxP3/Transcription Factor Staining Buffer Set (eBioscience) following the manufacturer's instructions. After permeabilization, cells were incubated with serial dilutions of fluorescently labeled (Pacific Blue™) AGEN1884w or an isotype control antibody ranging from 0.00003 μg/ml to 10 μg/ml for 45 minutes at 4° C. in the dark. The cells were washed twice before flow cytometric analysis using a Becton Dickinson LSRFortessa™. Data were analyzed using FlowJo software (Version 10). As shown in FIG. 2C, the antibody AGEN1884w bound to PHA-stimulated CD4+ human and cynomolgus T cells, but not rat or mouse T cells.

6.1.5 Ligand Blocking Activity

Figure 3A:
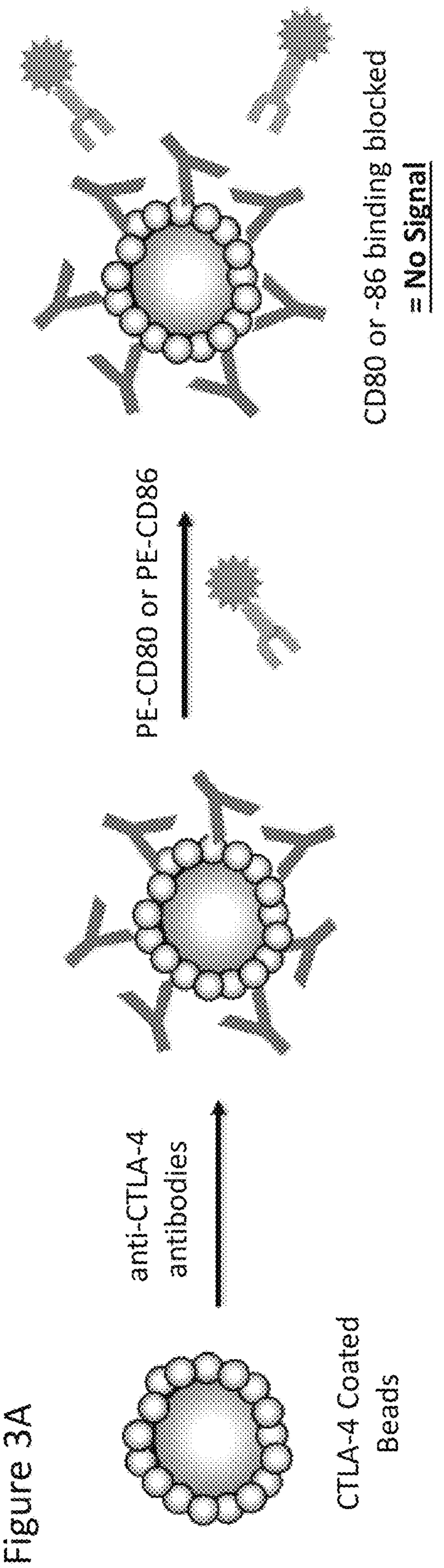

To determine whether anti-CTLA-4 antibodies block binding of ligands CD80 and CD86, a ranking assay setup was performed using suspension array technology (schematic shown in FIG. 3A). 1200 Luminex® beads in 5 μl assay buffer (Luminex Corp, #14 LC10014-01) were added to each well of 96-well half area plates (Corning, Inc., 3884). The beads were coupled with CTLA-4 antigen (rhCTLA-4-Fc, R&D, #7268-CT) via amine coupling with COOH bead surface. The coupling reaction was performed using 50 μg/ml of CTLA-4 antigen and $1\times10^7$ Luminex beads per ml. Standard NHS ester chemistry was used to form carbodiimide bonds between the primary amine groups of the antigen and the carboxyl groups on the bead surface (Luminex Xmap cookbook chapter 3).

Figure 3B:
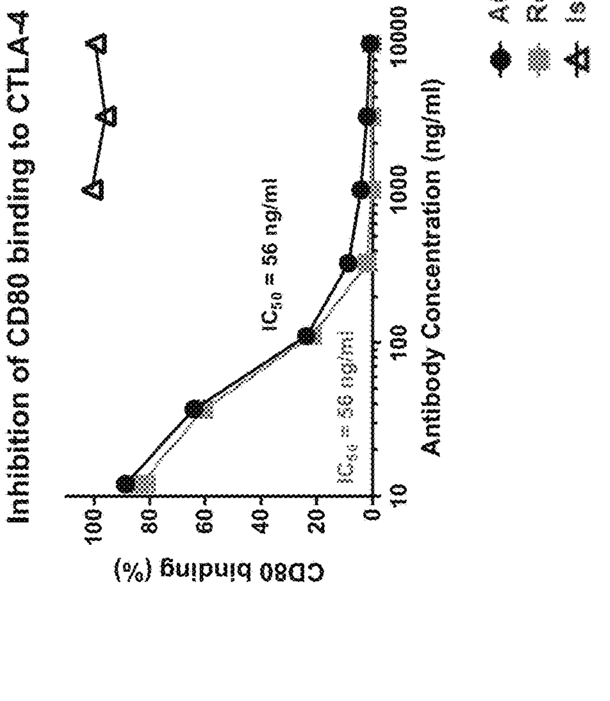
Figure 3C:
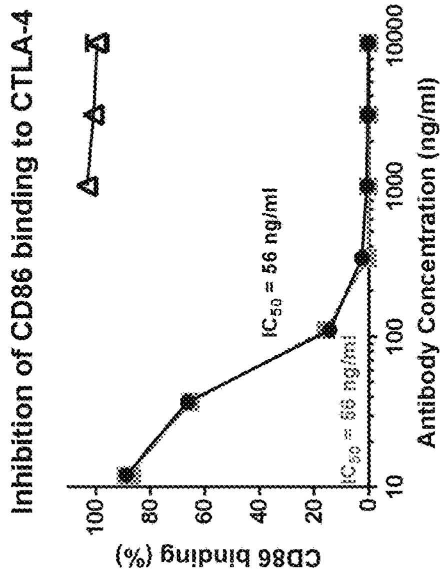

Antigen coupling for proteins is a simple two-step carbodiimide procedure during which microsphere carboxyl groups are first activated with EDC (1-Ethyl-3-[3-dimethylaminopropyl]carbodiimide hydrochloride) reagent in the presence of Sulfo-NHS (N-hydroxysulfosuccinimide) to form a sulfo-NHS-ester intermediate. The reactive intermediate is then replaced by reaction with the primary amine of the target molecule (antibody, protein or peptide) to form a covalent amide bond. The coupled beads were incubated with different concentrations of anti-CTLA-4 antibodies (concentrations of 9000 ng/ml to 12 ng/ml in 25 μl assay buffer per well before adding beads) for 1 hour at 20° C. and 650 rpm. The anti-CTLA-4 antibodies tested were AGEN1884, a reference anti-CTLA-4 $IgG_1$ antibody, and an $IgG_1$ isotype control antibody. Afterwards 30 μl of R-PE labeled CD80 (R&D Systems, #140-B1) or CD86 (R&D Systems, #141-B2) at a concentration of 1 nM was added to each well, giving a total well volume of 60 μl (1200 beads per well and a final concentration of 0.5 nM of labeled CD80 or CD86). The labeling of the ligand was done in-house using R-PE labeling kits (AbDSerotec, LYNX Rapid RPE Antibody Conjugation Kit, LNK023RPE) according to the manufacturer's protocol. Plates were analyzed using a Luminex® 200 system (Millipore). 100 beads were counted per well in 50 μl sample volume. Ligand blocking potential was calculated using the MFI values of the non-competed signal (100% binding) of the ligand only control. A PE detectable signal indicated ligand binding to the antigen. AGEN1884 inhibited the binding of CD80 (FIG. 3B) and CD86 (FIG. 3C) to CTLA-4 with an estimated IC50 of 56 ng/ml.

Figure 3D:
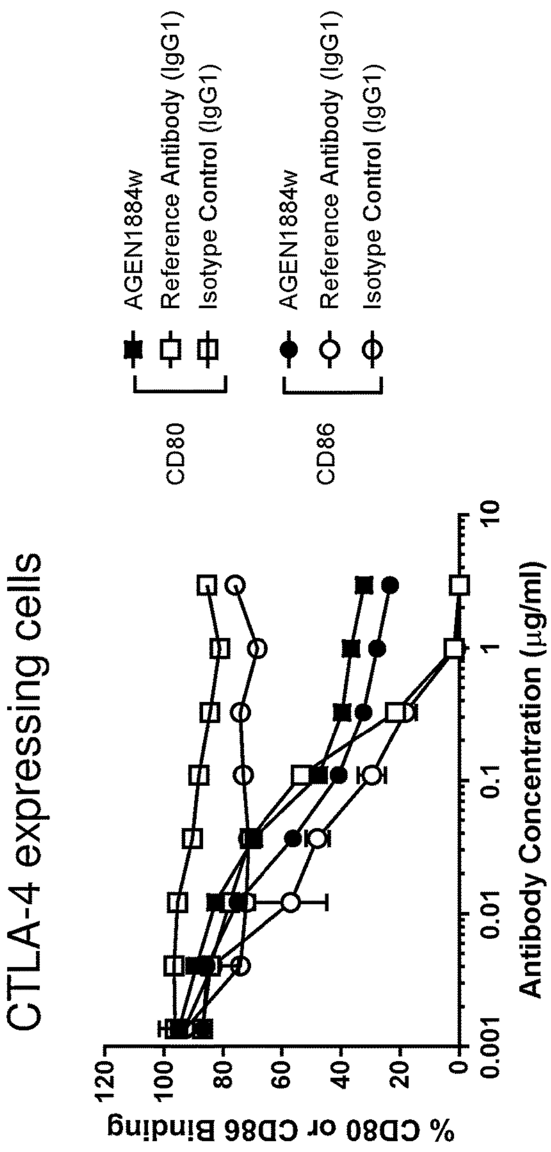

Next, the ability of the anti-CTLA-4 antibodies to block the binding of recombinant CD80-Fc and CD86-Fc to cell-surface expressed CTLA-4 was examined. Briefly, CTLA-4 expressing T cells (Jurkat) were incubated with increasing concentrations of AGEN1884w, a reference anti-CTLA-4 $IgG_1$ antibody, or an $IgG_1$ isotype control antibody (0, 0.001, 0.004, 0.012, 0.037, 0.11, 0.33, 0.99, and 2.96 μg/ml), followed by a fixed concentration (0.625 μg/ml) of fluorescently labeled CD80-Fc or CD86-Fc. The percent of cells bound by CD80-Fc or CD86-Fc was determined by flow cytometry. As shown in FIG. 3D, AGEN1884w and a reference anti-CTLA-4 $IgG_1$ antibody inhibited the binding of CD80-Fc and CD86-Fc to Jurkat cells expressing CTLA-4.

Figure 3E:
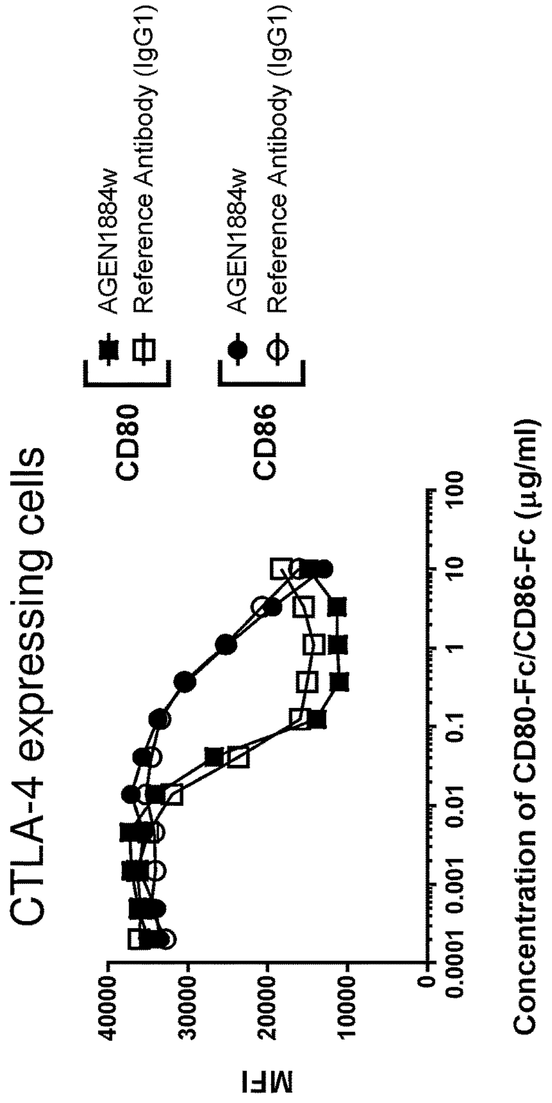

Further, the anti-CTLA-4 antibody AGEN1884w was examined for its ability to disrupt pre-formed complexes of cell surface expressed CTLA-4 and recombinant CD80 or CD86. Briefly, Jurkat cells engineered to constitutively express CTLA-4 on the cell surface were incubated with serially diluted CD80-Fc or CD86-Fc (R&D Systems) (10 to 0.0002 μg/ml) for 30 minutes at 4° C. in a 96-well round bottom plate. After washing, a fixed concentration (67 nM) of fluorescently labeled (PerCP-CY5.5) AGEN1884w or a reference anti-CTLA-4 $IgG_1$ antibody was added and the plate was incubated for 30 minutes at 4° C. The plate was washed again and the cells were re-suspended in 100 μl of 1% paraformaldehyde (Alfa Aear) in PBS. Samples were analyzed using a Becton Dickinson FACSCanto™ flow cytometer and data were analyzed using FlowJo software (Version 10). The antibody AGEN1884w disrupted performed complexes of CTLA-4 and CD80 or CD86 in a dose dependent manner (FIG. 3E).

6.1.6 Effect of Anti-CTLA-4 Antibodies on Human T Cells Following *Staphylococcus* Enterotoxin A (SEA) Stimulation The functional activity of anti-CTLA-4 antibodies on primary human T cells was assessed following *Staphylococcus* Enterotoxin A (SEA) stimulation. Cryopreserved PBMCs ($10^5$ cells/well) in RPMI1640 supplemented with penicillin, streptomycin, and 10% FBS (Hyclone) were added to 96-well NUNCLON delta surface plates (NUNC™). The cells were cultured in the presence of increasing antibody concentrations of 3.2, 16, 80, 400, 2000, 10000, and 50000 ng/ml and 100 ng/ml of SEA (Toxin Technologies) for 5 days at 37° C., 5% $CO_2$, and 97% humidity. The antibodies tested were AGEN1884w, a reference anti-CTLA-4 $IgG_1$ antibody, and an $IgG_1$ isotype control. Clarified supernatant was collected and stored at −80° C. until analysis. The titers of IL-2 were generated by electrochemiluminescence (MSD).

Figure 4A:
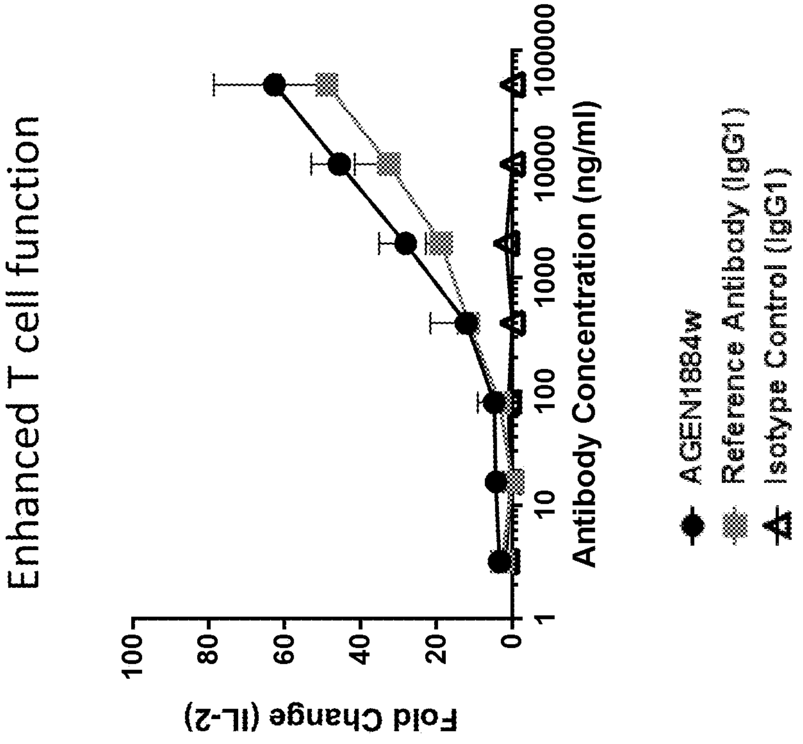

As shown in FIG. 4A, AGEN1884w increased IL-2 production of T cells in the presence of SEA stimulation.

6.1.7 Effect of Anti-CTLA-4 Antibody on IL-2-Luciferase Reporter Cell Line

Figure 4B:
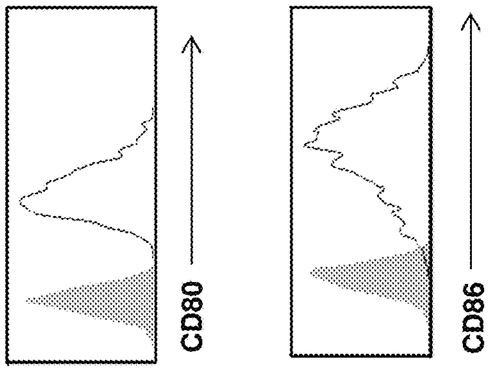

The functional activity of the anti-CTLA-4 antibody AGEN1884w was further analyzed using an IL-2-luciferase reporter assay. Briefly, a human T cell line (Jurkat) that endogenously expressed CD28 was engineered to constitutively express cell surface CTLA-4 and a luciferase reporter gene driven by an IL-2 promoter. The engineered Jurkat cell line was co-cultured with an antigen presenting cell line (Raji) that expressed CD80 and CD86. T cell receptor (TCR) triggering (Signal 1) was achieved with a mouse anti-human CD3 antibody and a goat anti-mouse IgG (H+L) antibody; and costimulatory signaling (Signal 2) was provided in trans by CD80 and CD86 expressed on Raji cells. The expression of CD80 and CD86 on Raji cells was confirmed by flow cytometry (FIG. 4B). Cross-linking of the TCR on the Jurkat T cell line triggered IL-2 expression leading to luciferase production, a surrogate marker for T cell activation. Co-culture of these two cell lines resulted in engagement of the inhibitory co-receptor CTLA-4 (expressed on Jurkat cells) with its natural ligands CD80 and CD86 (expressed on Raji cells) inhibiting T cell activation, demonstrated by a lack of luciferase expression. This inhibition was relieved upon addition of increasing concentrations of AGEN1884w (0 to 300 μg/ml) due to AGEN1884w blocking the interaction of CTLA-4 with its ligands CD80 and CD86 and shifting the interaction of these ligands with the costimulatory T cell co-receptor CD28. Luciferase expression was quantified using Bio-Glo™ reagent and the resulting data were used to determine maximum fold response values (fold increase with AGEN1884w compared with an $IgG_1$ isotype control antibody).

Figure 4C:
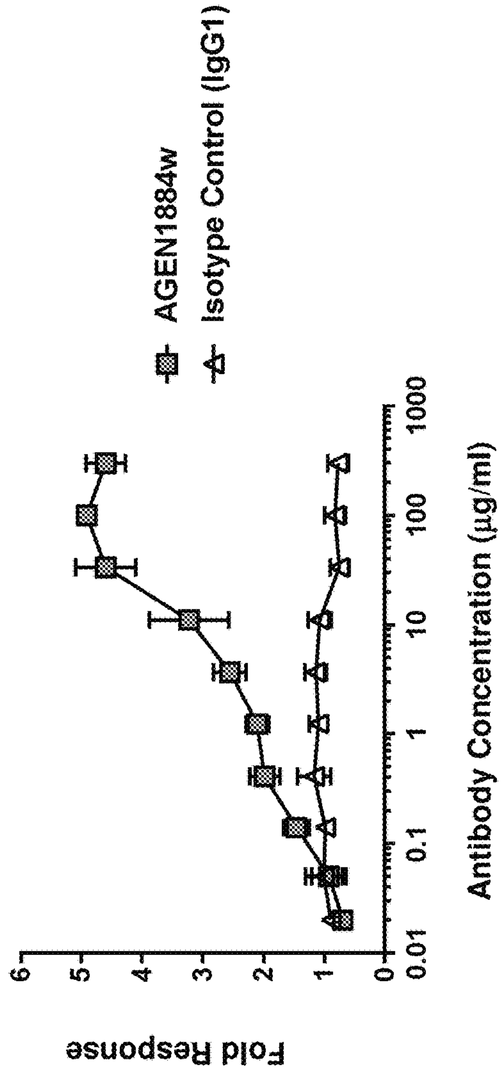

As shown in FIG. 4C, the anti-CTLA-4 antibody AGEN1884w dose-dependently released CTLA-4 mediated inhibition of T cells in this IL-2-luciferase reporter assay.

6.1.8 Lack of Agonistic Activity of Anti-CTLA-4 Antibody

The potential of AGEN1884w to mediate CTLA-4 forward signaling was evaluated. Primary CD3-expressing human T cells were isolated from peripheral blood mononuclear cells using Miltenyi Pan T cell microbead kit and cultured with a plate-bound anti-CD3 antibody (clone SP34, 10 μg/ml) to activate TCR signaling. AGEN1884w or an $IgG_1$ isotype control antibody was included in the context of TCR activation in either soluble or plate-bound formats (0.003 to 50 μg/ml). After four days in culture and a final 6-hour incubation with Brefeldin A (BD GolgiPlug™), cells were stained with fluorochrome conjugated antibodies against surface lineage markers, including an anti-CD3 antibody (APC Cy7, clone SP34), an anti-CD8 antibody (PE Cy7, clone SK1), and an anti-CD4 antibody (PercP Cy5.5, clone L200) followed by permeabilization of the cells with Cytofix-Cytoperm™ (Beckton Dickinson). For evaluation of intracellular cytokine production, cells were stained with an anti-IFNγ antibody (Alexa fluor 647, clone B27) and an anti-TNFα antibody (PE, clone Mab 11). Cells were acquired for flow cytometric analysis using a FACSCanto II and data analyses were performed with Flowjo Version 10.

Figure 4D:
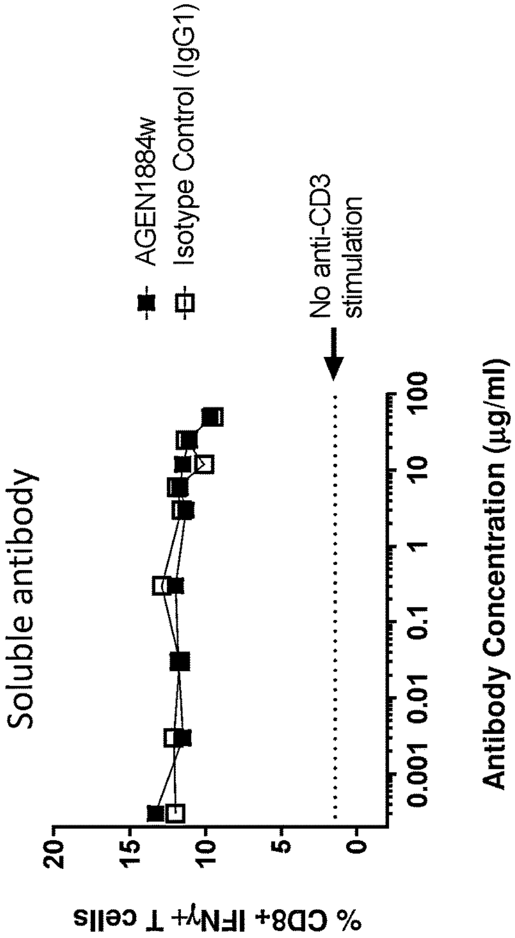
Figure 4E:
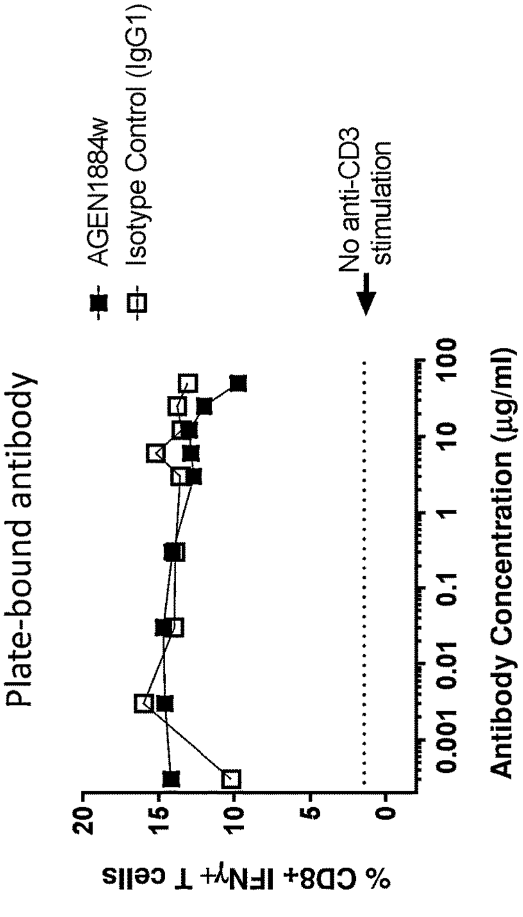

Increasing concentrations of either soluble (FIG. 4D) or plate-bound (FIG. 4E) AGEN1884w had no impact on the percentage of CD8+ IFNγ+ T cells, as compared to the $IgG_1$ isotype control antibody. At concentrations as high as 50 μg/ml, AGEN1884w did not act as a CTLA-4 agonist antibody.

6.1.9 Combination with Anti-LAG-3 Antibody or Anti-PD-1 Antibody

Figure 4F:
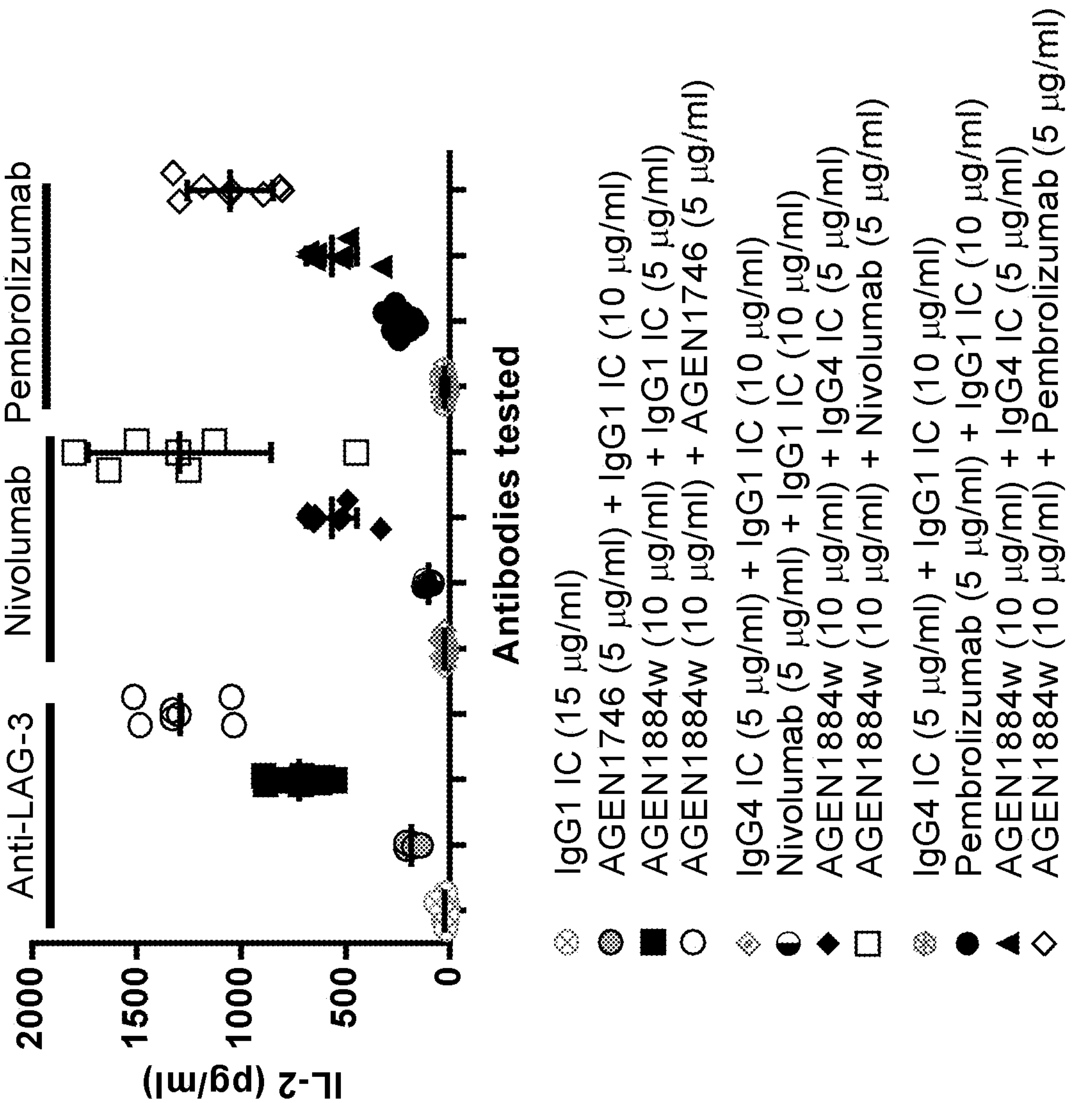

Next, the anti-CTLA-4 antibody AGEN1884w was examined for its synergy with an anti-LAG-3 antagonist antibody or anti-PD-1 antagonist antibodies using PBMCs sub-optimally stimulated with *Staphylococcus* Enterotoxin A (SEA). Briefly, cryopreserved human PBMCs (Research Blood Components) were plated at $10^5$ cells/well in RPMI1640 supplemented with Normocin™ (Invivogen #ant-nr) and 10% heat-inactivated FBS (Gibco, Invitrogen Corporation) in a 96-well NUNCLON delta surface plates (NUNC™). Cells were cultured with 100 ng/ml SEA (Toxin Technologies) in the presence of 10 μg/ml soluble AGEN1884w or an $IgG_1$ isotype control together with 5 μg/ml an anti-LAG-3 $IgG_1$ antibody AGEN1746, Nivolumab (lot AAB5719, Myoderm), Pembrolizumab (lot 7002688300, Myoderm), an $IgG_1$ isotype control, or an $IgG_4$ isotype control for 5 days at 37° C., 5% $CO_2$, and 97% humidity. The antibodies tested and their respective concentrations are shown in FIG. 4F. The anti-LAG-3 antibody AGEN1746 used in this assay was generated based on the variable regions of the antibody 25F7 provided in U.S. Application Publication No. US 2011/0150892 (herein incorporated by reference). AGEN1746 comprises a heavy chain of the amino acid sequence of SEQ ID NO: 91 and a light chain of the amino acid sequence of SEQ ID NO: 92 (Table 8). Clarified supernatants were collected and stored at −80° C. until analysis. The IL-2 cytokine was detected using AlphaLISA (Perkin Elmer). Mean and standard deviation of IL-2 concentration were calculated.

TABLE 8

Sequences of anti-LAG-3 antibody AGEN1746

| SEQ ID NO: | Description | Amino acid sequence |
|---|---|---|
| 91 | AGEN1746 heavy chain | QVQLQQWGAGLLKPSETLSLTCAVYGGSFSDYYWNWIR QPPGKGLEWIGEINHNGNTNSNPSLKSRVTLSLDTSKNQF SLKLRSVTAADTAVYYCAFGYSDYEYNWFDPWGQGTLV TVSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKRVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSREEMTKNQVSLTCLVKGFYPSDIAVEWESNGQPENNY KTTPPVLDSDGSFFLYSKLTVDKSRWQQGNVFSCSVMHE ALHNHYTQKSLSLSPG |
| 92 | AGEN1746 light chain | EIVLTQSPATLSLSPGERATLSCRASQSISSYLAWYQQKPG QAPRLLIYDASNRATGIPARFSGSGSGTDFTLTISSLEPEDF AVYYCQQRSNWPLTFGQGTNLEIKRSVAAPSVFIFPPSDE QLKSGTASVVCLLNNFYPREAKVQWKVDNALQSGNSQE SVTEQDSKDSTYSLSSTLTLSKADYEKHKVYACEVTHQG LSSPVTKSFNRGEC |

As shown in FIG. 4F, combination of the anti-CTLA-4 antibody AGEN1884w with the anti-LAG-3 antibody AGEN1746, the anti-PD-1 antibody Nivolumab, or the anti-PD-1 antibody Pembrolizumab enhanced IL-2 production from PBMCs sub-optimally stimulated with the SEA superantigen over single-agent treatment.

6.2 Example 2

Comparison of Anti-CTLA-4 Antibodies with IgG1 or IgG2 Constant Region

In this example, AGEN1884w, which is a human $IgG_1$ antibody, was converted to a human $IgG_2$ antibody, AGEN2041w. The antibody AGEN2041w shares the same heavy chain variable region and the same light chain as AGEN1884w but comprises a human $IgG_2$ constant region. The antibody AGEN2041w comprises a heavy chain sequence of SEQ ID NO: 94 and a light chain sequence of SEQ ID NO: 13.

In addition, a number of AGEN1884w with mutated Fc regions were also tested to examine the impact of FcγR interaction on the antagonistic activity of anti-CTLA-4 antibodies. AGEN1884w-N297A comprises a heavy chain sequence of SEQ ID NO: 95 and a light chain sequence of SEQ ID NO: 13. AGEN1884w-S267E/L328F comprises a heavy chain sequence of SEQ ID NO: 96 and a light chain sequence of SEQ ID NO: 13. AGEN1884w-S239D/A330L/I332E comprises a heavy chain sequence of SEQ ID NO: 97 and a light chain sequence of SEQ ID NO: 13. All the residues are numbered according to the EU numbering system.

6.2.1 Binding, Ligand Blocking, and Selectivity Analysis of Anti-CTLA-4 Antibodies with $IgG_2$ Constant Region The affinity of the anti-CTLA-4 antibody AGEN2041w, a reference anti-CTLA-4 $IgG_1$ antibody, and a reference anti-CTLA-4 $IgG_2$ antibody was analyzed by surface plasmon resonance as described in Section 6.1.1. The CTLA-4 antigens tested were recombinant human CTLA-4-Fc (R&D Systems, #7268-CT), recombinant human CTLA-4 (Sino Biological, #11159-H08H), recombinant cynomolgus CTLA-4-Fc (Sino Biological, #90213-C02H), and recombinant cynomolgus CTLA-4 (Sino Biological, #90213-C08H). The affinity values were listed in FIG. 5A.

Next, the binding of AGEN2041w to Jurkat cells over-expressing human CTLA-4 was analyzed in a flow cytometry assay similar to the assay described in Section 6.1.2. Briefly, Jurkat cells over-expressing human CTLA-4 (Promega) were stained first with serial dilutions of AGEN2041w, a reference anti-CTLA-4 $IgG_2$ antibody, or an $IgG_2$ isotype control and then with APC-conjugated mouse anti-human kappa antibody (Invitrogen). The samples were acquired on a FACSCanto II (BD Biosciences) and mean fluorescence intensities (MFI) were analyzed using FlowJo software (FlowJo, LLC). AGEN2041w bound to Jurkat cells over-expressing human CTLA-4 (FIG. 5B).

The ligand blocking activity of AGEN2041w, a reference anti-CTLA-4 $IgG_2$ antibody, and an $IgG_2$ isotype control was examined using suspension array technology as described in Section 6.1.5. As shown in FIG. 5C, AGEN2041w inhibited the binding of CD80 and CD86 to CTLA-4.

The selectivity of AGEN2041w and a reference anti-CTLA-4 $IgG_2$ antibody was compared with an $IgG_2$ isotype control antibody using suspension array technology as described in Section 6.1.3. As shown in FIGS. 5D and 5E, AGEN2041w binds specifically to human and cynomolgus CTLA-4. No significant binding to related family members (recombinant human CD28, ICOS, BTLA, and PD-1; and recombinant cynomolgus PD-1) was observed.

6.2.2 Effect of Anti-CTLA-4 Antibodies with $IgG_1$ or $IgG_2$ Constant Region on Human T Cells Following *Staphylococcus* Enterotoxin A (SEA) Stimulation The functional activities of anti-CTLA-4 antibodies AGEN1884w and AGEN2041w were tested in a primary human PBMC assay for the induction of IL-2. The assay was conducted as described in Section 6.1.6. Briefly, human PBMCs were cultured in the presence of increasing antibody concentrations of 0.016, 0.08, 0.4, 2.0, 10, 50, and 250 μg/ml and 100 ng/ml of SEA (Toxin Technologies) for 5 days. The antibodies tested were anti-CTLA-4 antibodies AGEN1884w and AGEN2041w, an $IgG_1$ isotype control, and an $IgG_2$ isotype control. The titer of IL-2 was determined by electrochemiluminescence (MSD).

Figure 6B:
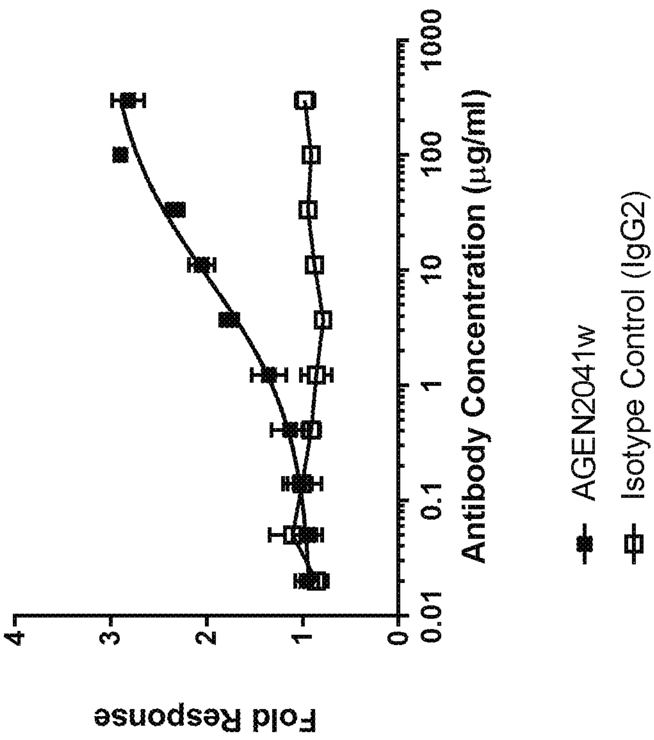
Figure 6A:
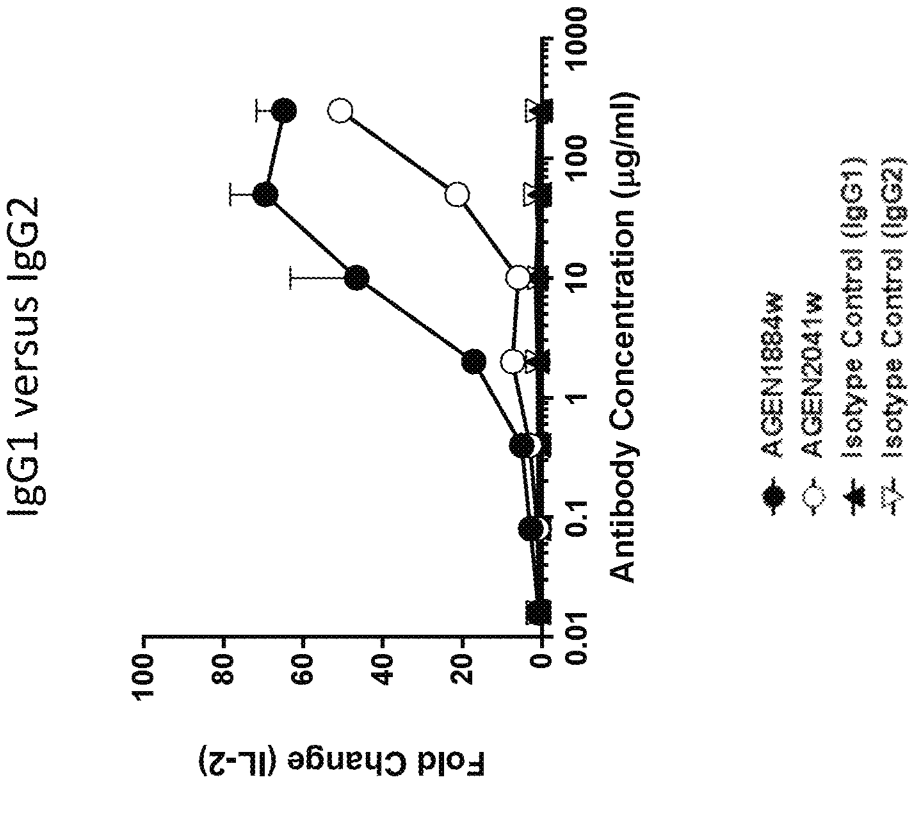

As shown in FIG. 6A, both AGEN1884w and AGEN2041w stimulated IL-2 production following SEA stimulation.

6.2.3 Effect of Anti-CTLA-4 Antibody with IgG2 Constant Region on IL-2-Luciferase Reporter Cell Line Next, the functional activity of the anti-CTLA-4 antibody AGEN2041w was evaluated using an IL-2-luciferase reporter assay similar to the one described above. In brief, T cells (Jurkat) genetically engineered to express surface CTLA-4 and a luciferase reporter gene downstream of an IL-2 promoter were added to wells containing increasing concentrations of AGEN2041w or an IgG2 isotype control. Subsequently, Raji cells, which endogenously express CD80 and CD86, and were genetically engineered to express "T Cell Activator", were added to cell culture. "T Cell Activator" is a proprietary cell surface receptor that binds T cell receptors (TCR) in an antigen independent manner leading to T cell activation. Stimulation of the TCR on the genetically engineered Jurkat cell line triggers IL-2 expression leading to luciferase production. Addition of AGEN2041w to this assay blocks the engagement of CTLA-4 (expressed on Jurkat cells) with its natural ligands CD80 and CD86 (expressed on Raji cells), augmenting luciferase production. Luciferase concentrations were quantified using Bio-Glo™ and the resulting data were used to determine maximum fold response values (fold increase with AGEN2041w compared with basal luciferase activity without antibodies).

As shown in FIG. 6B, increasing concentrations of AGEN2041w resulted in enhanced T cell activation in a dose-dependent manner. In contrast, the $IgG_2$ isotype control did not enhance luciferase expression even at the highest concentration tested.

6.2.4 Characterization of AGEN1884w Produced by a Stable Clone

In this example, AGEN1884w produced by a stable clone 105 (AGEN1884w-105) was examined for binding to cell-surface expressed CTLA-4 and for functional activity in a primary human PBMC assay.

Figure 7B:
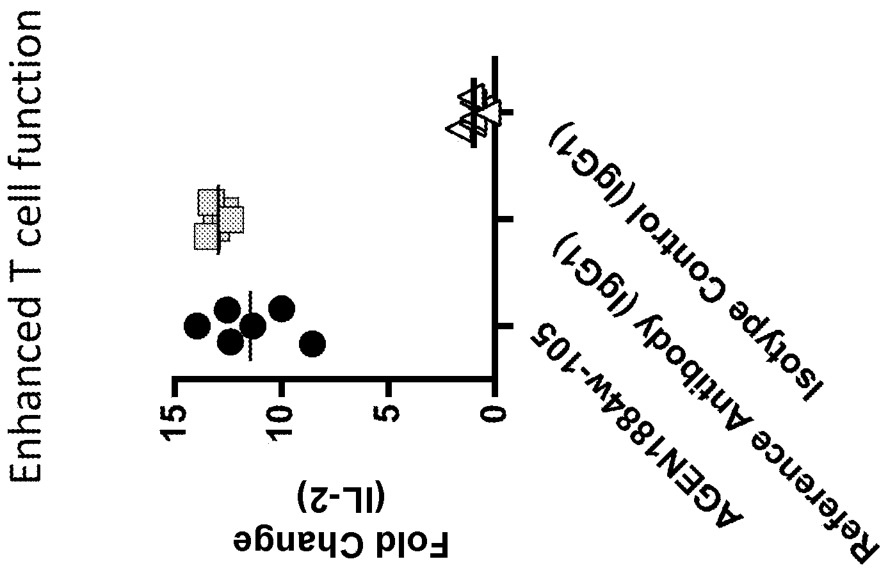
Figure 7A:
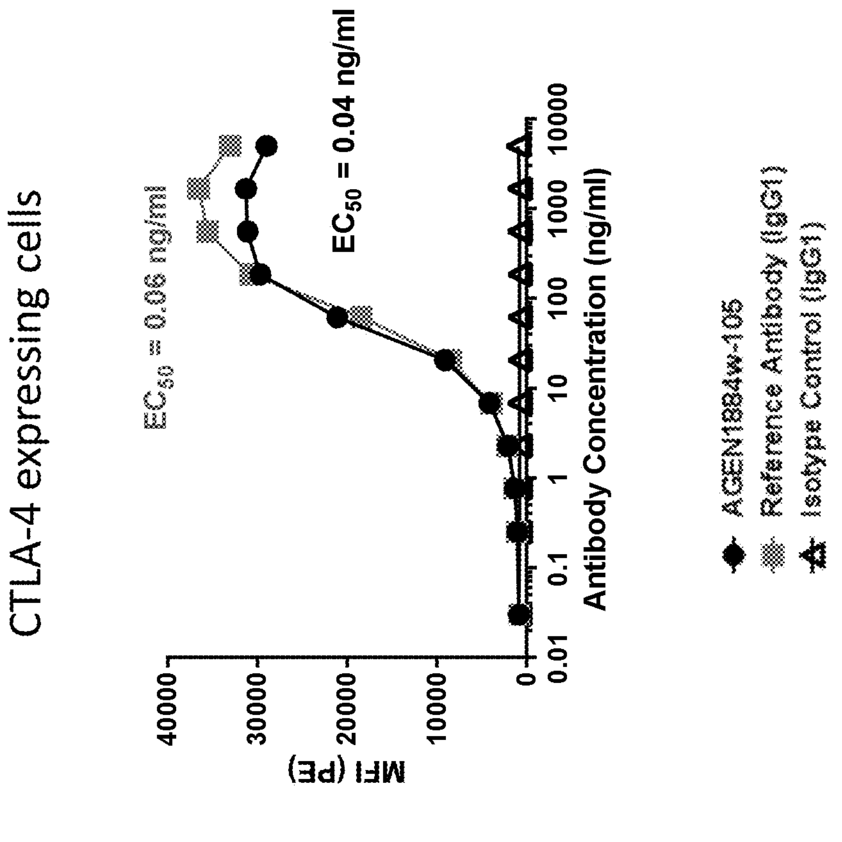

The binding of AGEN1884w-105 to Jurkat cells over-expressing human CTLA-4 was analyzed in a flow cytometry assay similar to the assay described in Section 6.1.2. Briefly, Jurkat cells over-expressing human CTLA-4 (Promega) were stained first with serial dilutions of AGEN1884w-105, a reference anti-CTLA-4 $IgG_1$ antibody, or an $IgG_1$ isotype control and then with PE-conjugated mouse anti-human kappa antibody (Invitrogen). The samples were acquired on a FACSCanto II (BD Biosciences) and mean fluorescence intensities (MFI) were analyzed using FlowJo software (FlowJo, LLC). AGEN1884w-105 bound to Jurkat cells over-expressing human CTLA-4 (FIG. 7A).

The ability of AGEN1884w-105 to induce IL-2 production was examined in an assay similar to the assay described in Section 6.1.6. Briefly, human PBMCs were cultured for 5 days in the presence of 100 ng/ml of SEA (Toxin Technologies) and 20 μg/ml of AGEN1884w-105, a reference anti-CTLA-4 $IgG_1$ antibody, or an $IgG_1$ isotype control. The titer of IL-2 was determined by electrochemiluminescence (MSD). As shown in FIG. 7B, AGEN1884w-105 induced IL-2 production following SEA stimulation.

6.2.5 Binding of Anti-CTLA-4 Antibodies to Surface-Expressed Fc Gamma Receptors

The binding of anti-CTLA-4 antibodies to human FcγRIIA, FcγRIIB, and FcγRIIIA expressed on the surface of CHO cells was measured by flow cytometry. Briefly, CHO cells were transfected with cDNA encoding for human $Fc\gamma RIIA^{H131}$, FcγRIIB, or $Fc\gamma RIIIA^{V158}$, generating the following CHO cell lines: $rCHO\text{-}huFc\gamma RIIA^{+}$, $rCHO\text{-}huFc\gamma RIIB^{+}$, and $rCHO\text{-}huFc\gamma RIIIA^{+}$. Binding of a dose titration of antibodies ranging from 0.0056-1000 μg/ml was performed and the primary antibodies were detected with an anti-human F(ab') secondary antibody conjugated with Phycoerythrin (PE) (Jackson Immune Research). The samples were tested by flow cytometry and the PE mean fluorescence intensity (MFI) values were analyzed and used to generate binding curves. The antibodies tested were AGEN1884w, AGEN2041w, a reference anti-CTLA-4 $IgG_1$ antibody, and an $IgG_1$ isotype control antibody. AGEN1884w produced in two different growth media was used in this study: the growth media CD FortiCHO™ from Life Technologies Inc./Thermo (AGEN1884w-FortiCHO) and the growth media PowerCHO™ 2 from Lonza (AGEN1884w-PowerCHO). The reference anti-CTLA-4 $IgG_1$ antibody contains a different $IgG_1$ allotype from the one in AGEN1884w. The $IgG_1$ isotype control antibody was only tested at 1000 μg/ml.

Figure 8A:
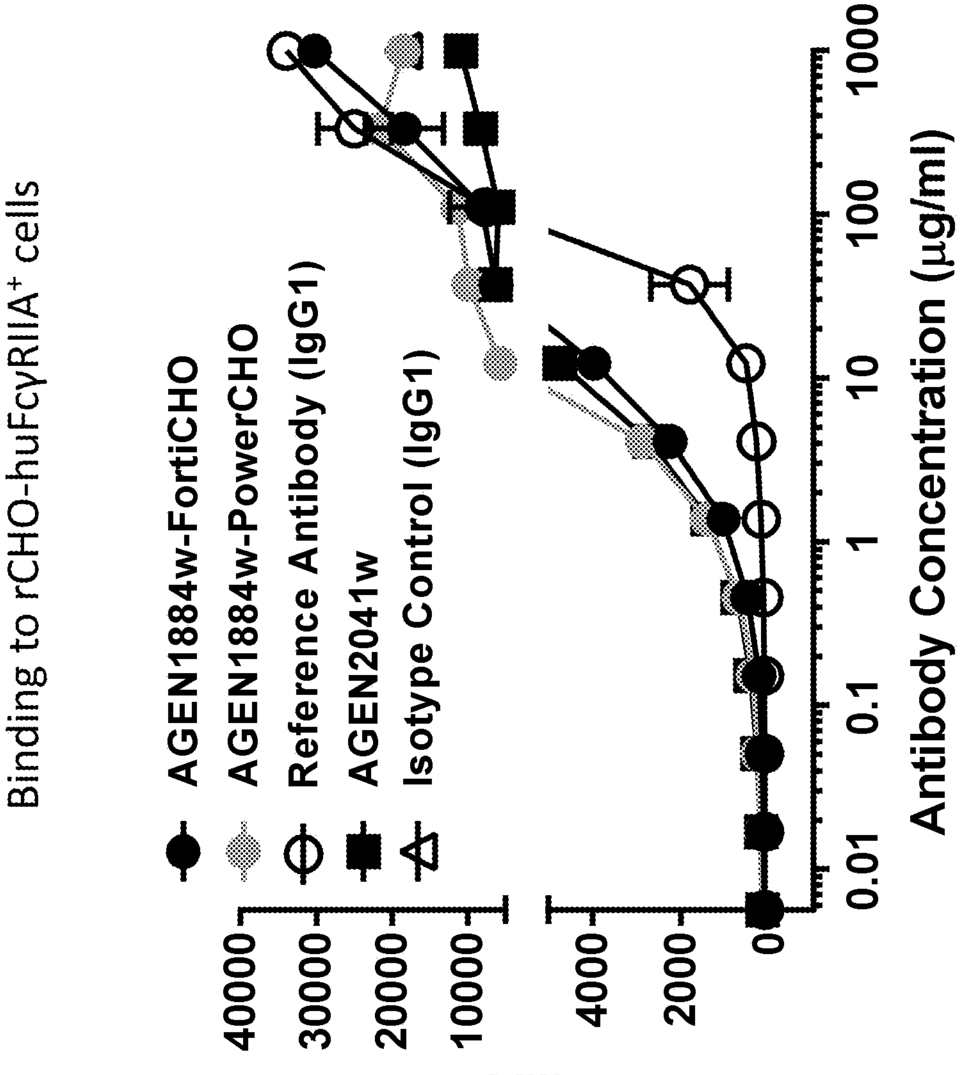
Figure 8B:
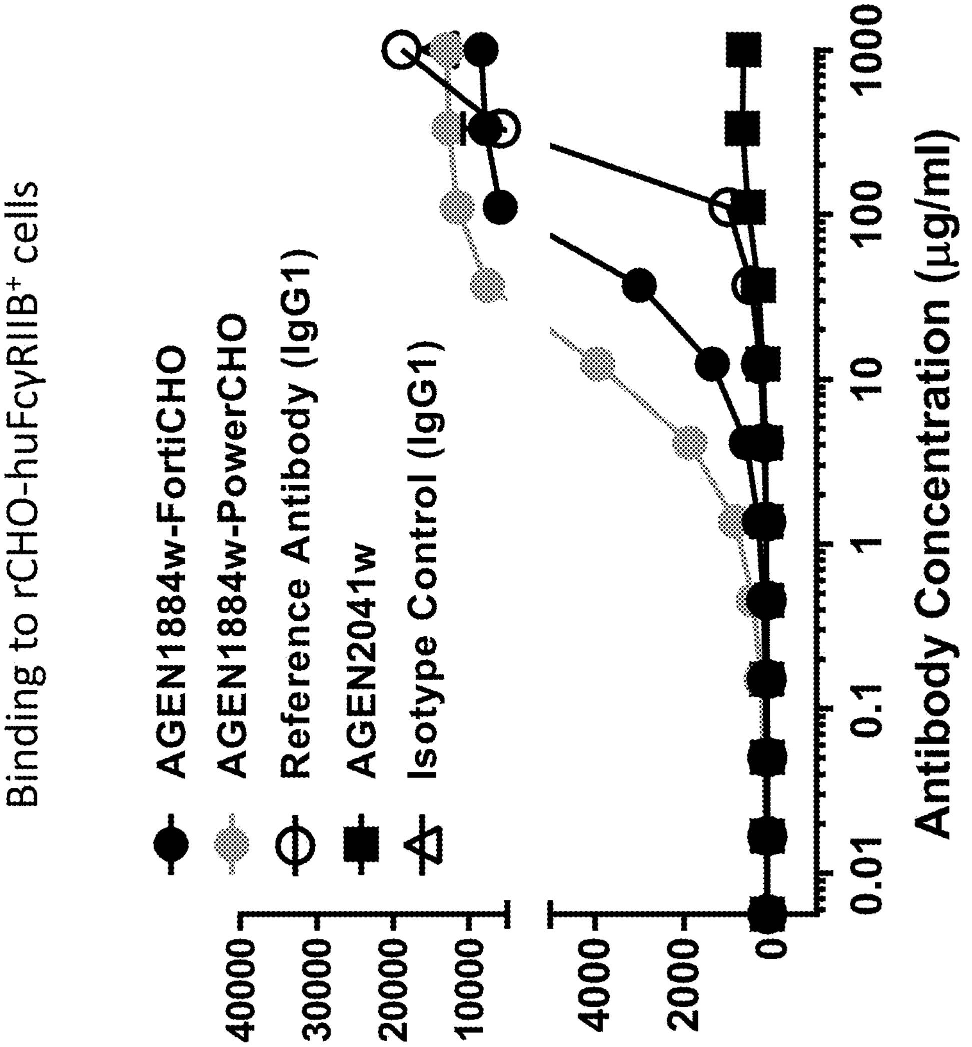
Figure 8C:
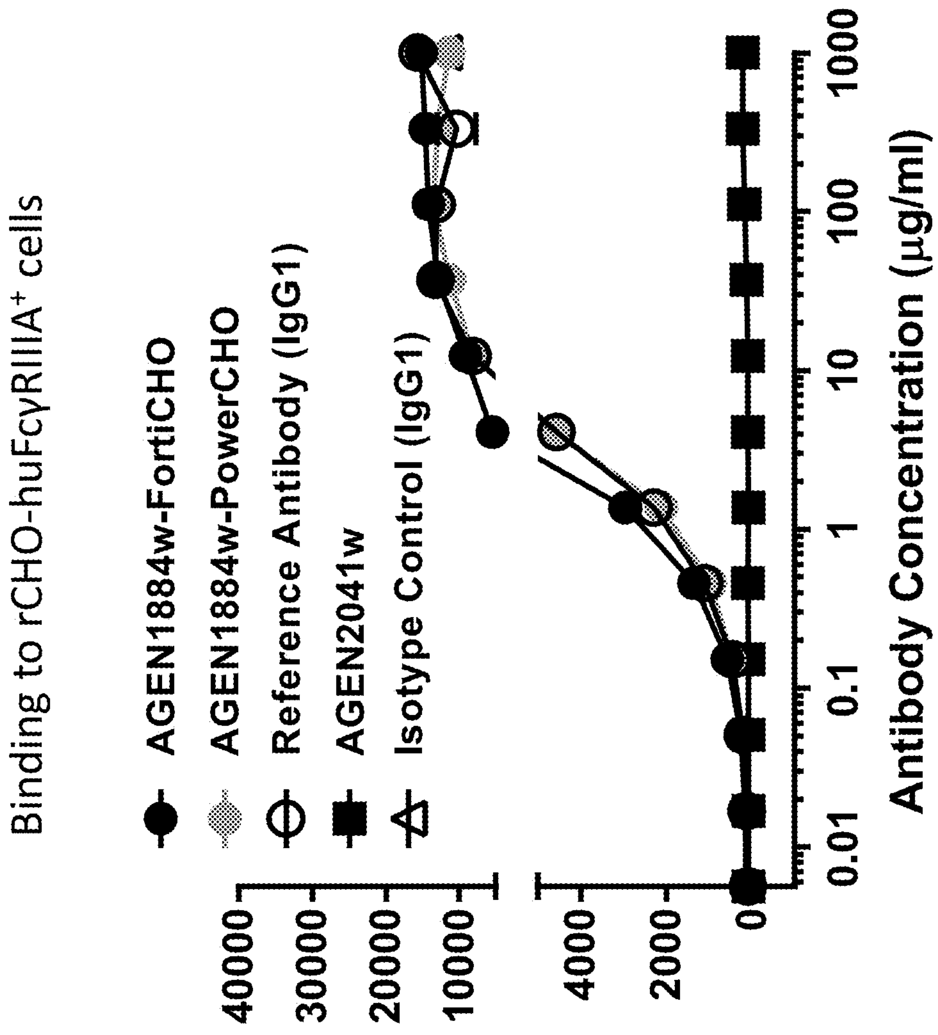

As shown in FIG. 8A, AGEN1884w-FortiCHO, AGEN1884w-PowerCHO, and AGEN2041w exhibited enhanced binding to $Fc\gamma RIIA^{H131}$-expressing cells than the reference anti-CTLA-4 $IgG_1$ antibody did. Similarly, the binding of AGEN1884w-PowerCHO and AGEN1884w-FortiCHO to FcγRIIB-expressing cells was stronger than that of the reference anti-CTLA-4 $IgG_1$ antibody (FIG. 8B). All the $IgG_1$ antibodies, AGEN1884w-FortiCHO, AGEN1884w-PowerCHO, and the reference anti-CTLA-4 $IgG_1$ antibody, bound similarly to $Fc\gamma RIIIA^{V158}$ expressed on the cell surface (FIG. 8C). AGEN2041w showed weaker binding to FcγRIIB (FIG. 8B) and $Fc\gamma RIIIA^{V158}$ (FIG. 8C) than the $IgG_1$ antibodies did.

6.2.6 Binding of Anti-CTLA-4 Antibodies to Recombinant Fc Gamma Receptors

The binding of the anti-CTLA-4 antibodies, AGEN1884w-FortiCHO, AGEN1884w-PowerCHO, AGEN2041w, and a reference anti-CTLA-4 $IgG_1$ antibody, to human FcγRIIA and FcγRIIIA was measured using surface plasmon resonance (BIAcore® 3000).

For binding to FcγRIIA, the direct immobilization method to a CM5 chip was applied using standard amine chemistry. The recombinant human FcγRIIA-His protein was diluted in sodium acetate solution, pH 4.0, to a concentration of 10 μg/ml and immobilized to flow cell 2 and 4 using an injection of 8 minutes at a flow rate of 5 μl/min. Flow cell 1 and 3, used as the reference flow cells, were sham-coupled, i.e., amine coupling reagents were run over the flow cells as in flow cell 2 and 4 without FcγRIIA. The performance of the immobilized FcγRIIA surfaces was tested using 1 mg/ml of Trastuzumab in HBS-EP Biacore running buffer over each flow cell for an injection of 0.5 minutes at a flow rate of 100 μl/min.

For binding to FcγRIIIA, the capture method was carried out through an immobilized anti-tetra His antibody to a CM5 chip. The mouse anti-His antibody was diluted in sodium acetate solution, pH 5.0, to a concentration of 10 μg/ml and immobilized to all four flow cells using a 5-minute injection at a flow rate of 10 μl/min through the standard amine chemistry. The recombinant human FcγRIIIA-His protein was captured to the chip surface by injecting a solution of FcγRIIIA-His at a concentration of 1 μg/ml for 2 minutes at a flow rate of 5 μl/min.

All the test antibodies were buffer exchanged into Biacore running buffer before analysis. The protein concentrations of the buffer exchanged samples and intermediate stock solutions were determined by measuring absorbance at 280 nm using a Nanodrop 1000 spectrophotometer.

Each sample was analyzed in an 8-point concentration series starting at 1000 μg/ml for a 2-fold dilution. The data were collected and processed using Biacore control software version 4.1 and BIAevaluation software version 4.1. The dose response curves were fitted to a five parameter logistic (5PL) model. The default curve weighting factors used were:

$$\text{Variance}=0.02\times\text{response (RU)}^{1.8}$$

The binding data were also analyzed using StatLIA version 3.2. Parallelism was assessed with the chi-squared test ($P<0.01$) in StatLIA.

Figure 9A:
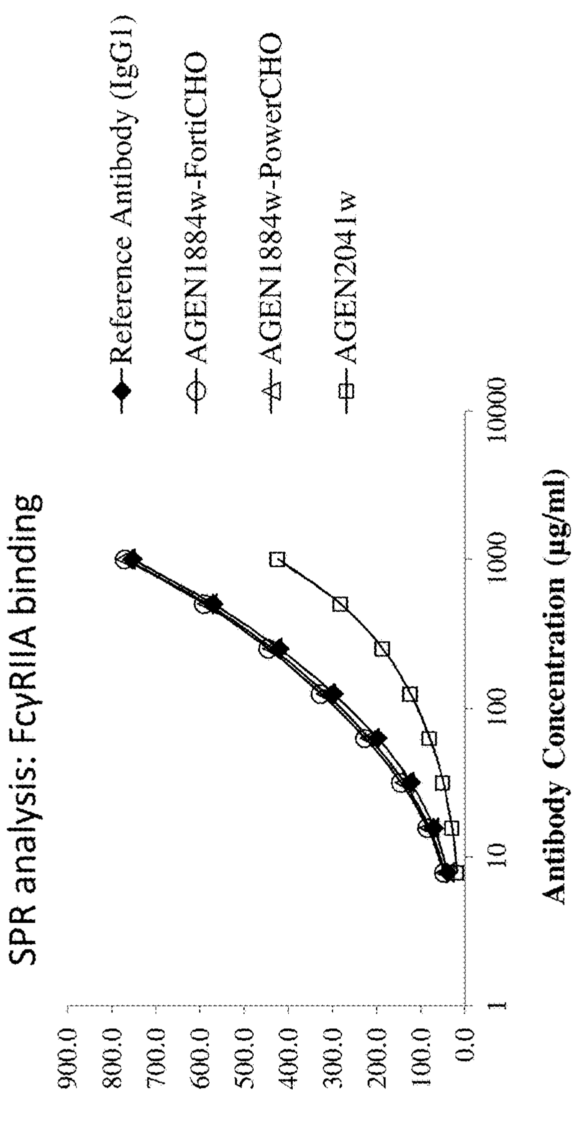
Figure 9B:
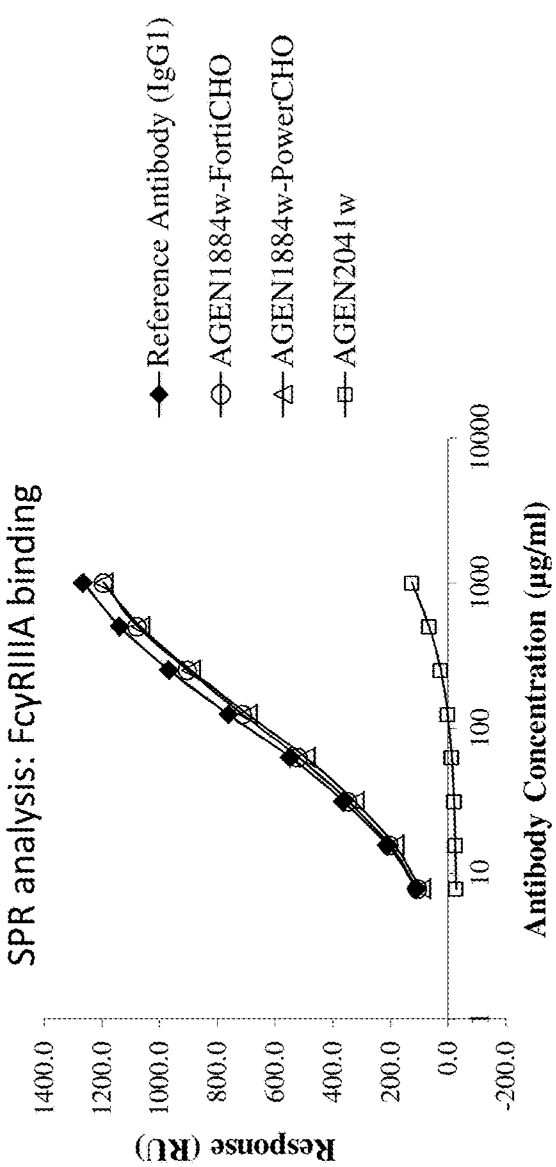

The mean response (resonance unit) of AGEN1884w-FortiCHO, AGEN1884w-PowerCHO, AGEN2041w, and a reference anti-CTLA-4 $IgG_1$ antibody for human FcγRIIA and human FcγRIIIA were shown in FIGS. 9A and 9B, respectively.

Figure 10A:
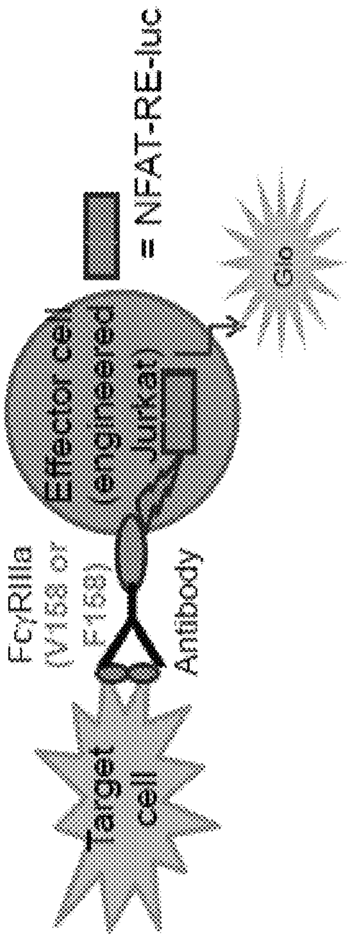
Figure 10B:
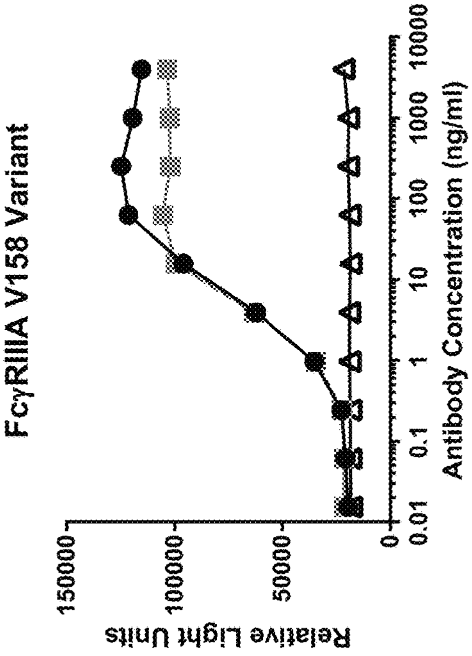

6.2.7 Effect of Anti-CTLA-4 Antibodies on Fc Gamma Receptor IIIA Reporter Cell Line The ability of AGEN1884w to co-engage CTLA-4 and signal via activating Fc gamma receptors was evaluated using a reporter cell line expressing Fc gamma receptor IIIA (FcγRIIIA) (Promega) together with target cells (assay schematic shown in FIG. 10A). In this assay, Jurkat cells expressing human CTLA-4 were used as target cells. Engineered Jurkat cells stably expressing FcγRIIIA, either the V158 variant (high affinity) or the F158 variant (low affinity), and an NFAT response element driving expression of firefly luciferase were used as effector cells. The assay was conducted according to the manufacturer's instructions. Briefly, 25 μl of target cells (25,000 cells) expressing CTLA-4 were mixed with 25 μl of serially diluted antibodies starting at 4 μg/ml in 96-well white flat bottom plates. 150,000 effector cells in 25 μl were then added to the well and the plates were incubated at 37° C. overnight. Binding of the antibody/antigen complex, wherein the antigen is located on the surface of the target cells, to FcγRIIIA signals to the promoter/reporter construct of the effector cells and results in luciferase gene transcription. On the next day, the plates were taken out of the incubator and let cool for 30 minutes. 75 μl of room temperature Bio-Glo reagent (Promega) was added to each well, luminescence was measured by EnVision Multimode Plate Reader (Perkin Elmer), and relative light units (RLU) were recorded. The antibodies tested were AGEN1884w-105 or AGEN 1884w (AGEN1884w-105 for FIGS. 10B, 10C, 10F, and 10G, and AGEN1884w for FIGS. 10D and 10E); AGEN1884w-N297A (FIGS. 10F and 10G); AGEN2041w (FIGS. 10D and 10E); a reference anti-CTLA-4 $IgG_1$ antibody (FIGS. 10B and 10C); and an $IgG_1$ isotype control antibody (FIGS. 10B-10G).

Figure 10C:
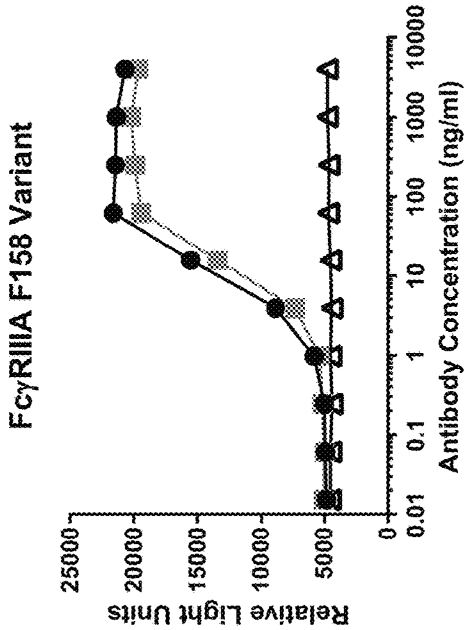
Figure 10C:
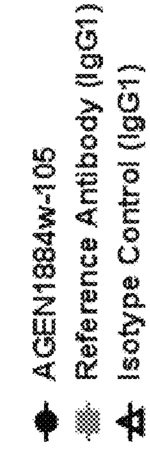
Figures 10D, 10E:
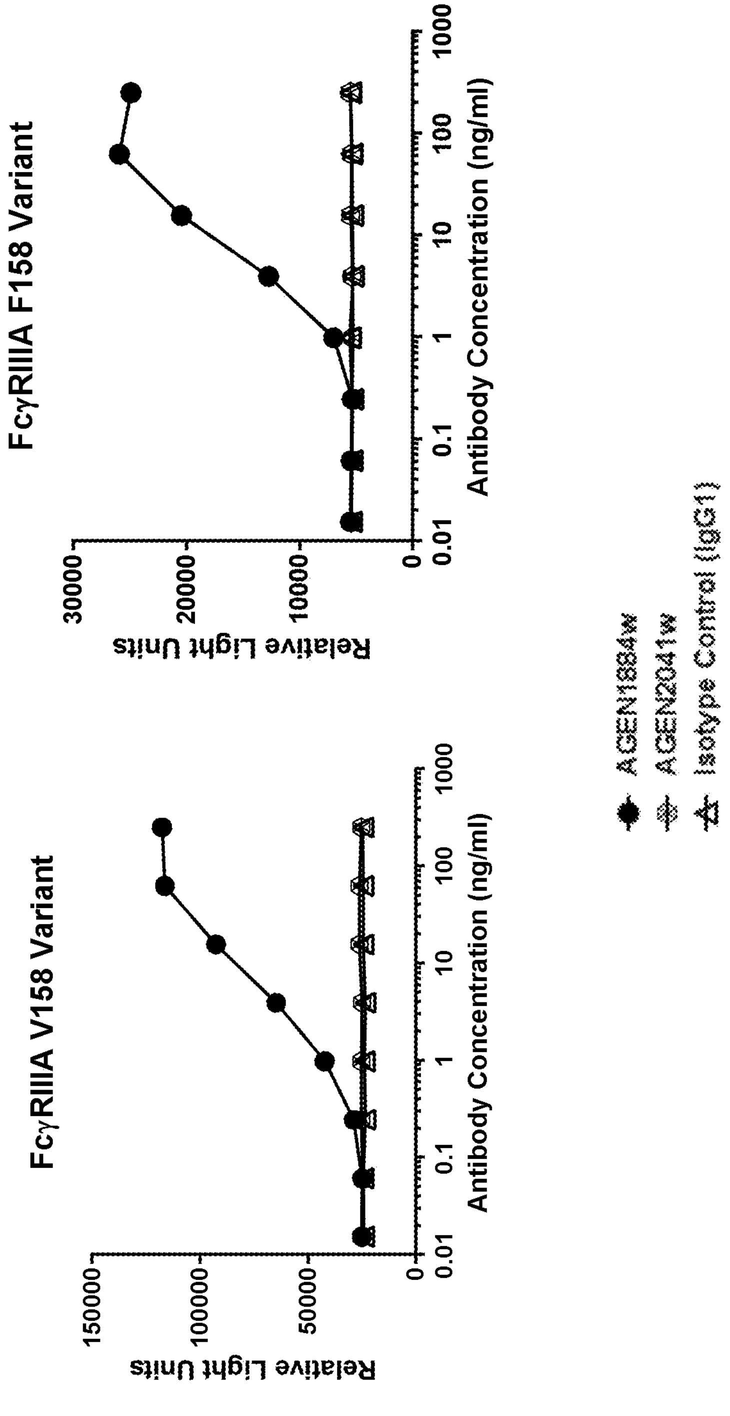
Figure 10G:
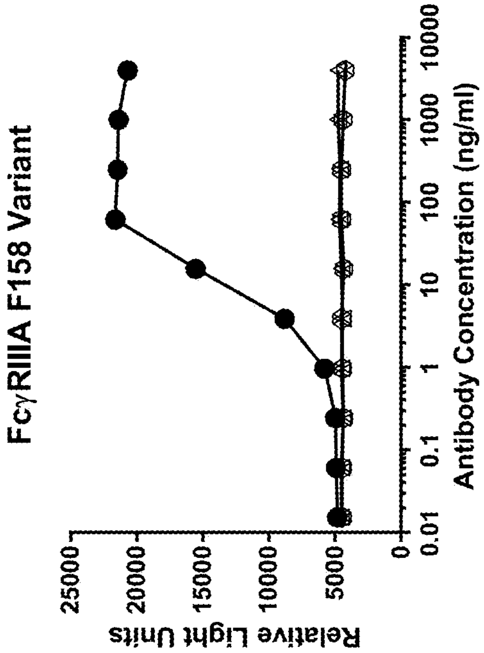
Figure 10F:
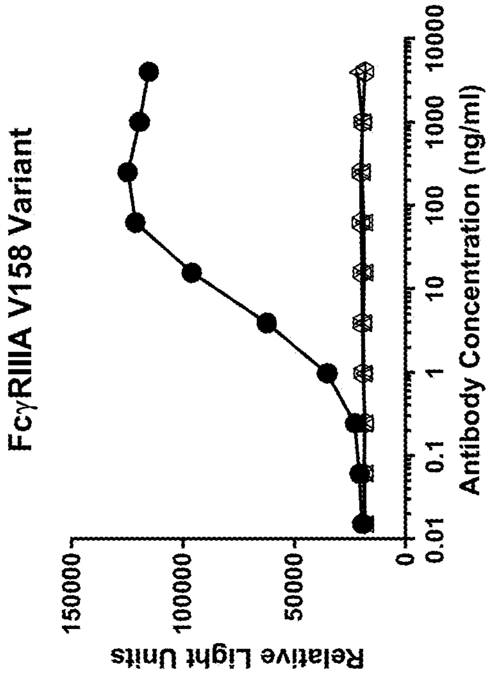
Figure 10F:
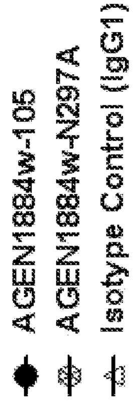

When bound to cells expressing CTLA-4, the $IgG_1$ antibody AGEN1884w-105 activated both the FcγRIIIA V158 variant (FIG. 10B) and the FcγRIIIA F158 variant (FIG. 10C). As expected, the $IgG_2$ antibody AGEN2041w did not signal via FcγRIIIA (FIGS. 10D and 10E). To confirm the specificity of this reporter assay, an Fc receptor (FcR)-silent variant of AGEN1884w (AGEN1884w-N297A) was tested in the same assay and this mutant did not signal via FcγRIIIA either (FIGS. 10F and 10G).

6.2.8 Effect of Anti-CTLA-4 Antibodies on Fc Gamma Receptor IIA Reporter Cell Line Next, the ability of AGEN2041w to co-engage CTLA-4 and signal via FcγRIIA was evaluated using a reporter cell line expressing FcγRIIA (Promega) together with target cells (Jurkat cells expressing human CTLA-4). Jurkat cells expressing FcγRIIA with the high affinity 131 H/H polymorphism and an NFAT response element driving expression of firefly luciferase were used as effector cells. Briefly, 25 μl of target cells ($6\times10^6$ cells/ml) were mixed with 25 μl of serially diluted antibodies starting at 0.1 μg/ml in duplicate wells of 96-well white assay plates. The antibodies tested were AGEN2041w, a reference anti-CTLA-4 IgG2 antibody, and an $IgG_2$ isotype control antibody. Then, 25 μl of effector cells ($6\times10^6$ cells/ml) were added to each well, resulting in a 1:1 effector to target ratio. The plates were incubated for 20 hours at 37° C. and 5% $CO_2$. After this incubation, Bio-Glo Luciferase Assay Reagent (Promega) was thawed at room temperature and 75 μl was added to each well. Within 5-10 minutes, luminescence was measured using the EnVision multilabel plate reader (PerkinElmer). Background luminescence was subtracted from each sample reading and the adjusted relative light units (RLU) were recorded.

Figure 11:
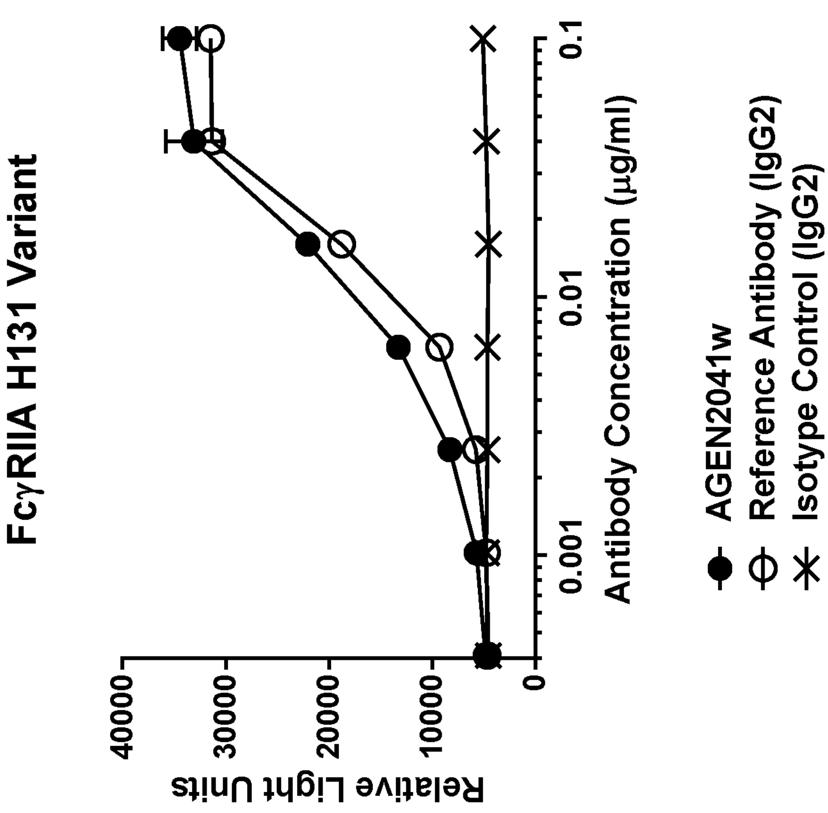

As shown in FIG. 11, when bound to cells expressing CTLA-4, the IgG2 antibody AGEN2041w activated $Fc\gamma RIIA^{H131}$.

6.2.9 Effect of Fc Gamma Receptor Binding on the Antagonistic Activity of Anti-CTLA-4 Antibodies In this example, the effect of FcγR binding on the antagonistic activity of anti-CTLA-4 antibodies was examined.

Figure 12A:
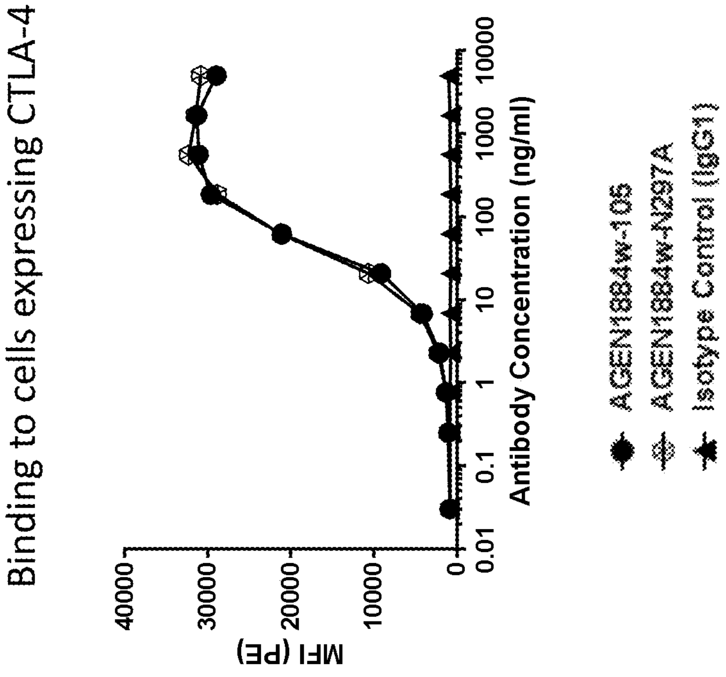

First, the binding of AGEN1884w-105 and AGEN1884w-N297A to cell-surface expressed CTLA-4 was compared in a flow cytometry assay similar to the assay described in Section 6.1.2. Briefly, Jurkat cells over-expressing human CTLA-4 (Promega) were stained first with serial dilutions of AGEN1884w-105, AGEN1884w-N297A, or an $IgG_1$ isotype control and then with PE-conjugated mouse anti-human kappa antibody (Invitrogen). The samples were acquired on a FACSCanto II (BD Biosciences) and mean fluorescence intensities (MFI) were analyzed using FlowJo software (FlowJo, LLC). AGEN1884w-105 and AGEN1884w-N297A showed similar binding to Jurkat cells over-expressing human CTLA-4 (FIG. 12A).

Next, the dependency on Fc receptor (FcR) engagement for in vitro functional activity was assessed in an assay similar to the assay described in Section 6.1.6. Briefly, human PBMCs were cultured for 5 days in the presence of 100 ng/ml of SEA (Toxin Technologies) and 20 μg/ml of AGEN1884w-105, AGEN1884w-N297A, or an $IgG_1$ isotype control. The titer of IL-2 was determined by electrochemiluminescence (MSD).

Figure 12B:
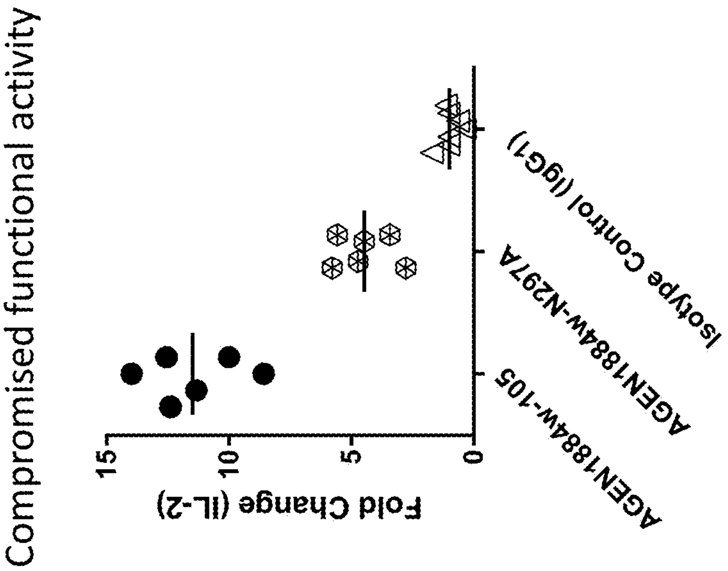

Despite similar binding to cell-surface expressed CTLA-4 (FIG. 12A), AGEN1884w-N297A showed reduced potentiation of IL-2 secretion as compared with that of AGEN1884w-105 in the primary human PBMC assay (FIG. 12B).

As further evidence of the requirement for FcR engagement for the functional activities, anti-CTLA-4 antibodies were tested for their ability to induce IL-2 secretion in the presence or absence of FcR blockers.

Figure 13B:
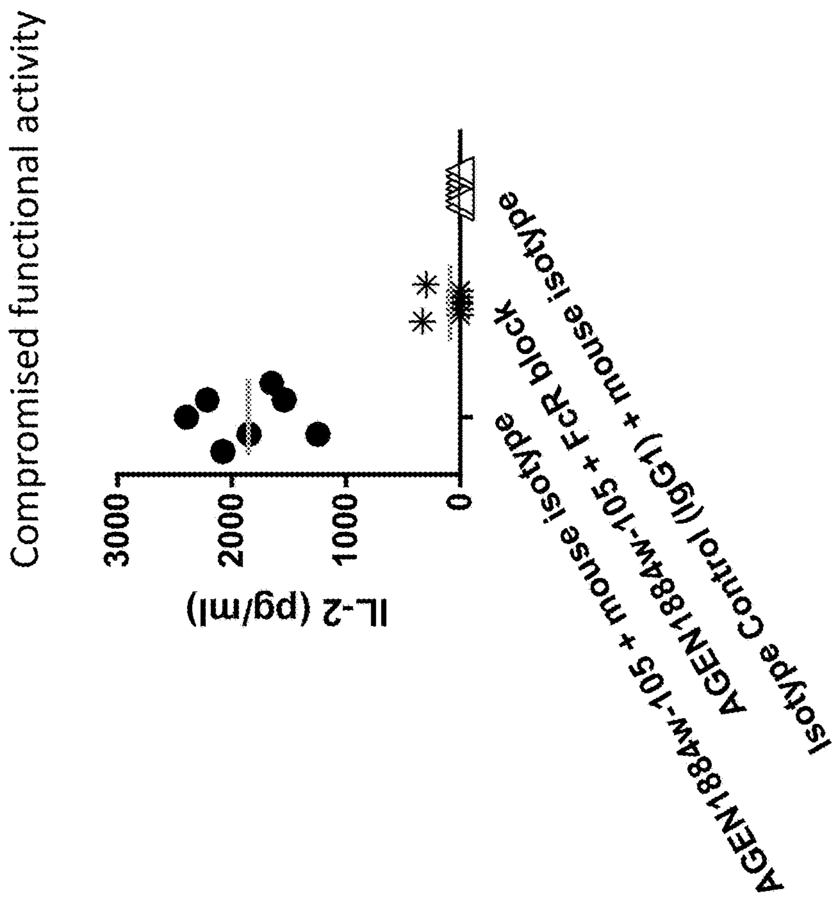
Figure 13A:
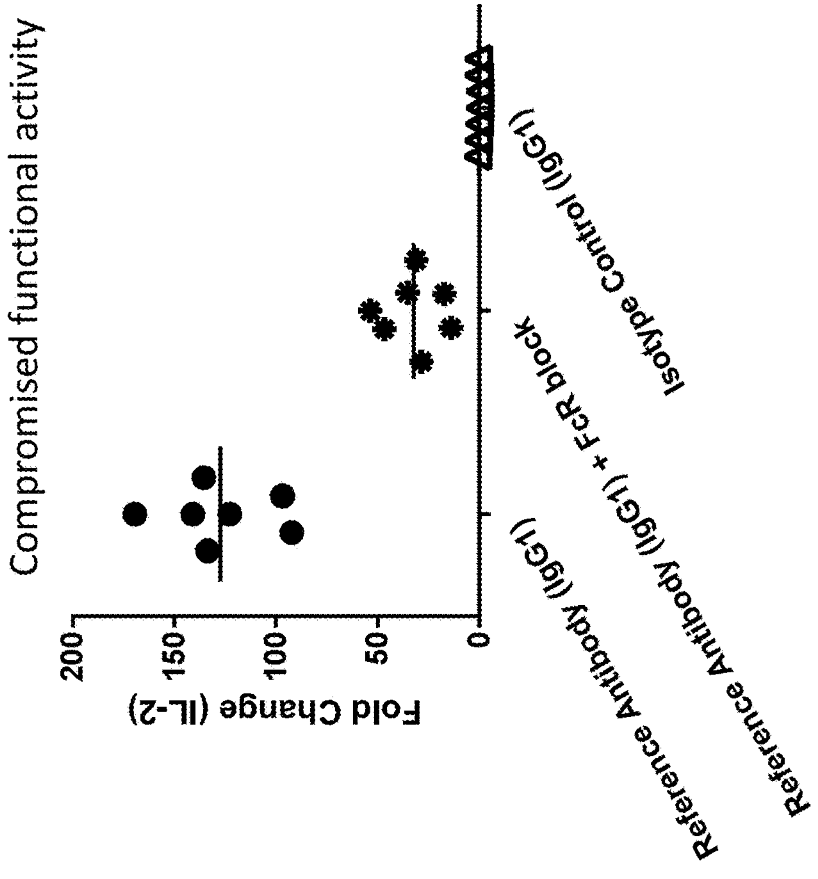

Cryopreserved PBMCs ($10^5$ cells/well) in RPMI1640 supplemented with penicillin, streptomycin, and 10% FBS (Hyclone) were added to 96-well NUNCLON delta surface plates (NUNC™). The cells were cultured with 100 ng/ml of SEA (Toxin Technologies) and 10 μg/ml of anti-CTLA-4 $IgG_1$ antibody or human $IgG_1$ isotype control, in the presence or absence of FcR blockers for 5 days at 37° C., 5% $CO_2$, and 97% humidity. The anti-CTLA-4 antibodies tested were a reference $IgG_1$ antibody (FIG. 13A) and AGEN1884w-105 (FIG. 13B). The FcR blockers were anti-CD16 (Biolegend #302013), anti-CD32 (R&D #AF1330), and anti-CD64 (R&D #AF1257) antibodies (10 μg/ml each) (FIG. 13A) or anti-CD32 antibody (eBiosciences #16-0329-81) alone (FIG. 13B). In the control groups in FIG. 13B, AGEN1884w-105 and the human $IgG_1$ isotype control were also incubated with a mouse $IgG_1$ isotype control (Biolegend #400124) as indicated in the figure. Clarified supernatant was collected and stored at −80° C. until analysis. The titers of IL-2 were generated by electrochemiluminescence (MSD).

FcR blockade, using antibodies against CD16, CD32, and CD64 (FIG. 13A) or using an antibody against CD32 (FIG. 13B), diminished the ability of anti-CTLA-4 antibodies to induce IL-2 secretion in this primary human PBMC assay.

Next, the functional activity of a number of anti-CTLA-4 antibodies with mutated Fc regions was tested using PBMCs. Briefly, cryopreserved human PBMCs (Research Blood Components) were plated at $10^5$ cells/well in RPMI1640 supplemented with Normocin™ (Invivogen) and 10% heat-inactivated FBS (Gibco, Invitrogen Corporation) in 96-well NUNCLON delta surface plates (NUNC™). The cells were cultured for 5 days at 37° C., 5% $CO_2$, and 97% humidity in the presence of 142 ng/ml of SEA (Toxin Technologies) and 10 μg/ml of AGEN1884w, AGEN1884w-N297A, AGEN1884w-S267E/L328F, AGEN1884w-S239D/A330L/I332E, AGEN2041w, an $IgG_1$ isotype control antibody, or an $IgG_2$ isotype control antibody. Clarified supernatant was collected and stored at −80° C. until analysis. The concentrations of IL-2 were measured by ELISA.

Figure 14:
FIG. 14 is a graph showing IL-2 production of human PBMCs upon *Staphylococcus* Enterotoxin A (SEA) stimulation in response to 10 μg/ml of AGEN1884w, AGEN1884w-N297A, AGEN1884w-S267E/L328F, AGEN1884w-S239D/A330L/I332E, AGEN2041w, an $IgG_1$ isotype control antibody, or an $IgG_2$ isotype control antibody. The mean values (bar) of IL-2 production are shown for each antibody tested.

AGEN1884w with the triple mutation S239D/A330L/I332E in the Fc region, which enhances binding to FcγRIIIA, stimulated more IL-2 secretion than AGEN1884w with the wild type $IgG_1$ Fc region (FIG. 14).

6.2.10 Fc Mediated Effector Cell Potential

In this example, the antibody AGEN1884w was analyzed for its ability to mediate NK cell cytotoxicity. In brief, Jurkat cells engineered to constitutively express CTLA-4 on the cell surface (target cells) were cultured at $1\times10^4$ cells/well in 96-well round bottom plates. Increasing concentrations of AGEN1884w, a reference anti-CTLA-4 $IgG_1$ antibody, or an isotype control antibody (all at 0 to 10 μg/ml), and $5\times10^4$ NK92-FcγRIIIA cells (effector cells) were added to the target cells. After incubating for 6 hours at 37° C. and 5% $CO_2$, lysis of target cells was assessed by photometric quantification of lactate dehydrogenase (LDH) released in the supernatant using a Cytotoxicity Detection Kit (LDH) (Roche) following the manufacturer's instructions. Data were acquired using a SoftMax® Pro Microplate Data Acquisition & Analysis Software. All antibody concentrations were tested in triplicate.

Figure 15:
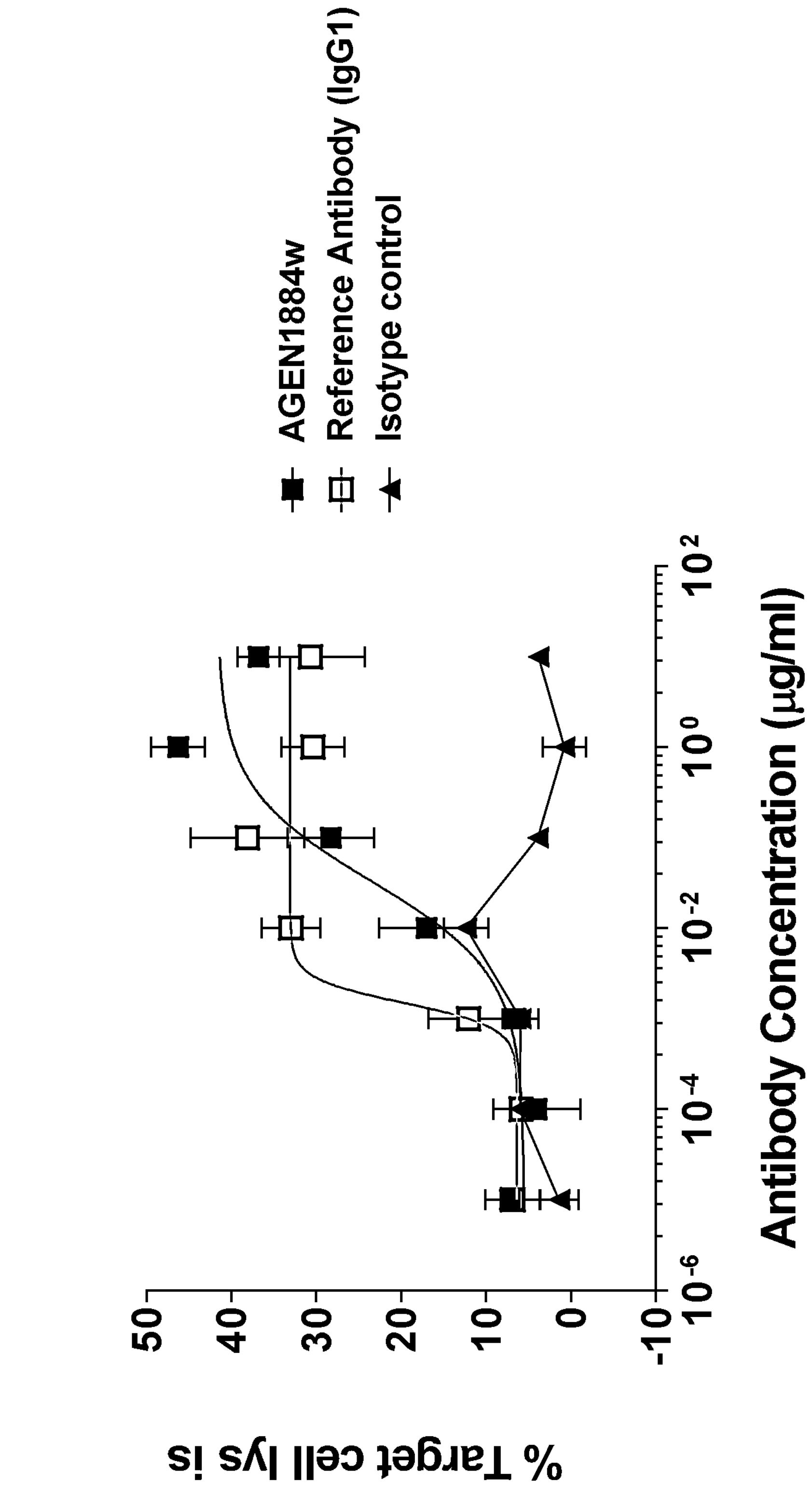
FIG. 15 is a graph showing percent of target cell lysis in the presence of effector cells together with a dose titration of AGEN1884w, a reference anti-CTLA-4 $IgG_1$ antibody, or an isotype control antibody. Jurkat cells engineered to constitutively express CTLA-4 on the cell surface were used as target cells and NK92-FcγRIIIA cells were used as effector cells.

As shown in FIG. 15, the antibody AGEN1884w effectively mediated lysis of CTLA-4 expressing target cells in the presence of effector cells.

6.2.11 Epitope Mapping of Anti-CTLA-4 Antibody

The interaction of the Fab fragment of AGEN1884w (AGEN1884w-Fab) with the extracellular domain of human CTLA-4 was studied by hydrogen-deuterium exchange (HDX) mass spectrometry. CTLA-4 extracellular domain alone or in combination with AGEN1884w-Fab, in phosphate buffered saline solution at pH 7.4, was diluted with a ten-fold volume of deuterium oxide labeling buffer and incubated for varying periods of time (0, 60, 300, 1800, and 7200 seconds) at room temperature. Exchange of deuterium for hydrogen was quenched by adding one volume of 4 M guanidine hydrochloride, 0.85 M TCEP (tris(2-carboxyethyl)phosphine) buffer and final pH was 2.5. Samples were then subjected to on-column pepsin/protease type XIII digestion and LC-MS analysis. Mass spectra were recorded in MS only mode. For the calculation of deuterium incorporation, the mass spectra for a given peptide were combined across the extracted ion chromatogram peak and the weighted average m/z was calculated. The mass increase from the mass of the native peptide (0 minute) to the weighted averaged mass corresponds to the level of deuterium incorporation. The deuterium buildup curves over exchange time for all the peptides were plotted for further analysis and were compared with HDExaminer software.

Most of the CTLA-4 peptides displayed identical or similar deuterium levels with and without the anti-human CTLA-4 Fab present. Several peptide segments, however, were found to have significantly decreased deuterium incorporation upon Fab binding. All the residues in this paragraph are numbered according to SEQ ID NO: 77. Two regions, $Q^{80}VT^{82}$ (SEQ ID NO: 78) and $Y^{135}PPPYYLGIGNGTQI^{149}$ (SEQ ID NO: 79), experienced strong deuterium protection when human CTLA-4 was bound to Fab. The strongest decrease in deuterium uptake was observed at $Y^{140}L^{141}$ which thus appeared to be a main feature of the epitope of AGEN1884w on CTLA-4. Inspection of the sequences of human and cynomolgus monkey CTLA-4, both of which AGEN1884w binds strongly, reveals almost complete sequence identity in the two regions described above, except for a methionine substitution for leucine at position 141 (FIG. 17A). In contrast, AGEN1884w does not bind to any significant extent to either mouse or rat CTLA-4 (data not shown) which differ from human CTLA-4 at $Y^{140}LGI^{143}$ (SEQ ID NO: 80) at three out of four positions (FIG. 17A). Further selectivity data show that AGEN1884w binds with high specificity to human and cynolmolgus monkey CTLA-4 and not to other related CD28 family members including CD28, ICOS, BTLA, and PD-1 (data not shown). Sequence comparison among these related proteins shows that the non-CTLA-4 proteins all differ at the $Y^{140}LGI^{143}$ (SEQ ID NO: 80) sequence (FIG. 17B), further supporting the importance of this epitope to the binding of AGEN1884w.

6.2.12 T-Dependent Antibody Response (TDAR) Study in Cynomolgus Monkeys

An eight week TDAR study in cynomolgus monkeys was conducted to examine the ability of AGEN1884w and AGEN2041w to potentiate T cell-dependent antibody responses to a Hepatitis B vaccine (ENERIX-G®) (HBsAg). The HBsAg vaccine was administered in three subcutaneous injections at 10 μg per injection (30 μg in total) in the hind leg on Day 1 (prime) and Day 29 (boost). AGEN1884w (N=6) or AGEN2041w (N=6) was given twice by intravenous bolus injection (10 mg/kg) on Day 1 and Day 29, together with the vaccine antigens. Using the same dosing schedule, one control group of animals (N=3) were given the HBsAg vaccine in combination with 3 mg/kg of a reference anti-CTLA-4 $IgG_1$ antibody and another control group of animals (N=6) received the HBsAg with the control article: 20 mM tris hydrochloride, 100 mM NaCl, 1% mannitol, 0.10 mM DTPA, 0.01% polysorbate 80, pH 7.0, but no anti-CTLA-4 antibody. During the eight week study, anti-HBsAg (IgG) analyses were conducted on serum samples collected at selected time points across the study (Day −20, −7, Day +15, +29, +43, +59, and +69). The serum titers were measured by a colorimetric ELISA assay.

The animals given AGEN1884w, AGEN2041w, the reference anti-CTLA-4 $IgG_1$ antibody, or the control article had normal anamnestic responses with measurable antibody titers following the second vaccine dose, which peaked and declined thereafter (FIGS. 18A and 18B). However, AGEN1884w, AGEN2041w, and the reference anti-CTLA-4 $IgG_1$ antibody were shown to enhance the anti-HBsAg IgG response over the control article given in the absence of an anti-CTLA-4 antibody.

6.3 Example 3

Characterization of Anti-CTLA-4 Antibodies

In this example, the following 19 anti-CTLA-4 antibodies were characterized for binding and ligand blocking: AGEN1884, AGEN1885, AGEN1886, AGEN1887, AGEN1888, AGEN1889, AGEN1890, AGEN1891, AGEN1892, AGEN1893, AGEN1894, AGEN1895, AGEN1896, AGEN1897, AGEN1898, AGEN1899, AGEN1900, AGEN1901, and AGEN1902. The variable heavy chain and variable light chain sequences of these antibodies were disclosed in Table 6. FIGS. 19A and 19B show sequence alignment of the variable heavy chains and variable light chains, respectively.

6.3.1 Binding and Ligand Blocking Analysis of Anti-CTLA-4 Antibodies

The affinity of the 19 anti-CTLA-4 antibodies described above was analyzed by surface plasmon resonance in an assay similar to the one described in Section 6.1.1. The CTLA-4 antigen tested was recombinant human CTLA-4-Fc (R&D Systems, #7268-CT). The anti-CTLA-4 antibodies (6 μg/ml in running buffer) were captured to the chip surface of a CM5sensor chip. The 19 antibodies bound to recombinant human CTLA-4 with nM affinity (data not shown).

The ligand blocking activity of the 19 anti-CTLA-4 antibodies was examined using suspension array technology in an assay similar to the one described in Section 6.1.5. Ligand blocking was tested in the presence of different concentrations of anti-CTLA-4 antibodies (3,000 ng/ml to 12 ng/ml before adding beads). As shown in FIGS. 20A-20E, all of the 19 anti-CTLA-4 antibodies blocked the binding of CTLA-4 to CD80 and CD86.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

What is claimed:

1. A host cell comprising:

(a) a first isolated polynucleotide encoding an antibody heavy chain variable region of an antibody that specifically binds human CTLA-4 protein, wherein the antibody heavy chain variable region comprises complementarity determining regions CDRH1, CDRH2, and CDRH3, wherein (i) CDRH1 comprises the amino acid sequence of $SYX_1MX_2$ (SEQ ID NO: 22), wherein $X_1$ is S or A; and $X_2$ is N or S;

(ii) CDRH2 comprises the amino acid sequence of SISSSSSYIYYADSVKG (SEQ ID NO: 2); and (iii) CDRH3 comprises the amino acid sequence of VGLMGPFXI (SEQ ID NO: 23), wherein X is D or N; and (b) a second isolated polynucleotide encoding an antibody light chain variable region of an antibody that specifically binds human CTLA-4 protein, wherein the antibody light chain variable region comprises complementarity determining regions CDRL1, CDRL2, and CDRL3, wherein (i) CDRL1 comprises the amino acid sequence of $RASQSVX_1X_2YLX_3$ (SEQ ID NO: 24), wherein:

$X_1$ is S or G;

$X_2$ is R, S, or T; and $X_3$ is G or A;

(ii) CDRL2 comprises the amino acid sequence of $X_1X_2SX_3RAT$ (SEQ ID NO: 25), wherein:

$X_1$ is G or A;

$X_2$ is A or T; and $X_3$ is T, S, R, or N; and (iii) CDRL3 comprises the amino acid sequence of $QQYGX_1SPX_2T$ (SEQ ID NO: 26), wherein:

$X_1$ is S or T; and $X_2$ is W or F.

2. The host cell of claim 1, wherein the first isolated polynucleotide encodes an antibody heavy chain variable region comprising CDRH1, CDRH2, and CDRH3 amino acid sequences selected from the group consisting of SEQ ID NOs 1, 2 and 3; 27, 2 and 3; and 27, 2 and 28, respectively.

3. The host cell of claim 1, wherein the second isolated polynucleotide encodes an antibody light chain variable region comprising CDRL1, CDRL2, and CDRL3 amino acid sequences selected from the group consisting of SEQ ID NOs: 4, 5, and 6; 29, 32, and 36; 29, 33, and 37; 30, 31, and 6; 29, 34, and 6; and 29, 35, and 37, respectively.

4. The host cell of claim 1, wherein:

(a) the first isolated polynucleotide encodes an antibody heavy chain variable region comprising CDRH1, CDRH2, and CDRH3 amino acid sequences selected from the group consisting of SEQ ID NOs 1, 2 and 3; 27, 2 and 3; and 27, 2 and 28, respectively; and (b) the second isolated polynucleotide encodes an antibody light chain variable region comprising CDRL1, CDRL2, and CDRL3 amino acid sequences selected from the group consisting of SEQ ID NOs: 4, 5, and 6; 29, 32, and 36; 29, 33, and 37; 30, 31, and 6; 29, 34, and 6; and 29, 35, and 37, respectively.

5. The host cell of claim 1, wherein:

(i) the first isolated polynucleotide encodes an antibody heavy chain variable region comprising the CDRH1, CDRH2, and CDRH3 amino acid sequences of SEQ ID NOs: 1, 2, and 3, respectively; and the second isolated polynucleotide encodes an antibody light chain variable region comprising the CDRL1, CDRL2, and CDRL3 amino acid sequences of SEQ ID NOs: 4, 5, and 6, respectively;

(ii) the first isolated polynucleotide encodes an antibody heavy chain variable region comprising the CDRH1, CDRH2, and CDRH3 amino acid sequences of SEQ ID NOs: 1, 2, and 3, respectively; and the second isolated polynucleotide encodes an antibody light chain variable region comprising the CDRL1, CDRL2, and CDRL3 amino acid sequences of SEQ ID NOs: 29, 32, and 36, respectively;

(iii) the first isolated polynucleotide encodes an antibody heavy chain variable region comprising the CDRH1, CDRH2, and CDRH3 amino acid sequences of SEQ ID NOs: 1, 2, and 3, respectively; and the second isolated polynucleotide encodes an antibody light chain variable region comprising the CDRL1, CDRL2, and CDRL3 amino acid sequences of SEQ ID NOs: 29, 33, and 37, respectively;

(iv) the first isolated polynucleotide encodes an antibody heavy chain variable region comprising the CDRH1, CDRH2, and CDRH3 amino acid sequences of SEQ ID NOs: 27, 2, and 3, respectively; and the second isolated polynucleotide encodes an antibody light chain variable region comprising the CDRL1, CDRL2, and CDRL3 amino acid sequences of SEQ ID NOs: 4, 5, and 6, respectively;

(v) the first isolated polynucleotide encodes an antibody heavy chain variable region comprising the CDRH1, CDRH2, and CDRH3 amino acid sequences of SEQ ID NOs: 27, 2, and 3, respectively; and the second isolated polynucleotide encodes an antibody light chain variable region comprising the CDRL1, CDRL2, and CDRL3 amino acid sequences of SEQ ID NOs: 29, 33, and 37, respectively;

(vi) the first isolated polynucleotide encodes an antibody heavy chain variable region comprising the CDRH1, CDRH2, and CDRH3 amino acid sequences of SEQ ID NOs: 1, 2, and 3, respectively; and the second isolated polynucleotide encodes an antibody light chain variable region comprising the CDRL1, CDRL2, and CDRL3 amino acid sequences of SEQ ID NOs: 30, 31, and 6, respectively;

(vii) the first isolated polynucleotide encodes an antibody heavy chain variable region comprising the CDRH1, CDRH2, and CDRH3 amino acid sequences of SEQ ID NOs: 1, 2, and 3, respectively; and the second isolated polynucleotide encodes an antibody light chain variable region comprising the CDRL1, CDRL2, and CDRL3 amino acid sequences of SEQ ID NOs: 29, 34, and 6, respectively;

(viii) the first isolated polynucleotide encodes an antibody heavy chain variable region comprising the CDRH1, CDRH2, and CDRH3 amino acid sequences of SEQ ID NOs: 1, 2, and 3, respectively; and the second isolated polynucleotide encodes an antibody light chain variable region comprising the CDRL1, CDRL2, and CDRL3 amino acid sequences of SEQ ID NOs: 29, 35, and 37, respectively;

(ix) the first isolated polynucleotide encodes an antibody heavy chain variable region comprising the CDRH1, CDRH2, and CDRH3 amino acid sequences of SEQ ID NOs: 27, 2, and 28, respectively; and the second isolated polynucleotide encodes an antibody light chain variable region comprising the CDRL1, CDRL2, and CDRL3 amino acid sequences of SEQ ID NOs: 4, 5, and 6, respectively;

(x) the first isolated polynucleotide encodes an antibody heavy chain variable region comprising the CDRH1, CDRH2, and CDRH3 amino acid sequences of SEQ ID NOs: 27, 2, and 28, respectively; and the second isolated polynucleotide encodes an antibody light chain variable region comprising the CDRL1, CDRL2, and CDRL3 amino acid sequences of SEQ ID NOs: 29, 32, and 36, respectively;

(xi) the first isolated polynucleotide encodes an antibody heavy chain variable region comprising the CDRH1, CDRH2, and CDRH3 amino acid sequences of SEQ ID NOs: 27, 2, and 28, respectively; and the second isolated polynucleotide encodes an antibody light chain variable region comprising the CDRL1, CDRL2, and CDRL3 amino acid sequences of SEQ ID NOs: 29, 33, and 37, respectively; or (xii) the first isolated polynucleotide encodes an antibody heavy chain variable region comprising the CDRH1, CDRH2, and CDRH3 amino acid sequences of SEQ ID NOs: 27, 2, and 28, respectively; and the second isolated polynucleotide encodes an antibody light chain variable region comprising the CDRL1, CDRL2, and CDRL3 amino acid sequences of SEQ ID NOs: 29, 35, and 37, respectively.

6. The host cell of claim 1, wherein:

(a) the first isolated polynucleotide encodes an antibody heavy chain variable region comprising CDRH1, CDRH2, and CDRH3 amino acid sequences selected from the group consisting of SEQ ID NOs 1, 2 and 3, respectively; and (b) the second isolated polynucleotide encodes an antibody light chain variable region comprising CDRL1, CDRL2, and CDRL3 amino acid sequences selected from the group consisting of SEQ ID NOs: 4, 5, and 6, respectively.

7. The host cell of claim 1, wherein the first isolated polynucleotide encodes a heavy chain variable region comprising an amino acid sequence selected from the group consisting of SEQ ID NOs: 7, 38-42, and 72.

8. The host cell of claim 1, wherein the second isolated polynucleotide encodes a light chain variable region comprising an amino acid sequence selected from the group consisting of SEQ ID NOs: 8, 43-47, and 73.

9. The host cell of claim 1, wherein:

(a) the first isolated polynucleotide encodes an antibody heavy chain variable region comprising an amino acid sequence selected from the group consisting of SEQ ID NOs: 7, 38-42, and 72; and (b) the second isolated polynucleotide encodes an antibody light chain variable region comprising an amino acid sequence selected from the group consisting of SEQ ID NOs: 8, 43-47, and 73.

10. The host cell of claim 1, wherein:

(i) the first isolated polynucleotide encodes an antibody heavy chain variable region comprising the amino acid sequence of SEQ ID NO: 7; and the second isolated polynucleotide encodes an antibody light chain variable region comprising the amino acid sequence of SEQ ID NO: 8;

(ii) the first isolated polynucleotide encodes an antibody heavy chain variable region comprising the amino acid sequence of SEQ ID NO: 7; and the second isolated polynucleotide encodes an antibody light chain variable region comprising the amino acid sequence of SEQ ID NO: 44;

(iii) the first isolated polynucleotide encodes an antibody heavy chain variable region comprising the amino acid sequence of SEQ ID NO: 7; and the second isolated polynucleotide encodes an antibody light chain variable region comprising the amino acid sequence of SEQ ID NO: 45;

(iv) the first isolated polynucleotide encodes an antibody heavy chain variable region comprising the amino acid sequence of SEQ ID NO: 38; and the second isolated polynucleotide encodes an antibody light chain variable region comprising the amino acid sequence of SEQ ID NO: 8;

(v) the first isolated polynucleotide encodes an antibody heavy chain variable region comprising the amino acid sequence of SEQ ID NO: 38; and the second isolated polynucleotide encodes an antibody light chain variable region comprising the amino acid sequence of SEQ ID NO: 45;

(vi) the first isolated polynucleotide encodes an antibody heavy chain variable region comprising the amino acid sequence of SEQ ID NO: 39; and the second isolated polynucleotide encodes an antibody light chain variable region comprising the amino acid sequence of SEQ ID NO: 43;

(vii) the first isolated polynucleotide encodes an antibody heavy chain variable region comprising the amino acid sequence of SEQ ID NO: 39; and the second isolated polynucleotide encodes an antibody light chain variable region comprising the amino acid sequence of SEQ ID NO: 45;

(viii) the first isolated polynucleotide encodes an antibody heavy chain variable region comprising the amino acid sequence of SEQ ID NO: 39; and the second isolated polynucleotide encodes an antibody light chain variable region comprising the amino acid sequence of SEQ ID NO: 46;

(ix) the first isolated polynucleotide encodes an antibody heavy chain variable region comprising the amino acid sequence of SEQ ID NO: 39; and the second isolated polynucleotide encodes an antibody light chain variable region comprising the amino acid sequence of SEQ ID NO: 47;

(x) the first isolated polynucleotide encodes an antibody heavy chain variable region comprising the amino acid sequence of SEQ ID NO: 40; and the second isolated polynucleotide encodes an antibody light chain variable region comprising the amino acid sequence of SEQ ID NO: 43;

(xi) the first isolated polynucleotide encodes an antibody heavy chain variable region comprising the amino acid sequence of SEQ ID NO: 40; and the second isolated polynucleotide encodes an antibody light chain variable region comprising the amino acid sequence of SEQ ID NO: 8;

(xii) the first isolated polynucleotide encodes an antibody heavy chain variable region comprising the amino acid sequence of SEQ ID NO: 40; and the second isolated polynucleotide encodes an antibody light chain variable region comprising the amino acid sequence of SEQ ID NO: 44;

(xiii) the first isolated polynucleotide encodes an antibody heavy chain variable region comprising the amino acid sequence of SEQ ID NO: 40; and the second isolated polynucleotide encodes an antibody light chain variable region comprising the amino acid sequence of SEQ ID NO: 45;

(xiv) the first isolated polynucleotide encodes an antibody heavy chain variable region comprising the amino acid sequence of SEQ ID NO: 41; and the second isolated polynucleotide encodes an antibody light chain variable region comprising the amino acid sequence of SEQ ID NO: 8;

(Xv) the first isolated polynucleotide encodes an antibody heavy chain variable region comprising the amino acid sequence of SEQ ID NO: 41; and the second isolated polynucleotide encodes an antibody light chain variable region comprising the amino acid sequence of SEQ ID NO: 44;

(xvi) the first isolated polynucleotide encodes an antibody heavy chain variable region comprising the amino acid sequence of SEQ ID NO: 41; and the second isolated polynucleotide encodes an antibody light chain variable region comprising the amino acid sequence of SEQ ID NO: 45;

(xvii) the first isolated polynucleotide encodes an antibody heavy chain variable region comprising the amino acid sequence of SEQ ID NO: 41; and the second isolated polynucleotide encodes an antibody light chain variable region comprising the amino acid sequence of SEQ ID NO: 47;

(xviii) the first isolated polynucleotide encodes an antibody heavy chain variable region comprising the amino acid sequence of SEQ ID NO: 42; and the second isolated polynucleotide encodes an antibody light chain variable region comprising the amino acid sequence of SEQ ID NO: 43; or (xix) the first isolated polynucleotide encodes an antibody heavy chain variable region comprising the amino acid sequence of SEQ ID NO: 42; and the second isolated polynucleotide encodes an antibody light chain variable region comprising the amino acid sequence of SEQ ID NO: 45.

11. The host cell of claim 1, wherein:

(a) the first isolated polynucleotide encodes an antibody heavy chain variable region comprising the amino acid of SEQ ID NO: 7; and (b) the second isolated polynucleotide encodes an antibody light chain variable region comprising the amino acid sequence of SEQ ID NO: 8.

12. The host cell of claim 1, wherein the first isolated polynucleotide encodes an antibody heavy chain of an antibody that specifically binds human CTLA-4 protein, wherein the antibody heavy chain comprises an amino acid sequence selected from the group consisting of SEQ ID NOs: 12, 14, 93, and 94.

13. The host cell of claim 1, wherein the second isolated polynucleotide encodes an antibody light chain of an antibody that specifically binds human CTLA-4 protein, wherein the antibody light chain comprises an amino acid sequence selected from the group consisting of SEQ ID NOs: 13 and 15.

14. The host cell of claim 1, wherein:

(i) the first isolated polynucleotide encodes an antibody heavy chain comprising the amino acid sequence of SEQ ID NO: 93; and the second isolated polynucleotide encodes an antibody light chain comprising the amino acid sequence of SEQ ID NO: 13;

(ii) the first isolated polynucleotide encodes an antibody heavy chain comprising the amino acid sequence of SEQ ID NO: 12; and the second isolated polynucleotide encodes an antibody light chain comprising the amino acid sequence of SEQ ID NO: 15;

(iii) the first isolated polynucleotide encodes an antibody heavy chain comprising the amino acid sequence of SEQ ID NO: 93; and the second isolated polynucleotide encodes an antibody light chain comprising the amino acid sequence of SEQ ID NO: 15;

(iv) the first isolated polynucleotide encodes an antibody heavy chain comprising the amino acid sequence of SEQ ID NO: 14; and the second isolated polynucleotide encodes an antibody light chain comprising the amino acid sequence of SEQ ID NO: 13;

(v) the first isolated polynucleotide encodes an antibody heavy chain comprising the amino acid sequence of SEQ ID NO: 14; and the second isolated polynucleotide encodes an antibody light chain comprising the amino acid sequence of SEQ ID NO: 15

(vi) the first isolated polynucleotide encodes an antibody heavy chain comprising the amino acid sequence of SEQ ID NO: 94; and the second isolated polynucleotide encodes an antibody light chain comprising the amino acid sequence of SEQ ID NO: 13; or (vii) the first isolated polynucleotide encodes an antibody heavy chain comprising the amino acid sequence of SEQ ID NO: 94; and the second isolated polynucleotide encodes an antibody light chain comprising the amino acid sequence of SEQ ID NO: 15.

15. The host cell of claim 1, wherein:

(a) the first isolated polynucleotide encodes an antibody heavy chain comprising an amino acid sequence selected from the group consisting of SEQ ID NOs: 12, 14, 93, and 94; and (b) the second isolated polynucleotide encodes an antibody light chain comprising an amino acid sequence selected from the group consisting of SEQ ID NOs: 13 and 15.

16. The host cell of claim 1, wherein:

(a) the first isolated polynucleotide encodes an antibody heavy chain comprising the amino acid sequence of SEQ ID NO: 93; and (b) the second isolated polynucleotide encodes an antibody light chain comprising the amino acid sequence of SEQ ID NOs: 13.

17. A method of producing an antibody that specifically binds to human CTLA-4 protein, the method comprising culturing the host cell of claim 1 so that the first and second polynucleotides are expressed and the antibody is produced.

18. A method of producing an antibody that specifically binds to human CTLA-4 protein, the method comprising culturing the host cell of claim 6 so that the first and second polynucleotides are expressed and the antibody is produced.

19. A method of producing an antibody that specifically binds to human CTLA-4 protein, the method comprising culturing the host cell of claim 11 so that the first and second polynucleotides are expressed and the antibody is produced.

20. A method of producing an antibody that specifically binds to human CTLA-4 protein, the method comprising culturing the host cell of claim 16 so that the first and second polynucleotides are expressed and the antibody is produced.

* * * * *

SEQUENCE LISTING

```
<160> NUMBER OF SEQ ID NOS: 97

<210> SEQ ID NO 1
<211> LENGTH: 5
<212> TYPE: PRT
<213> ORGANISM: Artificial Sequence
<220> FEATURE:
<223> OTHER INFORMATION: obtained from a synthetic library

<400> SEQUENCE: 1

Ser Tyr Ser Met Asn
1               5


<210> SEQ ID NO 2
<211> LENGTH: 17
```

```
<212> TYPE: PRT
<213> ORGANISM: Artificial Sequence
<220> FEATURE:
<223> OTHER INFORMATION: obtained from a synthetic library

<400> SEQUENCE: 2

Ser Ile Ser Ser Ser Ser Ser Tyr Ile Tyr Tyr Ala Asp Ser Val Lys
1               5                   10                  15

Gly


<210> SEQ ID NO 3
<211> LENGTH: 9
<212> TYPE: PRT
<213> ORGANISM: Artificial Sequence
<220> FEATURE:
<223> OTHER INFORMATION: obtained from a synthetic library

<400> SEQUENCE: 3

Val Gly Leu Met Gly Pro Phe Asp Ile
1               5


<210> SEQ ID NO 4
<211> LENGTH: 11
<212> TYPE: PRT
<213> ORGANISM: Artificial Sequence
<220> FEATURE:
<223> OTHER INFORMATION: obtained from a synthetic library

<400> SEQUENCE: 4

Arg Ala Ser Gln Ser Val Ser Arg Tyr Leu Gly
1               5                   10


<210> SEQ ID NO 5
<211> LENGTH: 7
<212> TYPE: PRT
<213> ORGANISM: Artificial Sequence
<220> FEATURE:
<223> OTHER INFORMATION: obtained from a synthetic library

<400> SEQUENCE: 5

Gly Ala Ser Thr Arg Ala Thr
1               5


<210> SEQ ID NO 6
<211> LENGTH: 9
<212> TYPE: PRT
<213> ORGANISM: Artificial Sequence
<220> FEATURE:
<223> OTHER INFORMATION: obtained from a synthetic library

<400> SEQUENCE: 6

Gln Gln Tyr Gly Ser Ser Pro Trp Thr
1               5


<210> SEQ ID NO 7
<211> LENGTH: 118
<212> TYPE: PRT
<213> ORGANISM: Artificial Sequence
<220> FEATURE:
<223> OTHER INFORMATION: obtained from a synthetic library

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Gly Leu Met Gly Pro Phe Asp Ile Trp Gly Gln Gly Thr
100 105 110

Met Val Thr Val Ser Ser
115

<210> SEQ ID NO 8
<211> LENGTH: 107
<212> TYPE: PRT
<213> ORGANISM: Artificial Sequence
<220> FEATURE:
<223> OTHER INFORMATION: obtained from a synthetic library

<400> SEQUENCE: 8

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Arg Tyr
20 25 30

Leu Gly Trp Tyr Gln Gln Lys Pro Gly Gln Ala Pro Arg Leu Leu Ile
35 40 45

Tyr Gly Ala Ser Thr Arg Ala Thr Gly Ile Pro Asp Arg Phe Ser Gly
50 55 60

Ser Gly Ser Gly Thr Asp Phe Thr Leu Thr Ile Thr Arg Leu Glu Pro
65 70 75 80

Glu Asp Phe Ala Val Tyr Tyr Cys Gln Gln Tyr Gly Ser Ser Pro Trp
85 90 95

Thr Phe Gly Gln Gly Thr Lys Val Glu Ile Lys
100 105

<210> SEQ ID NO 9
<211> LENGTH: 98
<212> TYPE: PRT
<213> ORGANISM: Artificial Sequence
<220> FEATURE:
<223> OTHER INFORMATION: obtained from a synthetic library

<400> SEQUENCE: 9

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 10
<211> LENGTH: 96
<212> TYPE: PRT
<213> ORGANISM: Artificial Sequence
<220> FEATURE:
<223> OTHER INFORMATION: obtained from a synthetic library

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 11
<211> LENGTH: 96
<212> TYPE: PRT
<213> ORGANISM: Artificial Sequence
<220> FEATURE:
<223> OTHER INFORMATION: obtained from a synthetic library

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

<210> SEQ ID NO 12
<211> LENGTH: 448
<212> TYPE: PRT
<213> ORGANISM: Artificial Sequence
<220> FEATURE:
<223> OTHER INFORMATION: obtained from a synthetic library

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 13
<211> LENGTH: 214
<212> TYPE: PRT
<213> ORGANISM: Artificial Sequence
<220> FEATURE:
<223> OTHER INFORMATION: obtained from a synthetic library

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 444
<212> TYPE: PRT
<213> ORGANISM: Artificial Sequence
<220> FEATURE:
<223> OTHER INFORMATION: obtained from a synthetic library

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 15
<211> LENGTH: 214
<212> TYPE: PRT
<213> ORGANISM: Artificial Sequence
<220> FEATURE:
<223> OTHER INFORMATION: obtained from a synthetic library

<400> SEQUENCE: 15

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45
```

Tyr Gly Ala Ser Thr Arg Ala Thr Gly Ile Pro Asp Arg Phe Ser Gly
50 55 60

Ser Gly Ser Gly Thr Asp Phe Thr Leu Thr Ile Thr Arg Leu Glu Pro
65 70 75 80

Glu Asp Phe Ala Val Tyr Tyr Cys Gln Gln Tyr Gly Ser Ser Pro Trp
85 90 95

Thr Phe Gly Gln Gly Thr Lys Val Glu Ile Lys Arg Ser Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 16
<211> LENGTH: 8
<212> TYPE: PRT
<213> ORGANISM: Artificial Sequence
<220> FEATURE:
<223> OTHER INFORMATION: obtained from a synthetic library

<400> SEQUENCE: 16

Gly Phe Thr Phe Ser Ser Tyr Ser
1 5

<210> SEQ ID NO 17
<211> LENGTH: 8
<212> TYPE: PRT
<213> ORGANISM: Artificial Sequence
<220> FEATURE:
<223> OTHER INFORMATION: obtained from a synthetic library

<400> SEQUENCE: 17

Ile Ser Ser Ser Ser Ser Tyr Ile
1 5

<210> SEQ ID NO 18
<211> LENGTH: 11
<212> TYPE: PRT
<213> ORGANISM: Artificial Sequence
<220> FEATURE:
<223> OTHER INFORMATION: obtained from a synthetic library

<400> SEQUENCE: 18

Ala Arg Val Gly Leu Met Gly Pro Phe Asp Ile
1 5 10

<210> SEQ ID NO 19
<211> LENGTH: 6
<212> TYPE: PRT
<213> ORGANISM: Artificial Sequence
<220> FEATURE:
<223> OTHER INFORMATION: obtained from a synthetic library

<400> SEQUENCE: 19

Gln Ser Val Ser Arg Tyr
1               5

<210> SEQ ID NO 20
<211> LENGTH: 3
<212> TYPE: PRT
<213> ORGANISM: Artificial Sequence
<220> FEATURE:
<223> OTHER INFORMATION: obtained from a synthetic library

<400> SEQUENCE: 20

Gly Ala Ser
1

<210> SEQ ID NO 21
<211> LENGTH: 9
<212> TYPE: PRT
<213> ORGANISM: Artificial Sequence
<220> FEATURE:
<223> OTHER INFORMATION: obtained from a synthetic library

<400> SEQUENCE: 21

Gln Gln Tyr Gly Ser Ser Pro Trp Thr
1               5

<210> SEQ ID NO 22
<211> LENGTH: 5
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT
<222> LOCATION: (3)..(3)
<223> OTHER INFORMATION: can be Ser or Ala
<220> FEATURE:
<221> NAME/KEY: VARIANT
<222> LOCATION: (5)..(5)
<223> OTHER INFORMATION: can be Asn or Ser

<400> SEQUENCE: 22

Ser Tyr Xaa Met Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT
<222> LOCATION: (8)..(8)
<223> OTHER INFORMATION: can be Asp or Asn

<400> SEQUENCE: 23

Val Gly Leu Met Gly Pro Phe Xaa Ile
1               5

<210> SEQ ID NO 24
<211> LENGTH: 11
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT

```
<222> LOCATION: (7)..(7)
<223> OTHER INFORMATION: can be Ser or Gly
<220> FEATURE:
<221> NAME/KEY: VARIANT
<222> LOCATION: (8)..(8)
<223> OTHER INFORMATION: can be Arg, Ser or Thr
<220> FEATURE:
<221> NAME/KEY: VARIANT
<222> LOCATION: (11)..(11)
<223> OTHER INFORMATION: can be Gly or Ala

<400> SEQUENCE: 24

Arg Ala Ser Gln Ser Val Xaa Xaa Tyr Leu Xaa
1               5                   10


<210> SEQ ID NO 25
<211> LENGTH: 7
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT
<222> LOCATION: (1)..(1)
<223> OTHER INFORMATION: can be Gly or Ala
<220> FEATURE:
<221> NAME/KEY: VARIANT
<222> LOCATION: (2)..(2)
<223> OTHER INFORMATION: can be Ala or Thr
<220> FEATURE:
<221> NAME/KEY: VARIANT
<222> LOCATION: (4)..(4)
<223> OTHER INFORMATION: can be Thr, Ser, Arg or Asn

<400> SEQUENCE: 25

Xaa Xaa Ser Xaa Arg Ala Thr
1               5


<210> SEQ ID NO 26
<211> LENGTH: 9
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT
<222> LOCATION: (5)..(5)
<223> OTHER INFORMATION: can be Ser or Thr
<220> FEATURE:
<221> NAME/KEY: VARIANT
<222> LOCATION: (8)..(8)
<223> OTHER INFORMATION: can be Trp or Phe

<400> SEQUENCE: 26

Gln Gln Tyr Gly Xaa Ser Pro Xaa Thr
1               5


<210> SEQ ID NO 27
<211> LENGTH: 5
<212> TYPE: PRT
<213> ORGANISM: Artificial Sequence
<220> FEATURE:
<223> OTHER INFORMATION: obtained from a synthetic library

<400> SEQUENCE: 27

Ser Tyr Ala Met Ser
1               5


<210> SEQ ID NO 28
<211> LENGTH: 9
<212> TYPE: PRT
```

<213> ORGANISM: Artificial Sequence
<220> FEATURE:
<223> OTHER INFORMATION: obtained from a synthetic library

<400> SEQUENCE: 28

Val Gly Leu Met Gly Pro Phe Asn Ile
1 5

<210> SEQ ID NO 29
<211> LENGTH: 11
<212> TYPE: PRT
<213> ORGANISM: Artificial Sequence
<220> FEATURE:
<223> OTHER INFORMATION: obtained from a synthetic library

<400> SEQUENCE: 29

Arg Ala Ser Gln Ser Val Ser Ser Tyr Leu Ala
1 5 10

<210> SEQ ID NO 30
<211> LENGTH: 11
<212> TYPE: PRT
<213> ORGANISM: Artificial Sequence
<220> FEATURE:
<223> OTHER INFORMATION: obtained from a synthetic library

<400> SEQUENCE: 30

Arg Ala Ser Gln Ser Val Gly Thr Tyr Leu Ala
1 5 10

<210> SEQ ID NO 31
<211> LENGTH: 7
<212> TYPE: PRT
<213> ORGANISM: Artificial Sequence
<220> FEATURE:
<223> OTHER INFORMATION: obtained from a synthetic library

<400> SEQUENCE: 31

Gly Ala Ser Arg Arg Ala Thr
1 5

<210> SEQ ID NO 32
<211> LENGTH: 7
<212> TYPE: PRT
<213> ORGANISM: Artificial Sequence
<220> FEATURE:
<223> OTHER INFORMATION: obtained from a synthetic library

<400> SEQUENCE: 32

Ala Thr Ser Ser Arg Ala Thr
1 5

<210> SEQ ID NO 33
<211> LENGTH: 7
<212> TYPE: PRT
<213> ORGANISM: Artificial Sequence
<220> FEATURE:
<223> OTHER INFORMATION: obtained from a synthetic library

<400> SEQUENCE: 33

Gly Ala Ser Ser Arg Ala Thr
1 5

<210> SEQ ID NO 34
<211> LENGTH: 7
<212> TYPE: PRT
<213> ORGANISM: Artificial Sequence
<220> FEATURE:
<223> OTHER INFORMATION: obtained from a synthetic library

<400> SEQUENCE: 34

Ala Ala Ser Thr Arg Ala Thr
1               5

<210> SEQ ID NO 35
<211> LENGTH: 7
<212> TYPE: PRT
<213> ORGANISM: Artificial Sequence
<220> FEATURE:
<223> OTHER INFORMATION: obtained from a synthetic library

<400> SEQUENCE: 35

Gly Ala Ser Asn Arg Ala Thr
1               5

<210> SEQ ID NO 36
<211> LENGTH: 9
<212> TYPE: PRT
<213> ORGANISM: Artificial Sequence
<220> FEATURE:
<223> OTHER INFORMATION: obtained from a synthetic library

<400> SEQUENCE: 36

Gln Gln Tyr Gly Thr Ser Pro Trp Thr
1               5

<210> SEQ ID NO 37
<211> LENGTH: 9
<212> TYPE: PRT
<213> ORGANISM: Artificial Sequence
<220> FEATURE:
<223> OTHER INFORMATION: obtained from a synthetic library

<400> SEQUENCE: 37

Gln Gln Tyr Gly Ser Ser Pro Phe Thr
1               5

<210> SEQ ID NO 38
<211> LENGTH: 118
<212> TYPE: PRT
<213> ORGANISM: Artificial Sequence
<220> FEATURE:
<223> OTHER INFORMATION: obtained from a synthetic library

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Val Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser

115

<210> SEQ ID NO 39
<211> LENGTH: 118
<212> TYPE: PRT
<213> ORGANISM: Artificial Sequence
<220> FEATURE:
<223> OTHER INFORMATION: obtained from a synthetic library

<400> SEQUENCE: 39

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Val Gly Leu Met Gly Pro Phe Asp Ile Trp Gly Gln Gly Thr
100 105 110

Met Val Thr Val Ser Ser
115

<210> SEQ ID NO 40
<211> LENGTH: 118
<212> TYPE: PRT
<213> ORGANISM: Artificial Sequence
<220> FEATURE:
<223> OTHER INFORMATION: obtained from a synthetic library

<400> SEQUENCE: 40

Glu Val Gln Leu Leu Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Gly Leu Met Gly Pro Phe Asp Ile Trp Gly Gln Gly Thr
100 105 110

Met Val Thr Val Ser Ser
115

<210> SEQ ID NO 41
<211> LENGTH: 118
<212> TYPE: PRT
<213> ORGANISM: Artificial Sequence
<220> FEATURE:
<223> OTHER INFORMATION: obtained from a synthetic library

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Val Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asn Ile Trp Gly Gln Gly Thr
            100                 105                 110

Met Val Thr Val Ser Ser
        115


<210> SEQ ID NO 42
<211> LENGTH: 118
<212> TYPE: PRT
<213> ORGANISM: Artificial Sequence
<220> FEATURE:
<223> OTHER INFORMATION: obtained from a synthetic library

<400> SEQUENCE: 42

Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115


<210> SEQ ID NO 43
<211> LENGTH: 107
<212> TYPE: PRT
<213> ORGANISM: Artificial Sequence
<220> FEATURE:
<223> OTHER INFORMATION: obtained from a synthetic library

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Thr Tyr
            20                  25                  30

Leu Ala Trp Tyr Gln His Lys Val Gly Gln Ala Pro Arg Leu Leu Ile
        35                  40                  45

Tyr Gly Ala Ser Arg Arg Ala Thr Gly Ile Pro Asp Arg Phe Ser Gly
```

```
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105


<210> SEQ ID NO 44
<211> LENGTH: 107
<212> TYPE: PRT
<213> ORGANISM: Artificial Sequence
<220> FEATURE:
<223> OTHER INFORMATION: obtained from a synthetic library

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Ser Leu Leu Ile
        35                  40                  45

Tyr Ala Thr Ser Ser Arg Ala Thr Gly Ile Pro Asp Arg Phe Ser Gly
    50                  55                  60

Ser Val Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Thr Ser Pro Trp
                85                  90                  95

Thr Phe Gly Gln Gly Thr Lys Val Glu Ile Lys
            100                 105


<210> SEQ ID NO 45
<211> LENGTH: 107
<212> TYPE: PRT
<213> ORGANISM: Artificial Sequence
<220> FEATURE:
<223> OTHER INFORMATION: obtained from a synthetic library

<400> SEQUENCE: 45

Glu Ile Val Leu Thr Gln Ser Pro Ala Thr Leu Ser Phe Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Phe Thr Ile Ser Arg Leu Glu Pro
65                  70                  75                  80

Glu Asp Phe Ala Val Tyr Tyr Cys Gln Gln Tyr Gly Ser Ser Pro Phe
                85                  90                  95

Thr Phe Gly Pro Gly Thr Lys Val Asp Ile Lys
            100                 105


<210> SEQ ID NO 46
<211> LENGTH: 107
<212> TYPE: PRT
<213> ORGANISM: Artificial Sequence
<220> FEATURE:
```

<223> OTHER INFORMATION: obtained from a synthetic library

<400> SEQUENCE: 46

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Asp Arg Phe Ser Gly
    50                  55                  60

Ser Ala Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105
```

<210> SEQ ID NO 47
<211> LENGTH: 107
<212> TYPE: PRT
<213> ORGANISM: Artificial Sequence
<220> FEATURE:
<223> OTHER INFORMATION: obtained from a synthetic library

<400> SEQUENCE: 47

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Phe
                85                  90                  95

Thr Phe Gly Pro Gly Thr Lys Val Asp Ile Lys
            100                 105
```

<210> SEQ ID NO 48
<211> LENGTH: 30
<212> TYPE: PRT
<213> ORGANISM: Artificial Sequence
<220> FEATURE:
<223> OTHER INFORMATION: obtained from a synthetic library

<400> SEQUENCE: 48

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 49
<211> LENGTH: 14
<212> TYPE: PRT
<213> ORGANISM: Artificial Sequence
<220> FEATURE:
<223> OTHER INFORMATION: obtained from a synthetic library

<400> SEQUENCE: 49

Trp Val Arg Gln Ala Pro Gly Lys Gly Leu Glu Trp Val Ser
1               5                   10

<210> SEQ ID NO 50
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 50

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 51
<211> LENGTH: 11
<212> TYPE: PRT
<213> ORGANISM: Artificial Sequence
<220> FEATURE:
<223> OTHER INFORMATION: obtained from a synthetic library

<400> SEQUENCE: 51

Trp Gly Gln Gly Thr Met Val Thr Val Ser Ser
1               5                   10

<210> SEQ ID NO 52
<211> LENGTH: 30
<212> TYPE: PRT
<213> ORGANISM: Artificial Sequence
<220> FEATURE:
<223> OTHER INFORMATION: obtained from a synthetic library

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 53
<211> LENGTH: 14
<212> TYPE: PRT
<213> ORGANISM: Artificial Sequence
<220> FEATURE:
<223> OTHER INFORMATION: obtained from a synthetic library

<400> SEQUENCE: 53

Trp Val Arg Gln Ala Pro Gly Lys Gly Leu Val Trp Val Ser
1               5                   10

<210> SEQ ID NO 54
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 54

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: obtained from a synthetic library

<400> SEQUENCE: 55

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 56
<211> LENGTH: 30
<212> TYPE: PRT
<213> ORGANISM: Artificial Sequence
<220> FEATURE:
<223> OTHER INFORMATION: obtained from a synthetic library

<400> SEQUENCE: 56

```
Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Ser
            20                  25                  30
```

<210> SEQ ID NO 57
<211> LENGTH: 23
<212> TYPE: PRT
<213> ORGANISM: Artificial Sequence
<220> FEATURE:
<223> OTHER INFORMATION: obtained from a synthetic library

<400> SEQUENCE: 57

```
Glu Ile Val Leu Thr Gln Ser Pro Gly Thr Leu Ser Leu Ser Pro Gly
1               5                   10                  15

Glu Arg Ala Thr Leu Ser Cys
            20
```

<210> SEQ ID NO 58
<211> LENGTH: 15
<212> TYPE: PRT
<213> ORGANISM: Artificial Sequence
<220> FEATURE:
<223> OTHER INFORMATION: obtained from a synthetic library

<400> SEQUENCE: 58

```
Trp Tyr Gln Gln Lys Pro Gly Gln Ala Pro Arg Leu Leu Ile Tyr
1               5                   10                  15
```

<210> SEQ ID NO 59
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 59

```
Gly Ile Pro Asp Arg Phe Ser Gly Ser Gly Ser Gly Thr Asp Phe Thr
1               5                   10                  15

Leu Thr Ile Thr Arg Leu Glu Pro Glu Asp Phe Ala Val Tyr Tyr Cys
            20                  25                  30
```

<210> SEQ ID NO 60
<211> LENGTH: 10
<212> TYPE: PRT
<213> ORGANISM: Artificial Sequence
<220> FEATURE:
<223> OTHER INFORMATION: obtained from a synthetic library

<400> SEQUENCE: 60

Phe Gly Gln Gly Thr Lys Val Glu Ile Lys
1               5                   10

<210> SEQ ID NO 61
<211> LENGTH: 23
<212> TYPE: PRT
<213> ORGANISM: Artificial Sequence
<220> FEATURE:
<223> OTHER INFORMATION: obtained from a synthetic library

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 62
<211> LENGTH: 15
<212> TYPE: PRT
<213> ORGANISM: Artificial Sequence
<220> FEATURE:
<223> OTHER INFORMATION: obtained from a synthetic library

<400> SEQUENCE: 62

Trp Tyr Gln His Lys Val Gly Gln Ala Pro Arg Leu Leu Ile Tyr
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 63

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 64
<211> LENGTH: 15
<212> TYPE: PRT
<213> ORGANISM: Artificial Sequence
<220> FEATURE:
<223> OTHER INFORMATION: obtained from a synthetic library

<400> SEQUENCE: 64

Trp Tyr Gln Gln Lys Pro Gly Gln Ala Pro Ser Leu Leu Ile Tyr
1               5                   10                  15

<210> SEQ ID NO 65
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 65

```
Gly Ile Pro Asp Arg Phe Ser Gly Ser Val Ser Gly Thr Asp Phe Thr
1               5                   10                  15

Leu Thr Ile Ser Arg Leu Glu Pro Glu Asp Phe Ala Val Tyr Tyr Cys
            20                  25                  30


<210> SEQ ID NO 66
<211> LENGTH: 23
<212> TYPE: PRT
<213> ORGANISM: Artificial Sequence
<220> FEATURE:
<223> OTHER INFORMATION: obtained from a synthetic library

<400> SEQUENCE: 66

Glu Ile Val Leu Thr Gln Ser Pro Ala Thr Leu Ser Phe Ser Pro Gly
1               5                   10                  15

Glu Arg Ala Thr Leu Ser Cys
            20


<210> SEQ ID NO 67
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 67

Gly Ile Pro Asp Arg Phe Ser Gly Ser Gly Ser Gly Thr Asp Phe Thr
1               5                   10                  15

Phe Thr Ile Ser Arg Leu Glu Pro Glu Asp Phe Ala Val Tyr Tyr Cys
            20                  25                  30


<210> SEQ ID NO 68
<211> LENGTH: 10
<212> TYPE: PRT
<213> ORGANISM: Artificial Sequence
<220> FEATURE:
<223> OTHER INFORMATION: obtained from a synthetic library

<400> SEQUENCE: 68

Phe Gly Pro Gly Thr Lys Val Asp Ile Lys
1               5                   10


<210> SEQ ID NO 69
<211> LENGTH: 23
<212> TYPE: PRT
<213> ORGANISM: Artificial Sequence
<220> FEATURE:
<223> OTHER INFORMATION: obtained from a synthetic library

<400> SEQUENCE: 69

Glu Ile Val Leu Thr Gln Ser Pro Ala Thr Leu Ser Val Ser Pro Gly
1               5                   10                  15

Glu Arg Ala Thr Leu Ser Cys
            20


<210> SEQ ID NO 70
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 70

Gly Ile Pro Asp Arg Phe Ser Gly Ser Ala Ser Gly Thr Asp Phe Thr
```

1 5 10 15

Leu Thr Ile Ser Arg Leu Glu Pro Glu Asp Phe Ala Val Tyr Tyr Cys
20 25 30

<210> SEQ ID NO 71
<211> LENGTH: 32
<212> TYPE: PRT
<213> ORGANISM: Artificial Sequence
<220> FEATURE:
<223> OTHER INFORMATION: obtained from a synthetic library

<400> SEQUENCE: 71

Gly Ile Pro Ala Arg Phe Ser Gly Ser Gly Ser Gly Thr Asp Phe Thr
1 5 10 15

Leu Thr Ile Ser Ser Leu Glu Pro Glu Asp Phe Ala Val Tyr Tyr Cys
20 25 30

<210> SEQ ID NO 72
<211> LENGTH: 118
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT
<222> LOCATION: (5)..(5)
<223> OTHER INFORMATION: can be Val or Leu
<220> FEATURE:
<221> NAME/KEY: VARIANT
<222> LOCATION: (13)..(13)
<223> OTHER INFORMATION: can be Lys or Gln
<220> FEATURE:
<221> NAME/KEY: VARIANT
<222> LOCATION: (19)..(19)
<223> OTHER INFORMATION: can be Arg or Thr
<220> FEATURE:
<221> NAME/KEY: VARIANT
<222> LOCATION: (33)..(33)
<223> OTHER INFORMATION: can be Ser or Ala
<220> FEATURE:
<221> NAME/KEY: VARIANT
<222> LOCATION: (35)..(35)
<223> OTHER INFORMATION: can be Asn or Ser
<220> FEATURE:
<221> NAME/KEY: VARIANT
<222> LOCATION: (46)..(46)
<223> OTHER INFORMATION: can be Glu or Val
<220> FEATURE:
<221> NAME/KEY: VARIANT
<222> LOCATION: (78)..(78)
<223> OTHER INFORMATION: can be Ser or Thr
<220> FEATURE:
<221> NAME/KEY: VARIANT
<222> LOCATION: (106)..(106)
<223> OTHER INFORMATION: can be Asp or Asn

<400> SEQUENCE: 72

Glu Val Gln Leu Xaa Glu Ser Gly Gly Gly Leu Val Xaa Pro Gly Gly
1 5 10 15

Ser Leu Xaa Leu Ser Cys Ala Ala Ser Gly Phe Thr Phe Ser Ser Tyr
20 25 30

Xaa Met Xaa Trp Val Arg Gln Ala Pro Gly Lys Gly Leu Xaa Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Xaa Leu Tyr
65 70 75 80

Leu Gln Met Asn Ser Leu Arg Ala Glu Asp Thr Ala Val Tyr Tyr Cys

```
            85                  90                  95

Ala Arg Val Gly Leu Met Gly Pro Phe Xaa Ile Trp Gly Gln Gly Thr
            100                 105                 110

Met Val Thr Val Ser Ser
        115
```

```
<210> SEQ ID NO 73
<211> LENGTH: 107
<212> TYPE: PRT
<213> ORGANISM: Artificial Sequence
<220> FEATURE:
<223> OTHER INFORMATION: obtained from a synthetic library
<220> FEATURE:
<221> NAME/KEY: VARIANT
<222> LOCATION: (9)..(9)
<223> OTHER INFORMATION: can be Gly or Ala
<220> FEATURE:
<221> NAME/KEY: VARIANT
<222> LOCATION: (13)..(13)
<223> OTHER INFORMATION: can be Leu, Val or Phe
<220> FEATURE:
<221> NAME/KEY: VARIANT
<222> LOCATION: (30)..(30)
<223> OTHER INFORMATION: can be Ser or Gly
<220> FEATURE:
<221> NAME/KEY: VARIANT
<222> LOCATION: (31)..(31)
<223> OTHER INFORMATION: can be Arg, Thr or Ser
<220> FEATURE:
<221> NAME/KEY: VARIANT
<222> LOCATION: (34)..(34)
<223> OTHER INFORMATION: can be Gly or Ala
<220> FEATURE:
<221> NAME/KEY: VARIANT
<222> LOCATION: (38)..(38)
<223> OTHER INFORMATION: can be Gln or His
<220> FEATURE:
<221> NAME/KEY: VARIANT
<222> LOCATION: (40)..(40)
<223> OTHER INFORMATION: can be Pro or Val
<220> FEATURE:
<221> NAME/KEY: VARIANT
<222> LOCATION: (45)..(45)
<223> OTHER INFORMATION: can be Arg or Ser
<220> FEATURE:
<221> NAME/KEY: VARIANT
<222> LOCATION: (50)..(50)
<223> OTHER INFORMATION: can be Gly or Ala
<220> FEATURE:
<221> NAME/KEY: VARIANT
<222> LOCATION: (51)..(51)
<223> OTHER INFORMATION: can be Ala or Thr
<220> FEATURE:
<221> NAME/KEY: VARIANT
<222> LOCATION: (53)..(53)
<223> OTHER INFORMATION: can be Thr, Arg, Ser or Asn
<220> FEATURE:
<221> NAME/KEY: VARIANT
<222> LOCATION: (60)..(60)
<223> OTHER INFORMATION: can be Asp or Ala
<220> FEATURE:
<221> NAME/KEY: VARIANT
<222> LOCATION: (66)..(66)
<223> OTHER INFORMATION: can be Gly, Val or Ala
<220> FEATURE:
<221> NAME/KEY: VARIANT
<222> LOCATION: (73)..(73)
<223> OTHER INFORMATION: can be Leu or Phe
<220> FEATURE:
<221> NAME/KEY: VARIANT
<222> LOCATION: (76)..(76)
<223> OTHER INFORMATION: can be Thr or Ser
<220> FEATURE:
<221> NAME/KEY: VARIANT
<222> LOCATION: (77)..(77)
<223> OTHER INFORMATION: can be Arg or Ser
```

<220> FEATURE:
<221> NAME/KEY: VARIANT
<222> LOCATION: (93)..(93)
<223> OTHER INFORMATION: can be Ser or Thr
<220> FEATURE:
<221> NAME/KEY: VARIANT
<222> LOCATION: (96)..(96)
<223> OTHER INFORMATION: can be Trp or Phe
<220> FEATURE:
<221> NAME/KEY: VARIANT
<222> LOCATION: (100)..(100)
<223> OTHER INFORMATION: can be Gln or Pro
<220> FEATURE:
<221> NAME/KEY: VARIANT
<222> LOCATION: (105)..(105)
<223> OTHER INFORMATION: can be Glu or Asp

<400> SEQUENCE: 73

```
Glu Ile Val Leu Thr Gln Ser Pro Xaa Thr Leu Ser Xaa Ser Pro Gly
1               5                   10                  15

Glu Arg Ala Thr Leu Ser Cys Arg Ala Ser Gln Ser Val Xaa Xaa Tyr
            20                  25                  30

Leu Xaa Trp Tyr Gln Xaa Lys Xaa Gly Gln Ala Pro Xaa Leu Leu Ile
        35                  40                  45

Tyr Xaa Xaa Ser Xaa Arg Ala Thr Gly Ile Pro Xaa Arg Phe Ser Gly
    50                  55                  60

Ser Xaa Ser Gly Thr Asp Phe Thr Xaa Thr Ile Xaa Xaa Leu Glu Pro
65                  70                  75                  80

Glu Asp Phe Ala Val Tyr Tyr Cys Gln Gln Tyr Gly Xaa Ser Pro Xaa
                85                  90                  95

Thr Phe Gly Xaa Gly Thr Lys Val Xaa Ile Lys
            100                 105
```

<210> SEQ ID NO 74
<211> LENGTH: 448
<212> TYPE: PRT
<213> ORGANISM: Artificial Sequence
<220> FEATURE:
<223> OTHER INFORMATION: obtained from a synthetic library

<400> SEQUENCE: 74

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 75
<211> LENGTH: 448
<212> TYPE: PRT
<213> ORGANISM: Artificial Sequence
<220> FEATURE:
<223> OTHER INFORMATION: obtained from a synthetic library

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Glu His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Phe Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 76
<211> LENGTH: 448
<212> TYPE: PRT
<213> ORGANISM: Artificial Sequence
<220> FEATURE:
<223> OTHER INFORMATION: obtained from a synthetic library

<400> SEQUENCE: 76

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 77
<211> LENGTH: 223
<212> TYPE: PRT
<213> ORGANISM: Homo sapiens

<400> SEQUENCE: 77

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 78
<211> LENGTH: 3
<212> TYPE: PRT
<213> ORGANISM: Homo sapiens

<400> SEQUENCE: 78

Gln Val Thr
1


<210> SEQ ID NO 79
<211> LENGTH: 15
<212> TYPE: PRT
<213> ORGANISM: Homo sapiens

<400> SEQUENCE: 79

Tyr Pro Pro Pro Tyr Tyr Leu Gly Ile Gly Asn Gly Thr Gln Ile
1               5                   10                  15
```

<210> SEQ ID NO 80
<211> LENGTH: 4
<212> TYPE: PRT
<213> ORGANISM: Homo sapiens

<400> SEQUENCE: 80

Tyr Leu Gly Ile
1

<210> SEQ ID NO 81
<211> LENGTH: 7
<212> TYPE: PRT
<213> ORGANISM: Homo sapiens

<400> SEQUENCE: 81

Met Tyr Pro Pro Pro Tyr Tyr
1               5

<210> SEQ ID NO 82
<211> LENGTH: 9
<212> TYPE: PRT
<213> ORGANISM: Homo sapiens

<400> SEQUENCE: 82

Tyr Pro Pro Pro Tyr Tyr Leu Gly Ile
1               5

<210> SEQ ID NO 83
<211> LENGTH: 10
<212> TYPE: PRT
<213> ORGANISM: Homo sapiens

<400> SEQUENCE: 83

Tyr Leu Gly Ile Gly Asn Gly Thr Gln Ile
1               5                   10

<210> SEQ ID NO 84
<211> LENGTH: 223
<212> TYPE: PRT
<213> ORGANISM: Macaca mulatta

<400> SEQUENCE: 84

Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
            20                  25                  30

Val Phe Ser Lys Ala Met His Val Ala Gln Pro Ala Val Val Leu Ala
        35                  40                  45

Asn Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Met Gly Ile Gly
    130                 135                 140

Asn Gly Thr Gln Ile Tyr Val Ile Asp Pro Glu Pro Cys Pro Asp Ser

```
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 85
<211> LENGTH: 223
<212> TYPE: PRT
<213> ORGANISM: Mus musculus

<400> SEQUENCE: 85

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Ser Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 86
<211> LENGTH: 223
<212> TYPE: PRT
<213> ORGANISM: Rattus norvegicus

<400> SEQUENCE: 86

Met Ala Cys Leu Gly Leu Gln Arg Tyr Lys Thr His Leu Gln Leu Pro
1               5                   10                  15

Ser Arg Thr Trp Pro Phe Gly Val Leu Leu Ser Leu Leu Phe Ile Pro
            20                  25                  30

Ile Phe Ser Glu Ala Ile Gln Val Thr Gln Pro Ser Val Val Leu Ala
```

```
        35                  40                  45

Ser Ser His Gly Val Ala Ser Phe Pro Cys Glu Tyr Ala Ser Ser His
    50                  55                  60

Asn Thr Asp Glu Val Arg Val Thr Val Leu Arg Gln Thr Asn Asp Gln
65                  70                  75                  80

Val Thr Glu Val Cys Ala Thr Thr Phe Thr Val Lys Asn Thr Leu Gly
                85                  90                  95

Phe Leu Asp Asp Pro Phe Cys Ser Gly Thr Phe Asn Glu Ser Arg Val
            100                 105                 110

Asn Leu Thr Ile Gln Gly Leu Arg Ala Ala Asp Thr Gly Leu Tyr Phe
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Val Thr Ala Val Ser Leu Asn Arg Thr Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 87
<211> LENGTH: 220
<212> TYPE: PRT
<213> ORGANISM: Homo sapiens

<400> SEQUENCE: 87

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190
```

Asn Met Thr Pro Arg Arg Pro Gly Pro Thr Arg Lys His Tyr Gln Pro
195 200 205

Tyr Ala Pro Pro Arg Asp Phe Ala Ala Tyr Arg Ser
210 215 220

<210> SEQ ID NO 88
<211> LENGTH: 199
<212> TYPE: PRT
<213> ORGANISM: Homo sapiens

<400> SEQUENCE: 88

Met Lys Ser Gly Leu Trp Tyr Phe Phe Leu Phe Cys Leu Arg Ile Lys
1 5 10 15

Val Leu Thr Gly Glu Ile Asn Gly Ser Ala Asn Tyr Glu Met Phe Ile
20 25 30

Phe His Asn Gly Gly Val Gln Ile Leu Cys Lys Tyr Pro Asp Ile Val
35 40 45

Gln Gln Phe Lys Met Gln Leu Leu Lys Gly Gly Gln Ile Leu Cys Asp
50 55 60

Leu Thr Lys Thr Lys Gly Ser Gly Asn Thr Val Ser Ile Lys Ser Leu
65 70 75 80

Lys Phe Cys His Ser Gln Leu Ser Asn Asn Ser Val Ser Phe Phe Leu
85 90 95

Tyr Asn Leu Asp His Ser His Ala Asn Tyr Tyr Phe Cys Asn Leu Ser
100 105 110

Ile Phe Asp Pro Pro Pro Phe Lys Val Thr Leu Thr Gly Gly Tyr Leu
115 120 125

His Ile Tyr Glu Ser Gln Leu Cys Cys Gln Leu Lys Phe Trp Leu Pro
130 135 140

Ile Gly Cys Ala Ala Phe Val Val Val Cys Ile Leu Gly Cys Ile Leu
145 150 155 160

Ile Cys Trp Leu Thr Lys Lys Lys Tyr Ser Ser Ser Val His Asp Pro
165 170 175

Asn Gly Glu Tyr Met Phe Met Arg Ala Val Asn Thr Ala Lys Lys Ser
180 185 190

Arg Leu Thr Asp Val Thr Leu
195

<210> SEQ ID NO 89
<211> LENGTH: 289
<212> TYPE: PRT
<213> ORGANISM: Homo sapiens

<400> SEQUENCE: 89

Met Lys Thr Leu Pro Ala Met Leu Gly Thr Gly Lys Leu Phe Trp Val
1 5 10 15

Phe Phe Leu Ile Pro Tyr Leu Asp Ile Trp Asn Ile His Gly Lys Glu
20 25 30

Ser Cys Asp Val Gln Leu Tyr Ile Lys Arg Gln Ser Glu His Ser Ile
35 40 45

Leu Ala Gly Asp Pro Phe Glu Leu Glu Cys Pro Val Lys Tyr Cys Ala
50 55 60

Asn Arg Pro His Val Thr Trp Cys Lys Leu Asn Gly Thr Thr Cys Val
65 70 75 80

Lys Leu Glu Asp Arg Gln Thr Ser Trp Lys Glu Glu Lys Asn Ile Ser
85 90 95

```
Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser


<210> SEQ ID NO 90
<211> LENGTH: 288
<212> TYPE: PRT
<213> ORGANISM: Homo sapiens

<400> SEQUENCE: 90

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175
```

```
Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 91
<211> LENGTH: 449
<212> TYPE: PRT
<213> ORGANISM: Artificial Sequence
<220> FEATURE:
<223> OTHER INFORMATION: obtained from a synthetic library

<400> SEQUENCE: 91

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 92
<211> LENGTH: 214
<212> TYPE: PRT
<213> ORGANISM: Artificial Sequence
<220> FEATURE:
<223> OTHER INFORMATION: obtained from a synthetic library

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 93
<211> LENGTH: 447
<212> TYPE: PRT
<213> ORGANISM: Artificial Sequence
<220> FEATURE:
<223> OTHER INFORMATION: obtained from a synthetic library

<400> SEQUENCE: 93

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 94
<211> LENGTH: 443
<212> TYPE: PRT
<213> ORGANISM: Artificial Sequence
<220> FEATURE:
<223> OTHER INFORMATION: obtained from a synthetic library

<400> SEQUENCE: 94

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Gly Leu Met Gly Pro Phe Asp Ile Trp Gly Gln Gly Thr
100 105 110

Met Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Asn Phe Gly Thr Gln Thr Tyr Thr Cys Asn Val Asp His Lys Pro Ser
195 200 205

Asn Thr Lys Val Asp Lys Thr Val Glu Arg Lys Cys Cys Val Glu Cys
210 215 220

Pro Pro Cys Pro Ala Pro Pro Val Ala Gly Pro Ser Val Phe Leu Phe

```
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 95
<211> LENGTH: 447
<212> TYPE: PRT
<213> ORGANISM: Artificial Sequence
<220> FEATURE:
<223> OTHER INFORMATION: obtained from a synthetic library

<400> SEQUENCE: 95

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Ala Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 96
<211> LENGTH: 447
<212> TYPE: PRT
<213> ORGANISM: Artificial Sequence
<220> FEATURE:
<223> OTHER INFORMATION: obtained from a synthetic library

<400> SEQUENCE: 96

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr

```
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Glu His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Phe Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 97
<211> LENGTH: 447
<212> TYPE: PRT
<213> ORGANISM: Artificial Sequence
<220> FEATURE:
<223> OTHER INFORMATION: Obtained from a synthetic library

<400> SEQUENCE: 97

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Gly Leu Met Gly Pro Phe Asp Ile Trp Gly Gln Gly Thr
100 105 110

Met Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Asp
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Leu Pro Glu Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

-continued

```
Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445
```